(12) United States Patent
Burgess et al.

(10) Patent No.: US 12,324,818 B2
(45) Date of Patent: Jun. 10, 2025

(54) GENERATION OF ALVEOLAR EPITHELIAL TYPE 1 (AT1) CELLS

(71) Applicant: TRUSTEES OF BOSTON UNIVERSITY, Boston, MA (US)

(72) Inventors: Claire Burgess, Boston, MA (US); Darrell Kotton, Newton, MA (US)

(73) Assignee: TRUSTEES OF BOSTON UNIVERSITY

( * ) Notice: Subject to any disclaimer, the term of this patent is extended or adjusted under 35 U.S.C. 154(b) by 0 days.

(21) Appl. No.: 18/541,448

(22) Filed: Dec. 15, 2023

(65) Prior Publication Data

US 2024/0261337 A1 Aug. 8, 2024

Related U.S. Application Data

(60) Provisional application No. 63/434,299, filed on Dec. 21, 2022.

(51) Int. Cl.
*A61K 35/42* (2015.01)
*C12N 5/071* (2010.01)
*C12N 15/86* (2006.01)

(52) U.S. Cl.
CPC ............ *A61K 35/42* (2013.01); *C12N 5/0688* (2013.01); *C12N 15/86* (2013.01); *C12N 2500/90* (2013.01); *C12N 2501/11* (2013.01); *C12N 2501/117* (2013.01); *C12N 2501/119* (2013.01); *C12N 2501/727* (2013.01); *C12N 2513/00* (2013.01); *C12N 2740/15043* (2013.01)

(58) Field of Classification Search
CPC ...... A61K 35/42; C12N 5/0688; C12N 5/068; C12N 5/096
USPC ....................................................... 435/377
See application file for complete search history.

(56) References Cited

U.S. PATENT DOCUMENTS

| | | |
|---|---|---|
| 2014/0329318 A1 | 11/2014 | Rajagopal |
| 2015/0175972 A1 | 6/2015 | Jabbari |
| 2015/0247124 A1 | 9/2015 | Snoeck |
| 2017/0275592 A1 | 9/2017 | Sachs |
| 2018/0208903 A1 | 7/2018 | Kotton |
| 2020/0216906 A1 | 7/2020 | Gujral |
| 2022/0273822 A1 | 9/2022 | Tang |

FOREIGN PATENT DOCUMENTS

WO 2018085275 A1 5/2018

OTHER PUBLICATIONS

Kastan, May 2021, Nature Communications, 12:3100, 12 pages.*
Nantie, Development (2018) 145, dev163105, 10 pages.*
Penkala, Cell Stem Cell. Oct. 7, 2021; 28(10): 1775-1789.*
Alysandratos, Cell Reports 36, 109636, Aug. 31, 2021.*
Jacob, Cell Stem Cell. Oct. 5, 2017; 21(4): 472-488.*
Gokey et al., 2021, iScience 24, 102967, Sep. 24, 2021, 22 pages.*
Barilla et al. "Poster Session Abstracts No. 395: Application of IPSC-Derived Airway Epithelium for Evaluating the Response of Rare or Unknown CFTR Mutations to Modulators." Pediatric Pulmonology 55(S2): S193 (2020).
Chen et al. "A three-dimensional model of human lung development and disease from pluripotent stem cells." Nature Cell Biology 19(5): 542-549 (2017).
Dye et al. "In vitro generation of human pluripotent stem cell derived lung organoids." elife 4: e05098 pp. 1-25 (2015).
Fulcher et al. "Human nasal and tracheo-bronchial respiratory epithelial cell culture." In S. Randal, M. Fulcher (eds.) Epithelial Cell Culture Protocols: Second Edition, Methods in Molecular Biology, vol. 945. Chapter 8: 109-21 (2012).
Fulcher et al. "Well-differentiated human airway epithelial cell cultures." In J. Picot (ed.) Methods in Molecular Medicine, vol. 107: Human Cell Culture Protocols, Second Edition. Chapter 13: 183-206 (2005).
Gowers et al. "Optimized isolation and expansion of human airway epithelial basal cells from endobronchial biopsy samples." Journal of Tissue Engineering and Regenerative Medicine 12(1): e313-e317 (2018).
Hawkins et al. "Derivation of airway basal stem cells from human pluripotent stem cells." Cell Stem Cell 28(1): 79-95 (2021).
Hawkins et al. "Prospective isolation of NKX2-1-expressing human lung progenitors derived from pluripotent stem cells." The Journal of Clinical Investigation 127(6): 2277-2294 (2017).
Katasura et al., "Human Lung Stem Cell-Based Alveolospheres Provide Insights into SARS-CoV-2-Mediated Interereon Responses and Pneumocyte Dysfunction" Cell Stem Cell 27:890-904 (2020).
Konishi et al. "Directed induction of functional multi-ciliated cells in proximal airway epithelial spheroids from human pluripotent stem cells." Stem Cell Reports 6(1): 18-25 (2016).
Longmire et al. "Efficient derivation of purified lung and thyroid progenitors from embryonic stem cells." Cell Stem Cell 10(4): 398-411 (2012).
McCauley et al. "Derivation of Epithelial-Only Airway Organoids from Human Pluripotent Stem Cells." Current Protocols in Stem Cell Biology 45(1): e51 pp. 1-27 (2018).
McCauley et al. "Efficient derivation of functional human airway epithelium from pluripotent stem cells via temporal regulation of Wnt signaling." Cell Stem Cell 20(6): 844-857.e1-e6 (2017).
McCauley et al. "Single-cell transcriptomic profiling of pluripotent stem cell-derived SCGB3A2+ airway epithelium." Stem Cell Reports 10(5): 1579-1595 (2018).
Miller et al. "In vitro and in vivo development of the human airway at single-cell resolution." Developmental Cell 53(1): 117-128 (2010).
Montoro et al. "A revised airway epithelial hierarchy includes CFTR-expressing ionocytes." Nature 560(7718): 319-324 (2018).

(Continued)

*Primary Examiner* — Valarie E Bertoglio
(74) *Attorney, Agent, or Firm* — NIXON PEABODY LLP; Ronald I. Eisenstein; Nicole D. Kling

(57) ABSTRACT

The technology described herein is directed to methods of producing or differentiating AT1 cells, and AT1 cells made by the methods described herein.

13 Claims, 121 Drawing Sheets

Specification includes a Sequence Listing.

(56) References Cited

OTHER PUBLICATIONS

Mou et al. "Dual SMAD signaling inhibition enables long-term expansion of diverse epithelial basal cells." Cell Stem Cell 19(2): 217-231 (2016).

Nikolic et al. "Human embryonic lung epithelial tips are multipotent progenitors that can be expanded in vitro as long-term self-renewing organoids." Elife 6: e26575 pp. 1-33 (2017).

Ornitz et al. "The fibroblast growth factor signaling pathway." Wiley Interdisciplinary Reviews: Developmental Biology 4(3): 215-266 (2015).

Plasschaert et al. "A single-cell atlas of the airway epithelium reveals the CFTR-rich pulmonary ionocyte." Nature 560(7718): 377-381 (2018).

Rock et al. "Basal cells as stem cells of the mouse trachea and human airway epithelium." Proceedings of the National Academy of Sciences 106(31): 12771-12775 (2009).

Suprynowicz et al. "Conditional cell reprogramming involves non-canonical β-catenin activation and mTOR-mediated inactivation of Akt." PloS One 12(7): e0180897 pp. 1-23 (2017).

Volckaert et al. "Localized Fgf10 expression is not required for lung branching morphogenesis but prevents differentiation of epithelial progenitors." Development 140(18): 3731-3742 (2013).

Yang et al. "Spatial-temporal lineage restrictions of embryonic p63+ progenitors establish distinct stem cell pools in adult airways." Developmental Cell 44(6): 752-761 (2018).

Zhang et al. "Long-term in vitro expansion of epithelial stem cells enabled by pharmacological inhibition of PAK1-ROCK-Myosin II and TGF-β signaling." Cell Reports 25(3): 598-610 (2018).

Tadokoro et al. "BMP signaling and cellular dynamics during regeneration of airway epithelium from basal progenitors." Development 143(5): 764-773 Jan. 19, 2016.

Horani et al. "Rho-associated protein kinase inhibition enhances airway epithelial Basal-cell proliferation and lentivirus transduction." American journal of respiratory cell and molecular biology 49(3): 341-347 May 28, 2013.

Miller et al. "Basal stem cell fate specification is mediated by SMAD signaling in the developing human lung." bioRxiv (461103): 1-46 Nov. 4, 2018.

Burgess et al. "Generation of human alveolar epithelial type I cells from pluripotent cells" BioRxiv 2023.01.19.524655 (Jan. 21, 2023).

* cited by examiner

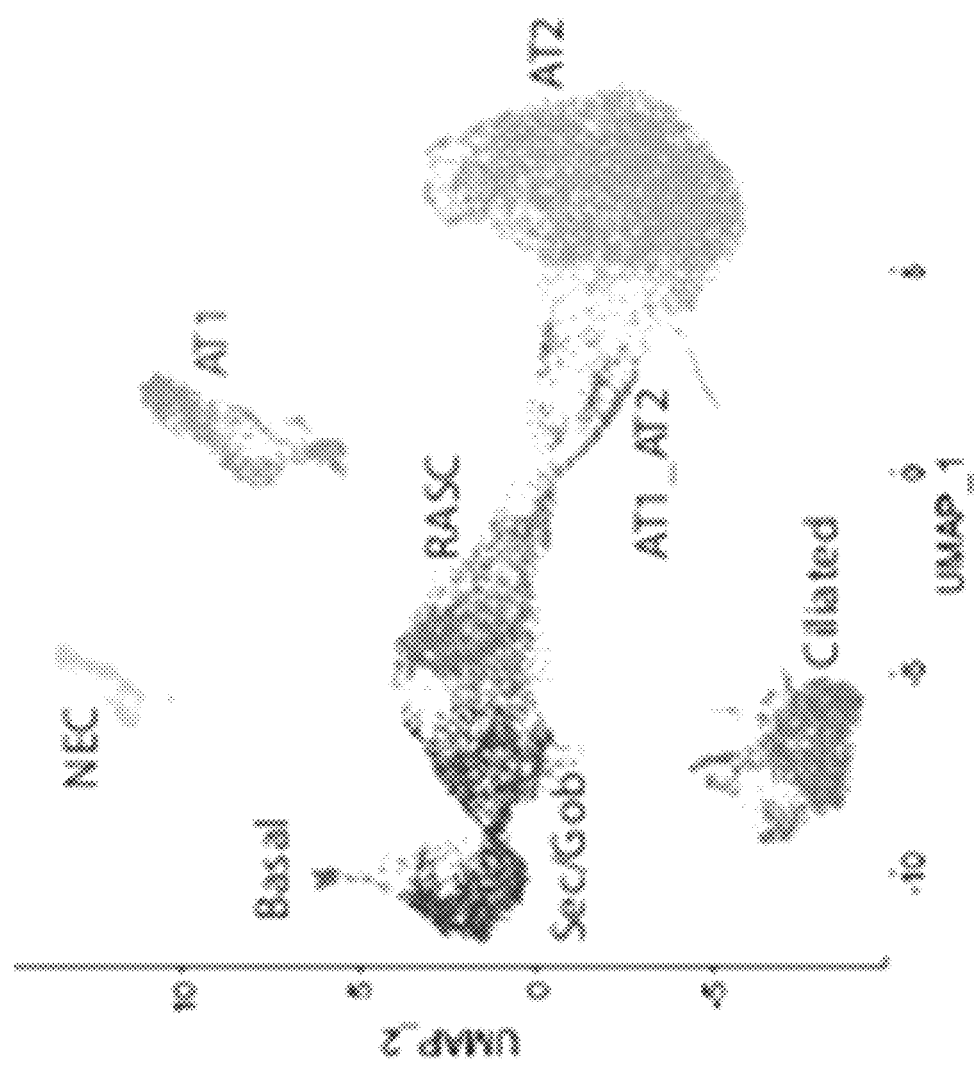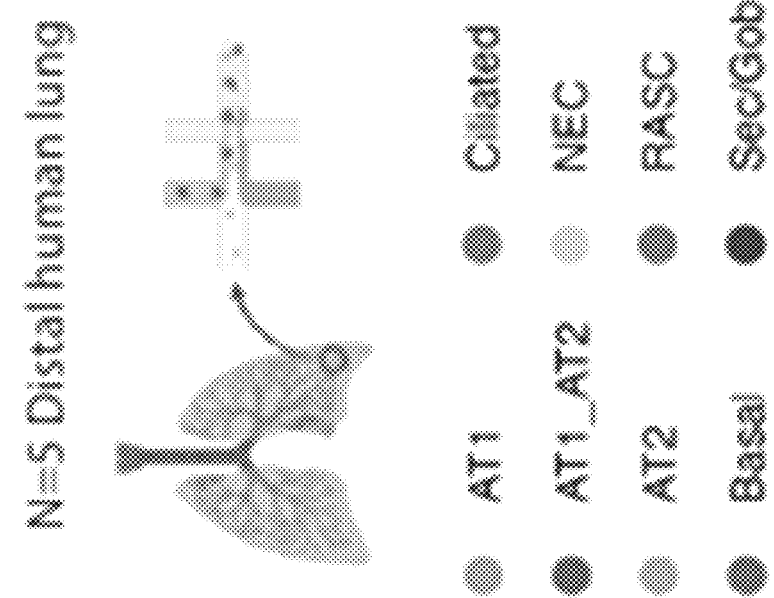
Fig. 1A

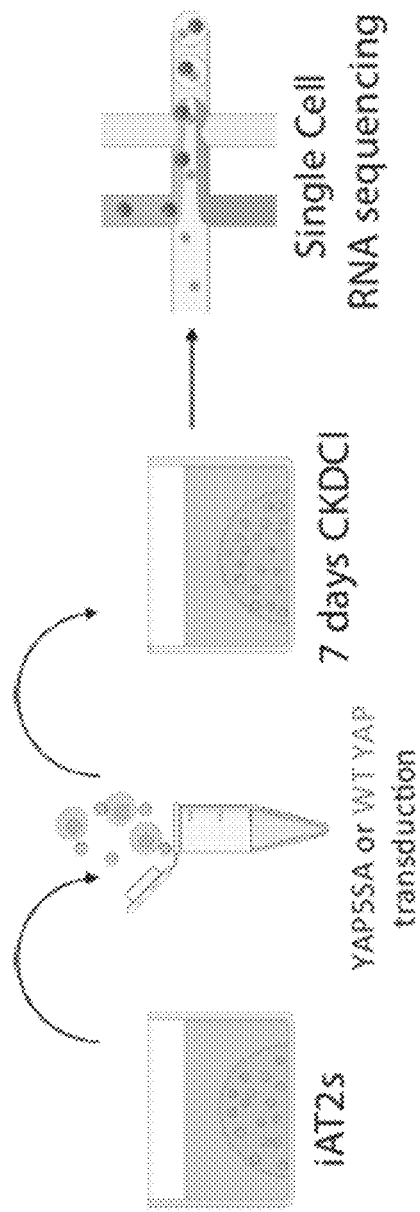
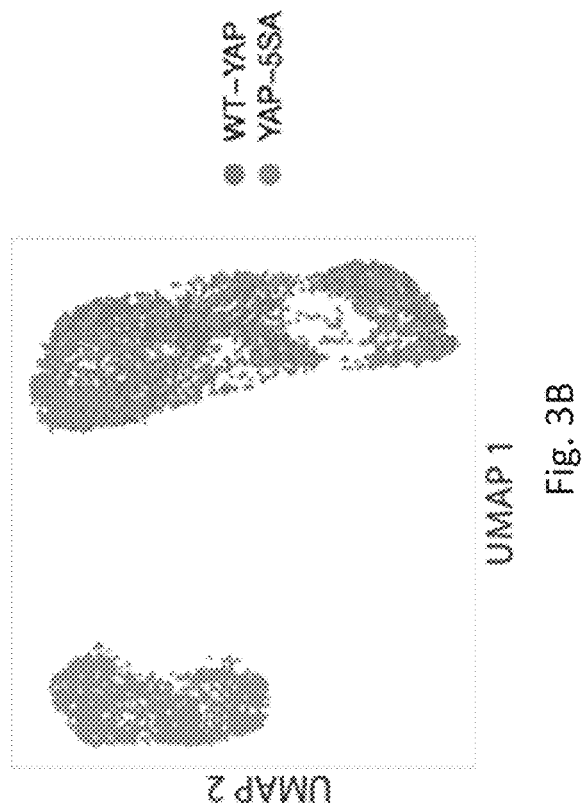

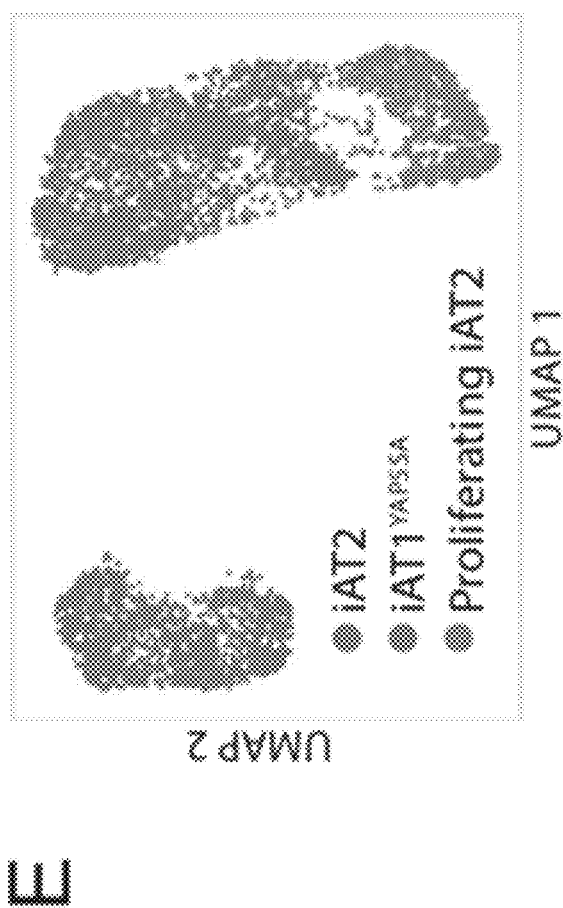
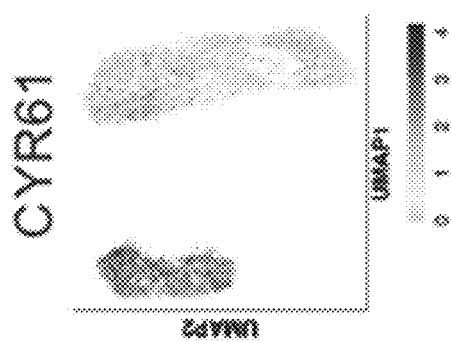
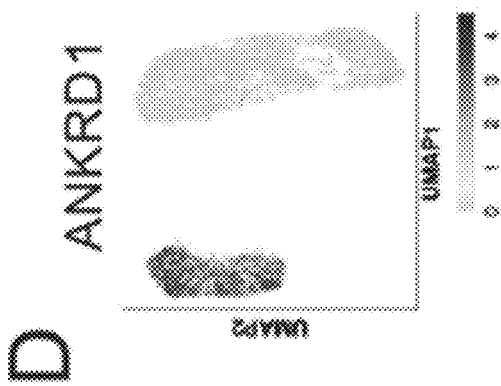
Figs. 3D-3E

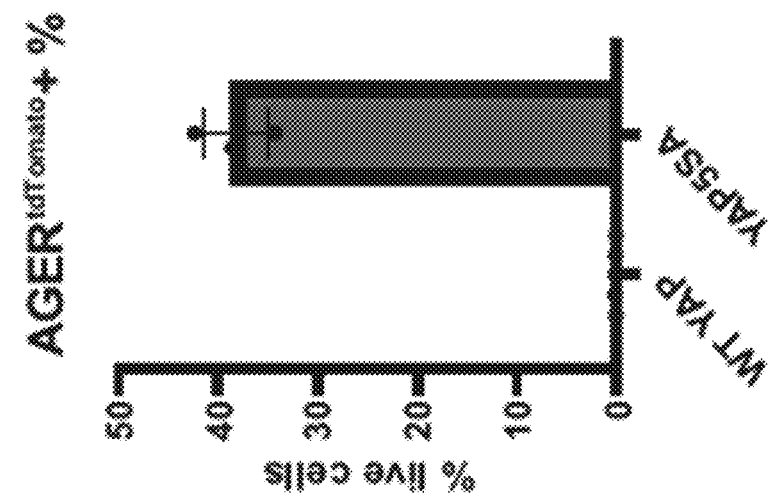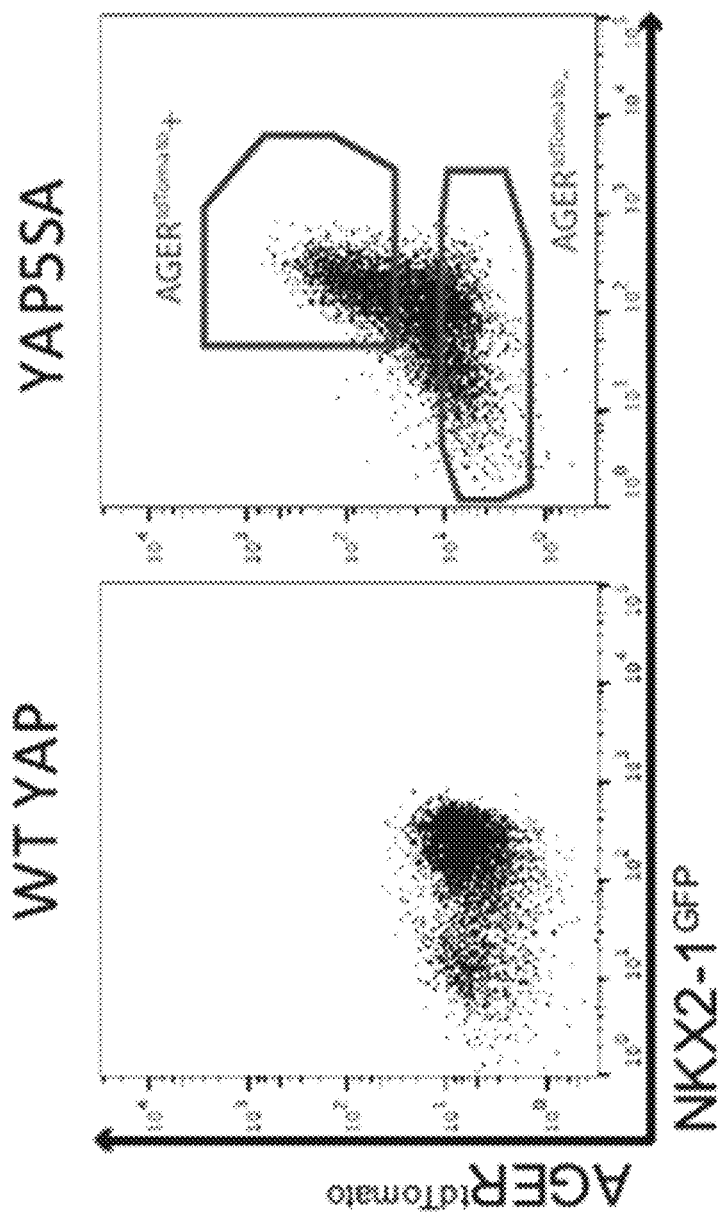
Fig. 4D

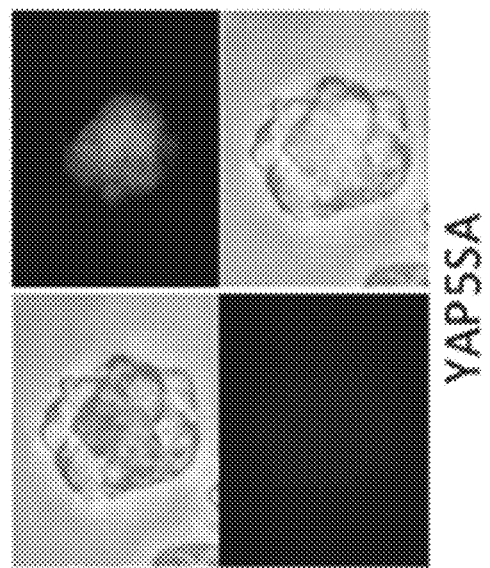
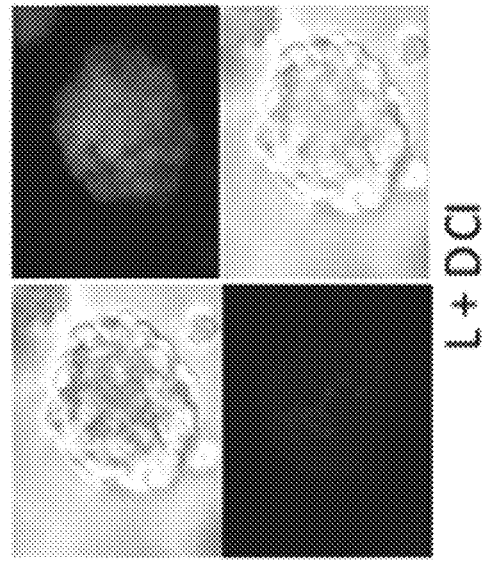
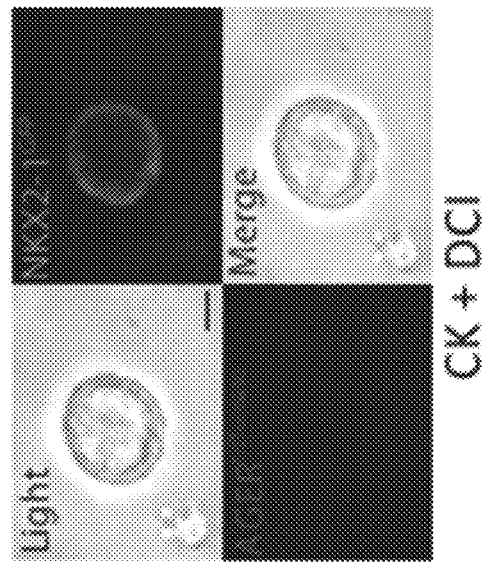
Fig. 5C

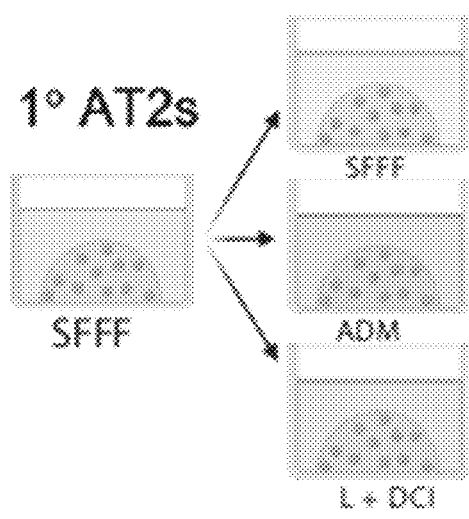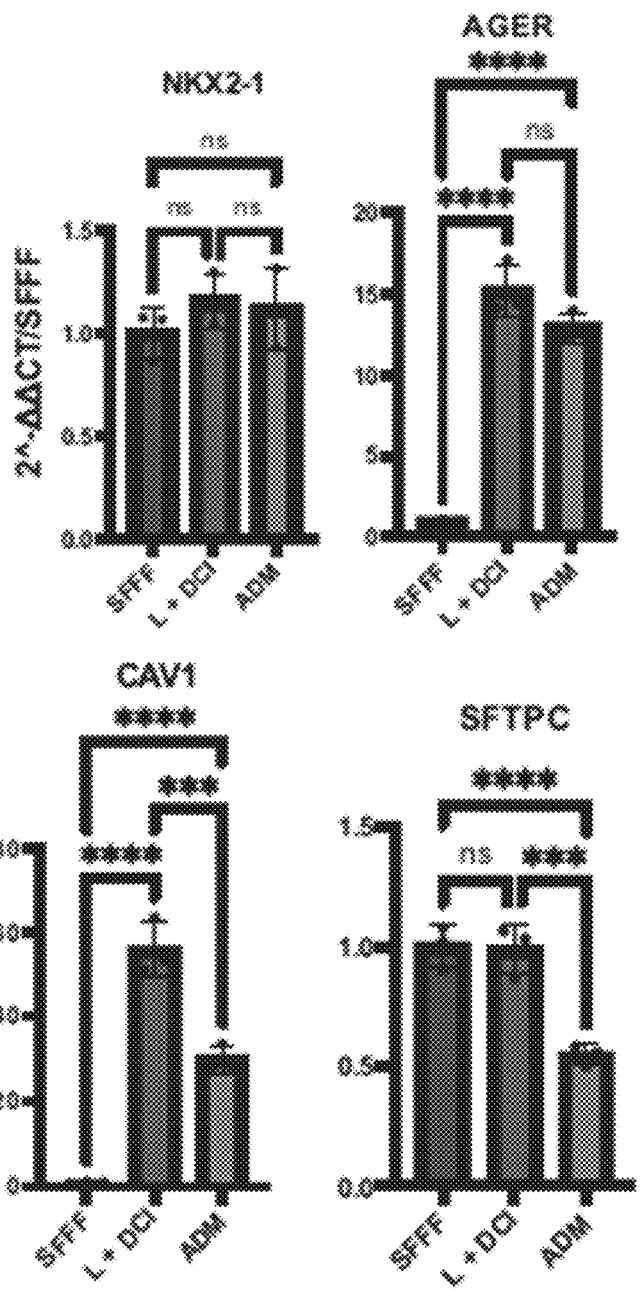
Fig. 5H

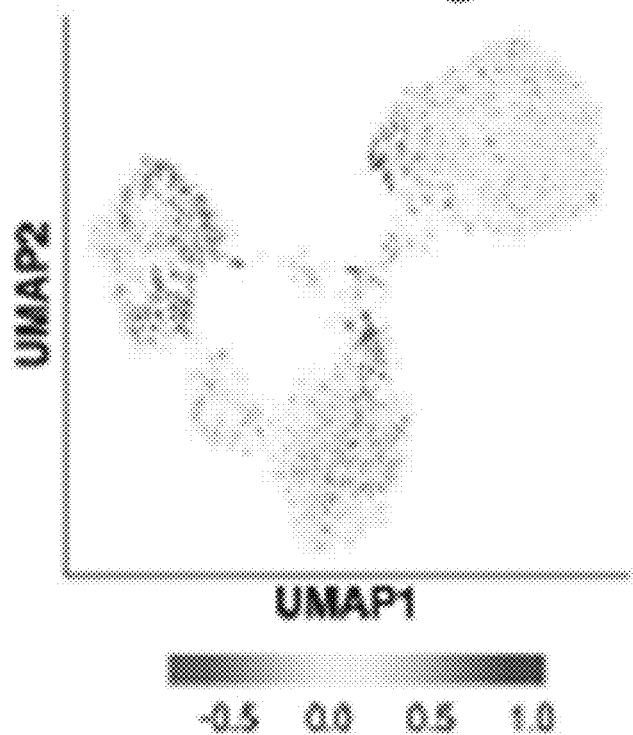
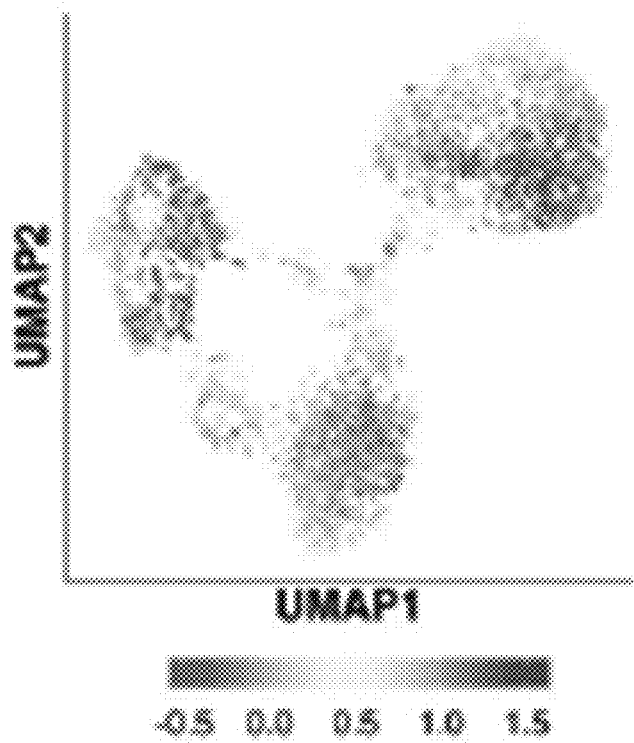
Fig. 7F

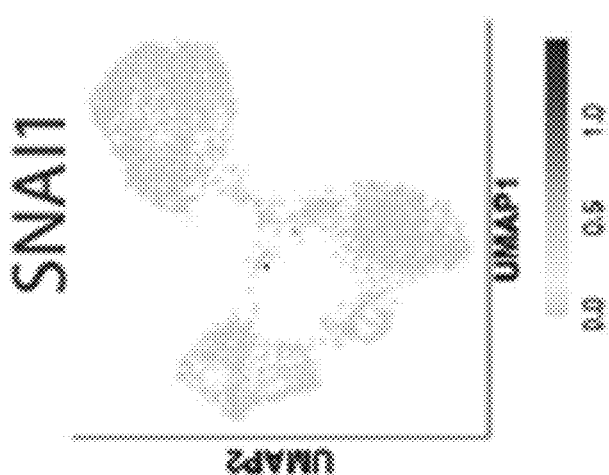
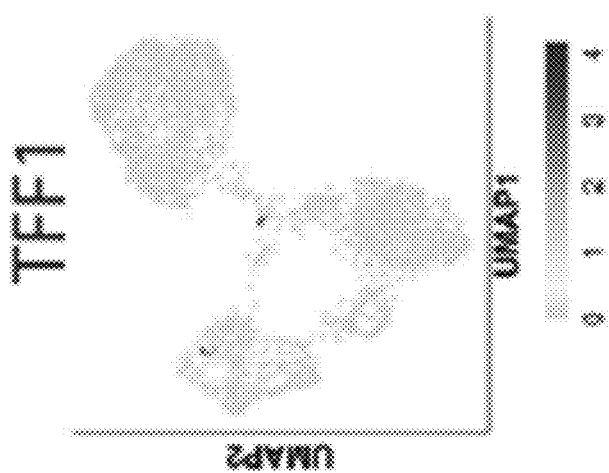
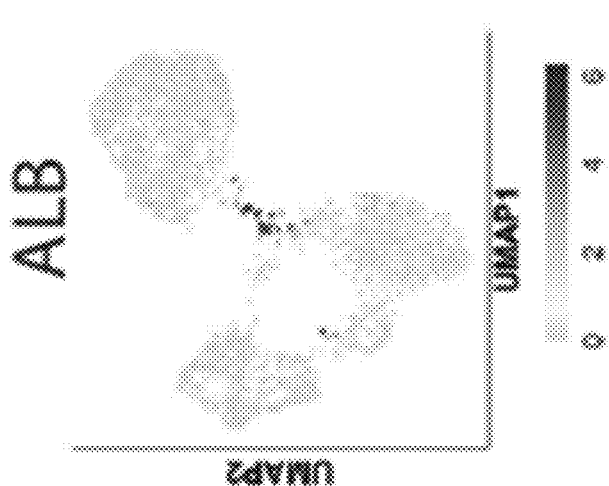
Fig. 16D

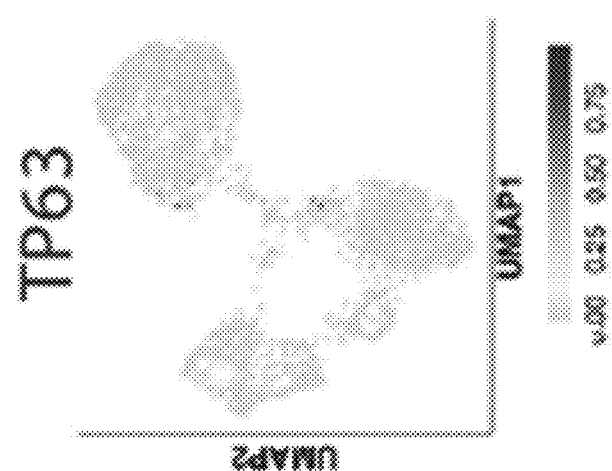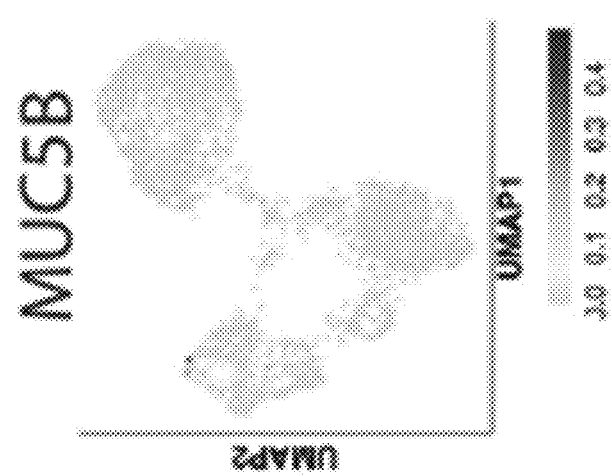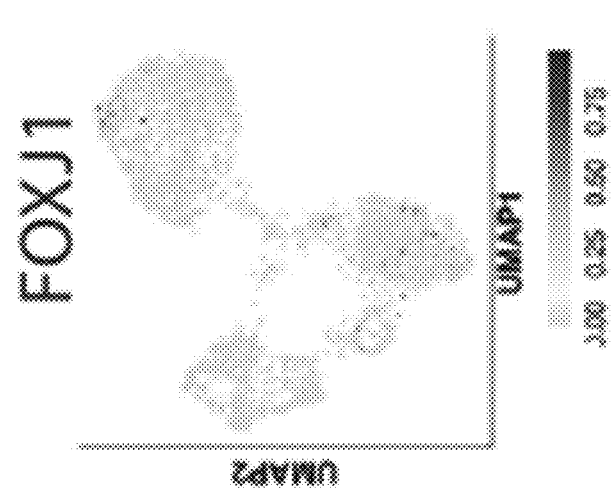
Fig. 16E

SEQUENCE LISTING

```
Sequence total quantity: 19
SEQ ID NO: 1            moltype = AA  length = 504
FEATURE                 Location/Qualifiers
source                  1..504
                        mol_type = protein
                        organism = Homo sapiens
SEQUENCE: 1
MDPGQQPPPQ PAPQGQGQPP SQPPQGQGPP SGPGQPAPAA TQAAPQAPPA GHQIVHVRGD   60
SETDLEALFN AVMNPKTANV PQTVPMRLRK LPDSFFKPPE PKSHSRQAST DAGTAGALTP  120
QHVRAHSSPA SLQLGAVSPG TLTPTGVVSG PAATPTAQHL RQSSFEIPDD VPLPAGWEMA  180
KTSSGQRYFL NHIDQTTTWQ DPRKAMLSQM NVTAPTSPPV QQNMMNSASG PLPDGWEQAM  240
TQDGEIYYIN HKNKTTSWLD PRLDPRFAMN QRISQSAPVK QPPPLAPQSP QGGVMGGSNS  300
NQQQQMRLQQ LQMEKERLRL KQQELLRQAM RNINPSTANS PKCQELALRS QLPTLEQDGG  360
TQNPVSSPGM SQELRTMTTN SSDPFLNSGT YHSRDESTDS GLSMSSYSVP RTPDDFLNSV  420
DEMDTGDTIN QSTLPSQQNR FPDYLEAIPG TNVDLGTLEG DGMNIEGEEL MPSLQEALSS  480
DILNDMESVL AATKLDKESF LTWL                                        504

SEQ ID NO: 2            moltype =    length =
```

```
SEQUENCE: 2
000

SEQ ID NO: 3                 moltype = AA   length = 488
FEATURE                      Location/Qualifiers
source                       1..488
                             mol_type = protein
                             organism = Homo sapiens
SEQUENCE: 3
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASG PLPDGWEQAM   240
TQDGEIYYIN HKNKTTSWLD PRLDPRFAMN QRISQSAPVK QPPPLAPQSP QGGVMGGSNS   300
NQQQQMRLQQ LQMEKERLRL KQQELLRQEL ALRSQLPTLE QDGGTQNPVS SPGMSQELRT   360
MTTNSSDPFL NSGTYHSRDE STDSGLSMSS YSVPRTPDDF LNSVDEMDTG DTINQSTLPS   420
QQNRFPDYLE AIPGTNVDLG TLEGDGMNIE GEELMPSLQE ALSSDILNDM ESVLAATKLD   480
KESFLTWL                                                           488

SEQ ID NO: 4                 moltype = AA   length = 326
FEATURE                      Location/Qualifiers
source                       1..326
                             mol_type = protein
                             organism = Homo sapiens
SEQUENCE: 4
MAKTSSGQRY FLNHIDQTTT WQDPRKAMLS QMNVTAPTSP PVQQNMMNSA SGPLPDGWEQ    60
AMTQDGEIYY INHKNKTTSW LDPRLDPRFA MNQRISQSAP VKQPPPLAPQ SPQGGVMGGS   120
NSNQQQQMRL QQLQMEKERL RLKQQELLRQ AMRNINPSTA NSPKCQELAL RSQLPTLEQD   180
GGTQNPVSSP GMSQELRTMT TNSSDPFLNS GTYHSRDEST DSGLSMSSYS VPRTPDDFLN   240
SVDEMDTGDT INQSTLPSQQ NRFPDYLEAI PGTNVDLGTL EGDGMNIEGE ELMPSLQEAL   300
SSDILNDMES VLAATKLDKE SFLTWL                                       326

SEQ ID NO: 5                 moltype = AA   length = 466
FEATURE                      Location/Qualifiers
source                       1..466
                             mol_type = protein
                             organism = Homo sapiens
SEQUENCE: 5
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASA MNQRISQSAP   240
VKQPPPLAPQ SPQGGVMGGS NSNQQQQMRL QQLQMEKERL RLKQQELLRQ AMRNINPSTA   300
NSPKCQELAL RSQLPTLEQD GGTQNPVSSP GMSQELRTMT TNSSDPFLNS GTYHSRDEST   360
DSGLSMSSYS VPRTPDDFLN SVDEMDTGDT INQSTLPSQQ NRFPDYLEAI PGTNVDLGTL   420
EGDGMNIEGE ELMPSLQEAL SSDILNDMES VLAATKLDKE SFLTWL                  466

SEQ ID NO: 6                 moltype = AA   length = 454
FEATURE                      Location/Qualifiers
source                       1..454
                             mol_type = protein
                             organism = Homo sapiens
SEQUENCE: 6
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASA MNQRISQSAP   240
VKQPPPLAPQ SPQGGVMGGS NSNQQQQMRL QQLQMEKERL RLKQQELLRQ VRPQELALRS   300
QLPTLEQDGG TQNPVSSPGM SQELRTMTTN SSDPFLNSGT YHSRDESTDS GLSMSSYSVP   360
RTPDDFLNSV DEMDTGDTIN QSTLPSQQNR FPDYLEAIPG TNVDLGTLEG DGMNIEGEEL   420
MPSLQEALSS DILNDMESVL AATKLDKESF LTWL                              454

SEQ ID NO: 7                 moltype = AA   length = 470
FEATURE                      Location/Qualifiers
source                       1..470
                             mol_type = protein
                             organism = Homo sapiens
SEQUENCE: 7
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASA MNQRISQSAP   240
VKQPPPLAPQ SPQGGVMGGS NSNQQQQMRL QQLQMEKERL RLKQQELLRQ VRPQAMRNIN   300
PSTANSPKCQ ELALRSQLPT LEQDGGTQNP VSSPGMSQEL RTMTTNSSDP FLNSGTYHSR   360
DESTDSGLSM SSYSVPRTPD DFLNSVDEMD TGDTINQSTL PSQQNRFPDY LEAIPGTNVD   420
LGTLEGDGMN IEGEELMPSL QEALSSDILN DMESVLAATK LDKESFLTWL              470

SEQ ID NO: 8                 moltype = AA   length = 492
FEATURE                      Location/Qualifiers
```

```
source                  1..492
                        mol_type = protein
                        organism = Homo sapiens
SEQUENCE: 8
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASG PLPDGWEQAM   240
TQDGEIYYIN HKNKTTSWLD PRLDPRFAMN QRISQSAPVK QPPPLAPQSP QGGVMGGSNS   300
NQQQQMRLQQ LQMEKERLRL KQQELLRQVR PQELALRSQL PTLEQDGGTQ NPVSSPGMSQ   360
ELRTMTTNSS DPFLNSGTYH SRDESTDSGL SMSSYSVPRT PDDFLNSVDE MDTGDTINQS   420
TLPSQQNRFP DYLEAIPGTN VDLGTLEGDG MNIEGEELMP SLQEALSSDI LNDMESVLAA   480
TKLDKESFLT WL                                                      492

SEQ ID NO: 9            moltype = AA   length = 508
FEATURE                 Location/Qualifiers
source                  1..508
                        mol_type = protein
                        organism = Homo sapiens
SEQUENCE: 9
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASG PLPDGWEQAM   240
TQDGEIYYIN HKNKTTSWLD PRLDPRFAMN QRISQSAPVK QPPPLAPQSP QGGVMGGSNS   300
NQQQQMRLQQ LQMEKERLRL KQQELLRQVR PQAMRNINPS TANSPKCQEL ALRSQLPTLE   360
QDGGTQNPVS SPGMSQELRT MTTNSSDPFL NSGTYHSRDE STDSGLSMSS YSVPRTPDDF   420
LNSVDEMDTG DTINQSTLPS QQNRFPDYLE AIPGTNVDLG TLEGDGMNIE GEELMPSLQE   480
ALSSDILNDM ESVLAATKLD KESFLTWL                                     508

SEQ ID NO: 10           moltype = AA   length = 450
FEATURE                 Location/Qualifiers
source                  1..450
                        mol_type = protein
                        organism = Homo sapiens
SEQUENCE: 10
MDPGQQPPPQ PAPQGQGQPP SQPPQGQGPP SGPGQPAPAA TQAAPQAPPA GHQIVHVRGD    60
SETDLEALFN AVMNPKTANV PQTVPMRLRK LPDSFFKPPE PKSHSRQAST DAGTAGALTP   120
QHVRAHSSPA SLQLGAVSPG TLTPTGVVSG PAATPTAQHL RQSSFEIPDD VPLPAGWEMA   180
KTSSGQRYFL NHIDQTTTWQ DPRKAMLSQM NVTAPTSPPV QQNMMNSASA MNQRISQSAP   240
VKQPPPLAPQ SPQGGVMGGS NSNQQQQMRL QQLQMEKERL RLKQQELLRQ ELALRSQLPT   300
LEQDGGTQNP VSSPGMSQEL RTMTTNSSDP FLNSGTYHSR DESTDSGLSM SSYSVPRTPD   360
DFLNSVDEMD TGDTINQSTL PSQQNRFPDY LEAIPGTNVD LGTLEGDGMN IEGEELMPSL   420
QEALSSDILN DMESVLAATK LDKESFLTWL                                   450

SEQ ID NO: 11           moltype = DNA   length = 25
FEATURE                 Location/Qualifiers
source                  1..25
                        mol_type = other DNA
                        organism = synthetic construct
SEQUENCE: 11
caccgccagg ctccaactgc tgttc                                         25

SEQ ID NO: 12           moltype = DNA   length = 25
FEATURE                 Location/Qualifiers
source                  1..25
                        mol_type = other DNA
                        organism = synthetic construct
SEQUENCE: 12
caccgatggc tgccggaaca gcagt                                         25

SEQ ID NO: 13           moltype = DNA   length = 25
FEATURE                 Location/Qualifiers
source                  1..25
                        mol_type = other DNA
                        organism = synthetic construct
SEQUENCE: 13
caccgctgtg gcctccgccc taggt                                         25

SEQ ID NO: 14           moltype = DNA   length = 25
FEATURE                 Location/Qualifiers
source                  1..25
                        mol_type = other DNA
                        organism = synthetic construct
SEQUENCE: 14
ctgatcccct cagacattct cagga                                         25

SEQ ID NO: 15           moltype = DNA   length = 17
FEATURE                 Location/Qualifiers
```

```
source                1..17
                      mol_type = other DNA
                      organism = synthetic construct
SEQUENCE: 15
gagctgccgc tgccggt                                                              17

SEQ ID NO: 16         moltype = DNA  length = 20
FEATURE               Location/Qualifiers
source                1..20
                      mol_type = other DNA
                      organism = synthetic construct
SEQUENCE: 16
acttgtgtag cgccaagtgc                                                           20

SEQ ID NO: 17         moltype = DNA  length = 20
FEATURE               Location/Qualifiers
source                1..20
                      mol_type = other DNA
                      organism = synthetic construct
SEQUENCE: 17
acacacactc gcctcctgtt                                                           20

SEQ ID NO: 18         moltype = DNA  length = 20
FEATURE               Location/Qualifiers
source                1..20
                      mol_type = other DNA
                      organism = synthetic construct
SEQUENCE: 18
aggactcttg tcccaaaggc                                                           20

SEQ ID NO: 19         moltype = DNA  length = 20
FEATURE               Location/Qualifiers
source                1..20
                      mol_type = other DNA
                      organism = synthetic construct
SEQUENCE: 19
ctggggtgtg gggttaaagt                                                           20
```

GENERATION OF ALVEOLAR EPITHELIAL TYPE 1 (AT1) CELLS

CROSS-REFERENCE TO RELATED APPLICATIONS

This application claims benefit under 35 U.S.C. § 119(c) of U.S. Provisional Application No. 63/434,299 filed Dec. 21, 2022, the contents of which are incorporated herein by reference in their entirety.

GOVERNMENT SUPPORT

This invention was made with Government support under Grant No. HL158193 awarded by the National Institutes of Health. The Government has certain rights in the invention.

SEQUENCE LISTING

The instant application contains a Sequence Listing which has been submitted electronically in XML format and is hereby incorporated by reference in its entirety. Said XML copy, created on Dec. 6, 2023, is named 701586-000110US-PT_SL.xml and is 20,300 bytes in size.

TECHNICAL FIELD

The technology described herein relates to differentiation of AT1 lung cells.

BACKGROUND

AT1 cells are flattened epithelial cells that permit oxygen to diffuse from the lungs into the bloodstream. Damage to AT1s in response to toxic inhalational exposures, radiation, or a variety of infections can lead to respiratory failure and severe diseases such as Acute Respiratory Distress Syndrome (ARDS). Impaired differentiation of AT1 cells has also been implicated in fibrotic lung diseases. Hence, a better understanding of the normal differentiation and biology of human AT1s could provide insights for resolving such lung diseases.

However, due to the thin flat shape of AT1s and their quiescent, terminally differentiated phenotype, they are difficult to isolate from lung tissue and to maintain in culture. As a result, relatively little is known about the cell biology, origins, and fates of human AT1s due in part to difficulties in accessing and culturing this key cell type which is naturally located deep within distal lung tissue.

SUMMARY

As described herein, the inventors have created methods of producing AT1 cells in vitro, providing a ready source of AT1 cells for studies of lung biology and lung disease treatments.

In one aspect of any of the embodiments, described herein is a method comprising at least one of: a) inducing ectopic Yes Associated Protein (YAP) expression in at least one AT2 cell and/or lung epithelial progenitor cell; and b) maintaining at least one AT2 cell and/or lung epithelial progenitor cell in a medium comprising a Large Tumor Suppressor Kinase (LATS) inhibitor.

In some embodiments of any of the aspects, the method comprises inducing ectopic Yes Associated Protein (YAP) expression in at least one AT2 cell and/or lung epithelial progenitor cell; and maintaining at least one AT2 cell and/or lung epithelial progenitor cell in a medium comprising a Large Tumor Suppressor Kinase (LATS) inhibitor. In some embodiments of any of the aspects, the method comprises inducing ectopic Yes Associated Protein (YAP) expression in at least one AT2 cell and/or lung epithelial progenitor cell. In some embodiments of any of the aspects, the method comprises maintaining at least one AT2 cell and/or lung epithelial progenitor cell in a medium comprising a Large Tumor Suppressor Kinase (LATS) inhibitor.

In some embodiments of any of the aspects, the method comprises inducing ectopic Yes Associated Protein (YAP) expression in at least one AT2 cell and/or lung epithelial progenitor cell; and maintaining at least one AT2 cell or lung epithelial progenitor cell in a medium comprising a Large Tumor Suppressor Kinase (LATS) inhibitor. In some embodiments of any of the aspects, the method comprises inducing ectopic Yes Associated Protein (YAP) expression in at least one AT2 cell or lung epithelial progenitor cell. In some embodiments of any of the aspects, the method comprises maintaining at least one AT2 cell or lung epithelial progenitor cell in a medium comprising a Large Tumor Suppressor Kinase (LATS) inhibitor.

In some embodiments of any of the aspects, the method comprises inducing ectopic Yes Associated Protein (YAP) expression in at least one AT2 cell and/or lung epithelial progenitor cell; and maintaining at least one AT2 cell in a medium comprising a Large Tumor Suppressor Kinase (LATS) inhibitor. In some embodiments of any of the aspects, the method comprises inducing ectopic Yes Associated Protein (YAP) expression in at least one AT2 cell. In some embodiments of any of the aspects, the method comprises maintaining at least one AT2 cell in a medium comprising a Large Tumor Suppressor Kinase (LATS) inhibitor.

In some embodiments of any of the aspects, the method comprises inducing ectopic Yes Associated Protein (YAP) expression in at least one lung epithelial progenitor cell; and maintaining at least one AT2 cell and/or lung epithelial progenitor cell in a medium comprising a Large Tumor Suppressor Kinase (LATS) inhibitor. In some embodiments of any of the aspects, the method comprises inducing ectopic Yes Associated Protein (YAP) expression in at least one lung epithelial progenitor cell. In some embodiments of any of the aspects, the method comprises maintaining at least one lung epithelial progenitor cell in a medium comprising a Large Tumor Suppressor Kinase (LATS) inhibitor.

In some embodiments of any of the aspects, the YAP comprises mutation of the serine of at least one HXRXXS consensus sequence. In some embodiments of any of the aspects, the YAP comprises mutation of the serine of at least one HXRXXS consensus sequence to alanine. In some embodiments of any of the aspects, the YAP comprises mutation of the serine of every HXRXXS consensus sequence. In some embodiments of any of the aspects, the YAP comprises mutation of the serine of every HXRXXS consensus sequence to alanine. In some embodiments of any of the aspects, the YAP comprises mutation of each serine corresponding to S61, S109, S127, S164, and S397 of SEQ ID NO: 1. In some embodiments of any of the aspects, the YAP comprises mutation of each serine corresponding to S61, S109, S127, S164, and S397 of SEQ ID NO: 1 to alanine.

In some embodiments of any of the aspects, inducing comprises contacting the at least one AT2 cell and/or lung epithelial progenitor cell with an expression vector encoding a YAP protein. In some embodiments of any of the aspects, the expression vector is a viral vector. In some embodiments of any of the aspects, the expression vector is a lentiviral vector.

In some embodiments of any of the aspects, the medium is a complete serum free defined medium. In some embodiments of any of the aspects, the LATS inhibitor is selected from the group consisting of: LATS-IN-1 (TRULI; N-(3-benzylthiazol-2(3H)-ylidene)-1H-pyrrolo[2,3-b]pyridine-3-carboxamide); GA-017; and TDI-011536. In some embodiments of any of the aspects, the medium does not comprise, or the at least one AT2 cell and/or lung epithelial progenitor cell is not in contact with, CHIR99021 and/or keratinocyte growth factor (KGF) protein. In some embodiments of any of the aspects, the medium does not comprise, or the at least one AT2 cell and/or lung epithelial progenitor cell is not in contact with, ectopic epidermal growth factor (EGF) protein and/or ectopic fibroblast growth factor 10 (FGF10) protein. In some embodiments of any of the aspects, the medium further comprises, or the at least one AT2 cell and/or lung epithelial progenitor cell is further contacted with, ectopic epidermal growth factor (EGF) protein and/or ectopic fibroblast growth factor 10 (FGF10) protein. In some embodiments of any of the aspects, the maintaining at least one AT2 cell and/or lung epithelial progenitor cell in a medium comprising a LATS inhibitor induces YAP signaling.

In some embodiments of any of the aspects, the at least one AT2 cell is a human AT2 cell. In some embodiments of any of the aspects, the at least one AT2 cell is a primary AT2 cell. In some embodiments of any of the aspects, the at least one AT2 cell is an induced AT2 cell. In some embodiments of any of the aspects, the at least one lung epithelial progenitor cell is a human lung epithelial progenitor cell. In some embodiments of any of the aspects, the lung epithelial progenitor cell is a primary lung epithelial progenitor cell. In some embodiments of any of the aspects, the lung epithelial progenitor cell is an induced lung epithelial progenitor cell.

In some embodiments of any of the aspects, the method further comprises contacting the at least one AT2 cell and/or lung epithelial progenitor cell, or a cell produced by the method, with a nucleic acid encoding a reporter protein. In some embodiments of any of the aspects, the method further comprises contacting an AT1 cell produced by the method with a virus. In some embodiments of any of the aspects, the method further comprises contacting an AT1 cell produced by the method with smoke. In some embodiments of any of the aspects, the method further comprises contacting an AT1 cell produced by the method with Transforming Growth Factor Beta (TGFβ) and/or bleomycin. In some embodiments of any of the aspects, the at least one AT2 cell and/or lung epithelial progenitor cell comprises a PF inducing mutation.

In one aspect of any of the embodiments, described herein is an AT1 cell made by any one of the methods described herein. In some embodiments of any of the aspects, the AT1 cell made by any one of the methods described herein comprises lower expression of PDPN relative to a primary AT1 cell.

In one aspect of any of the embodiments, described herein is a method of treating a lung disease in a subject in need thereof, the method comprising administering to the subject an AT1 cell produced according to the any one of the methods described herein. In some embodiments of any of the aspects, the lung disease is selected from the group consisting of: acute respiratory distress syndrome (ARDS), pulmonary fibrosis, interstitial lung diseases, acute inhalational lung injuries, childhood interstitial lung diseases, and bronchopulmonary dysplasia. In some embodiments of any of the aspects, the AT1 cell is derived from a cell obtained from the subject. In some embodiments of any of the aspects, the at least one AT2 cell and/or lung epithelial progenitor cell was genetically modified to correct a mutation that contributed to the lung disease.

In one aspect of any of the embodiments, described herein is a method of identifying a treatment as effective in treating lung disease, the method comprising: contacting an AT1 produced according to any one of the methods described herein with a candidate treatment agent; identifying the candidate treatment agent as effective if one or more of the following phenotypes is observed in the AT1 cell contacted with the candidate treatment agent as compared to an AT1 cell not contacted with the candidate treatment agent:
  increased cell survival;
  increased cell survival in the presence of cellular stressors;
  decreased release of toxic agents;
  improved cellular pathology arising from a genetic mutation in the AT1 cell;
  increased AT1 cell differentiation;
  decreased AT1 cell proliferation in the presence of carcinogens; and/or
  increased secretion of cytoprotective agents.

In some embodiments of any of the aspects, the AT1 cell is derived from a cell obtained from an individual subject and the treatment is identified as an effective treatment for that individual subject.

In one aspect of any of the embodiments, described herein is an AT1 cell produced according to any one of the methods described herein, for administration to the subject in need of treatment for a lung disease. In some embodiments of any of the aspects, the lung disease is selected from the group consisting of: acute respiratory distress syndrome (ARDS), pulmonary fibrosis, interstitial lung diseases, acute inhalational lung injuries, childhood interstitial lung diseases, and bronchopulmonary dysplasia. In some embodiments of any of the aspects, the AT1 cell is derived from a cell obtained from the subject. In some embodiments of any of the aspects, the at least one AT2 cell and/or lung epithelial progenitor cell was genetically modified to correct a mutation that contributed to the lung disease.

BRIEF DESCRIPTION OF THE DRAWINGS

FIGS. 1A-1F depict transcriptomic profiling at single cell resolution of primary adult human AT1s. FIG. 1A) Uniform Manifold Approximation and Projection (UMAP) embedding of 15769 primary distal lung epithelial cells (dataset previously published in Basil et al). N=5 including, 1401 AT1s and 7039 AT2s. FIG. 1B) Expression of AT2 specific marker genes, SFTPC, LAMP3, ABCA3; canonical AT1 marker genes AGER, CAV1, PDPN; mouse-specific AT1 marker genes HOPX, AQP5; lung epithelial marker NKX2-1; and more recent human AT1 marker genes ANKRD1, CLIC5, and RTKN2. FIG. 1C) Heatmap showing average expression for each cell type of top differentially upregulated human AT1 genes compared to all distal lung cells. FIG. 1D) Expression of selected AT1 and AT2 genes across all lung cell types. FIG. 1E) Expression of YAP (YAP1) and TAZ (WWTR1) and known downstream Hippo signaling markers across lung epithelial cell types. FIG. 1F) Violin plot showing AGER expression across indicated cell types.

FIG. 2A) Diagram of lentiviral vector encoding dual promoters driving activated nuclear-specific mutated YAP (YAP5SA), the blue fluorophore tagBFP, and LoxP site. FIG. 2B) Directed differentiation protocol for producing iAT2s as previously published. Ref 61 of Example 2 (Stem Cell Technologies Stem Diff endoderm kit, "DS/SB"=Dorsomorphin and SB43152, CBRa=Chir, BMP4, Retinoic Acid, CK+DCI=Chir, rhKGF, Dexamethasone, Cyclic AMP, IBMX, 3D plating in Growth Factor ReducedMatrigel.) FIG. 2C) Expression of indicated genes by RT-qPCR relative to Day 0 iPSCs in whole well RNA extracts taken 14 days post YAP5SA or mock lentiviral transduction of SPC2B2 iAT2s (>90% SFTPCtdTomato+ prior to lentiviral transduction, N=3 transductions. Student's t test). FIG. 2D) Representative live cell imaging of SPC2B2 iAT2s following transduction with either WT YAP or YAP5SA lentivirus. (Brightfield/SFTPC-tdTomato overlay, scale bar=500 um). FIG. 2E) Whole-well gene expression by RT-qPCR over time following WT YAP vs. YAP5SA lentiviral transduction of SPC2B2 iAT2s, relative to Day 0 iPSCs. N=3 transductions. FIG. 2F) Competition assay—SPC2B2 iAT2s were transduced with either a WT YAP-tagBFP or YAP5SA-GFP lentivirus and mixed 1:1 before 3D plating. Cells were assessed by FACS and passaged normally every 14 days for 3 passages (1 way ANOVA). FIG. 2G) Immunofluorescence staining for ProSFTPC and HTI-56 (Scale bar=100 um). $*p<0.05$, $p<0.01$, $*p<0.001$, and $****p<0.001$ for all panels.

FIGS. 3A-3H demonstrate that nuclear YAP overexpression drives a shift from AT2 to AT1 programs in a cell autonomous manner. FIG. 3A) Experimental schematic for single cell RNA sequencing of WT YAP and YAP5SA lentiviral transduced iAT2s 7 days post transduction. FIG. 3B) UMAP of transcriptomes profiled from WT YAP and YAP5SA exposed samples. FIG. 3C) Gene expression overlays of: AT2 marker SFTPC, AT1 markers AGER, PDPN, CLIC5, a 50 gene AT1 signature, and FIG. 3D) YAP downstream target genes ANKRD1 and CYR61. FIG. 3E) Louvain clustering at resolution 0.05 identifies 3 indicated clusters. FIG. 3F) Top 50 differentially upregulated genes for the clusters shown in FIG. 3E. FIG. 3G) Gene expression of specific AT2, AT1, and proliferation markers across the clusters shown in FIG. 3E ("pro. iAT2"=proliferating iAT2s). FIG. 3H) Dot plot showing expression levels and frequencies of the indicated genes in iPSC-derived cells compared to scRNA-seq profiles of human adult primary AT1, AT2, Transitional AT2 and KRT5−/KRT17+ populations previously published by Habermann et al (Ref 72 in Example 2).

FIGS. 4A-4F depict a bifluorescent NKX2-1GFP; AGERtdTomatoreporter iPSC line enables tracking and purification of iAT1YAP5SA cells. FIG. 4A) Gene editing strategy to generate the BU3 NKX2-1GFP/AGERtdTomato (NGAT) dual reporter iPSC line for tracking lung epithelial lineages and AT1-like cells. (BU3 NKX2-1GFPreporter previously published by Hawkins et al., Ref 24 in Example 2). FIG. 4B) BU3 NGAT iPSCs were differentiated into iAT2s and transduced with WT YAP or YAP5SA lentivirus. AGERtdTomato+ cells, appearing only in the YAP5SA well, were then sorted and analyzed after 14 days of outgrowth in CK+DCI. FIG. 4C) Live cell fluorescence microscopy of YAP5SA-transduced cells growing next to an un-transduced epithelial sphere showing GFP, tdTomato, and TagBFP fluorescence; Scale bar=200 um). FIG. 4D) Flow cytometry analysis of iAT2s (BU3 NGAT line) 14 days post WT YAP or YAP5SA lentiviral transduction showing sorting gate for AGERtdTomato+ and − cells with AGERtdTomato+ percentage quantified. FIG. 4E) Gene expression analysis of sorted cells from D, compared to WT YAP and YAP5SA unsorted cells by RT-qPCR. WT YAP=Unsorted WT YAP transduced cells, YAP5SA-pre=Unsorted YAP5SA transduced cells, TOM+=AGERtdTomato+ sorted cells, TOM−= AGERtdTomato− sorted cells. (1 way ANOVA). FIG. 4F) Immunofluorescence staining of NKX2-1 protein and tdTomato (αRFP) (Scale bar=50 um). $*p<0.05$. $p<0.01$. $*p<0.001$, and $****p<0.001$ for all panels.

FIGS. 5A-5L demonstrate serum-free medium-based induction of AGERtdTomato. FIG. 5A) BU3 NGAT iAT2s were passaged as usual into 3D Matrigel with CK+DCI+RI medium for 3 days. Medium was then kept the same or switched to LATS inhibitor-based media. CK DCI+L, DCI, or L DCI. (C=Chir, K=rhKGF, L=LATS-IN-1; "DCI" as defined in FIG. 2). FIG. 5B) Representative live fluorescence microscopy of iAT2s (BU3 NGAT clone) at 9 days after changing to the indicated medium, either without (FIG. 5B) or with (FIG. 5C) YAP5SA transduction (Scale bars=500 um in B; 50 um in FIG. 5C). FIG. 5D) Representative flow cytometry plots of NKX2-1GFP and AGERtdTomato 9 days post after changing to each indicate medium. FIG. 5E) Cell counts and flow cytometry quantification of AGER tdTomato+ percentage and Mean Fluorescence Intensity (MFI) 9 days post medium change. One way ANOVA, N=3 per condition. FIG. 5F) Gene expression of AT1 and AT2 markers by whole well RT-qPCR. (1 way ANOVA, N=3 per condition). FIG. 5G) Whole mount immunofluorescence microscopy of BU3 NGAT organoids in L+DCI. Scale bar=50 um. FIG. 5H) Primary adult human AT2 cells (1° AT2s) were cultured as described 5 and 7 days post plating, medium was changed to published, human-serum containing Alveolar Differentiation Media (ADM) or L+DCI. Whole well RT-qPCR of selected genes 7 days post medium change. 1 way ANOVA, N=3 per condition. FIG. 5I) Experimental schematic: BU3 NGAT iAT1s were grown in L+DCI for 10 days, sorted on AGERtdTomato, and then plated in 3D Matrigel in either L+DCI or CK+DCI. Outgrowths of sorted cells were analyzed after an additional 9 days. FIG. 5J) Representative flow cytometry plots of AGERtdTomato+ outgrowth from (FIG. 5I). FIG. 5K) Quantification of indicated fluorescence (FACS), cell counts, or transcript expression (FIG. 5LL; whole well RT-qPCR) of cells from (FIG. 5I). Control sorted iAT1s in L are freshly sorted AGERtdTomato+ cells after 9 days in L+DCI. (N=3 per condition; K=Student's t test; L=1 way ANOVA). $*p<0.05$, $p<0.01$, $*p<0.001$, and $****p<0.001$ for all panels.

FIG. 6A) Experimental schematic (left panel) showing SPC2B2 iAT2s were either grown in CK+DCI, transduced with YAP5SA lentivirus and grown in CK+DCI, or grown in CK+DCI for 3 days before switching to L+DCI. Nine days post passage live cells were profiled by scRNA-seq. UMAP visualization (right panel) of single cell transcriptomes by either original sample name (inset) or after Louvain clustering at resolution 0.05 into 3 clusters named iAT2, iAT1YAP5SA, and iAT1. FIG. 6B) Gene expression overlays of a human AT1 50-gene signature, a 22 gene YAP/TAZ signature67, an AT2 signature, or cell cycle phase. FIG. 6C) Violin plots quantifying expression of indicated markers across the clusters from (FIG. 6A). The first series is iAT1, second series is iAT1YAP5SA, and the third series id iAT2. FIG. 6D) Heatmap showing average expression (normalized by column) of genes in the AT1 50-gene set across the 3 Louvain clusters from (FIG. 6A). FIG. 6E) Dot plot of transcript expression levels and frequencies of YAP/TAZ downstream targets and TEADs across the 3 clusters from (FIG. 6A). FIG. 6F) Dot plot showing expression levels and frequencies of AT1, AT2, and YAP/TAZ targets in this dataset compared to human adult primary AT1, AT2, Transitional AT2, and KRT5-/KRT17+ scRNA-seq profiles previously published by Habermann et al.72 FIG. 6G) Expression of AT1 marker genes (RT-qPCR) in whole well RNA extracts of L+DCI-induced and YAP5SA-transduced iAT1s compared to bulk primary human distal lung tissue; fold change normalized to 18S ($2^{-DDCT}$) is calculated relative to iAT2s in CK+DDCT. (1 way ANOVA) *p<0.05, p<0.01, *p<0.001, and **** p<0.001 for all panels.

FIGS. 7A-7O demonstrate that iAT1s cultured at air-liquid interface (ALI) express AT1-like molecular and functional phenotypes. FIG. 7A) Experimental schematic indicating BU3 NGATiAT1s were cultured in 3D in L+DCI medium for 8-11 days before single cell passaging and replating onto transwell inserts in L+DCI medium. Upper chamber media was aspirated after 3 days (airlift) to form an air-liquid interface (ALI). FIG. 7F) UMAP overlays of YAP/TAZ 22 gene signature 67 and primary human AT1 50-gene signature (data not shown). FIG. 7I) Expression of transcripts encoding secreted ligands, comparing the samples from (FIG. 7E). FIG. 7O) Frequency distribution of cell surface areas of iAT2, iAT1 high density, and iAT1 low density. N=149, 139, and 79 respectively). * p<0.05, p<0.01, *p<0.001, and ****p<0.001 for all panels.

FIG. 8A) UMAP projection of all lung cells in previously published dataset by Basil et al. 52 (N=5, 58567 total cells, 1401 AT1s). FIGS. 8B-8S) Violin plots showing gene expression of selected AT1 marker genes across all lung cell types represented in dataset.

FIG. 9A) Whole well gene expression by RT-qPCR of EMT markers, airway lung lineage markers and non-lung endoderm markers 14 days post YAP5SA or mock lentiviral transduction of SPC2B2 iAT2s, relative to Day 0 iPSCs. (N=3 per condition, student's t test) FIG. 9B) Diagram of WT YAP and YAP5SA lentiviruses showing dual promoter system with tagBFP and LoxP site. YAP5SA-GFP lentivirus used for competition assay. *p<0.05, p<0.01, *p<0.001, and ****p<0.001 for all panels.

FIGS. 10A-10E depict single Cell RNA sequencing of YAP5SA transduced iAT2s. FIG. 10A) Sub plots of UMAP projections of WT YAP and YAP5SA wells to show lentiviral tagBFP expression in each condition. FIG. 10B) Heatmap of genes in the 50 AT1 gene signature across each population. FIGS. 10C-1 to 10C-3) Full heatmap of top 50 differentially upregulated genes in the iAT2, iAT1YAP5SA, and Proliferating iAT2 populations. FIGS. 10D1-10D2) Gene expression overlays of aberrant basaloidtransitional markers KRT17, SOX4, and CLDN4; Non-lung endoderm markers TFF1, PAX8, and AFP; and other lung markers TP63, MCUSB, FOXJ1, SCGB3A2, and NKX2-1. FIG. 10E) Enrichr analysis of top 92 (FDR>0.05, log FC>1) differentially upregulated genes in iAT1YAP5SApopulation using Tabula Sapiens dataset.

FIG. 11A) iAT2s were transduced with either WT YAP or YAP5SA lentivirus and then plated in 3D Matrigel in CK+DCI for 8 days. They were then infected at single cell with either Adeno-Cre to excise lentivirus or mock and replated into 3D Matrigel in CK+DCI for 12 days. FIG. 11B) Representative live cell imaging of SPC2B2 iAT2s following AdenoCre infection (SFTPCtdTomato/Phase Contrast overlay, scale bar=500 um). FIG. 11C) Quantification of flow cytometry analysis showing proliferation by 24 hr EDU and SFTPCtdTomatopercentage. (N=3, 1 way ANOVA). FIG. 11D) Cell counts per 50 uL droplet. FIGS. 11E-11F) Gene expression of YAP downstream targets, AT2 and AT1 markers by bulk RT-qPCR (N=3, 1 way ANOVA). * p<0.05, p<0.01, *p<0.001, and ****p<0.001 for all panels.

FIG. 12A) CRISPR targeting of tdTomato reporter to AGER locus and Cre excision of puromycin resistance cassette. Final clone does not include puromycin cassette by lack of Fp2→Rp2 band and has both long and short bands from Fp1→Fp2 showing one copy of unedited AGER and one copy of tdTomato reporter. FIG. 12B) Karyotype of BU3 NGAT iPSC line. FIG. 12C) Representative flow cytometry of NKX2-1GFP-outgrowth, iAT2s, WT YAP transduced and YAP5SA transduced cells in both BU3 NGAT and parent BU3 NG lines.

FIG. 13A) BU3 NGAT iAT2s were passaged into 3D Matrigel in CK+DCI for 3 days, and then media was switched to media containing LATS-IN-1 and either Chir or KGF and grown for a further 11 days. Representative flow cytometry of NKX2-1GFPand AGERtdTomato. FIG. 13B) Quantification of AGERtdTomatocompared to CK DCI+L and DCI+L quantification in FIGS. 5A-5L. (N=3 per condition, 1 way ANOVA). FIG. 13C) BU3 NGAT iAT2s were transduced with either WT YAP or YAP5SA lentivirus in suspension with polybrene for 4 hours and then replated into 3D Matrigel in CK DCI. After 5 days, media was changed to withdraw one or both growth factors from the media. Cells were analyzed 11 days post media change. FIG. 13D) Cell counts of WT YAP and YAP5SA transduced cells in different medias (2 way ANOVA). First series is CK+DCI, second series is C+DCI, third series is K+DCI, fourth series is DCI. FIG. 13E) Representative flow cytometry of NKX2-1GFP and AGERtdTomato. FIG. 13F) Quantification of AGERtd-Tomatopercentage and Mean Fluorescence Intensity following YAP5SA transduction. (2 way ANOVA). First series is CK+DCI, second series is C+DCI, third series is K+DCI, fourth series is DCI. FIGS. 13G-13H) Gene expression of AT1 markers, YAP downstream targets, and AT2 markers by whole well RT-qPCR. (N=3, 2 way ANOVA). First series is CK+DCI, second series is C+DCI, third series is K+DCI, fourth series is DCI.

FIG. 14AA) Quantification of AGERtdTomato expression by flow cytometry and cell counts of different concentrations of LATS-IN-1 added 3 days post passage, analyzed 9 days post media change. (N=3 per condition, 1 way ANOVA) FIG. 14B) Flow cytometry analysis and quantification of AGERtd-Tomatoin BU3 NGAT cells that were sorted on NKX2-1GFPon day 201 and replated into CK+DCI+RI before media was switched to L+DCI 3 days later. Cells were analyzed 11 days post media change. (N=3) FIG. 14C) Gene expression of YAP downstream targets. AT2 and AT1 markers in LATS inhibitor medias by whole well RT-qPCR. (1 way ANOVA). FIG. 14D) SPC2B2 iAT2s (>95% SFTPCtd-Tomato+) were passaged into CK+DCI and then switched media to L+DCI 3 days post passage. Representative flow cytometry of SFTPCtdTomatoreporter expression 8 days post media change. FIG. 14E) Quantification of SFTPCtd-Tomato and cell counts of SPC2B2 cells in CK+DCI and L+DCI (N=3 per condition, students t test). FIG. 14F) Gene expression by bulk RT-qPCR at 8 days post media change. (N=3) FIG. 14G) BU3 NGAT iAT2s were cultured in CK+DCI for three days post passage before changing to Alevolar Differentiation media (Katsura et al. 2020)5 or L+DCI and whole well RNA was taken for RT-qPCR 7 days post media change. (N=3, One way ANOVA).

FIGS. 15A-15E depict Single Cell RNA sequencing analysis of media and lentiviral induction of iAT1s. FIGS. 15A1-15A3) Heatmap showing top 50 differentially upregulated genes between iAT2, iAT1YAP5SA, and iAT1 populations. FIGS. 15B-15D) Gene expression overlays of lentiviral tagBFP, as well as transitional state markers, airway markers, and non-lung endoderm markers. FIG. 15E) Comparison of whole well RNA from iAT2, iAT1YAP5SA, and iAT1 populations compared to bulk primary human distal lung whole well RT-qPCR controlled to iAT2s in CK+DCI. (N=3, 1 way ANOVA).

FIGS. 16A-16I depict iAT1s at Air Liquid Interface (ALI). FIG. 16A) Heatmap showing average expression of genes in 50 gene primary adult human AT1 gene signature across populations iAT2 3D, iAT1 3D, and iAT1 ALI conditions. FIGS. 16B-16E) UMAP expression overlays of lung epithelial markers and Non-lung markers. FIG. 16F) Frequency distribution of cell surface arcas from high, medium, and low plating densities of iAT1s at ALI. Calculated using ImageJ on ZO-1 staining from ALIs fixed at day 10 post plating. N=457, 455, and 399 respectively across 3 different transwells. FIG. 16G) TEER of SPC2B2 iAT2s plated in CK+DCI at ALI as published76compared to iAT1s at high (200 k) and low (50 k) density plating in L+DCI. FIG. 16H) Surface area iAT2 vs iAT1 SPC2B2 N=3, averaged from ~30-50 cells per image. FIG. 16I) Immunofluorescence images of SPC2B2 iAT2s and iAT1s at high and low density. Scale bar=20 um. $*p<0.05$, $p<0.01$, $*p<0.001$, and $****p<0.001$ for all panels.

DETAILED DESCRIPTION

Figure 1B:
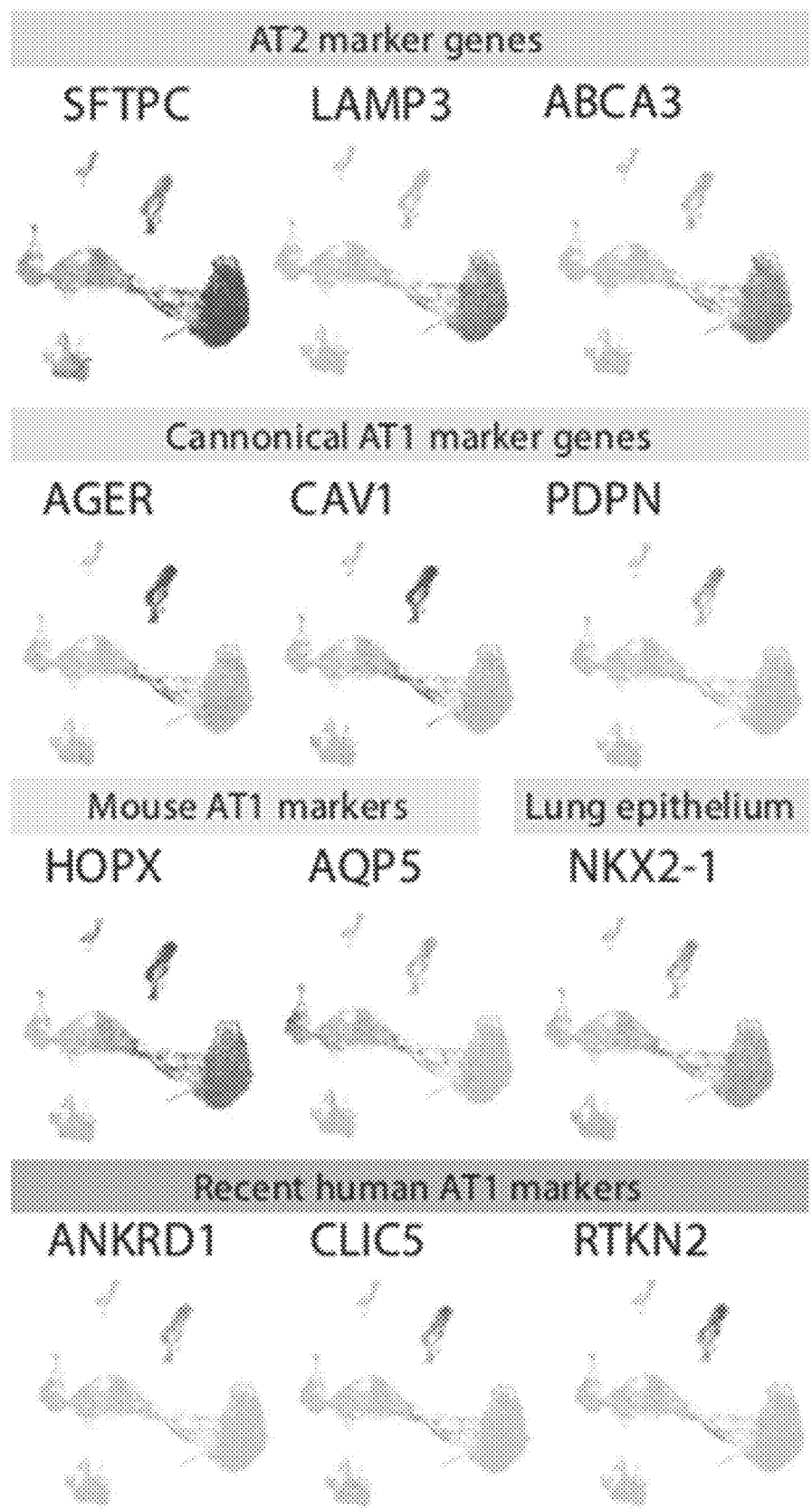

The inventors have created multiple methods of producing or differentiating AT1 cells in vitro. The AT1 cells produced by the instant methods express a molecular, morphologic, and functional phenotype reminiscent of human AT1 cells, including the capacity to form a flat epithelial barrier which produces characteristic extracellular matrix molecules and secreted ligands. The instant methods therefore provide an in vitro model of human alveolar epithelial differentiation and a source of human cells that until now have been challenging to viably obtain from patients.

The methods described herein relate to producing and/or differentiating AT1 cells. As used herein, "alveolar epithelial cell type I" or "AT1" refers to uniquely flattened (e.g., less than 0.1 µm thickness) lung epithelial cells that permit oxygen diffusion into the capillaries. In some embodiments of any of the aspects, an AT1 cell is AGER+, CAV1+, CLIC5+, and/or PDPN+. In some embodiments of any of the aspects, an AT1 cell is AGER+, CAV1+, CLIC5+, and PDPN+. Further discussion of AT1 characteristics and function can be found, e.g., in Yang et al. Development 143:54-65 (2016) and Wang et al. PNAS 115:2407-2412 (2018); each of which is incorporated by reference herein in its entirety.

An AT1 cell obtained and/or produced according to the method described herein can be an isolated cell, a member of a pure population of AT1 cells, or a member of a mixed population of cells. In some embodiments of any of the aspects, the AT1 cells can be provided as a member of a population of cells which are at least 50% AT1 cells, e.g., at least 50%, at least 60%, at least 70%, at least 80%, at least 90% AT1 cells or more.

The AT1 cells produced by the methods described herein can be stable in culture (e.g., viable and consistent in an AT1 cell phenotype) for at least 1 month, e.g., at least 1 month, at least 2 months, at least 3 months, or more.

Accordingly, in one aspect, described herein is method comprising at least one of:
  a) inducing ectopic Yes Associated Protein (YAP) expression in at least one AT2 cell and/or lung epithelial progenitor cell; and
  b) maintaining at least one AT2 cell and/or lung epithelial progenitor cell in a medium comprising a Large Tumor Suppressor Kinase (LATS) inhibitor.

In one aspect, described herein is a method comprising a) inducing ectopic Yes Associated Protein (YAP) expression in at least one AT2 cell and/or lung epithelial progenitor cell; and b) maintaining at least one AT2 cell and/or lung epithelial progenitor cell in a medium comprising a Large Tumor Suppressor Kinase (LATS) inhibitor. In one aspect, described herein is a method comprising inducing ectopic Yes Associated Protein (YAP) expression in at least one AT2 cell and/or lung epithelial progenitor cell. In one aspect, described herein is a method comprising maintaining at least one AT2 cell and/or lung epithelial progenitor cell in a medium comprising a Large Tumor Suppressor Kinase (LATS) inhibitor. In some embodiments of any of the aspects, the methods described herein can provide or result in differentiation and/or growth of an AT1 cell. In some embodiments of any of the aspects, the methods described herein can provide or result in differentiation of an AT1 cell. In some embodiments of any of the aspects, the methods described herein can provide or result in expansion of a population of AT1 cells.

As used herein, "alveolar epithelial cell type II" or "AT2" refers to an epithelial cell found in the alveoli which produces pulmonary surfactant. AT2s are characterized by high expression of, e.g., SFTPC, SFTPB, and ABCA3. In some embodiments of any of the aspects, an AT2 cell is a NKX2-1+/ SFTPC+ cell. In some embodiments of any of the aspects, an AT2 cell is a NKX2-1+/ SFTPCHi cell. As used herein "SFTPC" refers to pulmonary surfactant-associated protein C, a membrane protein which produces surfactant. Sequences for SFTPC genes, mRNA, and polypeptides are known for a number of species, e.g., human SFTPC (NCBI Gene ID No: 6440) mRNA (e.g., NCBI Ref Seq: NM_001172357.1; NM_001172410.1; NM_001317778.1; NM_001317779.1; NM_001317780.1; and NM_003018.3) and polypeptide (e.g., NCBI Ref Seq: NP_001165828.1; NP_001165881.1; NP_001304707.1; NP_001304708.1; NP_001304709.1; and NP_003009.2).

In some embodiments, the at least one AT2 cell is a human AT2 cell. In some embodiments. the at least one AT2 cell is a primary AT2 cell. In some embodiments, the at least one AT2 cell is an induced AT2 cell. Methods for producing induced AT2 cells are known in the art, e.g., as in U.S. Pat. No. 10,975,357; which is incorporated by reference herein in its entirety.

As used herein, the term "progenitor cell" refers to an immature or undifferentiated cell that has the potential to mature (differentiate) into a specific cell type, for example, a blood cell, a skin cell, a bone cell, or a hair cells. Progenitor cells have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. A progenitor cell also can proliferate to make more progenitor cells that are similarly immature or undifferentiated.

Accordingly, as used herein, "lung epithelial progenitor cell" refers to a progenitor cell with the differentiation potential to form one or more types of lung epithelial cells. In some embodiments of any of the aspects, lung epithelial progenitor cells can be NKX2-1$^+$FOXA2$^+$ cells. In some embodiments of any of the aspects, lung epithelial progenitor cells can be NKX2-1$^+$FOXA2$^+$ epithelial cells. In some embodiments of any of the aspects, lung epithelial progenitor cells can be NKX2-1$^+$FOXA2$^+$ epithelial cells that can give rise to cells that express mature lung epithelial markers (e.g., SFTPC, SCGB3A2, P63, SFTPB, HOPX, PDPN, SCGB1A1, FOXJ1). In some embodiments of any of the aspects, a lung epithelial progenitor cell is NKX2-1$^+$ and STPC$^-$. In some embodiments of any of the aspects, a lung epithelial progenitor cell is NKX2-1$^+$FOXA2$^+$ and STPC$^-$.

As used herein, "NKX2-1", "NK2 homeobox 1", or thyroid transcription factor 1 (TTF-1) refers to a transcription factor that controls gene expression specifically in the thyroid, lung, and diencephalon. It is also known as thyroid specific enhancer binding protein. Sequences are known for the sequence of NKX2-1 genes and polypeptides for a number of species, e.g., human NKX2-1 (NCBI Gene ID No: 7080) mRNA (e.g., NCBI Ref Seq: NM_001079668.2 and 2. NM_003317.3) and polypeptide (e.g., NCBI Ref Seq: NP_001073136.1 and NP_003308.1).

In some embodiments of any of the aspects, a NKX2-1+ cell is a cell expressing a detectable quantity of NKX2-1 polypeptide. In some embodiments of any of the aspects, a NKX2-1$^{Hi}$ cell belongs to a first subpopulation (NKX2-1$^{Hi}$) of cells expressing a relatively higher amount of NKX2-1 polypeptide as compared to a second subpopulation (NKX2-1$^{Lo}$) of cells expressing a relatively lower amount of NKX2-1 polypeptide, wherein both subpopulations are part of the same total population (e.g. a population of cells obtained from the same source). In some embodiments of any of the aspects wherein a NKX2-1+ cell is referred to, a NKX2-1$^{Hi}$ cell can be used as an alternative embodiment.

In some embodiments of any of the aspects, the NKX2-1+ lung epithelial progenitor cell is a CD47hi/CD26lo cell, wherein CD47 is a polypeptide of NCBI Gene ID: 961 or an ortholog thereof and CD26 is a polypeptide of NCBI Gene ID: 1803 or an ortholog thereof. In some embodiments of any of the aspects, a CD47hi/CD26lo cell is a cell sorted from a population of cells for a CD47hi/CD26lo phenotype. In some embodiments of any of the aspects, the NKX2-1+ lung epithelial progenitor cell is provided by sorting lung epithelial progenitor cells to isolate a CD47hi/CD26lo population.

Lung epithelial progenitor cells can be obtained from any source known in the art, e.g., by isolating such cells from a subject or tissue and/or by differentiating such cells from a less differentiated cell type, e.g., a stem cell or epithelial progenitor cell type. In some embodiments of any of the aspects, the lung epithelial progenitor cell is derived from a stem cell, an induced pluripotent stem cell (iPSC), an embryonic stem cell, and/or a somatic stem cell. In some embodiments, the lung epithelial progenitor cell is derived from a cell obtained from a subject, e.g., a subject having, diagnosed as having, or in need of treatment for a lung disease.

In some embodiments, the at least one lung epithelial progenitor cell is a human lung epithelial progenitor cell. In some embodiments, the at least one lung epithelial progenitor cell is a primary lung epithelial progenitor cell. In some embodiments, the at least one lung epithelial progenitor cell is an induced lung epithelial progenitor cell.

In some embodiments of any of the aspects, the at least one AT2 and/or at least one lung epithelial progenitor cell is not contacted or cultured with a feeder cell layer. In some embodiments of any of the aspects, a feeder cell layer is not present during any step of the methods described herein. In some embodiments of any of the aspects, a feeder cell layer is not added or provided during any step of the methods described herein.

In some embodiments of any of the aspects described herein, cells can be sorted and/or selected before or after any contacting or maintaining step described herein, e.g., lung epithelial progenitor cells can be sorted to increase the percentage of NKX2-1+ cells present in a population after differentiation from an iPSC and/or cells can be sorted after the contacting and/or maintaining steps to increase the percentage of AT1 cells present in a population. Methods of sorting and selecting cells are known in the art, e.g., FACs, flow cytometry, magnetic bead based sorting, and microfluidic chip based sorting using cell fluorescence, or the like.

The at least one AT2 and/or at least one lung epithelial progenitor cell can be provided as an isolated cell, as a member of a pure population of cells, or as a member of a mixed population of cells. The cells described herein can be eukaryotic cells, mammalian cells, or human cells. In some embodiments of any of the aspects, a cell described herein can be a human cell. In some embodiments of any of the aspects, a cell described herein can be a mammalian cell.

In some embodiments, the methods described herein comprise inducing expression in or contacting at least one AT2 cell. In some embodiments, the methods described herein comprise inducing expression in or contacting at least one lung epithelial progenitor cell. In some embodiments, the methods described herein comprise inducing expression in or contacting a pure culture of AT2 cells (e.g., a culture or population of cells that do not comprise any other type of cells). In some embodiments, the methods described herein comprise inducing expression in or contacting a pure culture of lung epithelial progenitor cells (e.g., a culture or population of cells that do not comprise any other type of cells). In some embodiments, the methods described herein comprise inducing expression in or contacting at least one AT2 cell and at least one lung epithelial progenitor cell.

As used herein, "Yes Associated Protein" or "YAP" or "YAP1" refers to a nuclear effector in the Hippo signaling pathway that physically interacts with Yes and Src kinases. Multiple isoforms of YAP are known, due to alternative splicing. Sequences for YAP genes, mRNA, and polypeptides are known for a number of species, e.g., human YAP (NCBI Gene ID No: 10413) mRNA (e.g., NCBI Ref Seq: NM_001130145.3, NM_001195044.2, NM_001195045.2, NM_001282097.2, NM_001282098.2, NM_0001282099.2, NM_001282100.2, NM_001282101.2, and NM_006106.5) and polypeptide (e.g., NCBI Ref Seq: NP_001123617.1, NP_001181973.1, NP_001181974.1, NP_001269026.1, NP_001269027.1, NP_001269028.1, NP_001269029.1, NP_001269030.1, and NP_006097.2).

```
YAP1 Isoform 1
                                                                     SEQ ID NO: 1
    1    mdpgqqpppq papqgqgqpp sqppqgqgpp sgpgqpapaa tqaapqappa ghqivhvrgd 61    setdlealfn avmnpktanv pqtvpmrlrk lpdsffkppe pkshsrqast dagtagaltp 121    qhvrahsspa slqlgavspg tltptgvvsg paatptaqhl rqssfeipdd vplpagwema 181    ktssgqryfl nhidqtttwq dprkamlsqm nvtaptsppv qqnmmnsasg plpdgweqam 241    tqdgeiyyin hknkttswld prldprfamn qrisqsapvk qppplapqsp qggvmggsns 301    nqqqqmrlqq lqmekerlrl kqqellrqam rninpstans pkcqelalrs qlptleqdgg 361    tqnpvsspgm sqelrtmttn ssdpflnsgt yhsrdestds glsmssysvp rtpddflnsv 421    demdtgdtin qstlpsqqnr fpdyleaipg tnvalgtleg dgmniegeel mpslqealss 481    dilndmesvl aatkldkesf ltwl YAP1 Isoform 3
                                                                     SEQ ID NO: 3
    1    mdpgqqpppq papqgqgqpp sqppqgqgpp sgpgqpapaa tqaapqappa ghqivhvrgd 61    setdlealfn avmnpktanv pqtvpmrlrk lpdsffkppe pkshsrqast dagtagaltp 121    qhvrahsspa slqlgavspg tltptgvvsg paatptaqhl rqssfeipdd vplpagwema 181    ktssgqryfl nhidqtttwq dprkamlsqm nvtaptsppv qqnmmnsasg plpdgweqam 241    tqdgeiyyin hknkttswld prldprfamn qrisqsapvk qppplapqsp qggvmggsns 301    nqqqqmrlqq lqmekerlrl kqqellrqel alrsqlptle qdggtqnpvs spgmsqelrt 361    mttnssdpfl nsgtyhsrde stdsglsmss ysvprtpddf lnsvdemdtg dtinqstlps 421    qqnrfpdyle aipgtnvdlg tlegdgmnie geelmpslqe alssdilndm esvlaatkld 481    kesfltwl YAP1 Isoform 4
                                                                     SEQ ID NO: 4
    1    maktssgqry flnhidqttt wqdprkamls qmnvtaptsp pvqqnmmnsa sgplpdgweq 61    amtqdgeiyy inhknkttsw ldprldprfa mnqrisqsap vkqppplapq spqggvmggs 121    nsnqqqqmrl qqlqmekerl rlkqqellrq amrninpsta nspkcqelal rsqlptleqd 181    ggtqnpvssp gmsqelrtmt tnssdpflns gtyhsrdest dsglsmssys vprtpddfln 241    svdemdtgdt inqstlpsqq nrfpdyleai pgtnvdlgtl egdgmniege elmpslqeal 301    ssdilndmes vlaatkldke sfltwl YAP1 Isoform 6
                                                                     SEQ ID NO: 5
    1    mdpgqqpppq papqgqgqpp sqppqgqgpp sgpgqpapaa tqaapqappa ghqivhvrgd 61    setdlealfn avmnpktanv pqtvpmrlrk lpdsffkppe pkshsrqast dagtagaltp 121    qhvrahsspa slqlgavspg tltptgvvsg paatptaqhl rqssfeipdd vplpagwema 181    ktssgqryfl nhidqtttwq dprkamlsqm nvtaptsppv qqnmmnsasa mnqrisqsap
```

-continued

```
241  vkqppplapq spqggvmggs nsnqqqqmrl qqlqmekerl rlkqqellrq amrninpsta
301  nspkcqelal rsqlptleqd ggtqnpvssp gmsqelrtmt tnssdpflns gtyhsrdest
361  dsglsmssys vprtpddfln svdemdtgdt inqstlpsqq nrfpdyleai pgtnvdlgtl
421  egdgmniege elmpslqeal ssdilndmes vlaatkldke sfltwl
```

YAP1 Isoform 5
SEQ ID NO: 6
```
  1  mdpgqqpppq papqgqgqpp sqppqgqgpp sgpgqpapaa tqaapqappa ghqivhvrgd
 61  setdlealfn avmnpktanv pqtvpmrlrk lpdsffkppe pkshsrqast dagtagaltp
121  qhvrahsspa slqlgavspg tltptgvvsg paatptaqhl rqssfeipdd vplpagwema
181  ktssgqryfl nhidqtttwq dprkamlsqm nvtaptsppv qqnmmnsasa mnqrisqsap
241  vkqppplapq spqggvmggs nsnqqqqmrl qqlqmekerl rlkqqellrq vrpqelalrs
301  qlptleqdgg tqnpvsspgm sqelrtmttn ssdpflnsgt yhsrdestds glsmssysvp
361  rtpddflnsv demdtgdtin qstlpsqqnr fpdyleaipg tnvalgtleg dgmniegeel
421  mpslqealss dilndmesvl aatkldkesf ltwl
```

YAP1 Isoform 7
SEQ ID NO: 7
```
  1  mdpgqqpppq papqgqgqpp sqppqgqgpp sgpgqpapaa tqaapqappa ghqivhvrgd
 61  setdlealfn avmnpktanv pqtvpmrlrk lpdsffkppe pkshsrqast dagtagaltp
121  qhvrahsspa slqlgavspg tltptgvvsg paatptaqhl rqssfeipdd vplpagwema
181  ktssgqryfl nhidqtttwq dprkamlsqm nvtaptsppv qqnmmnsasa mnqrisqsap
241  vkqppplapq spqggvmggs nsnqqqqmrl qqlqmekerl rlkqqellrq vrpqamrnin
301  pstanspkcq elalrsqlpt leqdggtqnp vsspgmsqel rtmttnssdp flnsgtyhsr
361  destdsglsm ssysvprtpd dflnsvdemd tgdtinqstl psqqnrfpdy leaipgtnvd
421  lgtlegdgmn iegeelmpsl qealssdiln dmesvlaatk ldkesfltwl
```

YAP1 Isoform 8
SEQ ID NO: 8
```
  1  mdpgqqpppq papqgqgqpp sqppqgqgpp sgpgqpapaa tqaapqappa ghqivhvrgd
 61  setdlealfn avmnpktanv pqtvpmrlrk lpdsffkppe pkshsrqast dagtagaltp
121  qhvrahsspa slqlgavspg tltptgvvsg paatptaqhl rqssfeipdd vplpagwema
181  ktssgqryfl nhidqtttwq dprkamlsqm nvtaptsppv qqnmmnsasg plpdgweqam
241  tqdgeiyyin hknkttswld prldprfamn qrisqsapvk qppplapqsp qggvmggsns
301  nqqqqmrlqq lqmekerlrl kqqellrqvr pqelalrsql ptleqdggtq npvsspgmsq
361  elrtmttnss dpflnsgtyh srdestdsgl smssysvprt pddflnsvde mdtgdtinqs
421  tlpsqqnrfp dyleaipgtn valgtlegdg mniegeelmp slqealssdi lndmesvlaa
481  tkldkesflt wl
```

YAP1 Isoform 9
SEQ ID NO: 9
```
  1  mdpgqqpppq papqgqgqpp sqppqgqgpp sgpgqpapaa tqaapqappa ghqivhvrgd
 61  setdlealfn avmnpktanv pqtvpmrlrk lpdsffkppe pkshsrqast dagtagaltp
121  qhvrahsspa slqlgavspg tltptgvvsg paatptaqhl rqssfeipdd vplpagwema
181  ktssgqryfl nhidqtttwq dprkamlsqm nvtaptsppv qqnmmnsasg plpdgweqam
241  tqdgeiyyin hknkttswld prldprfamn grisqsapvk qppplapqsp qggvmggsns
301  nqqqqmrlqq lqmekerlrl kqqellrqvr pqamrninps tanspkcqel alrsqlptle
361  qdggtqnpvs spgmsqelrt mttnssdpfl nsgtyhsrde stdsglsmss ysvprtpddf
```

-continued

```
421    lnsvdemdtg dtinqstlps qqnrfpdyle aipgtnvdlg tlegdgmnie geelmpslqe 481    alssdilndm esvlaatkld kesfltwl YAP1 Isoform 2
                                                                SEQ ID NO: 10
  1    mdpgqqpppq papqgqgqpp sqppqgqgpp sgpgqpapaa tqaapqappa ghqivhvrgd 61    setdlealfn avmnpktanv pqtvpmrlrk lpdsffkppe pkshsrqast dagtagaltp 121    qhvrahsspa slqlgavspg tltptgvvsg paatptaqhl rqssfeipdd vplpagwema 181    ktssgqryfl nhidqtttwq dprkamlsqm nvtaptsppv qqnmmnsasa mnqrisqsap 241    vkqppplapq spqggvmggs nsnqqqqmrl qqlqmekerl rlkqqellrq elalrsqlpt 301    leqdggtqnp vsspgmsqel rtmttnssdp flnsgtyhsr destdsglsm ssysvprtpd 361    dflnsvdemd tgdtinqstl psqqnrfpdy leaipgtnvd lgtlegdgmn iegeelmpsl 421    qealssdiln dmesvlaatk ldkesfltwl
```

In some embodiments of any of the aspects, a YAP protein comprises the sequence of SEQ ID NO: 1. In some embodiments of any of the aspects, a YAP protein consists of the sequence of SEQ ID NO: 1. In some embodiments of any of the aspects, a YAP protein consists essentially of the sequence of SEQ ID NO: 1.

In some embodiments of any of the aspects, a YAP protein comprises a sequence with at least 80%, at least 85%, at least 90%, at least 95%, at least 98%, or at least 99% sequence identity to the sequence of SEQ ID NO: 1. In some embodiments of any of the aspects, a YAP protein consists of a sequence with at least 80%, at least 85%, at least 90%, at least 95%, at least 98%, or at least 99% sequence identity to the sequence of SEQ ID NO: 1. In some embodiments of any of the aspects, a YAP protein consists essentially of a sequence with at least 80%, at least 85%, at least 90%, at least 95%, at least 98%, or at least 99% sequence identity to the sequence of SEQ ID NO: 1.

In some embodiments of any of the aspects, a YAP protein comprises a sequence with at least 80% sequence identity to the sequence of SEQ ID NO: 1. In some embodiments of any of the aspects, a YAP protein consists of a sequence with at least 80% sequence identity to the sequence of SEQ ID NO: 1. In some embodiments of any of the aspects, a YAP protein consists essentially of a sequence with at least 80% sequence identity to the sequence of SEQ ID NO: 1.

In some embodiments of any of the aspects, a YAP protein comprises a sequence with at least 95% sequence identity to the sequence of SEQ ID NO: 1. In some embodiments of any of the aspects, a YAP protein consists of a sequence with at least 95% sequence identity to the sequence of SEQ ID NO: 1. In some embodiments of any of the aspects, a YAP protein consists essentially of a sequence with at least 95% sequence identity to the sequence of SEQ ID NO: 1.

In some embodiments of any of the aspects, a YAP protein comprises the sequence of one of SEQ ID NOs: 1 and 3-10. In some embodiments of any of the aspects, a YAP protein consists of the sequence of one of SEQ ID NOs: 1 and 3-10. In some embodiments of any of the aspects, a YAP protein consists essentially of the sequence of one of SEQ ID NOs: 1 and 3-10.

In some embodiments of any of the aspects, a YAP protein comprises a sequence with at least 80%, at least 85%, at least 90%, at least 95%, at least 98%, or at least 99% sequence identity to the sequence of one of SEQ ID NOs: 1 and 3-10. In some embodiments of any of the aspects, a YAP protein consists of a sequence with at least 80%, at least 85%, at least 90%, at least 95%, at least 98%, or at least 99% sequence identity to the sequence of one of SEQ ID NOs: 1 and 3-10. In some embodiments of any of the aspects, a YAP protein consists essentially of a sequence with at least 80%, at least 85%, at least 90%, at least 95%, at least 98%, or at least 99% sequence identity to the sequence of one of SEQ ID NOs: 1 and 3-10.

In some embodiments of any of the aspects, a YAP protein comprises a sequence with at least 80% sequence identity to the sequence of one of SEQ ID NOs: 1 and 3-10. In some embodiments of any of the aspects, a YAP protein consists of a sequence with at least 80% sequence identity to the sequence of one of SEQ ID NOs: 1 and 3-10. In some embodiments of any of the aspects, a YAP protein consists essentially of a sequence with at least 80% sequence identity to the sequence of one of SEQ ID NOs: 1 and 3-10.

In some embodiments of any of the aspects, a YAP protein comprises a sequence with at least 95% sequence identity to the sequence of one of SEQ ID NOs: 1 and 3-10. In some embodiments of any of the aspects, a YAP protein consists of a sequence with at least 95% sequence identity to the sequence of one of SEQ ID NOs: 1 and 3-10. In some embodiments of any of the aspects, a YAP protein consists essentially of a sequence with at least 95% sequence identity to the sequence of one of SEQ ID NOs: 1 and 3-10.

YAP proteins comprise HXRXXS consensus sequences, where X is any amino acid. In a wild-type YAP, the serine residues of HXRXXS are phosphorylated by LATS to inhibit activity of YAP. Thus, mutation of the serine of one or more such consensus sequences in a YAP protein can increase YAP activity in a cell by lowering the ability of LATS to inhibit YAP. In some embodiments, a wild-type YAP referred to herein can be a protein of SEQ ID NO: 1. In some embodiments, a sequence or mutation described herein can be described as occurring at a position corresponding to a position in a reference sequence. In some embodiments, a sequence or mutation described herein can be described as occurring at a position corresponding to a position in SEQ ID NO: 1. As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

In some embodiments of any of the aspects, the YAP comprises mutation of the serine of at least one HXRXXS consensus sequence. In some embodiments of any of the aspects, the YAP comprises mutation of the serine of one HXRXXS consensus sequence present in the protein. In some embodiments of any of the aspects, the YAP comprises mutation of the serine of one HXRXXS consensus sequence present in the wild-type YAP. In some embodiments of any of the aspects, the YAP comprises mutation of the serine of every HXRXXS consensus sequence present in the protein. In some embodiments of any of the aspects, the YAP comprises mutation of the serine of every HXRXXS consensus sequence present in the wild-type YAP. In some embodiments of any of the aspects, the YAP does not comprise a HXRXXS consensus sequence.

In some embodiments of any of the aspects, the YAP comprises mutation of at least one of the serines corresponding to S61, S109, S127, S164, and S397 of SEQ ID NO: 1. In some embodiments of any of the aspects, the YAP comprises mutation of at least two of the serines corresponding to S61, S109, S127, S164, and S397 of SEQ ID NO: 1. In some embodiments of any of the aspects, the YAP comprises mutation of at least three of the serines corresponding to S61, S109, S127, S164, and S397 of SEQ ID NO: 1. In some embodiments of any of the aspects, the YAP comprises mutation of at least four of the serines corresponding to S61, S109, S127, S164, and S397 of SEQ ID NO: 1. In some embodiments of any of the aspects, the YAP comprises mutation of each serine corresponding to S61, S109, S127, S164, and S397 of SEQ ID NO: 1. In some embodiments of any of the aspects, the YAP comprises mutation of the serine corresponding to S61 of SEQ ID NO: 1. In some embodiments of any of the aspects, the YAP comprises mutation of the serine corresponding to S109 of SEQ ID NO: 1. In some embodiments of any of the aspects, the YAP comprises mutation of the serine corresponding to S127, of SEQ ID NO: 1. In some embodiments of any of the aspects, the YAP comprises mutation of the serine corresponding to S397 of SEQ ID NO: 1.

In some embodiments of any of the aspects, the mutation of serine in a YAP can be a mutation to any amino acid other than serine. In some embodiments of any of the aspects, the mutation of serine in a YAP can be a mutation to alanine.

Expression of a gene or protein can be induced by contacting a cell with a nucleic acid encoding the protein (e.g., a vector), contacting a cell with a nucleic acid encoding an agonist of the gene (e.g., a transcriptional regulator or enzyme that agonizes the protein), or contacting the cell with an inhibitor of a protein or nucleic acid that inhibits expression of the gene or protein. Such methods are known in the art.

In some embodiments of any of the aspects, inducing comprises contacting the at least one AT2 cell and/or lung epithelial progenitor cell with an expression vector encoding a YAP protein. In some embodiments of any of the aspects, the expression vector is a viral vector. In some embodiments of any of the aspects, the expression vector is a lentiviral vector.

As used herein, "Large Tumor Suppressor Kinase" or "LATS" refers to collectively to LATS1 and LATS2, kinases that phosphorylate YAP and TAZ. Sequences for LATS genes, mRNA, and polypeptides are known for a number of species, e.g., human LATS1 (NCBI Gene ID No: 9113) and human LATS2 (NCBI Gene ID No: 26524).

As used herein, "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target and/or the level of editing of a system described herein. In some embodiments of any of the aspects, the inhibitor can be an inhibitory nucleic acid; an aptamer; an antibody reagent; an antibody; or a small molecule. An inhibitor of a target described herein can inhibit the activity, expression, or accumulation of the target polypeptide. Inhibitors can include inhibitors that act directly on the target itself (e.g., that bind to the protein or transcript, e.g., direct inhibitors). In some embodiments of any of the aspects, an inhibitor of a specified target is an antibody, antibody reagent, or antigen-binding fragment thereof, that specifically binds to the target.

A LATS inhibitor can be effective in inhibiting both or one of LATS1 and LATS2. In some embodiments of any of the aspects, a LATS inhibitor inhibits LATS1 and LATS2. In some embodiments of any of the aspects, a LATS inhibitor inhibits LATS1 and does not inhibit LATS2. In some embodiments of any of the aspects, a LATS inhibitor inhibits LATS2 and does not inhibit LATS1.

Small molecule LATS inhibitors are known in the art. In some embodiments of any of the aspects, the LATS inhibitor is selected from the group consisting of: LATS-IN-1 (TRULI; N-(3-benzylthiazol-2(3H)-ylidene)-1H-pyrrolo[2,3-b]pyridine-3-carboxamide); GA-017; and TDI-011536.

In some embodiments of any of the aspects, the medium comprises one LATS inhibitor. In some embodiments of any of the aspects, the medium comprises two or more LATS inhibitors. In some embodiments of any of the aspects, the medium comprises the LATS inhibitor is present in the medium before the medium and cell are in contact with each other. In some embodiments of any of the aspects, the medium comprises the LATS inhibitor is added to the medium after the medium and cell are in contact with each other. In some embodiments of any of the aspects, the LATS inhibitor is added to the medium once. In some embodiments of any of the aspects, the LATS inhibitor is added to the medium multiple times during the maintaining step. In some embodiments of any of the aspects, the LATS inhibitor is added to the medium continuously during the maintaining step.

As described herein, LATS inhibition induces YAP signaling. Accordingly, in some of the embodiments, maintaining at least one AT2 cell and/or lung epithelial progenitor cell in a medium comprising a LATS inhibitor induces YAP signaling. In some of the embodiments, the amount of the LATS inhibitor is an amount sufficient to induce YAP signaling. In some of the embodiments, maintaining at least one AT2 cell and/or lung epithelial progenitor cell in a medium comprising a LATS inhibitor is performed for a time sufficient to induce YAP signaling. Methods for measuring YAP signaling are provided in the Examples herein.

In some embodiments of any of the aspects, the methods described herein comprise maintaining the AT2 cells after the contacting step.

As used herein. "maintaining" or "culturing" refers to continuing the viability of population of cells. A maintained population of cells will have a population of metabolically active cells. The number of these cells can be roughly stable over a period of at least 3 days or can grow.

Conditions for maintaining or culturing cells are known in the art, e.g., suitable media, temperatures, and humidity. By way of example, media suitable for maintaining or culturing lung cells can include complete serum free defined media. Exemplary, nonlimiting complete serum free defined media includes a mixture of Iscove's Modified Dulbecco's Medium (IMDM) Ham's F12, L-alanyl-L-glutamine dipeptide, B27 supplement, bovine serum albumin (BSA), ascorbic acid, 1-thioglycerol, and N2 supplement. A further complete serum free defined media includes a mixture of Iscove's Modified Dulbecco's Medium (IMDM) Ham's F12, L-alanyl-L-glutamine dipeptide, B27 supplement, bovine serum albumin (BSA), ascorbic acid, 1-thioglycerol, N2 supplement, and one or more antibiotics and/or antifungals. A further complete serum free defined media includes a mixture of Iscove's Modified Dulbecco's Medium (IMDM) Ham's F12, L-alanyl-L-glutamine dipeptide, B27 supplement, bovine serum albumin (BSA), ascorbic acid, 1-thioglycerol, N2 supplement, and Primocin.

In some embodiments of any of the aspects, a maintaining step comprises air-liquid interface (ALI) culture. In some embodiments of any of the aspects, a maintaining step comprises culture in a Transwell culture system. In some embodiments of any of the aspects, a maintaining step comprises culture in a medium comprising dexamethasone. 8-bromoadenosine 3',5'cyclic monophosphate sodium salt, and 0.1 mM 3-isobutyl-1-methylxanthine (IBMX). In some embodiments of any of the aspects, a maintaining step comprises culture in a medium comprising dexamethasone, 8-bromoadenosine 3',5'cyclic monophosphate sodium salt, 3-isobutyl-1-methylxanthine (IBMX), and a ROCK inhibitor. In some embodiments of any of the aspects, a maintaining step comprises culture in a medium comprising a ROCK inhibitor for the first 3 days and then in the absence of a ROCK inhibitor.

In some embodiments of any of the aspects, a maintaining step is continued for at least 3 days. In some embodiments of any of the aspects, a maintaining step is continued for at least 6 days. In some embodiments of any of the aspects, a maintaining step is continued for at least 10 days. In some embodiments of any of the aspects, a maintaining step is continued for at least 13 days. In some embodiments of any of the aspects, a maintaining step is continued for at least 16 days. In some embodiments of any of the aspects, a maintaining step is continued for up to 13 days. In some embodiments of any of the aspects, a maintaining step is continued for up to 16 days.

In some embodiments of any of the aspects, the medium does not comprise, or the at least one AT2 cell and/or lung epithelial progenitor cell is not in contact with, CHIR99021 and/or keratinocyte growth factor (KGF) protein.

In some embodiments of any of the aspects, the medium does not comprise CHIR99021 and/or keratinocyte growth factor (KGF) protein. In some embodiments of any of the aspects, the medium does not comprise either of CHIR99021 and keratinocyte growth factor (KGF) protein. In some embodiments of any of the aspects, the medium does not comprise CHIR99021. In some embodiments of any of the aspects, the medium does not comprise keratinocyte growth factor (KGF) protein.

In some embodiments of any of the aspects the at least one AT2 cell and/or lung epithelial progenitor cell is not in contact with CHIR99021 and/or keratinocyte growth factor (KGF) protein (e.g., during the inducing or maintaining steps). In some embodiments of any of the aspects the at least one AT2 cell and/or lung epithelial progenitor cell is not in contact with either of CHIR99021 and keratinocyte growth factor (KGF) protein (e.g., during the inducing or maintaining steps). In some embodiments of any of the aspects the at least one AT2 cell and/or lung epithelial progenitor cell is not in contact with CHIR99021 (e.g., during the inducing or maintaining steps). In some embodiments of any of the aspects the at least one AT2 cell and/or lung epithelial progenitor cell is not in contact with keratinocyte growth factor (KGF) protein (e.g., during the inducing or maintaining steps).

In some embodiments of any of the aspects, the medium does not comprise, or the at least one AT2 cell and/or lung epithelial progenitor cell is not in contact with, ectopic epidermal growth factor (EGF) protein and/or ectopic fibroblast growth factor 10 (FGF10) protein.

In some embodiments of any of the aspects, the medium does not comprise ectopic epidermal growth factor (EGF) protein and/or ectopic fibroblast growth factor 10 (FGF10) protein. In some embodiments of any of the aspects, the medium does not comprise either of ectopic epidermal growth factor (EGF) protein and ectopic fibroblast growth factor 10 (FGF10) protein. In some embodiments of any of the aspects, the medium does not comprise ectopic epidermal growth factor (EGF) protein. In some embodiments of any of the aspects, the medium does not comprise ectopic fibroblast growth factor 10 (FGF10) protein.

In some embodiments of any of the aspects, the at least one AT2 cell and/or lung epithelial progenitor cell is not in contact with ectopic epidermal growth factor (EGF) protein and/or ectopic fibroblast growth factor 10 (FGF10) protein (e.g., during the inducing or maintaining steps). In some embodiments of any of the aspects, the at least one AT2 cell and/or lung epithelial progenitor cell is not in contact with either of ectopic epidermal growth factor (EGF) protein and ectopic fibroblast growth factor 10 (FGF10) protein (e.g., during the inducing or maintaining steps). In some embodiments of any of the aspects, the at least one AT2 cell and/or lung epithelial progenitor cell is not in contact with ectopic epidermal growth factor (EGF) protein (e.g., during the inducing or maintaining steps). In some embodiments of any of the aspects, the at least one AT2 cell and/or lung epithelial progenitor cell is not in contact with ectopic fibroblast growth factor 10 (FGF10) protein (e.g., during the inducing or maintaining steps).

In some embodiments of any of the aspects, the medium further comprises, or the at least one AT2 cell and/or lung epithelial progenitor cell is further contacted with, ectopic epidermal growth factor (EGF) protein and/or ectopic fibroblast growth factor 10 (FGF10) protein.

In some embodiments of any of the aspects, the medium further comprises ectopic epidermal growth factor (EGF) protein and/or ectopic fibroblast growth factor 10 (FGF10) protein. In some embodiments of any of the aspects, the medium further comprises ectopic epidermal growth factor (EGF) protein and ectopic fibroblast growth factor 10 (FGF10) protein. In some embodiments of any of the aspects, the medium further comprises ectopic epidermal growth factor (EGF) protein. In some embodiments of any of the aspects, the medium further comprises ectopic fibroblast growth factor 10 (FGF10) protein.

In some embodiments of any of the aspects, the at least one AT2 cell and/or lung epithelial progenitor cell is further contacted with ectopic epidermal growth factor (EGF) protein and/or ectopic fibroblast growth factor 10 (FGF10) protein (e.g., during the inducing or maintaining steps). In some embodiments of any of the aspects, the at least one AT2 cell and/or lung epithelial progenitor cell is further contacted with ectopic epidermal growth factor (EGF) protein and ectopic fibroblast growth factor 10 (FGF10) protein (e.g., during the inducing or maintaining steps). In some embodiments of any of the aspects, the at least one AT2 cell and/or lung epithelial progenitor cell is further contacted with ectopic epidermal growth factor (EGF) protein (e.g., during the inducing or maintaining steps). In some embodiments of any of the aspects, the at least one AT2 cell and/or lung epithelial progenitor cell is further contacted with ectopic fibroblast growth factor 10 (FGF10) protein (e.g., during the inducing or maintaining steps).

As used herein, "differentiate", or "differentiating" is a relative term meaning a "differentiated cell" is a cell that has progressed further down the developmental pathway than its precursor cell, or to a different identity than the precursor cells. Thus in some embodiments, a lung epithelial precursor cell as this term is defined herein, can differentiate to an AT1 cell, which plays a characteristic role in lung tissue, and may or may not retain the capacity to proliferate further.

AT1 cells expressing a reporter protein can be utilized to study AT1 cell biology, including the response of AT1 cells to stimuli, injury, and or candidate therapeutics. Accordingly, in some embodiments of any of the aspects, the methods described herein can further comprise contacting the at least one AT2 cell and/or lung epithelial progenitor cell, or a cell produced by the method, with a nucleic acid encoding a reporter protein. In some embodiments of any of the aspects, the at least one AT2 cell and/or lung epithelial progenitor cell can comprise a nucleic acid encoding a reporter protein. A reporter gene encodes or produces a detectable signal or label. Detectable labels, methods of detecting them are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). Detectable labels can include, but are not limited to radioisotopes, bioluminescent compounds, chromophores, antibodies, chemiluminescent compounds, fluorescent compounds, metal chelates, and enzymes. In some embodiments of any of the aspects, the detectable label or signal is a fluorescent compound, e.g., a fluorescent dye molecule or fluorophore. In some embodiments of any of the aspects, the detectable label or signal is a radiolabel. In some embodiments of any of the aspects, the detectable label or signal is a chemiluminescent compound. In some embodiments of any of the aspects, the detectable label or signal is an enzymatic label, e.g., a enzyme that can produce a chemiluminescent signal, a color signal, or a fluorescent signal. In some embodiments of any of the aspects, a detectable label can be a spectral colorimetric label including, but not limited to colloidal gold or colored glass or plastic (e.g., polystyrene, polypropylene, and latex) beads.

A reporter gene encoding any fluorescent protein can be applicable in the technology described herein. The fluorescent protein includes, but is not limited to, for example, GFP, mCherry, Venus, and Cerulean. Examples of genes encoding fluorescent proteins that can be used in accordance with the compositions and methods described herein include, without limitation, those proteins provided in U.S. Patent Application No. 2012/0003630 (see Table 59), incorporated herein by reference.

Similarly, a reporter gene encoding any enzyme can be applicable as well. Enzymes that produce colored substrates ("colorimetric enzymes") can also be used for visualization and/or quantification. Enzymatic products can be quantified using spectrophotometers or other instruments that can take absorbance measurements including plate readers. Examples of genes encoding colorimetric enzymes that can be used in accordance with the compositions and methods described herein include, without limitation, lacZ alpha fragment, lacZ (encoding beta- galactosidase, full-length), and xylE. An enzyme (e.g., glucose oxidase) can also change the conductivity of a reaction volume, permitting an electrical or electronic readout (Malitesta et al., Anal Chem 1990, 62, 2735-2740). In another example, a nuclease enzyme can cleave a nucleic acid sequence such that an electronic and optical signal is generated. In yet another example, an enzyme can separate a fluorescence resonance energy transfer (FRET) or quenching pair to induce a change in fluorescence.

A reporter gene encoding any antigen for which a specific antibody is available or can be made can also be applicable. By way of example only, as antigens are expressed by the reporter gene, the antigens bind to an electrode coated with complementary antibodies, which produces an electronic signal. Conversely, a reporter gene can encode an antibody, which when expressed, binds to an electrode coated with the complementary antigen. For non-limiting examples of reporter genes, see Reporter Genes: A Practical Guide, D. Anson (Ed.), 2007, Humana Press, the contents of which are incorporated by reference for examples on reporter genes.

A reporter gene encoding luciferases can also be used in the technology described herein. Luciferases produce luminescence, which can be readily quantified using a plate reader or luminescence counter. Examples of genes encoding luciferases for that can be used in accordance with the compositions and methods described herein include, without limitation, Rluc and firefly luciferase (from *Photinus pyralis*).

The methods and cells described herein can be utilized to study disease or injury to AT1 cells. In some embodiments of any of the aspects, the methods described herein further comprise contacting an AT1 cell produced by the method with a virus. In some embodiments of any of the aspects, the methods described herein further comprise contacting an AT1 cell produced by the method with a virus contacting an AT1 cell produced by the method with smoke, e.g., cigarette smoke. In some embodiments of any of the aspects, the methods described herein further comprise contacting an AT1 cell produced by the method with Transforming Growth Factor Beta (TGFβ) and/or bleomycin. In some embodiments of any of the aspects, the methods described herein further comprise contacting an AT1 cell produced by the method with Transforming Growth Factor Beta (TGFβ). In some embodiments of any of the aspects, the methods described herein further comprise contacting an AT1 cell produced by the method with bleomycin. In some embodiments of any of the aspects, the at least one AT2 cell and/or lung epithelial progenitor cell comprises a pulmonary fibrosis (PF) inducing mutation. Mutations that induce pulmonary fibrosis, e.g., idiopathic pulmonary fibrosis are known in the art and include, e.g., telomerase pathway genes, mutations in SFTPC, and mutations in ABCA3. More discussion of such mutations can be found in, e.g., Kropski et al., European Respiratory Journal 45:1717-1727 (2015); Kaur et al. Front Med (Lausanne) 4:154 (2017); Schwartz Trans Am Clin Climatol Assoc 127:34-45 (2016); and Evans et al. Physiological Reviews 96:1567-1591 (2016); each of which is incorporated by reference herein its entirety.

In one aspect of any of the embodiments, described herein is an AT1 cell made by a method described herein. As demonstrated in the Examples herein, AT1 cells made by the methods described herein exhibit structural differences from naturally arising or primary AT1 cells. For example, in some embodiments of any of the aspects, an AT1 cell made by a method described herein comprises lower expression of Podoplanin (PDPN) relative to a primary AT1 cell. In some embodiments, lower expression is less than 50% of the expression in a primary AT1 cell. In some embodiments, lower expression is less than 25% of the expression in a primary AT1 cell. In some embodiments, lower expression is less than 10% of the expression in a primary AT1 cell. In some embodiments of any of the aspects, an AT1 cell made by a method described herein comprises higher expression of ANKRD1 relative to a primary AT1 cell. In some embodiments of any of the aspects, an AT1 cell made by a method described herein comprises higher expression of CYR61 relative to a primary AT1 cell. In some embodiments of any of the aspects, an AT1 cell made by a method described herein comprises higher expression of CTGF relative to a primary AT1 cell. In some embodiments, higher expression is more than 200% of the expression in a primary AT1 cell. In some embodiments, higher expression is more than 300% of the expression in a primary AT1 cell. In some embodiments, higher expression is more than 500% of the expression in a primary AT1 cell.

In some embodiments of any of the aspects, the compositions of the disclosure—comprising an AT1 cell made by a method described herein—exhibit markedly different characteristics/properties compared to their closest naturally occurring counterpart. That is, the compositions of the disclosure exhibit markedly different functional and/or structural characteristics/properties, as compared to their closest naturally occurring counterpart. For instance, the AT1 cells made by a method described herein are structurally different from an AT1 cell as it naturally exists in the lung, for at least the following reasons: said AT1 cells can be isolated and purified, such that it is not found in the milieu of the lung, said AT1 can be present at concentrations that do not occur in the lung, and said AT1 cells can be associated with acceptable carriers that do not occur in the lung.

A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In one aspect of any of the embodiments, described herein is a method of treating a lung disease in a subject in need thereof, the method comprising administering to the subject an AT1 cell, e.g., a AT1 cell produced according to a method described herein. As used herein "lung disease" refers to any pathology or condition affecting and/or arising in the lungs (e.g., including the bronchi, alveoli, pleura, muscles and/or nerves of the lung). In some embodiments of any of the aspects, the lung disease is not an infectious lung disease. In some embodiments of any of the aspects, a lung disease can be an AT1-associated lung disease, e.g., a disease characterized by damage to and/or dysfunction of the AT1 cells of the lung. In some embodiments of any of the aspects, the lung disease can be acute respiratory distress syndrome (ARDS), pulmonary fibrosis, interstitial lung diseases, acute inhalational lung injuries, childhood interstitial lung diseases, or bronchopulmonary dysplasia.

In some embodiments of any of the aspects, a therapeutically effective amount of AT1 cells are administered to the subject. In some embodiments of any of the aspects, the AT1 cell is derived from a cell obtained from the subject. In some embodiments of any of the aspects, the AT1 cells is autologous to the subject. In some embodiments of any of the aspects, the at least one AT2 cell and/or lung epithelial progenitor cell was genetically modified to correct a mutation that contributed to the lung disease. Such mutations are known in the art and readily identified by one of ordinary skill in the art and/or, e.g., by genetic testing of the subject.

In some embodiments of any of the aspects, the methods described herein relate to treating a subject having or diagnosed as having lung disease with an AT1 cell. Subjects having lung disease can be identified by a physician using current methods of diagnosing lung diseases. Symptoms and/or complications of, e.g., interstitial lung disease (ILD) which characterize these conditions and aid in diagnosis are well known in the art and include but are not limited to, reduced lung function, trouble breathing, or shortness of breath. Tests that may aid in a diagnosis of, e.g. ILD include, but are not limited to, pulmonary function tests, biopsies, chest xrays, and/or chest CTs. A family history of ILD, or exposure to risk factors for ILD (e.g. lung infections) can also aid in determining if a subject is likely to have ILD or in making a diagnosis of ILD.

The compositions and methods described herein can be administered to a subject having or diagnosed as having a lung disease. In some embodiments of any of the aspects, the methods described herein comprise administering an effective amount of compositions described herein, e.g. an AT1 cell to a subject in order to alleviate a symptom of a lung disease. As used herein, "alleviating a symptom of a lung disease" is ameliorating any condition or symptom associated with the lung disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

In some embodiments of any of the aspects described herein, the administration of an AT1 cells can improve and/or increase surfactant production in the lung. In some embodiments of any of the aspects described herein, an AT1 cell is administered to a subject in need of improved lung function.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease). or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for lung function, among others. The dosage can be determined by a physician and adjusted, as necessary, to suit observed effects of the treatment.

In some embodiments of any of the aspects, the technology described herein relates to a pharmaceutical composition comprising an AT1 cell and/or an AT1 cell produced by the methods described herein, and optionally a pharmaceutically acceptable carrier. In some embodiments of any of the aspects, the active ingredients of the pharmaceutical composition comprise an AT1 cell and/or an AT1 cell produced by the methods described herein as described herein. In some embodiments of any of the aspects, the active ingredients of the pharmaceutical composition consist essentially of an AT1 cell and/or an AT1 cell produced by the methods described herein as described herein. In some embodiments of any of the aspects, the active ingredients of the pharmaceutical composition consist of an AT1 cell and/or an AT1 cell produced by the methods described herein as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. an AT1 cell and/or an AT1 cell produced by the methods described herein as described herein.

In some embodiments of any of the aspects, the pharmaceutical composition comprising an AT1 cell and/or an AT1 cell produced by the methods described herein as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an AT1 cell and/or an AT1 cell produced by the methods described herein as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, a pharmaceutical composition comprising the cells, e.g., an AT1 cell and/or an AT1 cell produced by the methods described herein, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of cells can be apportioned into multiple infusions that cumulatively equal or exceed $10^5$, $10^6$, $10^7$, $10^8$, $10^9$, $10^{10}$, $10^{11}$, or $10^{12}$ cells.

In some embodiments of any of the aspects, the dosage can be from about $1\times10^5$ cells to about $1\times10^8$ cells per kg of body weight. In some embodiments of any of the aspects, the dosage can be from about $1\times10^6$ cells to about $1\times10^7$ cells per kg of body weight. In some embodiments of any of the aspects, the dosage can be about $1\times10^6$ cells per kg of body weight. In some embodiments of any of the aspects, one dose of cells can be administered. In some embodiments of any of the aspects, the dose of cells can be repeated, e.g., once, twice, or more. In some embodiments of any of the aspects, the dose of cells can be administered on, e.g., a daily, weekly, or monthly basis. AT1 cell compositions may be administered multiple times at dosages within these ranges. The cells may be allogeneic, syngeneic, xenogencic, or autologous to the patient undergoing therapy.

In some embodiments of any of the aspects, the methods described herein can further comprise administering a second agent and/or treatment to the subject, e.g. as part of a combinatorial therapy.

In certain embodiments, an effective dose of a composition comprising an AT1 cell and/or an AT1 cell produced by the methods described herein as described herein can be administered to a patient once. In certain embodiments, an effective dose of a composition comprising an AT1 cell and/or an AT1 cell produced by the methods described herein can be administered to a patient repeatedly.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an AT1 cell and/or an AT1 cell produced by the methods described herein can be administered over a period of time, such as over a 5 minute, 10 minute, 15 minute, 20 minute, or 25 minute period.

The dosage ranges for the administration of an AT1 cell and/or an AT1 cell produced by the methods described herein, according to the methods described herein depend upon, for example, the form of the composition, its potency, and the extent to which symptoms, markers, or indicators of a condition described herein are desired to be reduced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an AT1 cell and/or an AT1 cell produced by the methods described herein in, e.g. the treatment of a condition described herein, or to induce a response as described herein (e.g. lung function) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. surfactant production and/or lung function. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of murine models of lung diseases described herein. When using an experimental animal model, efficacy of treatment is evidenced when a statistically significant change in a marker is observed, e.g. surfactant production and/or lung function.

In one aspect, described herein is a kit comprising a composition as described herein, e.g., an AT1 cell and/or an AT1 cell produced by the methods described herein. A kit is any manufacture (e.g., a package or container) comprising at least one reagent, e.g., a cell, the manufacture being promoted, distributed, or sold as a unit for performing the methods described herein. The kits described herein can optionally comprise additional components useful for performing the methods described herein. By way of example, the kit can comprise fluids (e.g., buffers) suitable for a composition comprising an AT1 cell and/or an AT1 cell produced by the methods described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

In one aspect of any of the embodiments, described herein is a method of identifying a treatment as effective in treating a lung disease, the method comprising: a) contacting an AT1 cell (e.g., an AT1 cell produced according to a method described herein) with a candidate treatment agent; and b) identifying the candidate treatment agent as effective if one or more of the following phenotypes is observed in the AT1 cell contacted with the candidate treatment agent as compared to an AT1 cell not contacted with the candidate treatment agent:
  i) increased cell survival (e.g., an increase in the length of cell survival, average length of cell survival in population of AT1 cells, or rate of cell survival at a given time point in a population of AT1 cells);
  ii) increased cell survival in the presence of cellular stressors (e.g., wherein cellular stressors can be toxins, conditions that limit nutrients and/or function, conditions that mimic a lung disease pathology or etiology (e.g. excessive mucus levels), and/or stimuli that contribute to lung disease, e.g., cigarette smoke);
  iii) decreased release of toxic agents (e.g., inflammatory cytokines or chemokines, reactive oxygen species, or apoptotic factors);
  iv) improved cellular pathology arising from a genetic mutation in the AT1 cell (e.g., decreased signs or symptoms of a disease in an AT1 cell comprising a mutation associated with and/or causing a lung disease);
  v) increased AT1 cell differentiation (e.g., increased rate or speed of AT1 cell production in a method described herein);
  vi) decreased AT1 cell proliferation in the presence of carcinogens; and/or
  vii) increased secretion of cytoprotective agents (e.g., antiinflammtory cytokines or chemokines, antioxidant molecules or molecules involved in xenobiotic metabolism).

In some embodiments of any of the aspects, an AT1 cell is derived from a cell obtained from an individual subject and the treatment is identified as an effective treatment for that individual subject.

In some embodiments of any of the aspects, a reference made herein to an NCBI Reference Sequence is a reference to the sequence available on Dec. 15, 2023.

In one respect, the present invention relates to the herein described compositions, methods, and respective component(s) thereof, as essential to the technology, yet open to the inclusion of unspecified elements, essential or not ("comprising). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect of the full length polypeptide. Conservative substitution variants that maintain the activity of wildtype proteins will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant.

In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of wildtype activity. As to amino acid sequences, one of skill will recognize that individual substitutions, deletions or additions to a nucleic acid, peptide, polypeptide, or protein sequence which alters a single amino acid or a small percentage. (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype protein, e.g. 110%, 125%, 150%, 175%, 200%, 500%, 1000% or more.

One method of identifying amino acid residues which can be substituted is to align, for example, a human protein sequence to a homolog from one or more non-human species. Alignment can provide guidance regarding not only residues likely to be necessary for function but also, conversely. those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. the activity and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu;

Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments, a polypeptide can comprise one or more amino acid substitutions or modifications. In some embodiments, the substitutions and/or modifications can prevent or reduce proteolytic degradation and/or prolong half-life of the polypeptide in a subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4, -tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moities, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, a nucleic acid, polypeptide, or other agent described herein is exogenous. In some embodiments of any of the aspects, a nucleic acid, polypeptide, or other agent described herein is ectopic. In some embodiments of any of the aspects, a nucleic acid, polypeptide, or other agent described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid encoding a polypeptide as described herein (e.g. a YAP polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments of any of the aspects, an inhibitor is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like. In some embodiments of any of the aspects, the inhibitory nucleic acid can be a silencing RNA (siRNA), microRNA (miRNA), or short hairpin RNA (shRNA). Inhibitory nucleic acids can also include guide sequence molecules (e.g., a guide RNA) that function, e.g., in combination with an enzyme, to induce insertions, deletions, indels, and/or mutations of a target, thereby inhibiting the expression of the target.

In some embodiments of any of the aspects, an iNA comprises a sequence that is complementary to at least a portion of a target sequence described herein. In some embodiments of any of the aspects, an iNA comprises a sequence at least 15 nucleotides in length that is complementary to at least a portion of a target sequence described herein. In some embodiments of any of the aspects, an iNA comprises a sequence at least 20 nucleotides in length that is complementary to at least a portion of a target sequence described herein.

In some embodiments of any of the aspects, an iNA comprises a sequence that is the reverse complement to at least a portion of a target sequence described herein. In some embodiments of any of the aspects, an iNA comprises a sequence at least 15 nucleotides in length that is the reverse complement to at least a portion of a target sequence described herein. In some embodiments of any of the aspects, an iNA comprises a sequence at least 20 nucleotides in length that is the reverse complement to at least a portion of a target sequence described herein.

In some embodiments of any of the aspects, an iNA comprises a sequence that can specifically hybridize to at least a portion of a target sequence described herein. In some embodiments of any of the aspects, an iNA comprises a sequence at least 15 nucleotides in length that can specifically hybridize to at least a portion of a target sequence described herein. In some embodiments of any of the aspects, an iNA comprises a sequence at least 20 nucleotides in length that can specifically hybridize to at least a portion of a target sequence described herein.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target, e.g. LATS. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art. One skilled in the art would be able to design further siRNA, shRNA, or miRNA to target the nucleic acid sequence of LATS, e.g., using publicly available design tools, siRNA, shRNA, or miRNA is commonly made using companies such as Dharmacon (Layfayette, CO) or Sigma Aldrich (St. Louis, MO).

In some embodiments of the various aspects described herein, the inhibitory nucleic acid is a guide nucleic acid (gNA). As used herein, the terms "guide nucleic acid," "guide sequence," "crRNA," "guide RNA," "single guide RNA," "gRNA" or "CRISPR guide sequence" refer to a nucleic acid comprising a sequence that determines the specificity of an enzyme, e.g., the Cas DNA binding protein of a CRISPR/Cas system, to a polynucleotide target. The gNA can comprise a polynucleotide sequence with at least partial complementarity with a target nucleic acid sequence, sufficient to hybridize with the target nucleic acid sequence and to direct sequence-specific binding of an enzyme, e.g., a nuclease, to the target nucleic acid sequence.

In some embodiments, the enzyme directed by the gNA is a gene-editing protein, e.g., any nuclease that induces a nick or double-strand break into a desired recognition site. Such enzymes can be native or engineered. These breaks can then be repaired by the cell in one of two ways: non-homologous end joining and homology-directed repair (homologous recombination). In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence can be used as a template for repair of the cleaved target DNA sequence, resulting in the transfer of genetic information from the donor polynucleotide to the target DNA. Therefore, new nucleic acid material may be inserted/copied into the site. The modifications of the target DNA due to NHEJ and/or homology-directed repair can be used for gene correction, gene replacement, gene tagging, transgene insertion, nucleotide deletion, gene disruption, gene mutation, etc.

In one embodiment, the gene-editing protein is a CRISPR-associated nuclease. The native prokaryotic CRISPR-associated nuclease system comprises an array of short repeats with intervening variable sequences of constant length (i.e., clusters of regularly interspaced short palindromic repeats), and CRISPR-associated ("Cas") nuclease proteins. The RNA of the transcribed CRISPR array is processed by a subset of the Cas proteins into small guide RNAs, which generally have two components as discussed below. There are at least three different systems: Type I, Type II and Type III. The enzymes involved in the processing of the RNA into mature crRNA are different in the 3 systems. In the native prokaryotic system, the guide RNA ("gRNA") comprises two short, non-coding RNA species referred to as CRISPR RNA ("crRNA") and trans-acting RNA ("tracrRNA"). In an exemplary system, the gRNA forms a complex with a nuclease, for example, a Cas nuclease. The gRNA: nuclease complex binds a target polynucleotide sequence having a protospacer adjacent motif ("PAM") and a protospacer, which is a sequence complementary to a portion of the gRNA. The recognition and binding of the target polynucleotide by the gRNA: nuclease complex induces cleavage of the target.

Any CRISPR-associated nuclease can be used in the system and methods of the invention. CRISPR nuclease systems are known to those of skill in the art, e.g. Cas9, Cas12, Cas12a, or the like, see Patents/applications U.S. Pat. No. 8,993,233, US 2015/0291965, US 2016/0175462, US 2015/0020223, US 2014/0179770, U.S. Pat. Nos. 8,697,359; 8,771,945; 8,795,965; WO 2015/191693; U.S. Pat. No. 8,889,418; WO 2015/089351; WO 2015/089486; WO 2016/028682; WO 2016/049258; WO 2016/094867; WO 2016/094872; WO 2016/094874; WO 2016/112242; US 2016/0153004; US 2015/0056705; US 2016/0090607; US 2016/0029604; U.S. Pat. Nos. 8,865,406; 8,871,445; each of which are incorporated by reference in their entirety. The nuclease can also be a phage Cas nuclease, e.g., CasΦ (e.g., Pausch et al. Science 369:333-7 (2020); which is incorporated by reference herein in its entirety).

The full-length guide nucleic acid strand can be any length. For example, the guide nucleic acid strand can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments of the various aspects described herein, a nucleic acid strand is less than about 75, 50, 45, 40, 35, 30, 25, 20, 15, 12, or fewer nucleotides in length. For example, the guide nucleic acid sequence is 10-30 nucleotides long.

In addition to a sequence that is complementary to a target nucleic acid, in some embodiments, the gNA also comprises a scaffold sequence. Expression of a gNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gNA may be referred to as a single guide RNA (sgRNA).

In some embodiments of the various aspects described herein, the guide nucleic acid is designed using a guide design tool (e.g., Benchling™; Broad Institute GPP™; CasOFFinder™; CHOPCHOP™; CRISPOR™; Deskgen™; E-CRISP™; Gencious™; GenHub™; GUIDES™ (e.g., for library design); Horizon Discovery™; IDT™; Off-Spotter™; and Synthego™; which are available on the world wide web).

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L., et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4 position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2- [known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J, et al., (2005) Nucleic Acids Research 33(1): 439-447; Mook, O R. et al., (2007) Mol Canc Ther 6(3): 833-843; Grunweller, A, et al., (2003) Nucleic Acids Research 31(12):3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2)nNH2, O(CH2)nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta. 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide, iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein. "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine, 5-methylcytosine substitutions have been shown to increase nucleic acid duplex stability by 0.6-1.2° C. (Sanghvi, Y. S., Crooke, S. T, and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA. 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Bchmoaras et al., EMBO J, 1991, 10: 1111-1118; Kabanov et al., FEBS Lett., 1990, 259:327-330; Svinarchuk et al., Biochimie, 1993, 75:49-54), a phospholipid, e.g., di-hexadecyl-rac-glycerol or tricthyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyaminc or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

As used herein. "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.). The Encyclopedia of Molecular Cell Biology and Molecular Medicine, published by Blackwell Science Ltd., 1999-2012 (ISBN 9783527600908); and Robert A. Meyers (ed.). Molecular Biology and Biotechnology: a Comprehensive Desk Reference, published by VCH Publishers. Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeck, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A method comprising at least one of:
    a) inducing ectopic Yes Associated Protein (YAP) expression in at least one AT2 cell and/or lung epithelial progenitor cell; and
    b) maintaining at least one AT2 cell and/or lung epithelial progenitor cell in a medium comprising a Large Tumor Suppressor Kinase (LATS) inhibitor.
2. The method of any one of the preceding paragraphs, wherein the YAP comprises mutation of the serine of at least one HXRXXS consensus sequence.
3. The method of any one of the preceding paragraphs, wherein the YAP comprises mutation of the serine of at least one HXRXXS consensus sequence to alanine.
4. The method of any one of the preceding paragraphs, wherein the YAP comprises mutation of the serine of every HXRXXS consensus sequence.
5. The method of any one of the preceding paragraphs, wherein the YAP comprises mutation of the serine of every HXRXXS consensus sequence to alanine.
6. The method of any one of the preceding paragraphs, wherein the YAP comprises mutation of each serine corresponding to S61, S109, S127, S164, and S397 of SEQ ID NO: 1.
7. The method of any one of the preceding paragraphs, wherein the YAP comprises mutation of each serine corresponding to S61, S109, S127, S164, and S397 of SEQ ID NO: 1 to alanine.

8. The method of any one of the preceding paragraphs, wherein inducing comprises contacting the at least one AT2 cell and/or lung epithelial progenitor cell with an expression vector encoding a YAP protein.

9. The method of paragraph 8, wherein the expression vector is a viral vector.

10. The method of paragraph 8, wherein the expression vector is a lentiviral vector.

11. The method of any one of the preceding paragraphs, wherein the medium is a complete serum free defined medium.

12. The method of any one of the preceding paragraphs, wherein the LATS inhibitor is selected from the group consisting of:
LATS-IN-1 (TRULI; N-(3-benzylthiazol-2(3H)-ylidene)-1H-pyrrolo[2,3-b]pyridine-3-carboxamide); GA-017; and TDI-011536.

13. The method of any one of the preceding paragraphs, wherein the medium does not comprise, or the at least one AT2 cell and/or lung epithelial progenitor cell is not in contact with, CHIR99021 and/or keratinocyte growth factor (KGF) protein.

14. The method of any one of the preceding paragraphs, wherein the medium does not comprise, or the at least one AT2 cell and/or lung epithelial progenitor cell is not in contact with, ectopic epidermal growth factor (EGF) protein and/or ectopic fibroblast growth factor 10 (FGF10) protein.

15. The method of any one of the preceding paragraphs, wherein the medium further comprises, or the at least one AT2 cell and/or lung epithelial progenitor cell is further contacted with, ectopic epidermal growth factor (EGF) protein and/or ectopic fibroblast growth factor 10 (FGF10) protein.

16. The method of any one of the preceding paragraphs, whereby the maintaining at least one AT2 cell and/or lung epithelial progenitor cell in a medium comprising a LATS inhibitor induces YAP signaling.

17. The method of any one of the preceding paragraphs, wherein the at least one AT2 cell is a human AT2 cell.

18. The method of any one of the preceding paragraphs, wherein the at least one AT2 cell is a primary AT2 cell.

19. The method of any one of the preceding paragraphs, wherein the at least one AT2 cell is an induced AT2 cell.

20. The method of any one of the preceding paragraphs, wherein the at least one lung epithelial progenitor cell is a human lung epithelial progenitor cell.

21. The method of any one of the preceding paragraphs, wherein the lung epithelial progenitor cell is a primary lung epithelial progenitor cell.

22. The method of any one of the preceding paragraphs, wherein the lung epithelial progenitor cell is an induced lung epithelial progenitor cell.

23. The method of any one of the preceding paragraphs, further comprising contacting the at least one AT2 cell and/or lung epithelial progenitor cell, or a cell produced by the method, with a nucleic acid encoding a reporter protein.

24. The method of any one of the preceding paragraphs, further comprising contacting an AT1 cell produced by the method with a virus.

25. The method of any one of the preceding paragraphs, further comprising contacting an AT1 cell produced by the method with smoke.

26. The method of any one of the preceding paragraphs, further comprising contacting an AT1 cell produced by the method with Transforming Growth Factor Beta (TGFβ) and/or bleomycin.

27. The method of any one of the preceding paragraphs, wherein the at least one AT2 cell and/or lung epithelial progenitor cell comprises a PF inducing mutation.

28. An AT1 cell made by the method of any one of the preceding paragraphs.

29. The AT1 cell of paragraph 28, comprising lower expression of PDPN relative to a primary AT1 cell.

30. A method of treating a lung disease in a subject in need thereof, the method comprising administering to the subject an AT1 cell produced according to the method of any of paragraphs 1-27.

31. The method of paragraph 30, wherein the lung disease is selected from the group consisting of:
acute respiratory distress syndrome (ARDS), pulmonary fibrosis, interstitial lung diseases, acute inhalational lung injuries, childhood interstitial lung diseases, and bronchopulmonary dysplasia.

32. The method of any of paragraphs 30-31, wherein the AT1 cell is derived from a cell obtained from the subject.

33. The method of any of paragraphs 30-31, wherein the at least one AT2 cell and/or lung epithelial progenitor cell was genetically modified to correct a mutation that contributed to the lung disease.

34. A method of identifying a treatment as effective in treating lung disease, the method comprising:
contacting an AT1 produced according to the method of any of paragraphs 1-27 with a candidate treatment agent;
identifying the candidate treatment agent as effective if one or more of the following phenotypes is observed in the AT1 cell contacted with the candidate treatment agent as compared to an AT1 cell not contacted with the candidate treatment agent:
increased cell survival;
increased cell survival in the presence of cellular stressors;
decreased release of toxic agents;
improved cellular pathology arising from a genetic mutation in the AT1 cell;
increased AT1 cell differentiation;
decreased AT1 cell proliferation in the presence of carcinogens; and/or
increased secretion of cytoprotective agents.

35. The method of paragraph 34, wherein the AT1 cell is derived from a cell obtained from an individual subject and the treatment is identified as an effective treatment for that individual subject.

36. An AT1 cell produced according to the method of any of paragraphs 1-27, for administration to the subject in need of treatment for a lung disease.

37. The cell of paragraph 36, wherein the lung disease is selected from the group consisting of:
acute respiratory distress syndrome (ARDS), pulmonary fibrosis, interstitial lung diseases, acute inhalational lung injuries, childhood interstitial lung diseases, and bronchopulmonary dysplasia 38. The cell of any of paragraphs 36-37, wherein the AT1 cell is derived from a cell obtained from the subject.

39. The cell of any of paragraphs 36-38, wherein the at least one AT2 cell and/or lung epithelial progenitor cell was genetically modified to correct a mutation that contributed to the lung disease.

In some embodiments, the present technology may be defined in any of the following numbered paragraphs:

1. A method comprising at least one of:
   a) inducing ectopic Yes Associated Protein (YAP) expression in at least one AT2 cell and/or lung epithelial progenitor cell; and
   b) maintaining at least one AT2 cell and/or lung epithelial progenitor cell in a medium comprising a Large Tumor Suppressor Kinase (LATS) inhibitor.
2. The method of paragraph 1, wherein the YAP comprises:
   mutation of the serine of at least one HXRXXS consensus sequence;
   mutation of the serine of at least one HXRXXS consensus sequence to alanine;
   mutation of the serine of every HXRXXS consensus sequence;
   mutation of the serine of every HXRXXS consensus sequence to alanine;
   mutation of each serine corresponding to S61, S109, S127, S164, and S397 of SEQ ID NO: 1; or
   mutation of each serine corresponding to S61, S109, S127, S164, and S397 of SEQ ID NO: 1 to alanine.
3. The method of paragraph 1, wherein inducing comprises contacting the at least one AT2 cell and/or lung epithelial progenitor cell with an expression vector encoding a YAP protein.
4. The method of paragraph 1, wherein the medium is a complete serum free defined medium.
5. The method of paragraph 1, wherein the LATS inhibitor is selected from the group consisting of:
   LATS-IN-1 (TRULI; N-(3-benzylthiazol-2(3H)-ylidene)-1H-pyrrolo[2,3-b]pyridine-3-carboxamide); GA-017; and TDI-011536.
6. The method of paragraph 1, wherein the medium does not comprise, or the at least one AT2 cell and/or lung epithelial progenitor cell is not in contact with, CHIR99021 and/or keratinocyte growth factor (KGF) protein.
7. The method of paragraph 1, wherein the medium does not comprise, or the at least one AT2 cell and/or lung epithelial progenitor cell is not in contact with, ectopic epidermal growth factor (EGF) protein and/or ectopic fibroblast growth factor 10 (FGF10) protein.
8. The method of paragraph 1, wherein the medium further comprises, or the at least one AT2 cell and/or lung epithelial progenitor cell is further contacted with, ectopic epidermal growth factor (EGF) protein and/or ectopic fibroblast growth factor 10 (FGF10) protein.
9. The method of paragraph 1, whereby the maintaining at least one AT2 cell and/or lung epithelial progenitor cell in a medium comprising a LATS inhibitor induces YAP signaling.
10. The method of paragraph 1, wherein the at least one AT2 cell is a human AT2 cell, a primary AT2 cell, or an induced AT2 cell; and/or
    the at least one lung epithelial progenitor cell is a human lung epithelial progenitor cell; a primary lung epithelial progenitor cell; or an induced lung epithelial progenitor cell.
11. The method of paragraph 1, further comprising contacting the at least one AT2 cell and/or lung epithelial progenitor cell, or a cell produced by the method, with:
    a nucleic acid encoding a reporter protein;
    a virus;
    smoke; and/or
    Transforming Growth Factor Beta (TGFβ) and/or bleomycin.
12. The method of paragraph 1, wherein the at least one AT2 cell and/or lung epithelial progenitor cell comprises a PF inducing mutation.
13. An AT1 cell made by the method of paragraph 1.
14. The AT1 cell of paragraph 13, comprising lower expression of PDPN relative to a primary AT1 cell.
15. A method of treating a lung disease in a subject in need thereof, the method comprising administering to the subject an AT1 cell produced according to the method of paragraph 1.
16. The method of paragraph 15, wherein the lung disease is selected from the group consisting of:
    acute respiratory distress syndrome (ARDS), pulmonary fibrosis, interstitial lung diseases, acute inhalational lung injuries, childhood interstitial lung diseases, and bronchopulmonary dysplasia.
17. The method of any of paragraph 15, wherein the AT1 cell is derived from a cell obtained from the subject.
18. The method of any of paragraph 15, wherein the at least one AT2 cell and/or lung epithelial progenitor cell was genetically modified to correct a mutation that contributed to the lung disease.
19. A method of identifying a treatment as effective in treating lung disease, the method comprising:
    contacting an AT1 produced according to the method of paragraph 1 with a candidate treatment agent;
    identifying the candidate treatment agent as effective if one or more of the following phenotypes is observed in the AT1 cell contacted with the candidate treatment agent as compared to an AT1 cell not contacted with the candidate treatment agent:
    increased cell survival;
    increased cell survival in the presence of cellular stressors;
    decreased release of toxic agents;
    improved cellular pathology arising from a genetic mutation in the AT1 cell;
    increased AT1 cell differentiation;
    decreased AT1 cell proliferation in the presence of carcinogens; and/or
    increased secretion of cytoprotective agents.
20. The method of paragraph 19, wherein the AT1 cell is derived from a cell obtained from an individual subject and the treatment is identified as an effective treatment for that individual subject.

The technology described herein is further illustrated by the following examples which in no way should be construed as being further limiting.

EXAMPLES

Example 1

In the distal lung, alveolar epithelial type I cells (AT1s) are uniquely flattened to allow for the diffusion of oxygen into the capillaries. This structure has made them particularly challenging to study and isolate. As a result, there is a lack of established models for the study of human AT1 biology, and in contrast to alveolar type II cells (AT2s), little is known about the mechanisms regulating their differentiation. We sought to engineer a human in vitro model of AT1s through the directed differentiation of induced pluripotent stem cells (iPSC). Described herein are two systems to drive AT1 differentiation in human iPSC-derived iAT2s.

1) Lentiviral overexpression of nuclear YAP (YAP5SA) in iAT2s results in loss of AT2 program and gain of AT1 program only in cells transduced with the lentivirus, iAT2s growing in the same well but not transduced maintain iAT2 fate.
2) Complete, serum free defined media containing a LATS inhibitor (LATS-IN-1) thus avoiding the need for forced lentiviral-based over-expression to activate YAP signaling drives AT1 program in up to 97% of iAT2s.

iAT1 cells can be cultured in 3D matrigel or in 2D, submerged or at Air Liquid Interface.

This model permits better understanding of human AT1 biology. This can serve as a model for alveolar epithelial injury, including viral infection and smoke exposure. Other diseases such as Idiopathic Pulmonary Fibrosis are associated with aberrant differentiation of AT2 to AT1 cells which could be studied using this system.

Example 2

In one embodiment of the invention, lentiviral overexpression of nuclear YAP (YAP5SA) in iAT2 cells is employed to drive gain of AT1 program, resulting in AT1 cells.

In a second embodiment of the invention, a complete, serum free defined media containing a LATS inhibitor (for example, LATS-IN-1) is used to activate YAP signaling to create AT1 cells from both iPSC-derived iAT2s and cultured primary AT2 cells. In a further specific example of the invention, the media defined in FIGS. 5A-L is used.

Additionally, AT1 cells of the invention, which may optionally contain a fluorescent reporter, are utilized in 2D or 3D models of alveolar epithelial injury, including viral infection and smoke exposure as well as other diseases such as Idiopathic Pulmonary Fibrosis which are associated with aberrant differentiation of AT2 to AT1 cells.

In the distal lung, alveolar epithelial type I cells (AT1s) are uniquely flattened to allow for the diffusion of oxygen into the capillaries. This structure along with a quiescent, terminally differentiated phenotype has made AT1s particularly challenging to isolate or maintain in cell culture. As a result, there is a lack of established models for the study of human AT1 biology, and in contrast to alveolar type II cells (AT2s), little is known about the mechanisms regulating their differentiation. Here we engineer a human in vitro model of AT1s through the directed differentiation of induced pluripotent stem cells (iPSC). We first define the global transcriptomes of primary adult human AT1s, suggesting gene-set benchmarks and pathways, such as Hippo-LATS-YAP/TAZ signaling, that are enriched in these cells. Next, we differentiate iPSCs into AT2-like cells (iAT2s) and drive activated nuclear YAP signaling via lentiviral forced over-expression of a YAP5SA cassette, resulting in a broad transcriptomic shift from AT2 to AT1 gene programs.

To enable tracking and purification of these putative iPSC-derived AT1s (iAT1s), we use gene editing to generate a bifluorescent AT1 reporter iPSC line containing GFP and tdTomato fluorochromes targeted to the endogenous human NKX2-1 and AGER loci, respectively. We then employ this reporter line to develop a defined serum-free iAT1 differentiation medium containing a LATS inhibitor able to robustly recapitulate the differentiation of iAT2s into iAT1s with 97% efficiency, without requiring any lentiviral transduction. The resulting iAT1s express a molecular, morphologic, and functional phenotype reminiscent of human AT1 cells, including the capacity to form a flat epithelial barrier which produces characteristic extracellular matrix molecules and secreted ligands. Our results demonstrate a role for Hippo-LATS-YAP signaling in the differentiation of human AT1s and accomplishes the generation of viable AT1-like cells from iPSC-derived AT2 cells, providing an in vitro model of human alveolar epithelial differentiation and a potential source of human cells that until now have been challenging to viably obtain from patients.

The alveolar epithelium of the lung is vital for gas exchange and consists of two cell types. Alveolar epithelial type II cells (AT2s) are cuboidal and produce surfactant while the type I cells (AT1s) are uniquely flattened in order to allow for the diffusion of oxygen into the capillaries. AT1s make up 40% of the alveolar epithelial cell population but cover over 95% of the alveolar surface area. Despite their critical role comprising the vast majority of the lung's alveolar surface area, in contrast to AT2s relatively little is known about the cell biology, origins, and fates of human AT1s due in part to difficulties accessing and culturing this key cell type located deep within distal lung tissue.

The expansive and fragile structure of AT1s has made them particularly challenging to study. A single AT1 can cover the surface of one alveolus or penetrate pores of Kohn, crossing the alveolar septum to cover the luminal surfaces of two adjacent alveoli, making it difficult to identify individual AT1s with a single 2D cross-section.$_{1,2}$ Likewise, AT1s are easily shredded by methods such as cell sorting, leading to difficulties in isolating fresh primary AT1s for cell culture. Their putative terminally differentiated nature has limited efforts to maintain these cells in vitro with only a few prior reports suggesting successful expansion in culture as proliferating cells.$_{3,4}$ Current human models utilizing 2D plating and/or serum-containing media to produce "AT1-like" cells have not been fully validated for more than a few typical AT1 markers leaving in doubt the signaling mechanisms involved in their differentiation or maintenance.$_{5,6}$ AT1s are generally assumed to be replenished by adjacent cuboidal AT2s, based on a broad literature beginning in the 1970's that employed rodent models of lung injury to characterize the transition of AT2 progenitor cells into AT1 progeny in vivo[7,8] or after culturing in vitro.$_{9-12}$ The origin of AT1 cells in adult humans, however, has been less clear and more difficult to study. A variety of reports involving the in vitro 2D culture of isolated primary fetal or adult human AT2s have documented the rapid downregulation of AT2 marker transcripts and proteins, coincident with a flattened morphology. and upregulation of some "AT1 markers" of unclear specificity, leading to the currently accepted paradigm that AT1s are a "default state" of AT2s, if cultured in undefined (e.g. serum containing) conditions.$_{6,13-15}$ This default state has been called into question by more recent 3D culture models which observed little if any evidence of bona fide AT1 cells emerging from either primary human AT2 cells co-cultured with or without fibroblasts or from human induced pluripotent stem cell (iPSC)-derived AT2s (iAT2s), even after prolonged time in most culture conditions tested to date.[16-18] with three notable exceptions.[5,18-21]

The developmental origins of AT1 cells have also been challenging to discern.[22,23] Developmentally in both mice and humans, the lung epithelium derives from anterior foregut endoderm, from which NKX2-1+ primordial lung progenitor cells are specified at embryonic development day (E) 9.0 in mice or around 1 month of gestation in humans.[24-28] Lineage tracing in mice has shown that AT1s develop from these NKX2-1+ lung epithelial progenitor cells after proximal/distal airway patterning.[29] While some studies have suggested the existence of a bipotent progenitor cell as late as E18.5 that differentiates into both AT1 and alveolar epithelial type II cells (AT2s).[22,30] other studies have shown that specification between the two cell types happens much earlier, suggesting a distinct AT1 progenitor cell.[23] Several signaling pathways have been implicated as regulating murine AT1 development, such as Wnt and KGF as well as mechanotransduction through YAP/TAZ signaling.[6,15,31-34]

In adult lungs, lineage tracing in mice has shown that AT1s can be derived from mature AT2s after injury and during normal homeostasis.[22,35,36] In most models. AT2s divide symmetrically with one daughter cell then transdifferentiating directly into an AT1[7,22,36]; however, a recent report demonstrates this transition need not require cell division of the AT2 parent.[37] The exact signaling mechanisms driving AT1 differentiation in adults are still uncertain, although recent studies have implicated a wide variety of classical pathways such as Wnt, BMP, TGFb, FGF, and YAP/TAZ signaling.[31,38-44] Additionally, studies have shown that nuclear YAP/TAZ localization is necessary for the maintenance of the AT1 program, and that loss of YAP/TAZ in mature AT1 cells leads to reversion back into an AT2-like cell fate.[45,46]

Determining the origins of human AT1 cells during development, homeostasis, and after lung injury is particularly important since damage to AT1s in response to toxic inhalational exposures, radiation, or a variety of infections can lead to respiratory failure and severe diseases such as the Acute Respiratory Distress Syndrome (ARDS).[47] Impaired differentiation of AT1 cells has also recently been implicated in fibrotic lung diseases.[10,11,48,49] Hence, understanding normal differentiation of human AT1s could provide insights for resolving the aberrant transitional state found in fibrotic lung tissue. The engineering of laboratory mice carrying fluorochrome reporters or lineage tracing cassettes under the regulatory control of AT1 gene promoters has been invaluable in identifying, tracing, and isolating mouse AT1 cells during development and disease;$_{3,50,51}$ however, to date no comparable engineered human reporter has yet been generated to facilitate the study of human AT1s.

Here we report the in vitro generation of cells expressing the molecular and functional phenotypes of human AT1 cells via differentiation of iPSC derived AT2 (iAT2) cells. We first profile human lung explant tissues at single cell resolution to identify potential AT1-selective marker gene sets and AT1-enriched signaling pathways. We engineer an iPSC line carrying a tdTomato reporter targeted to the endogenous AGER locus, which is specifically upregulated in primary AT1s according to our gene set. The AGERtdTomatoreporter enables real time tracking and quantitation, of the resulting putative iPSC derived AT1s (iAT1s), facilitating the isolation of a pure population of cells. We find activated nuclear YAP expression is sufficient to drive the transcriptomic shift from iAT2 to iAT1 programs in a cell-autonomous manner in multiple iPSC lines. Further, we have developed a defined, serum-free differentiation medium containing a LATS inhibitor that recapitulates the above process, leading to robust and efficient differentiation of iAT2s into iAT1s.

Results

Figure 8A:
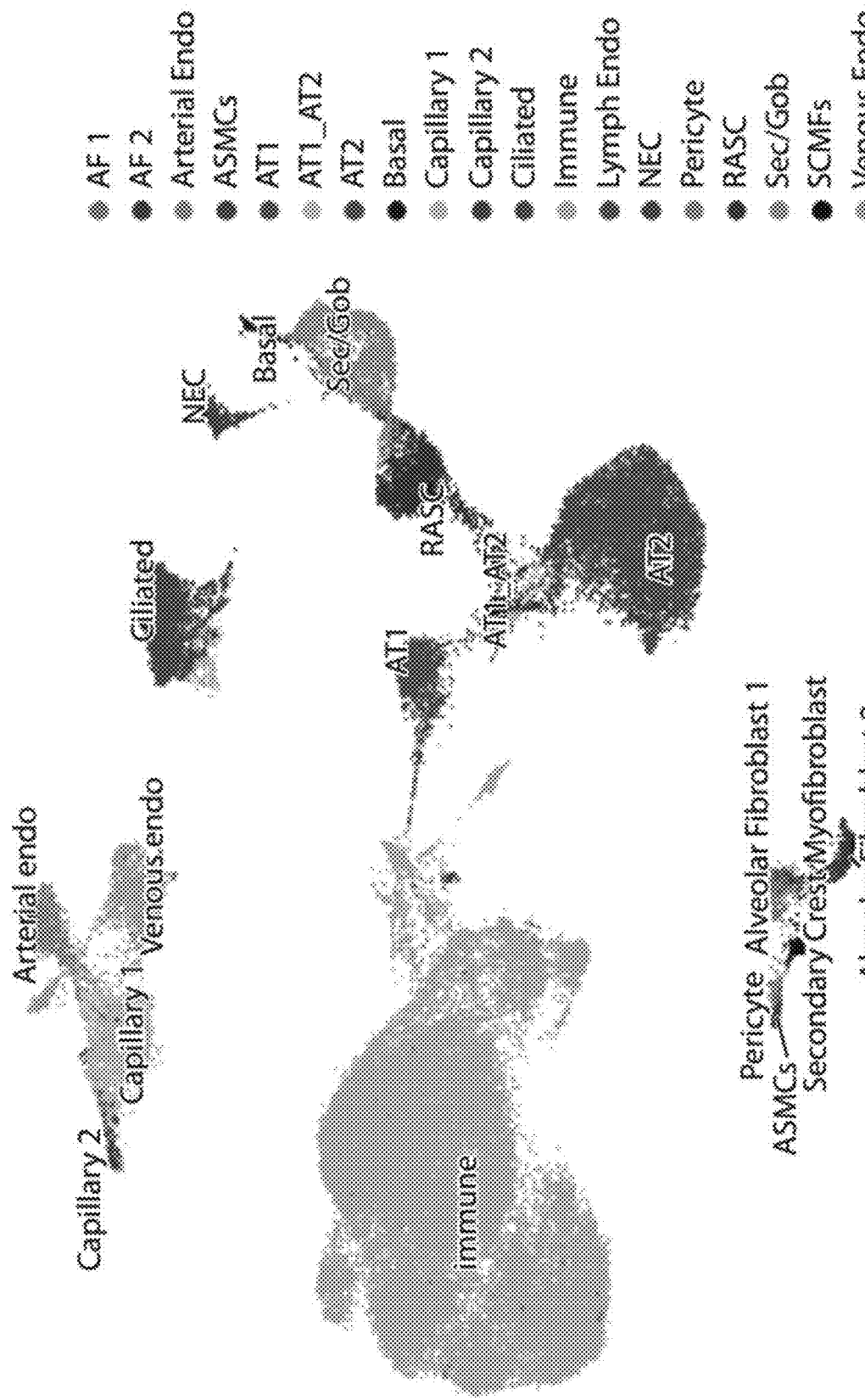
FIGS. 8A-8S depict human AT1 marker gene expression across all cell types in the lung.
Figure 8B:
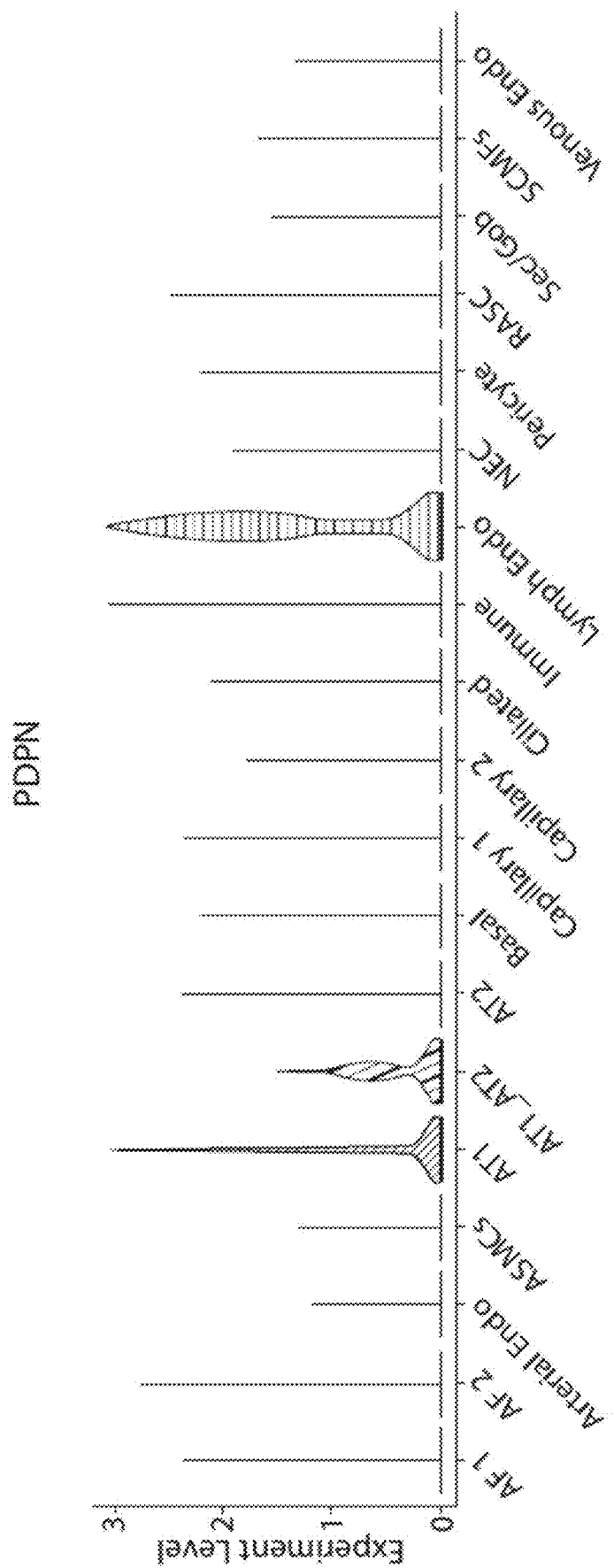
Figure 8C:
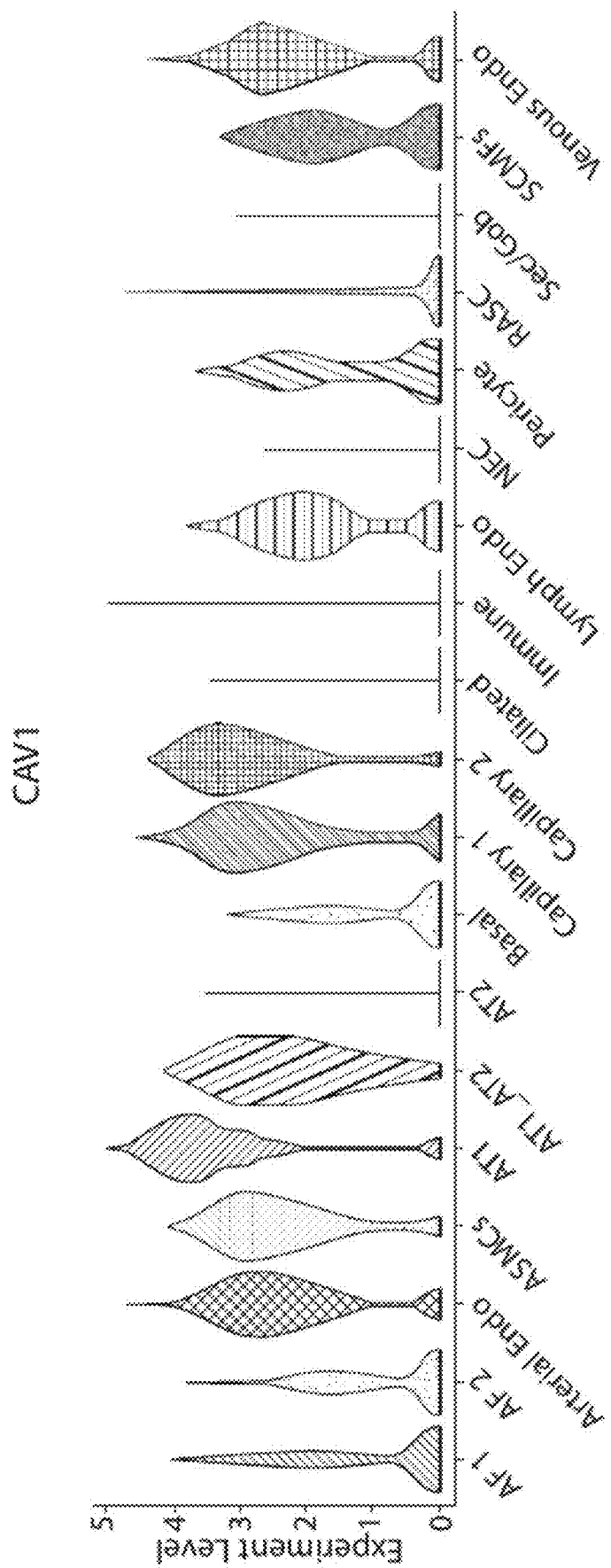
Figure 8D:
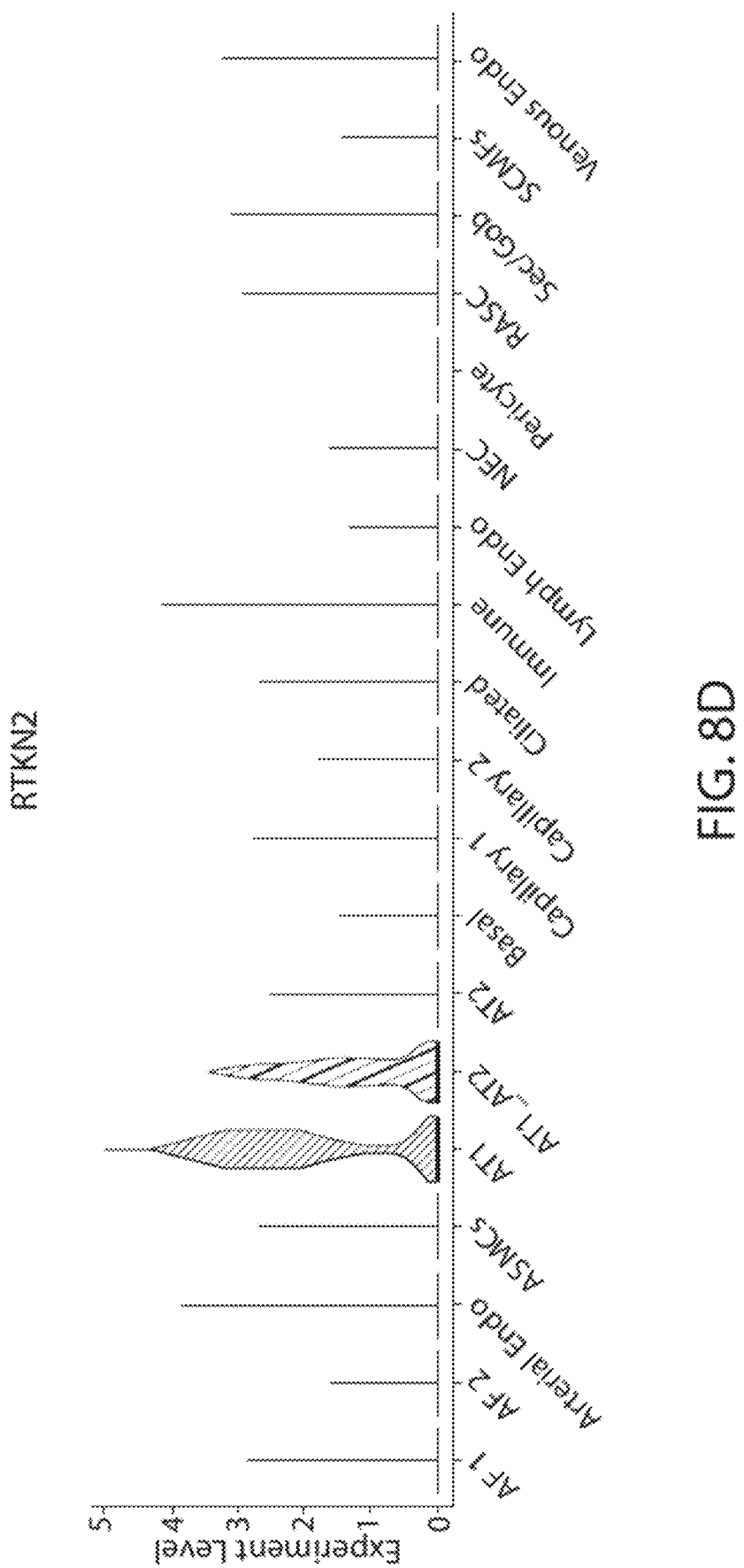
Figure 8E:
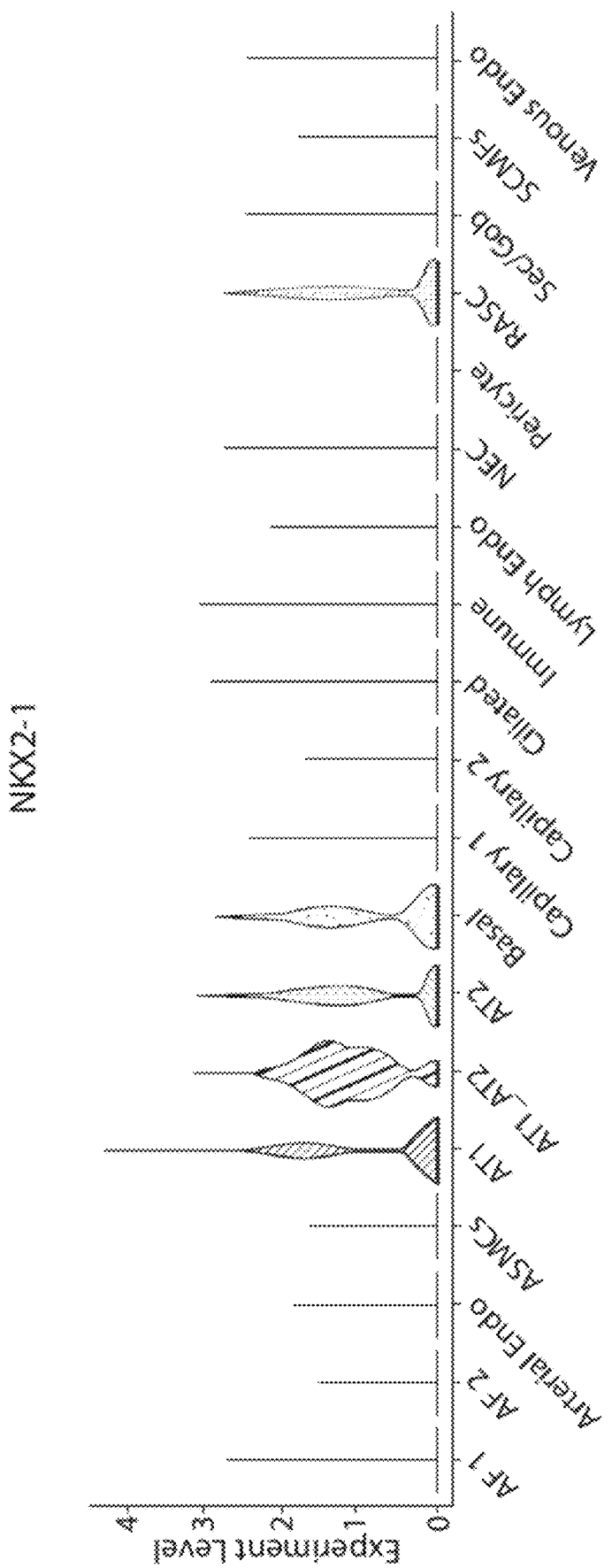
Figure 8F:
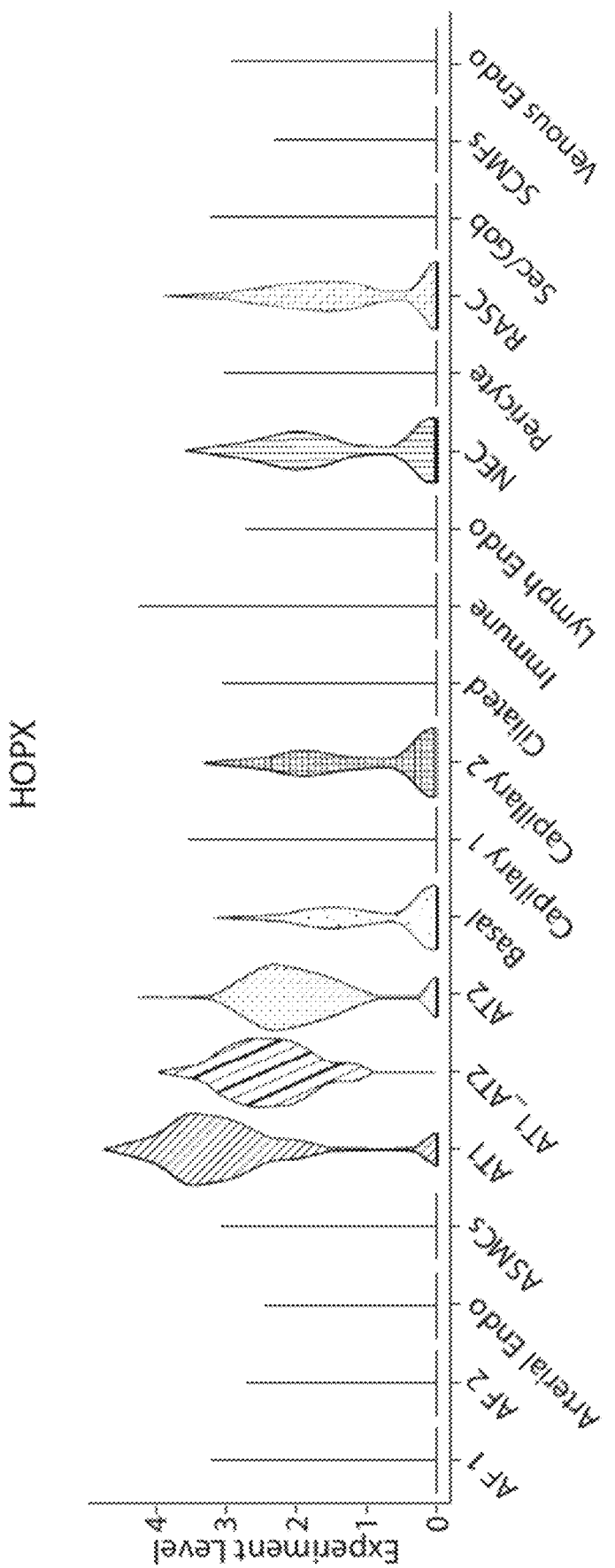
Figure 8G:
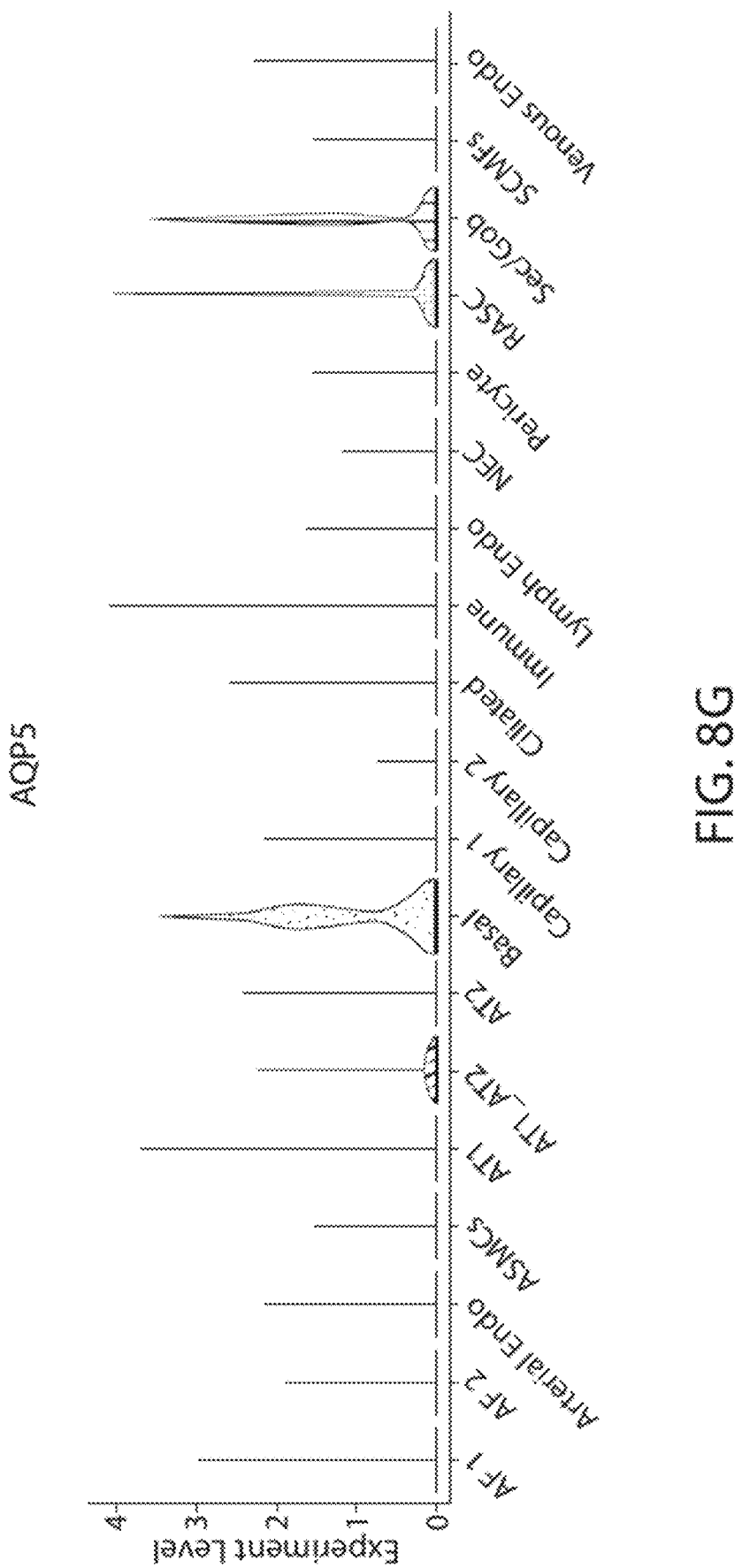
Figure 8H:
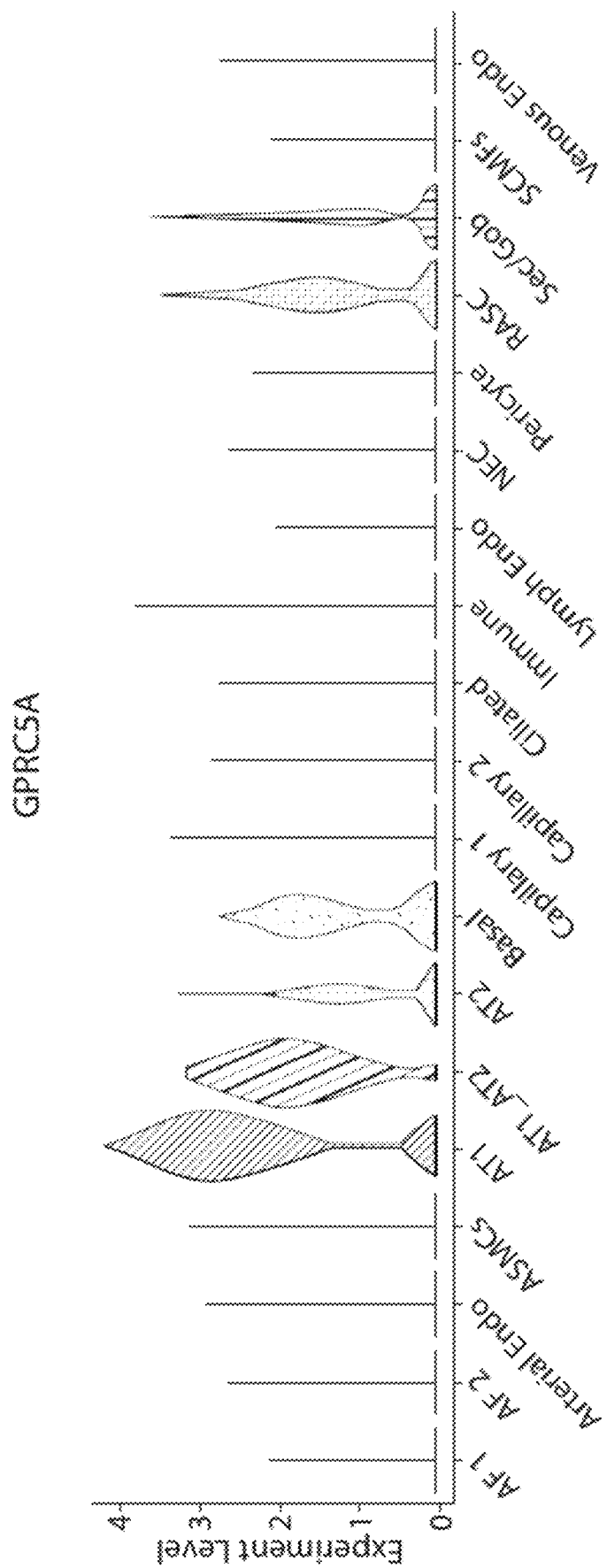
Figure 8I:
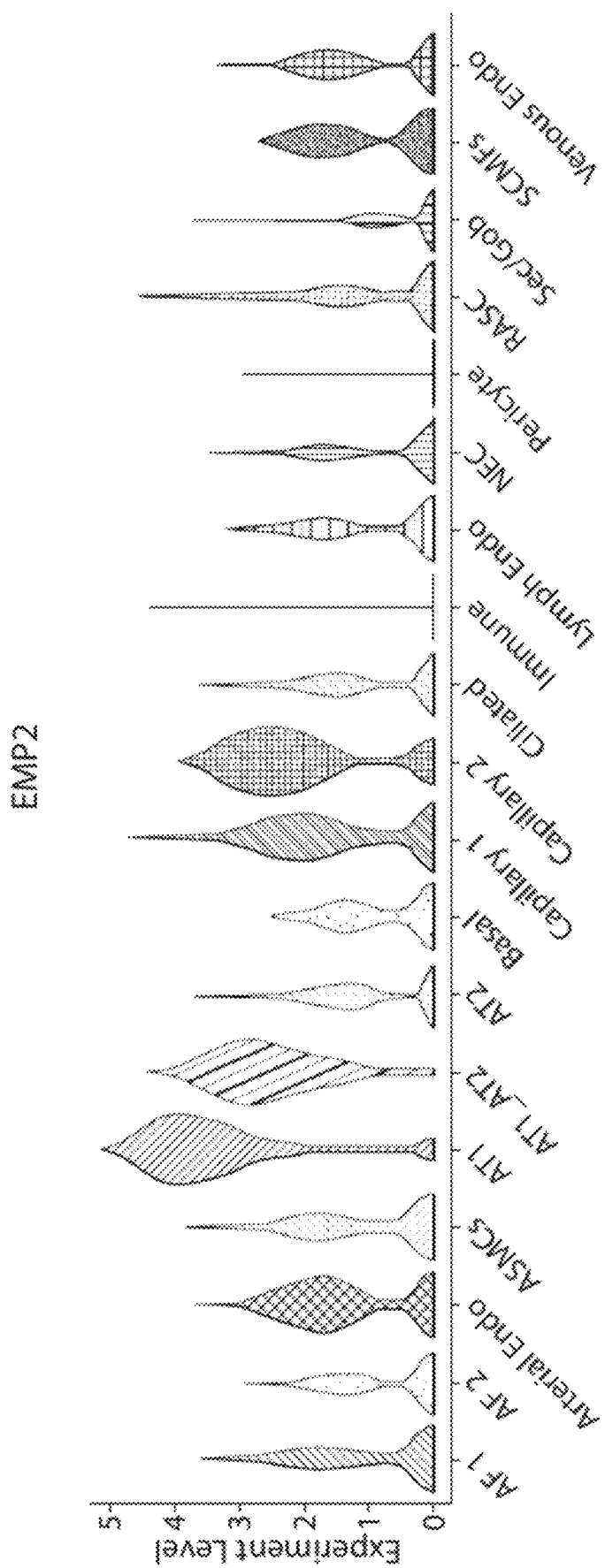
Figure 8J:
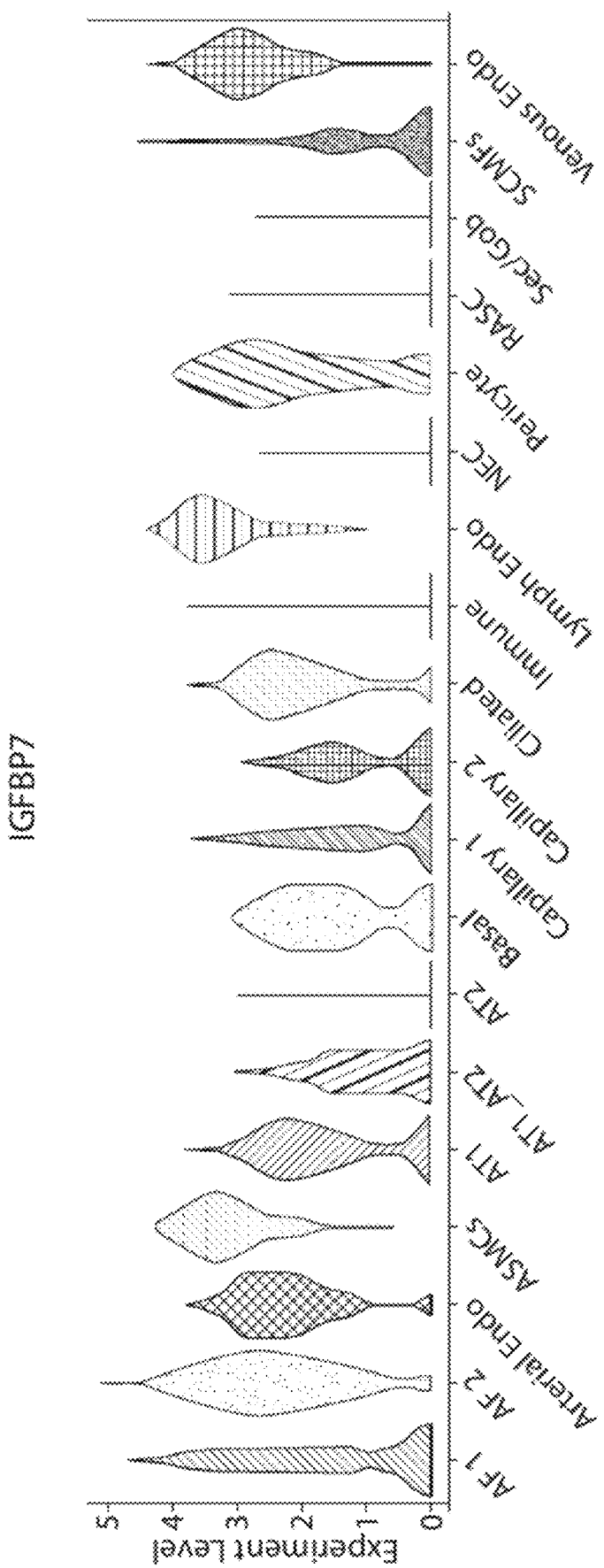
Figure 8K:
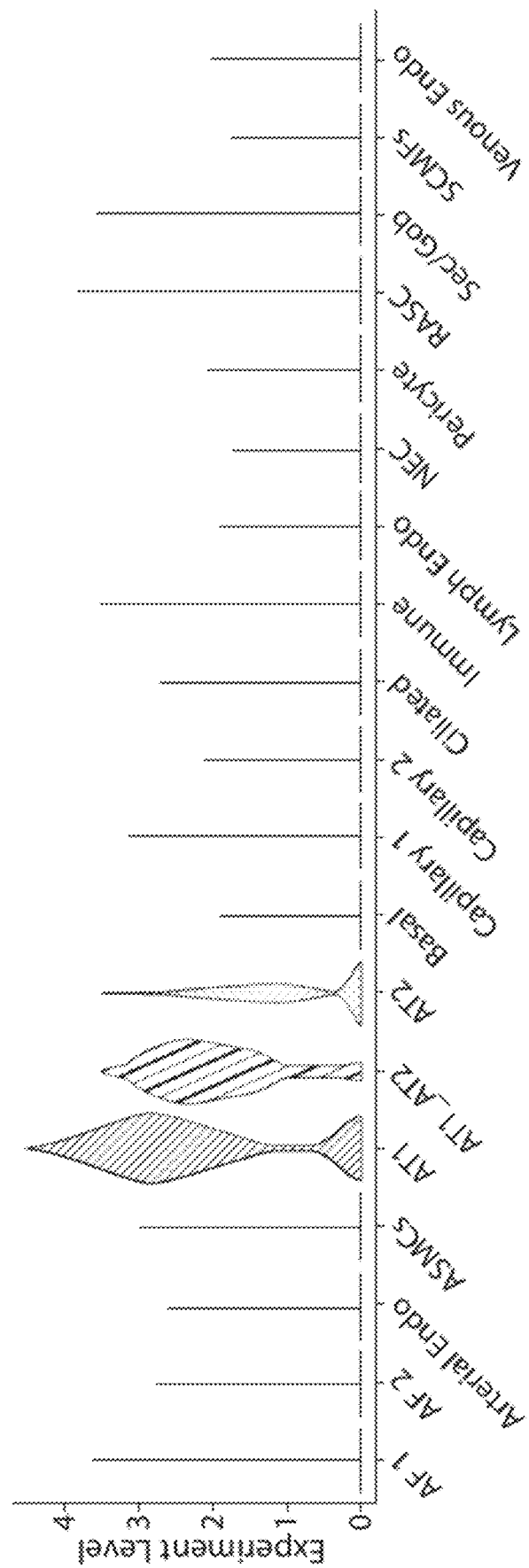
Figure 8L:
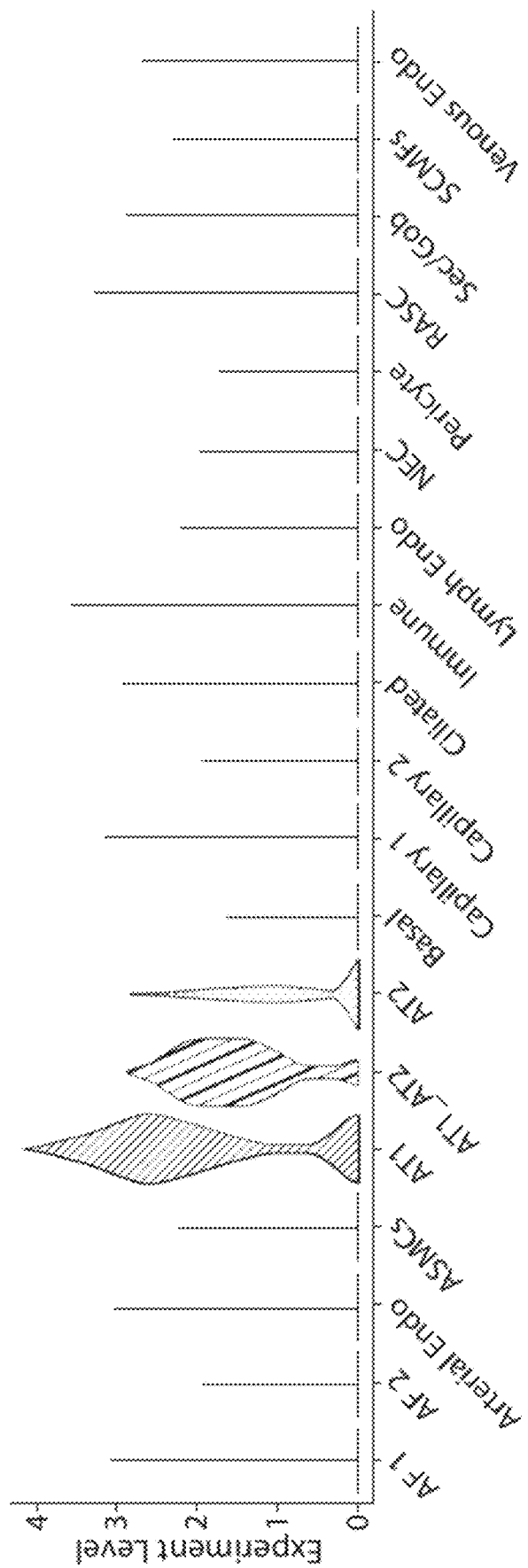
Figure 8M:
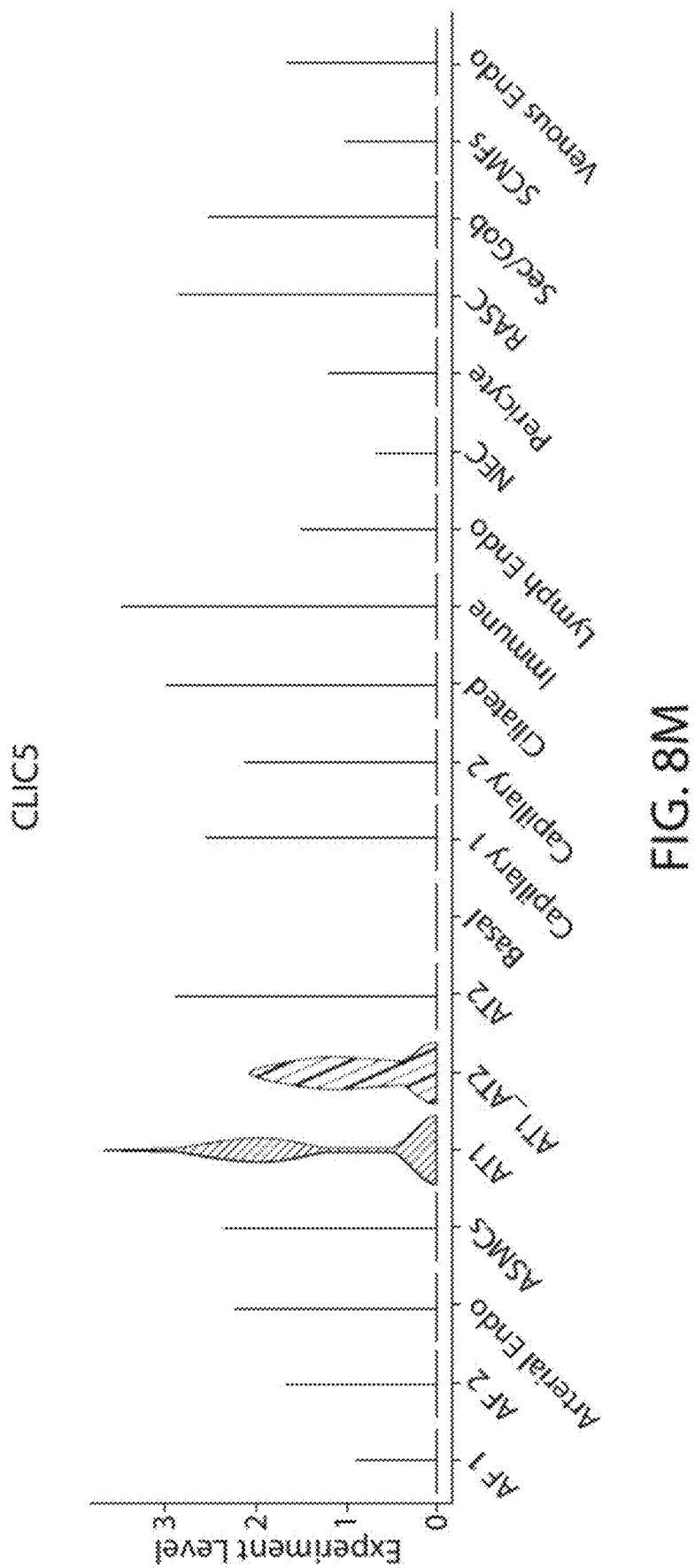
Figure 8N:
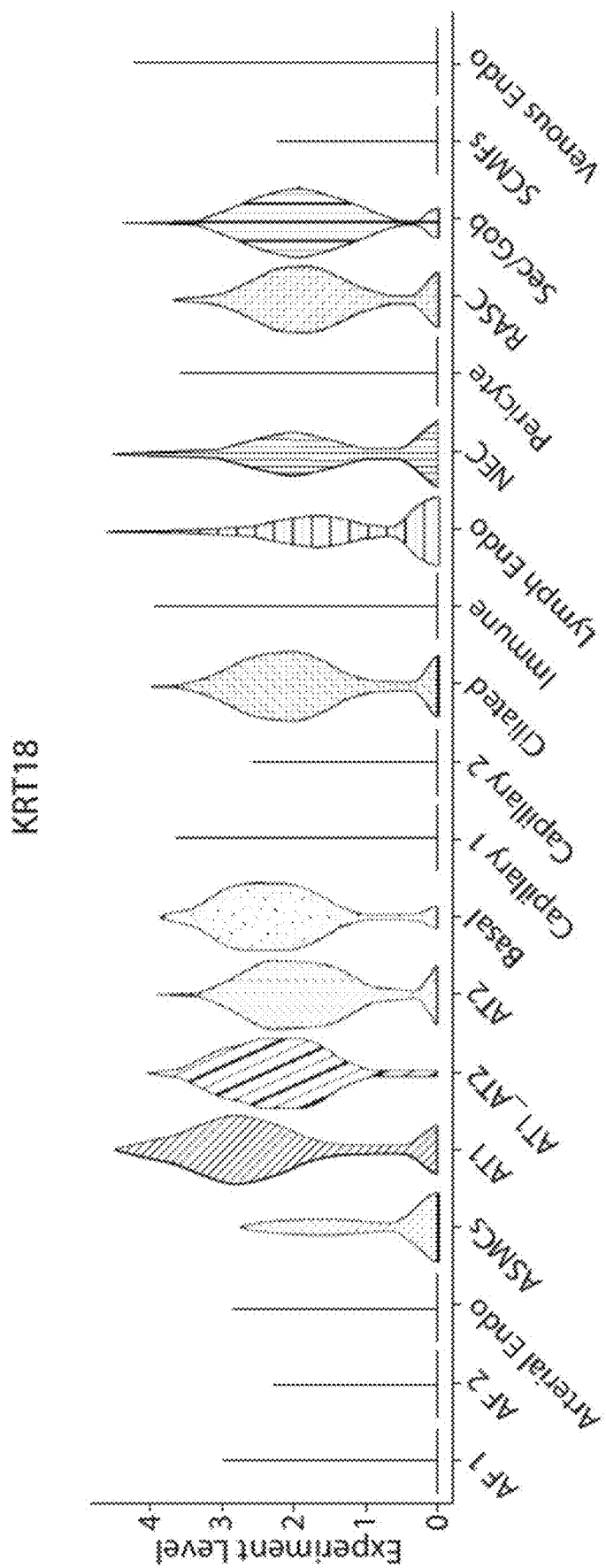
Figure 80:
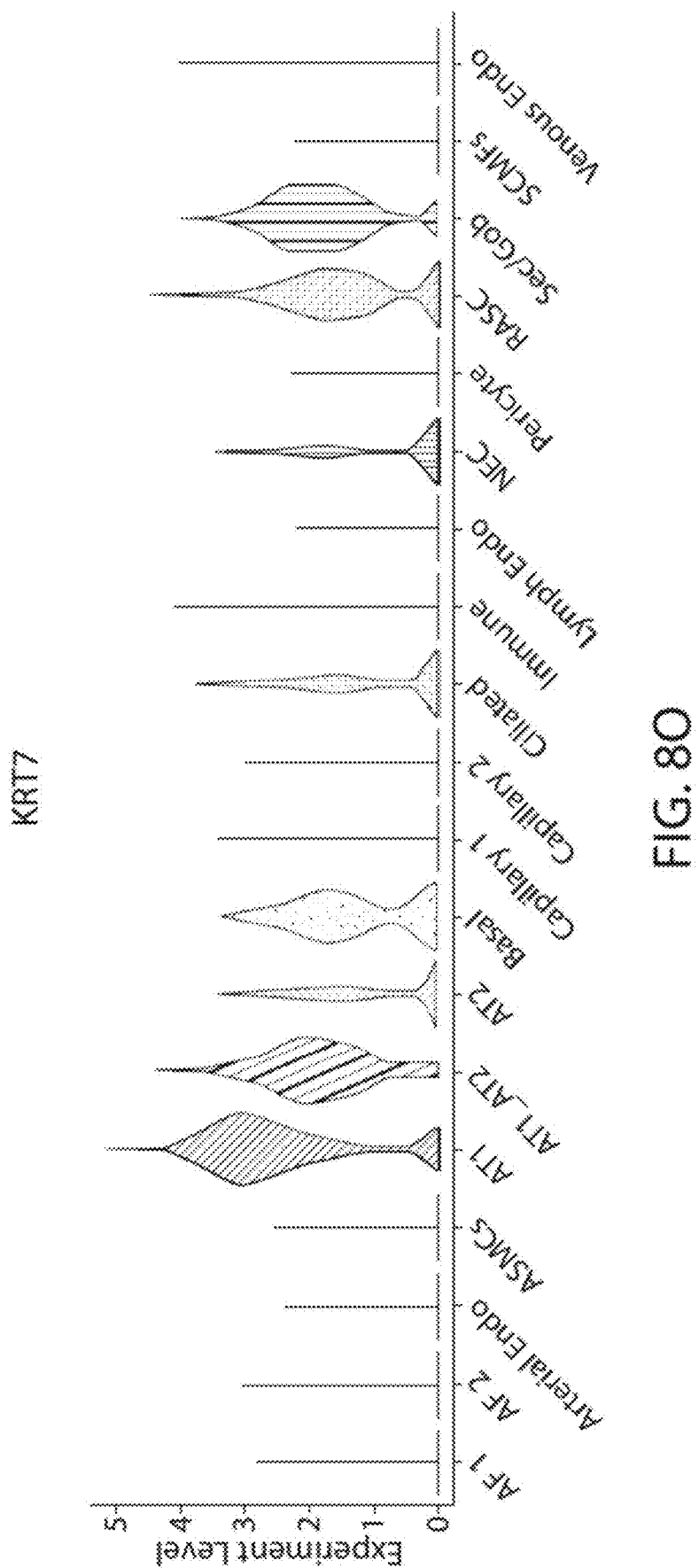
Figure 8P:
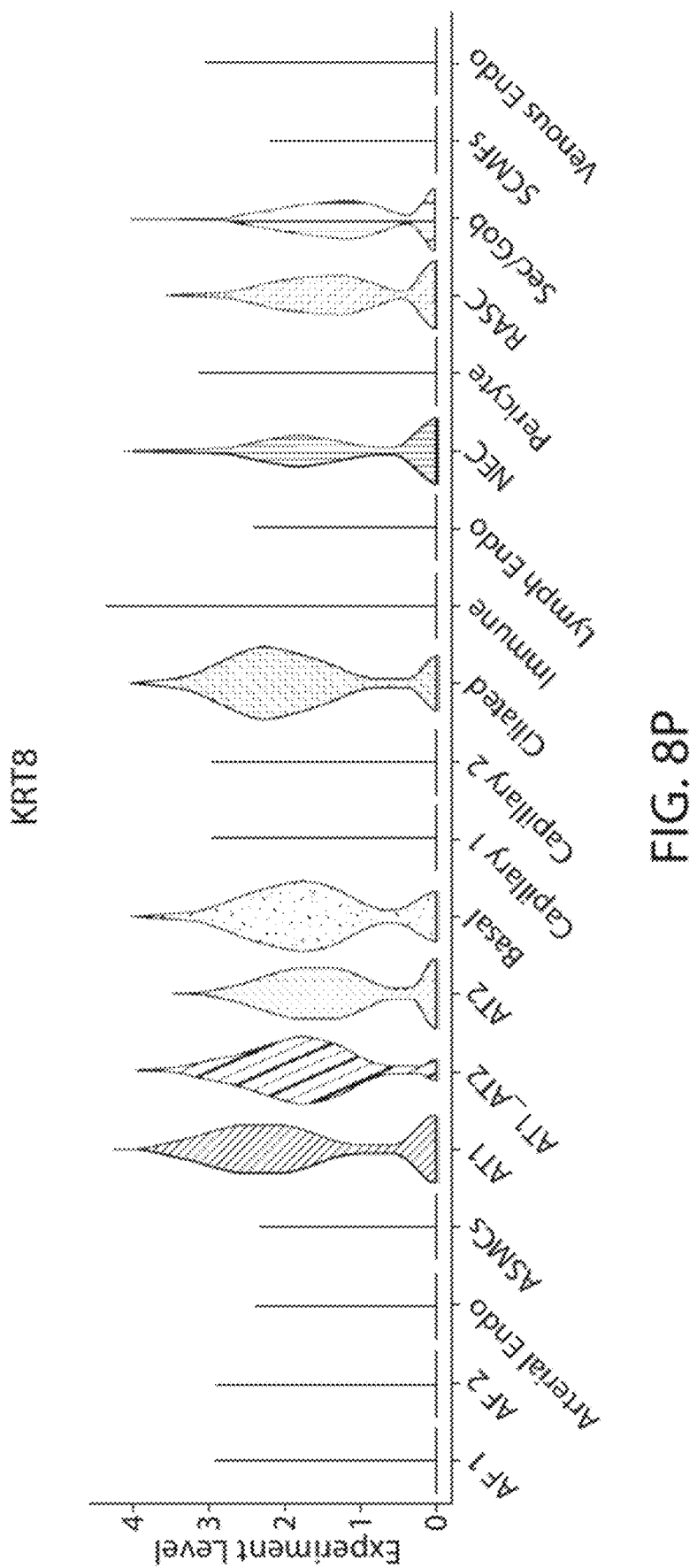
Figure 8Q:
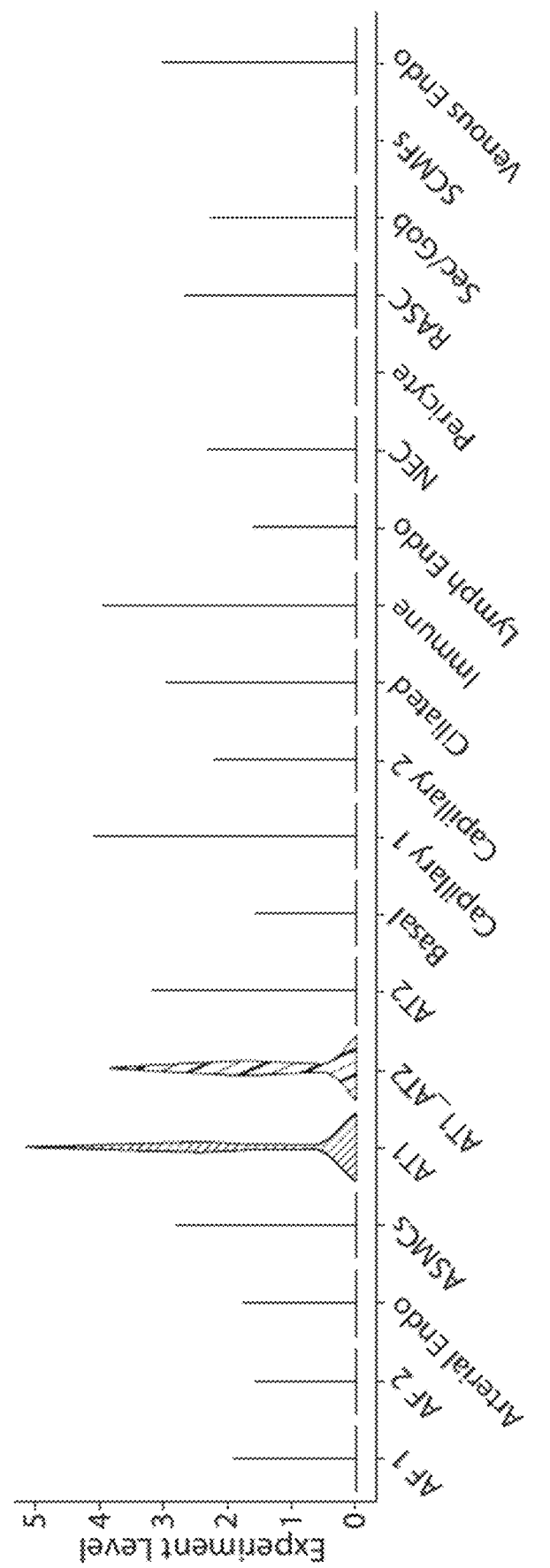
Figure 8R:
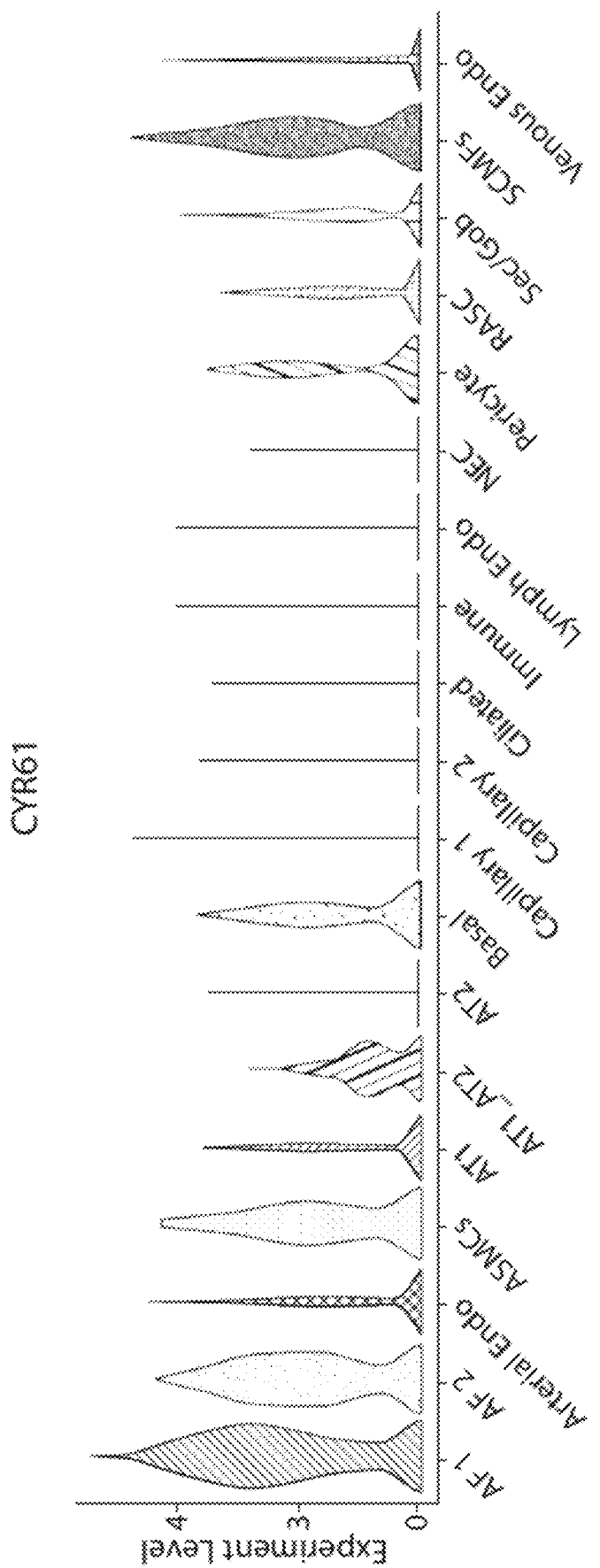
Figure 8S:
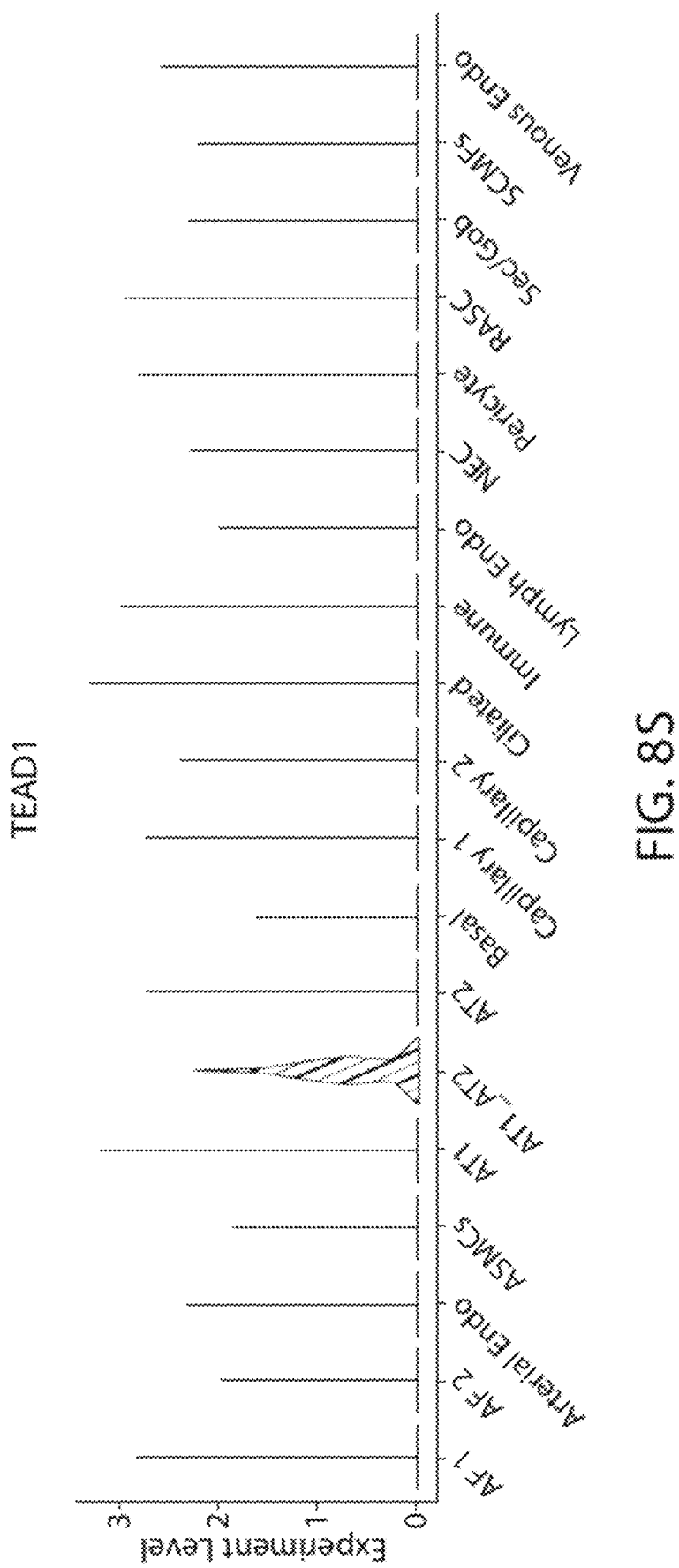

Single Cell RNA Sequencing Defines the Transcriptomic Program of Primary Human Alveolar Epithelial Type I Cells To understand the transcriptomic programs of human AT1s, we performed profiling by single cell RNA sequencing (scRNA-seq) of 5 distal human lung explant tissues (partial dataset published previously in Basil et al, Nature 2022),$_{52}$. After visualization of all pooled analyses, we identified 19 distinct epithelial, mesenchymal, and immune cell clusters, including 1401 AT1 cells, and annotated each cluster according to canonical lineage markers detailed previously for this dataset (FIG. 8A).$_{52}$ Selecting and reclustering all epithelial cells (UMAP; FIG. 1A), we visualized expression of previously reported putative AT1 markers (PDPN, CAV1, AGER, AQP5, and HOPX) and canonical AT2 (SFTPC, LAMP3, ABCA3) marker genes through overlayed UMAPs (FIG. 1B). We found some human AT1 markers (AGER, CAV1, PDPN, and RTKN2) shared similar qualitative clustered expression patterns to published mouse scRNA-seq atlases;$_{30,53}$ however, HOPX and AQP5, which have been well characterized as mouse AT1-specific markers.$_{3,9}$ lacked specificity as they were also expressed in other epithelial cells, such as AT2s for HOPX and airway cells for AQP5. (FIGS. 1B-1D, 8B-8S).

Figure 1C:
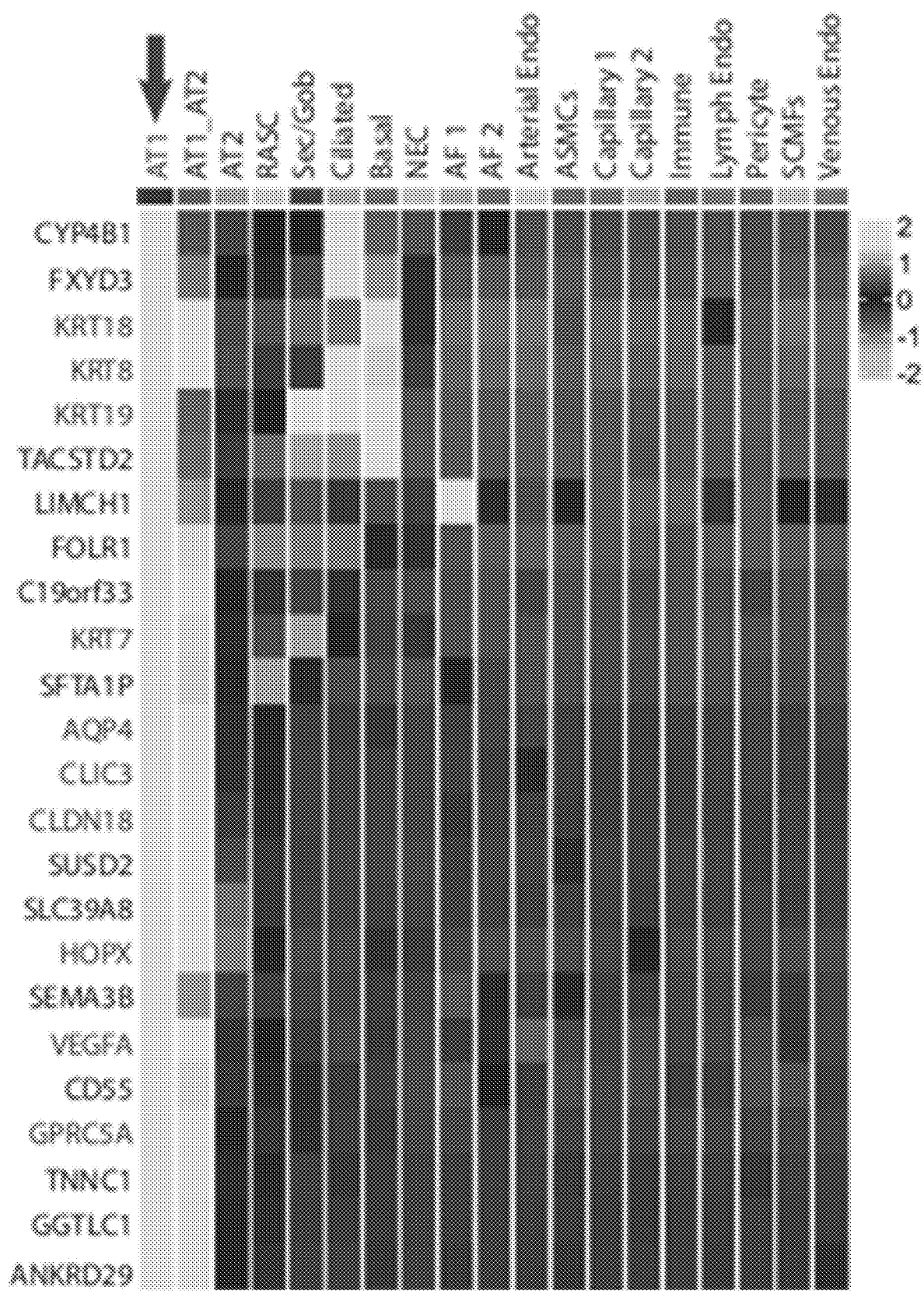
Figure 1C:
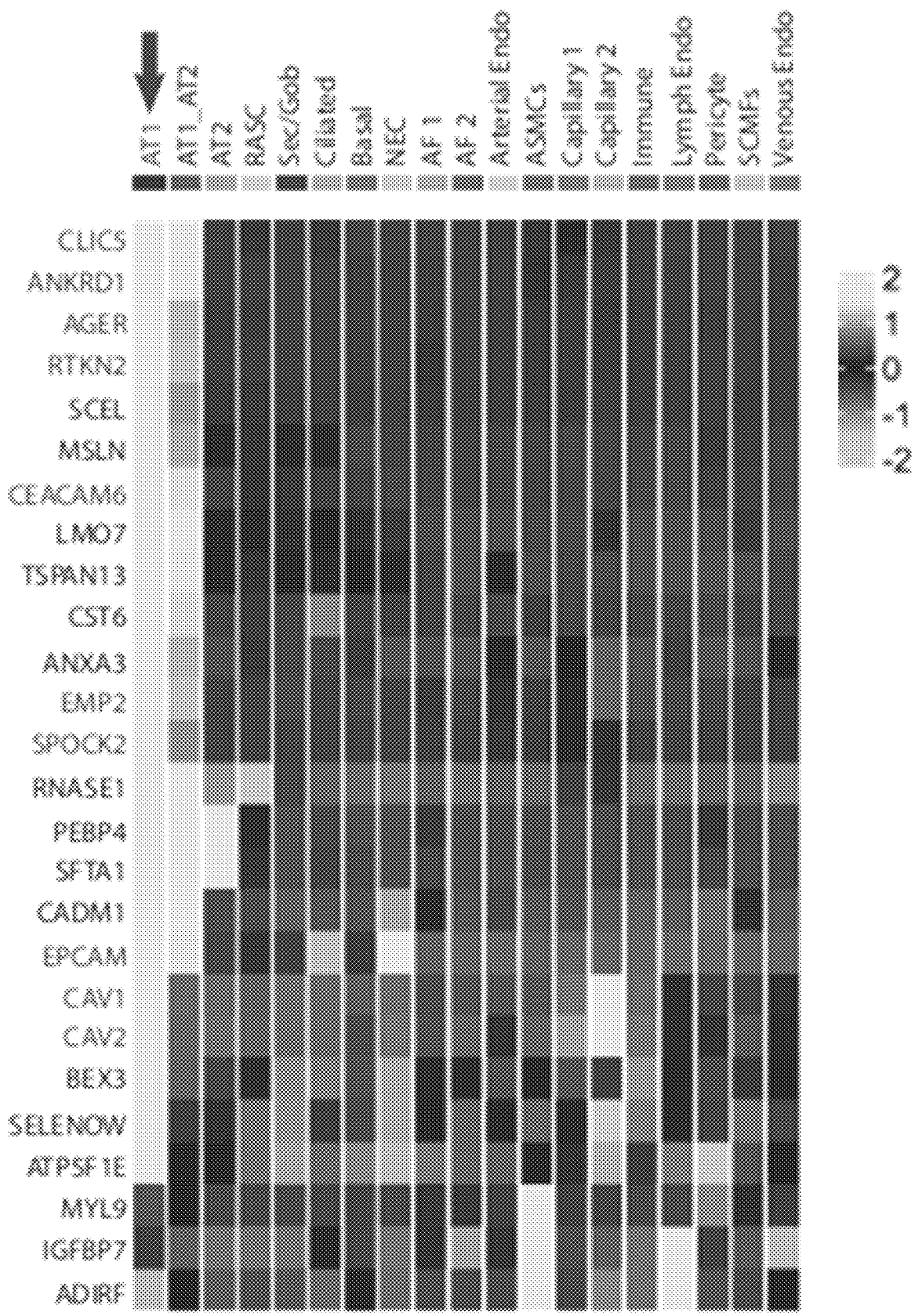
Figure 1D:
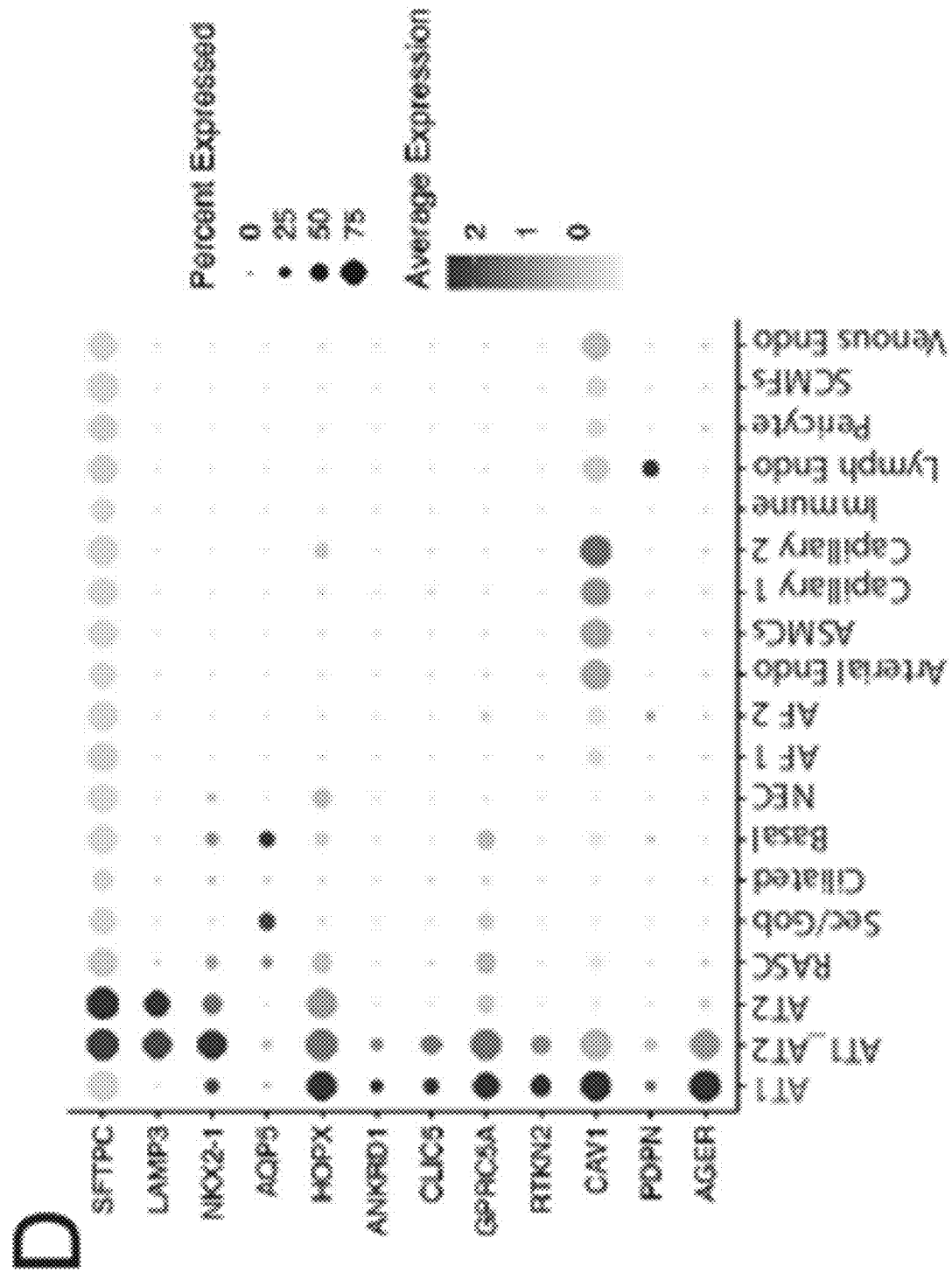

To generate unbiased candidate human AT1 marker 50-gene sets we identified differentially expressed transcripts enriched in AT1s using three pair-wise comparisons: 1) AT1s vs all lung cells, 2) AT1s vs. lung epithelial cells, and 3) AT1s vs AT2s (FIG. 1C). AGER was the top transcript significantly enriched in human AT1s in all 3 comparisons (ranked by log FC) with multiple caveolin (CAV1 and CAV2) and chloride intracellular channel (CLIC3 and CLIC5) gene family members upregulated in the top 50 genes as well (FIG. 1C). Although PDPN was not in the top 50 upregulated genes, likely due to its expression in lymphatic endothelium and basal cells, we still selected it as an informative AT1 marker because: 1) PDPN was significantly upregulated in all comparisons, and 2) PDPN has been extensively published as a canonical AT1 marker in other scRNA-seq atlases for both mice and humans.$_{23,30,53-55}$ To confirm the utility of the above markers, we compared their expression levels, frequencies, and relative specificities across all human lung epithelia (FIGS. 1D-1F, 8B-8S). Taken together, these analyses suggested AGER, CAV1, CLIC5, and PDPN as an informative 4-gene human AT1 marker set, in addition to the more extended 50-gene marker sets (data not shown), each able to reliably distinguish human AT1 cells.

Figure 1E:
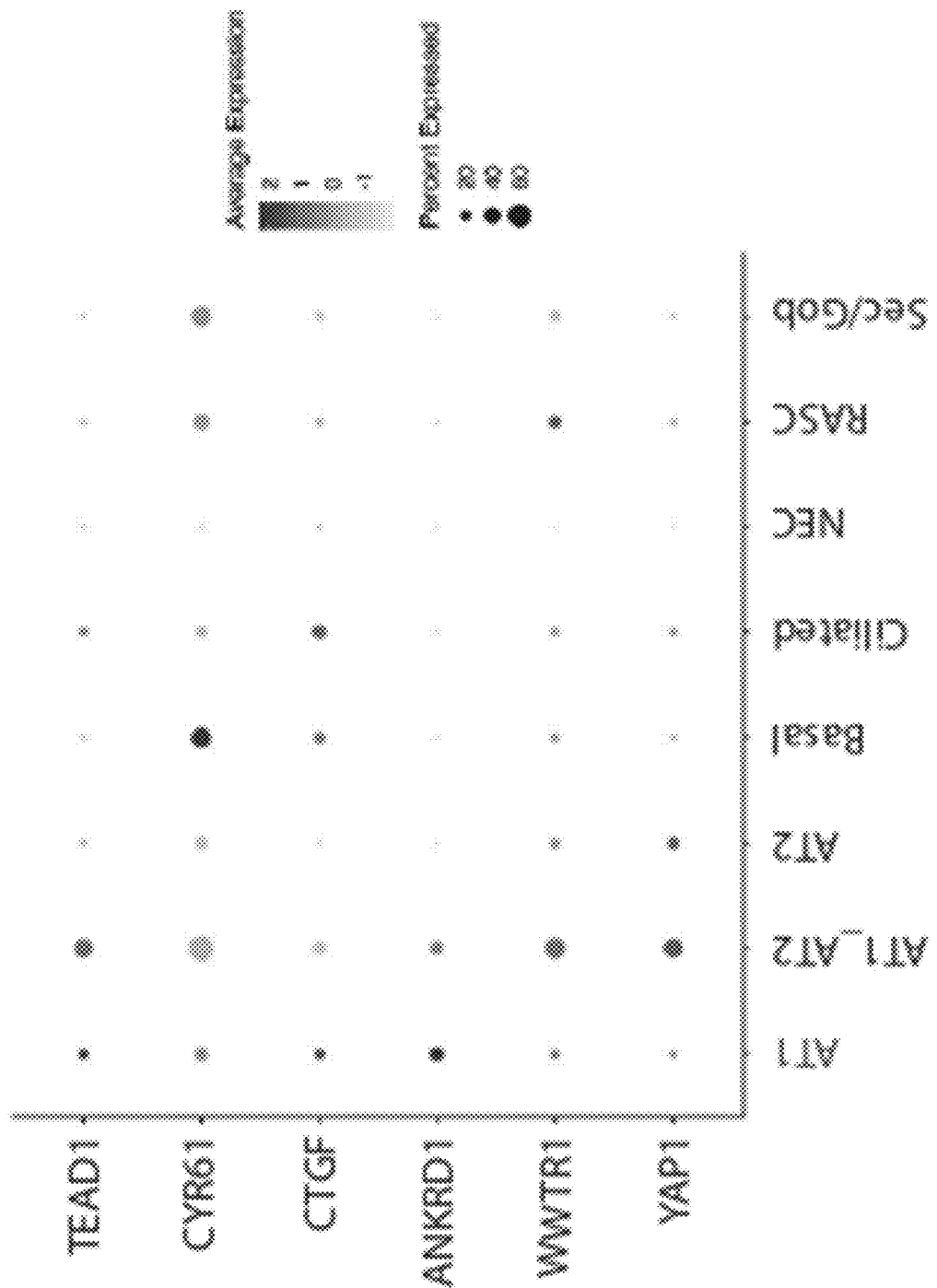
Figure 1F:
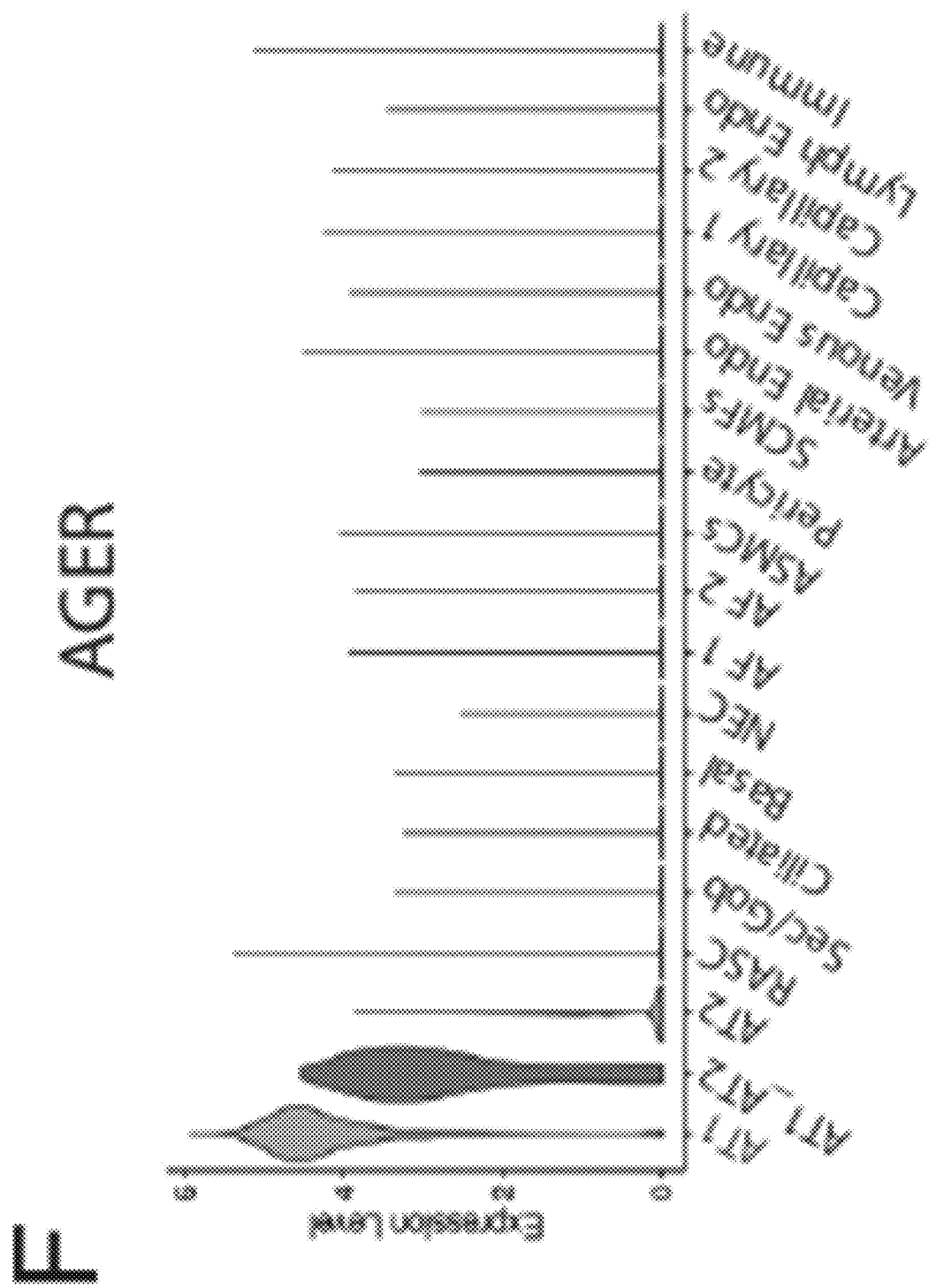

We noted the canonical Hippo signaling target gene, ANKRD1, was in the top 50 most enriched transcripts in AT1 cells in each of our comparisons, a finding in keeping with recent publications suggesting activated nuclear YAP/TAZ is important for the differentiation and maintenance of the mouse AT1 program.$_{45,56-59}$ Since Hippo signaling, including the activity of its transcriptional effectors YAP and TAZ, is typically regulated at the post-translational level, as expected YAP1 and TAZ (WWTR1) mRNAs were expressed broadly and not enriched in AT1s (FIG. 1E); however, their downstream targets including ANKRD1, CTGF, CYR61, and TEAD1 were all highly expressed in the AT1 population as well as in transitioning AT1_AT2 cells (FIG. 1E). Taken together these analyses: a) defined the transcriptomic programs of human AT1 cells, including multiple extended (50-gene) AT1 marker gene sets, b) validated a quartet of canonical human AT1 transcript markers (AGER, CAV1, CLIC5, and PDPN), and c) suggested that targets of Hippo kinase signaling (e.g., YAP/TAZ activation) distinguishes AT1 from AT2 cells in humans.

Nuclear Localization of YAP Leads to Activation of the AT1 Program in iAT2s

Figures 2A, 2B:
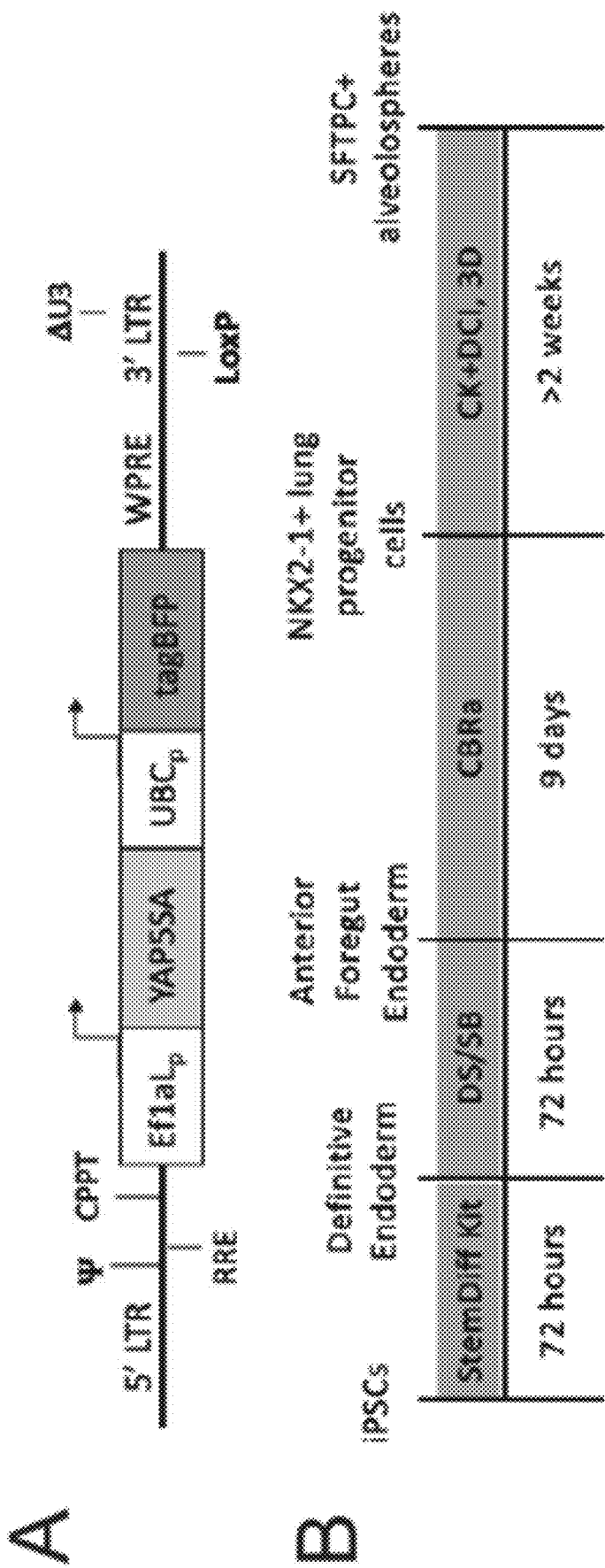
FIGS. 2A-2G demonstrate that iAT2s transduced with nuclear YAP overexpression lentivirus upregulate AT1 marker genes.
Figure 2C:
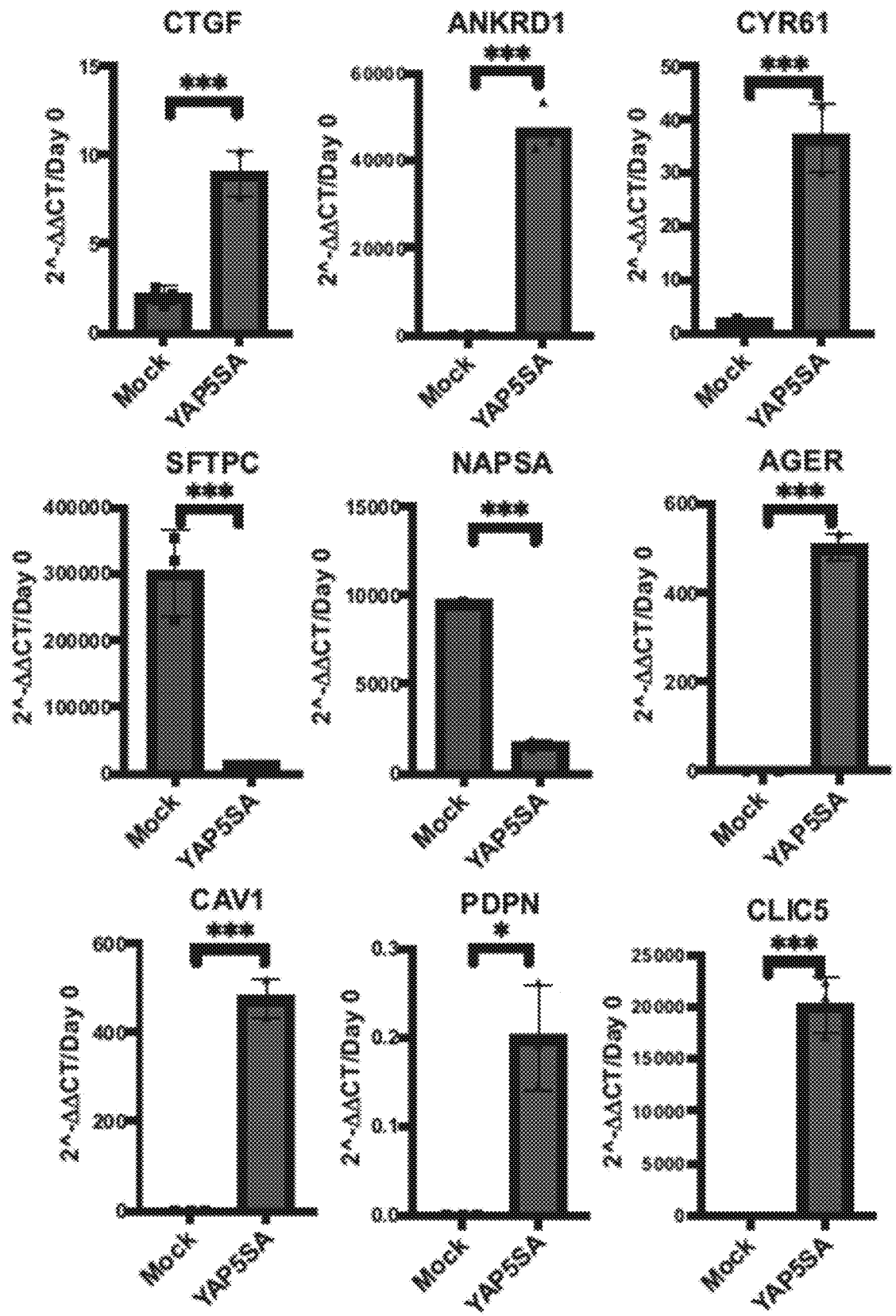
Figure 9A:
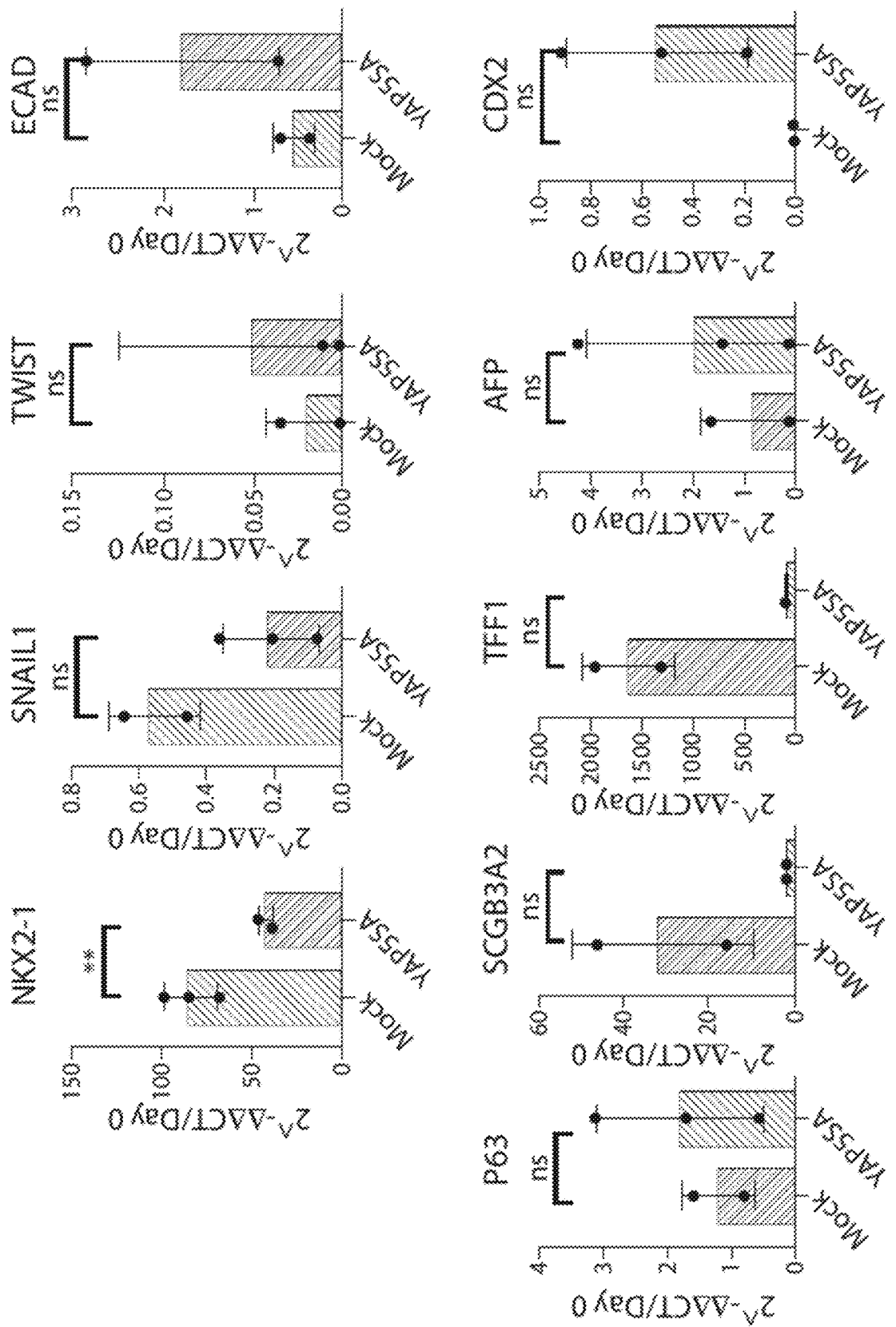
FIGS. 9A-9B depict YAP5SA transduction of SPC2B2 iAT2s.

In order to examine the role of Hippo signaling via nuclear YAP in the differentiation of human AT1s, we engineered a lentiviral vector encoding a constitutively active nuclear YAP cassette. YAP5SA, in which 5 serine residues have been mutated to alanines, preventing phosphorylation by LATS kinases[60] (FIG. 2A). We differentiated human iPSCs into iAT2s using our previously established protocol[16,61] (FIG. 2B), and transduced the resulting iAT2s (>95% SFTPCtdTomato+) with lentiviral YAP5SA vs. parallel untransduced controls (mock). After 12 days of outgrowth in 3D cultures maintained in our published iAT2 media (CK+DCI),[16] we observed significant upregulation of YAP target genes, CTGF, ANKRD1, and CYR61, in the YAP5SA transduced samples (FIG. 2C). YAP5SA over expression resulted in a significant decrease in the AT2 markers SFTPC and NAPSA, and a significant increase in the four AT1 marker set, AGER, CAV1, PDPN, and CLIC5 (FIG. 2C). While lung epithelial marker NKX2-1 was slightly decreased, we observed little to no expression of mesenchymal (SNAIL1 and TWIST), airway (P63, SCGB3A2), or non-lung endoderm (TFF1, AFP, CDX2) markers after lentiviral transduction (FIG. 9A). These results suggest that nuclear YAP activity promotes the loss of AT2 program and gain of AT1 markers in iAT2s.

Figure 2D:
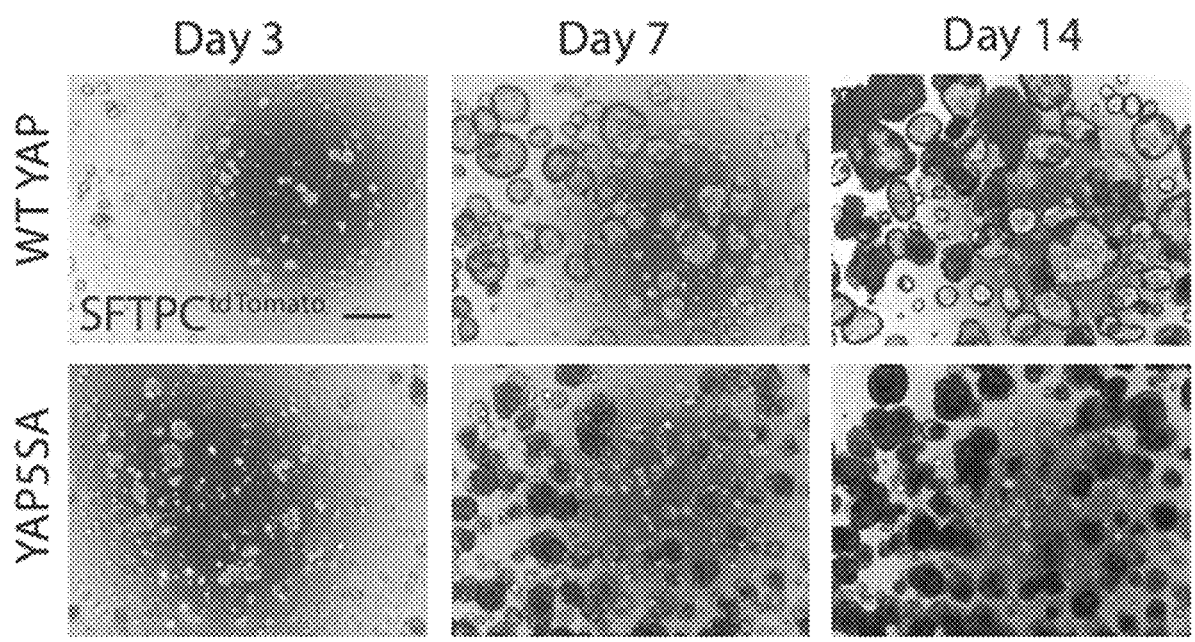

To better control for lentiviral forced overexpression of the YAP transcript, we generated a control lentivirus with the same construct encoding constitutively over-expressed WT YAP (FIG. 9B), which is predicted to be non-signaling as it is phosphorylated and degraded without nuclear translocation of YAP.[60] iAT2s transduced with negative control WT YAP continued to grow normally as monolayered epithelial spheres with visible lumens and retained SFTPCtdtomatoeporter expression, whereas YAP5SA transduced cells rapidly lost SFTPCtdtomato, and by 3 days post-transduction exhibited an altered morphology with aggregated clumps of cells lacking visible lumens (FIG. 2D). These morphological differences became more pronounced over time, as documented by microscopy at both 7- and 14-days post transduction (FIG. 2D).

Figure 2E:
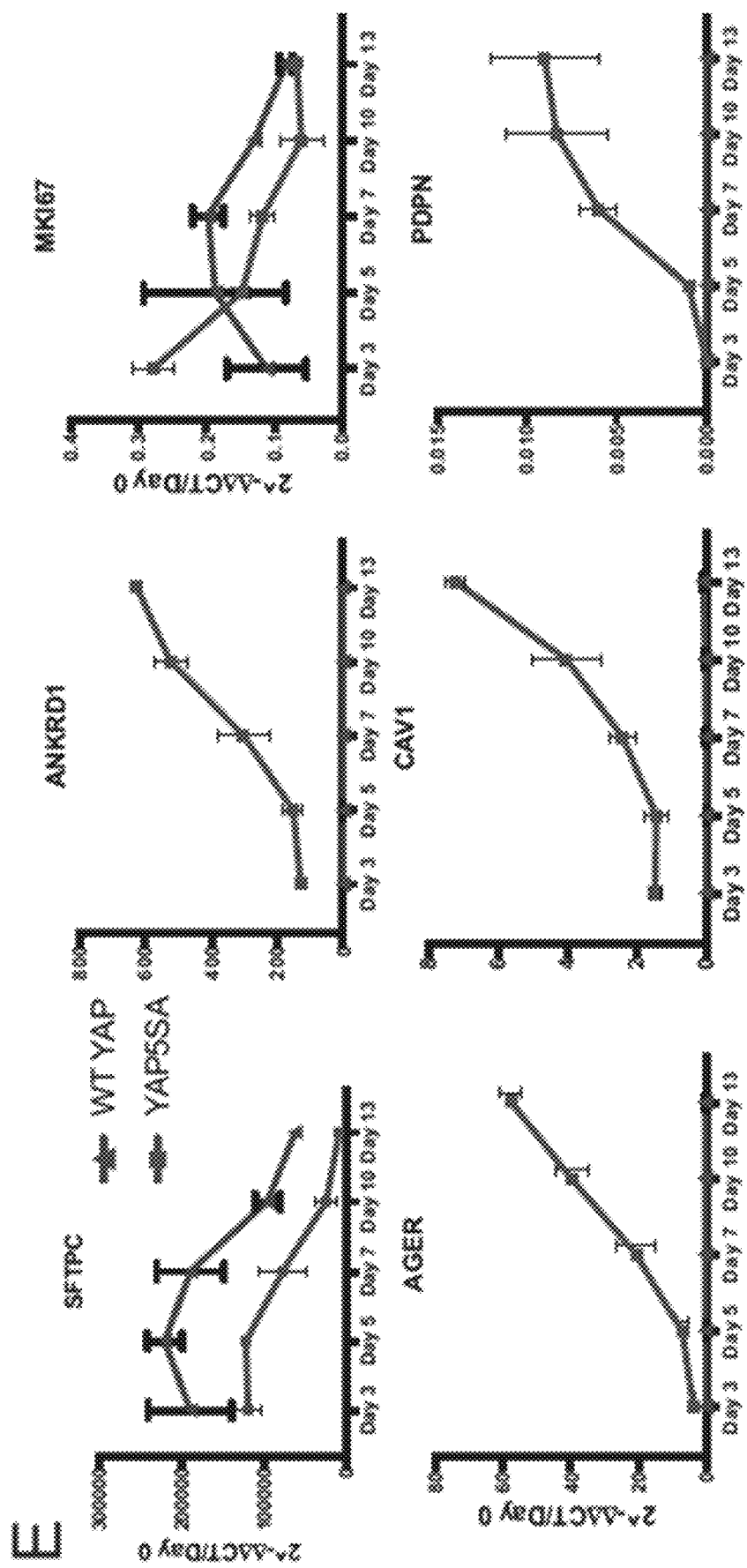

We hypothesized that activated nuclear YAP might be driving a transition in iAT2 transcriptomic programs from AT2-like to AT1-like. To further study the kinetics of this hypothesized transcriptomic shift following YAP5SA lentiviral transduction, we performed a time series gene expression analysis by taking whole well RNA extracts over a 2-week period post infection with lentiviral YAP5SA vs WT YAP. By day 3 after infection. SFTPC expression was already decreased in the YAP5SA infected well and continued to decrease over time. AT1 markers AGER, CAV1 and PDPN were significantly upregulated and continued to increase over time with only PDPN seeming to plateau by 2 weeks. YAP downstream target ANKRD1 followed a similarly increasing pattern (FIG. 2E).

Figure 2F:
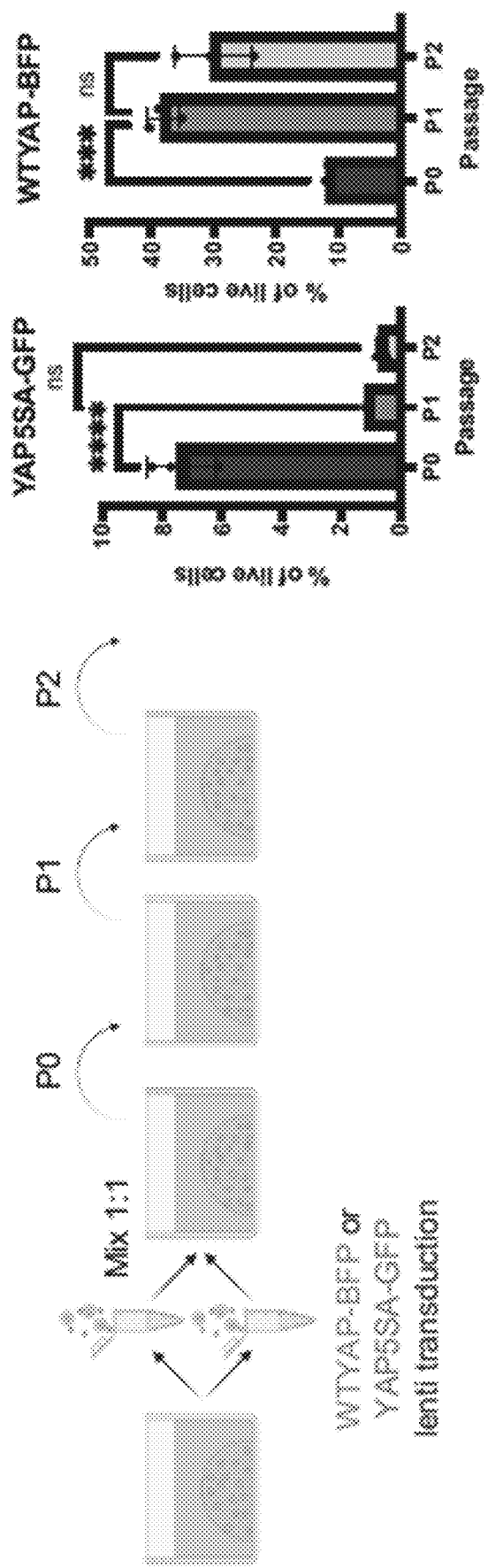
Figure 2G:
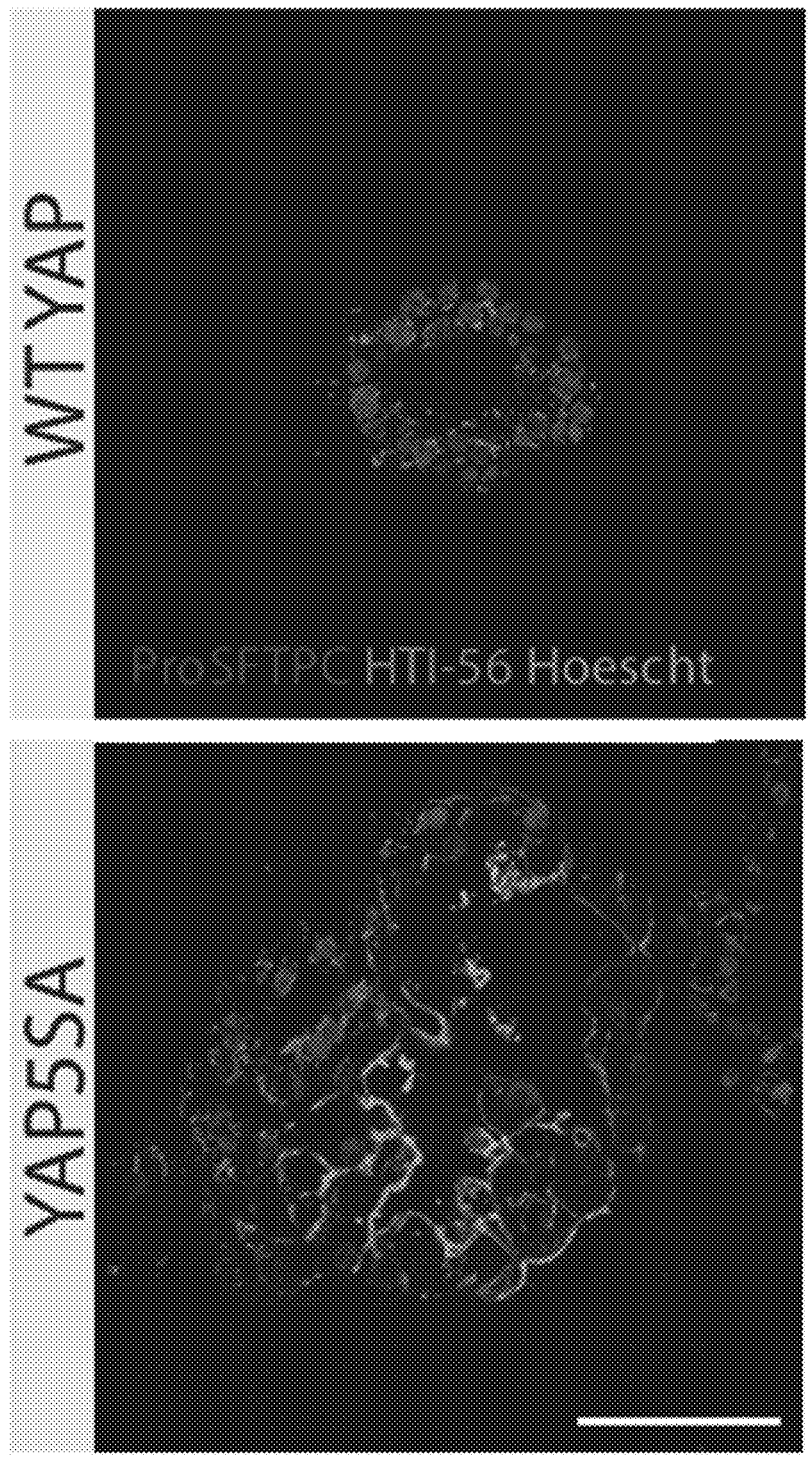
Figure 9B:
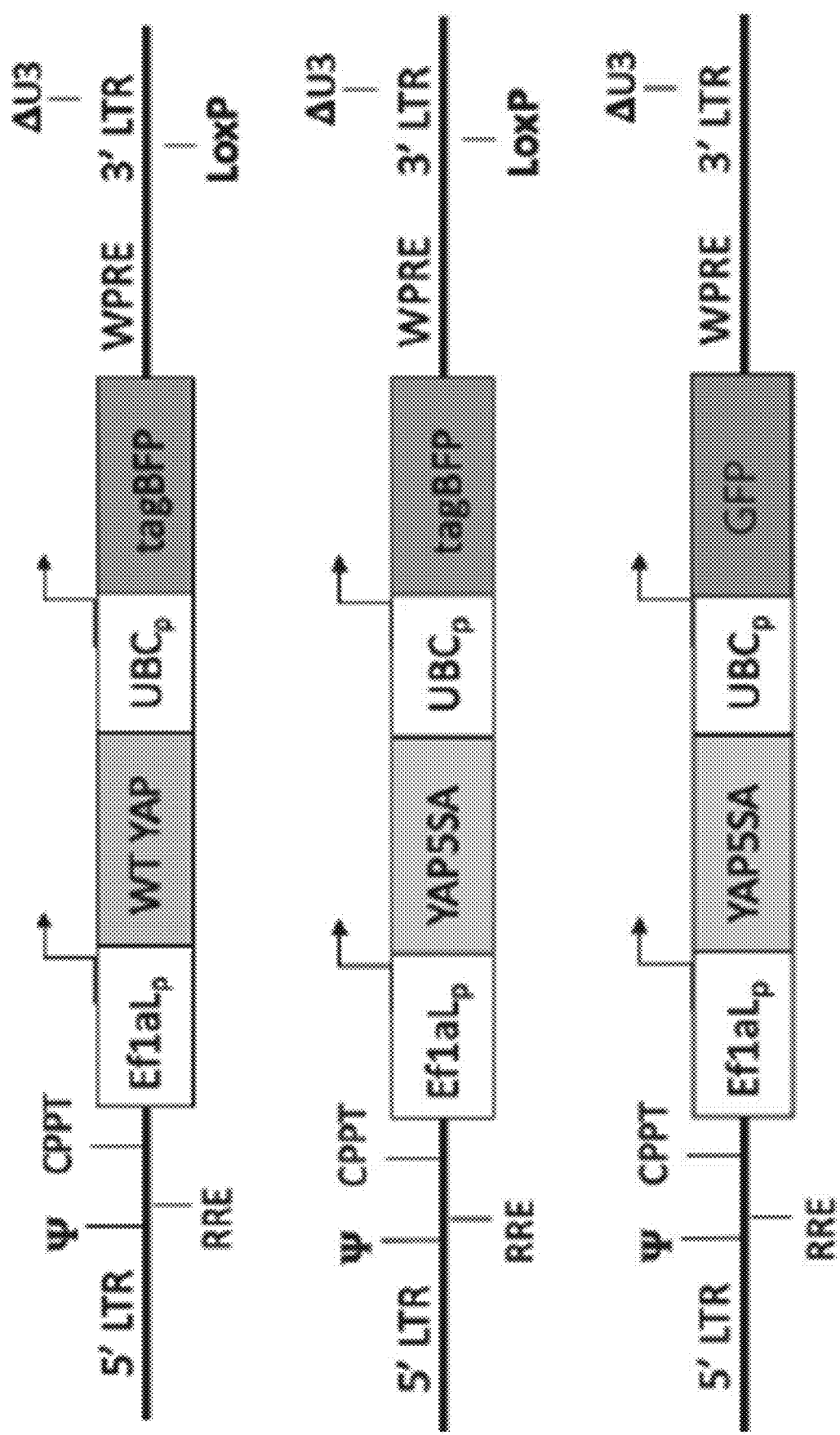

Consistent with the known non-proliferative, quiescent state that characterizes AT1s in vivo,[62] decreased proliferation in outgrowth cells was suggested by: 1) decreasing expression of MKI67 over time post YAP5SA transduction (FIG. 2E), and 2) loss of YAP5SA infected cells after serial passaging using a competition assay between iAT2s transduced with WT YAP-BFP vs. YAP5SA-GFP lentiviruses (FIGS. 2F, 9B). Emergence of the AT1 program in YAP5SA transduced cells in 3D culture was also evident at the protein level by immunostaining for the AT1 marker, HTI-56 (FIG. 2G). Whereas iAT2s exposed to the WT YAP lentivirus gave rise to epithelial spheres expressing only punctate proSFTPC cytoplasmic protein with no detectable HTI-56 staining, iAT2s exposed to YAP5SA lentivirus gave rise to subsets of organoids that exclusively contained either HTI-56 positive cells, or proSFTPC-positive cells, with other subsets of organoids containing a mixture of cells positive for either HTI-56 or proSFTPC (FIG. 2G).

YAP5SA-Induced Acquisition of the iAT1 Program Profiled by Single Cell RNA Sequencing To further evaluate the effect of nuclear YAP on the global transcriptomic programs of iPSC-derived alveolar epithelial cells and to understand the heterogeneity of the lentiviral transduced cells at single cell resolution, we repeated YAP5SA vs WT YAP lentiviral transduction experiments and performed profiling by single cell RNA sequencing (SPCB2 iPSC line; FIG. 3A). We analyzed the resulting cells at 7 days post transduction, because there were significant differences in all genes measured at that date by bulk RT-qPCR (FIG. 2E), and the cells were not yet overly confluent. All live cells were isolated for these profiles to allow examination of both transduced as well as non-transduced cells within the same well, which can serve as additional controls.

Figure 3C:
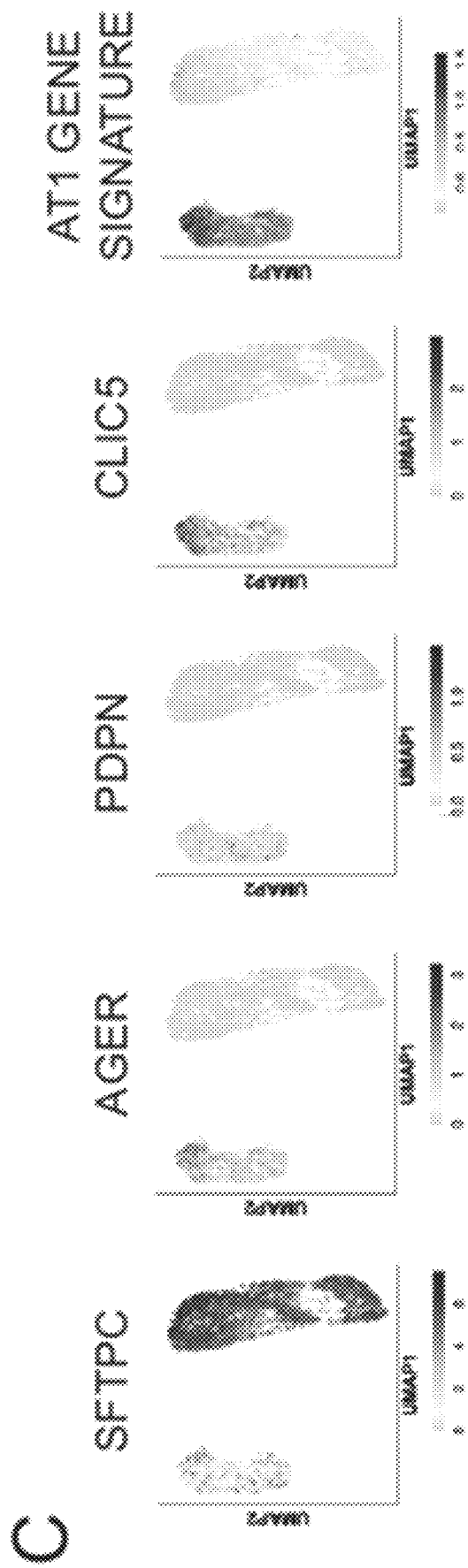
Figure 10A:
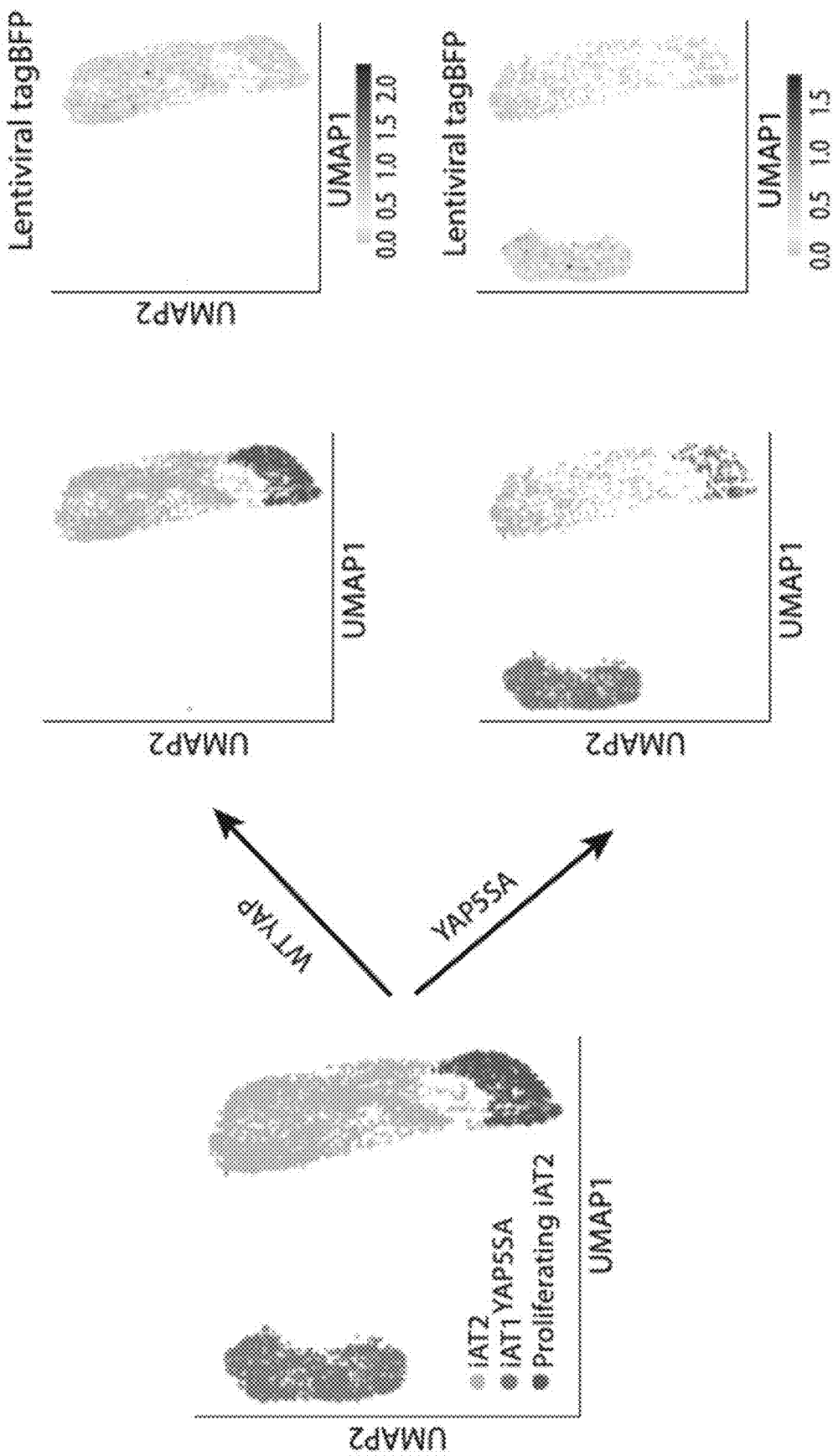
Figure 10B:
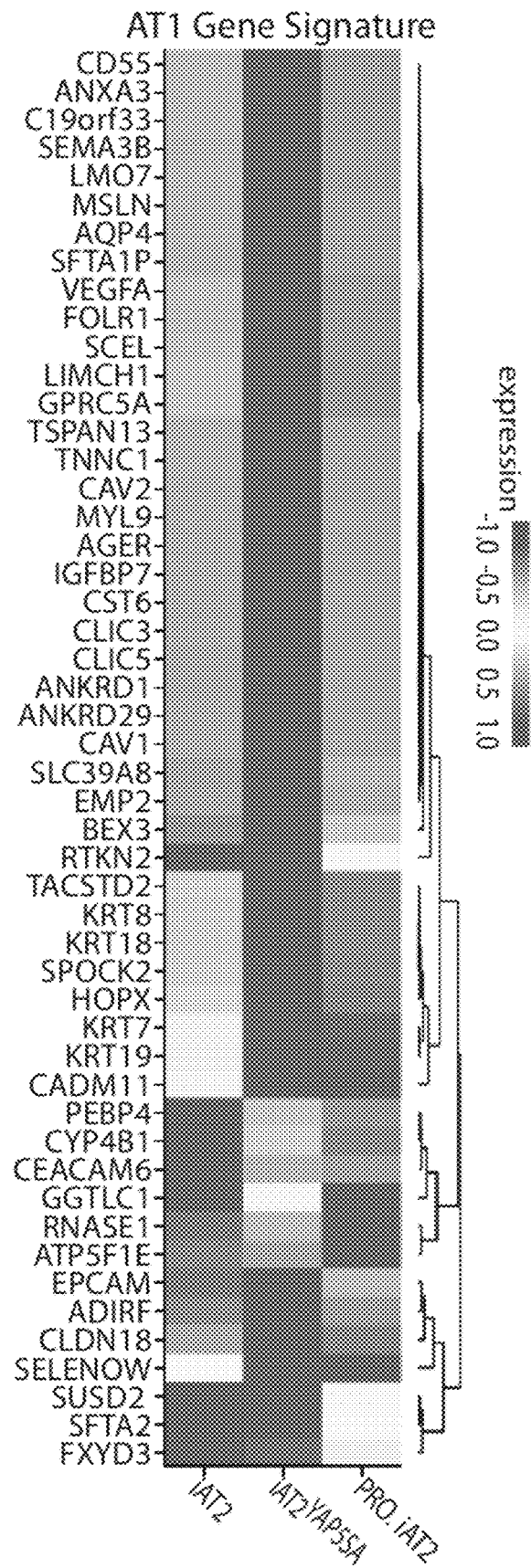

By UMAP analysis the WT YAP-transduced control iAT2 population clustered together regardless of lentiviral transduction as shown by lentiviral BFP expression (FIGS. 3B, 10A). This population showed high levels of expression of AT2 marker SFTPC (FIG. 3C), as expected. The population of cells exposed to YAP5SA lentivirus contained some cells clustered with the WT YAP cells and some that clustered separately (FIG. 3B), presumably resulting from whether each cell had been transduced vs not transduced. Consistent with this speculation, expression of the BFP reporter present in our lentiviral construct localized mostly to the newly emergent cell cluster (FIG. 10A). To screen for emergence of the AT1 program in the newly emerged cluster after YAP5SA transduction, we analyzed expression of AT1 markers AGER, PDPN, and CLIC5 as well as our AT1 50 gene set signature derived from the primary human lung dataset in FIG. 1 (FIGS. 3C-3G, 10B). We observed high AGER and AT1 gene expression in the new cluster made only from the YAP5SA-transduced cells with little to no expression in the WT YAP transduced cluster. This upregulation of the AT1 program coincided with high expression of YAP downstream targets ANKRD1 and CYR61 (FIG. 3D), and loss of expression of AT2 markers, such as SFTPC, SFTPB, and NAPSA (FIGS. 3C-3G).

Figure 3F:
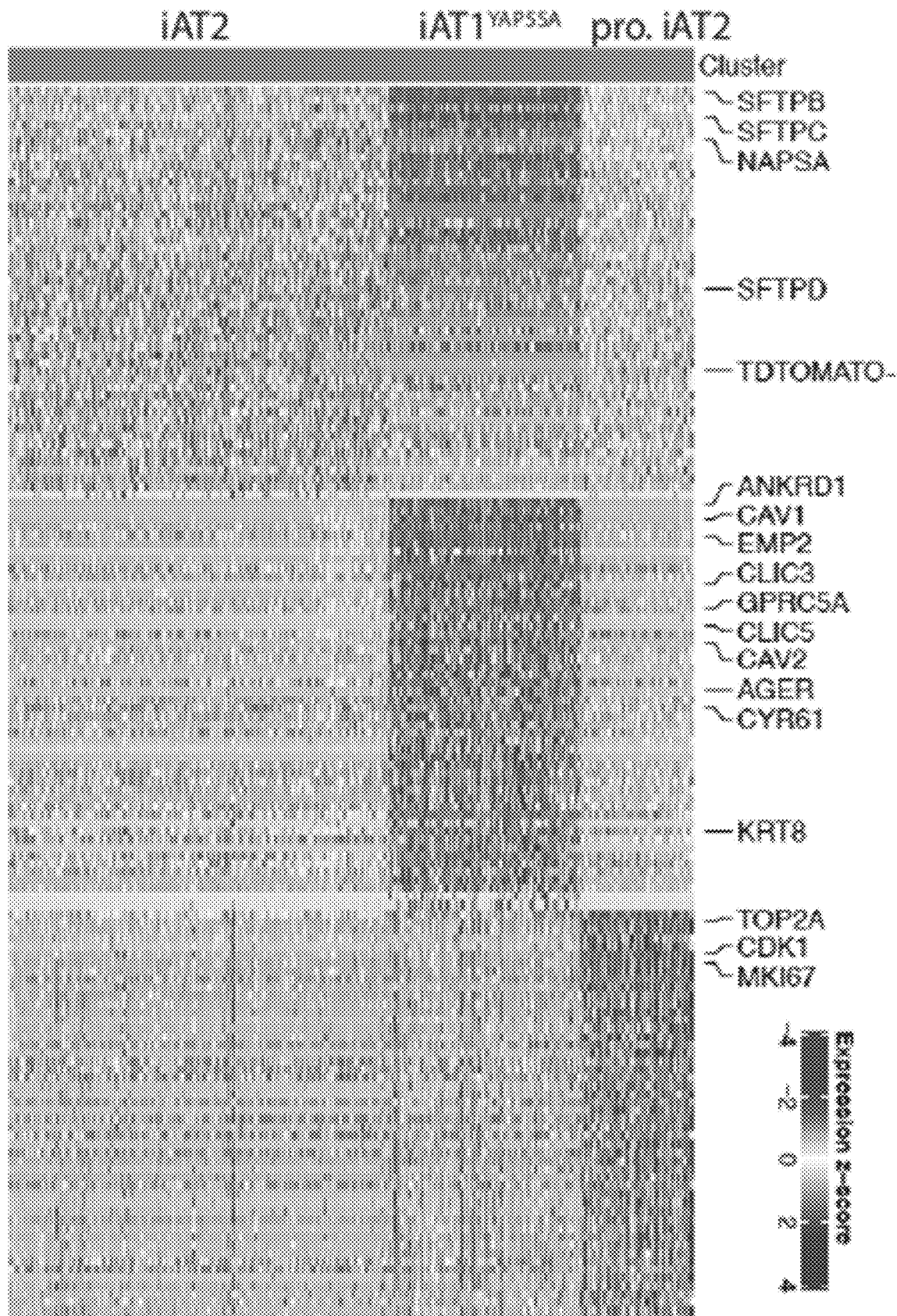
Figure 3G:
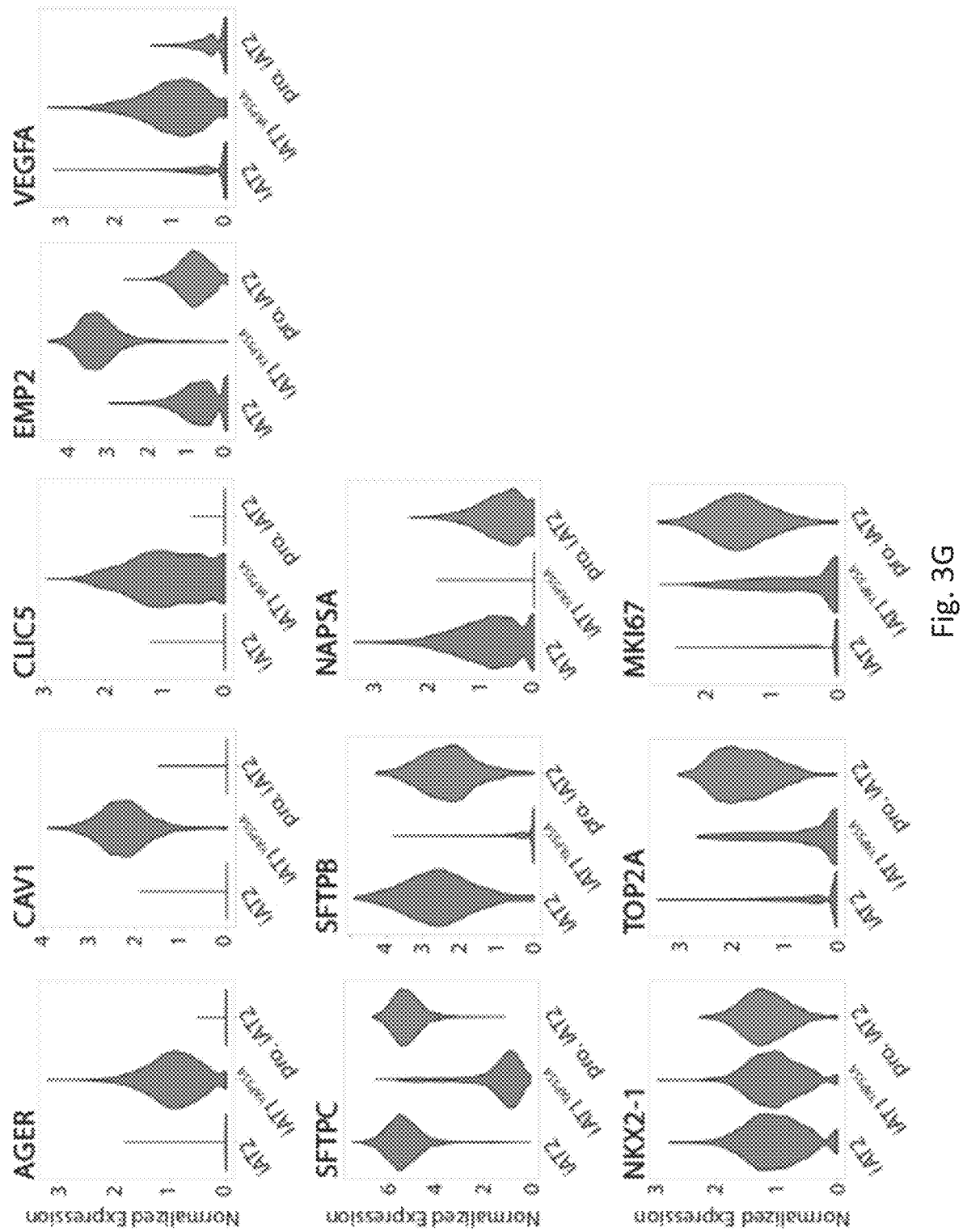
Figures 1, 10C:
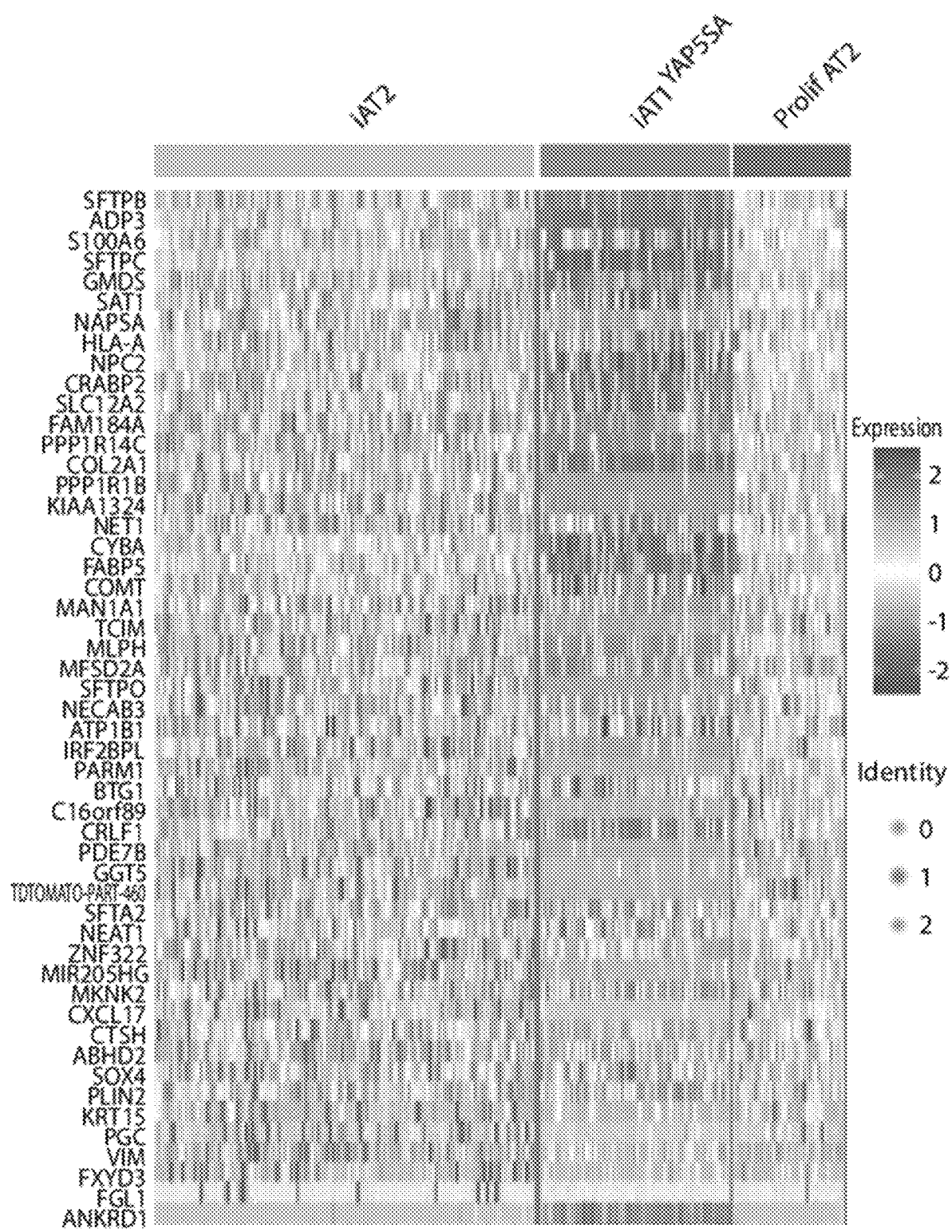
Figures 2, 10C:
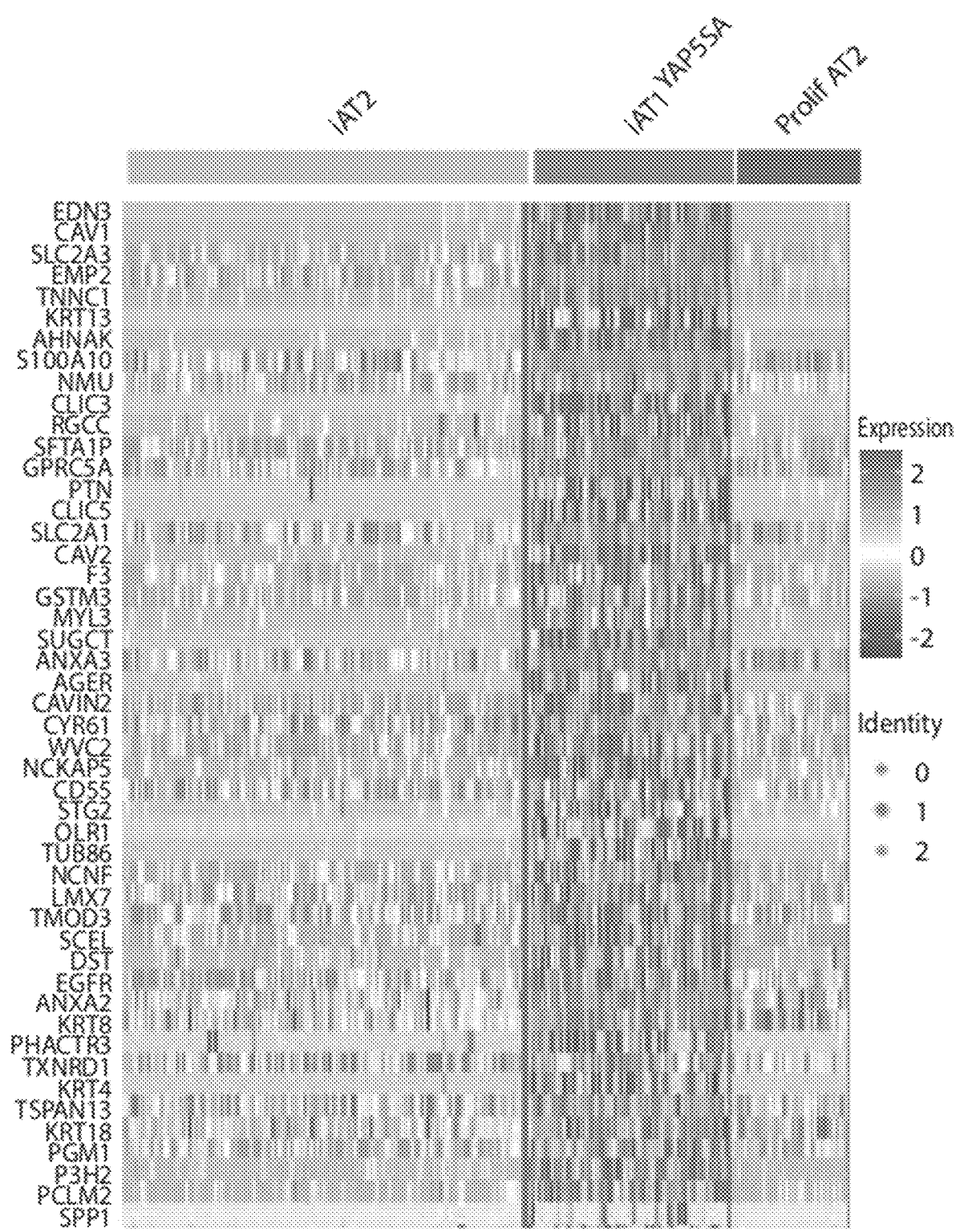
Figures 3, 10C:
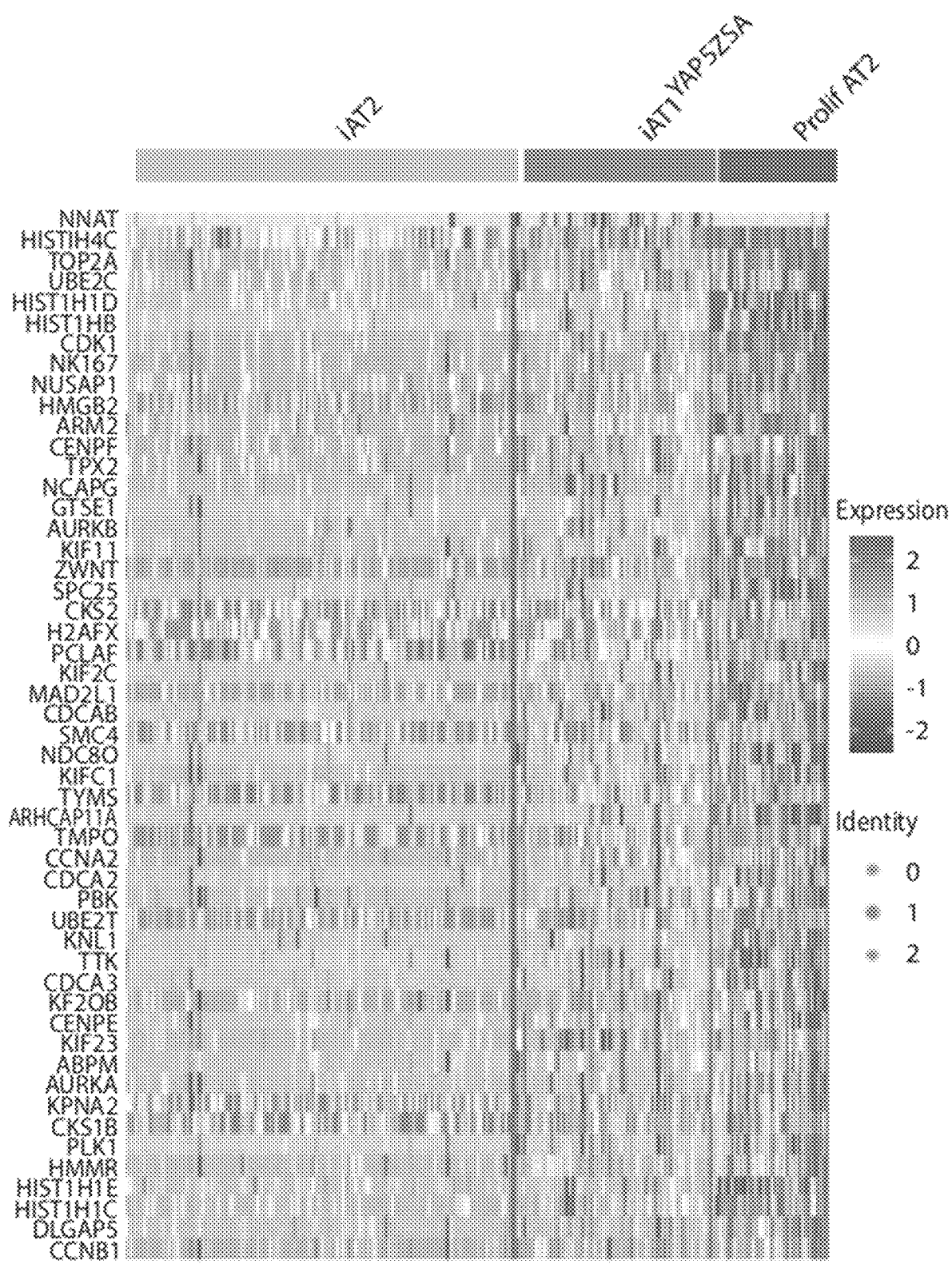
Figures 1, 10D:
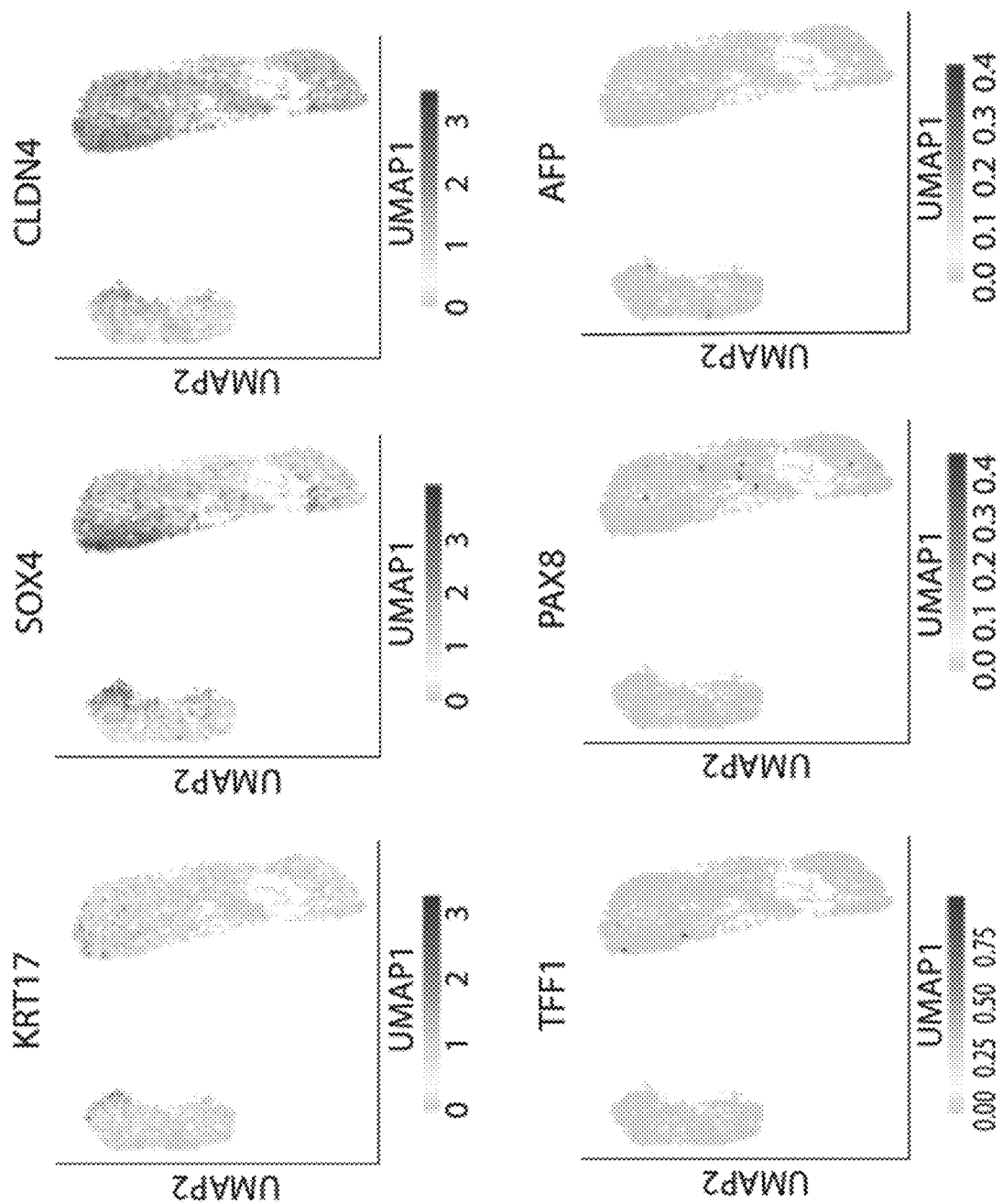
Figures 2, 10D:
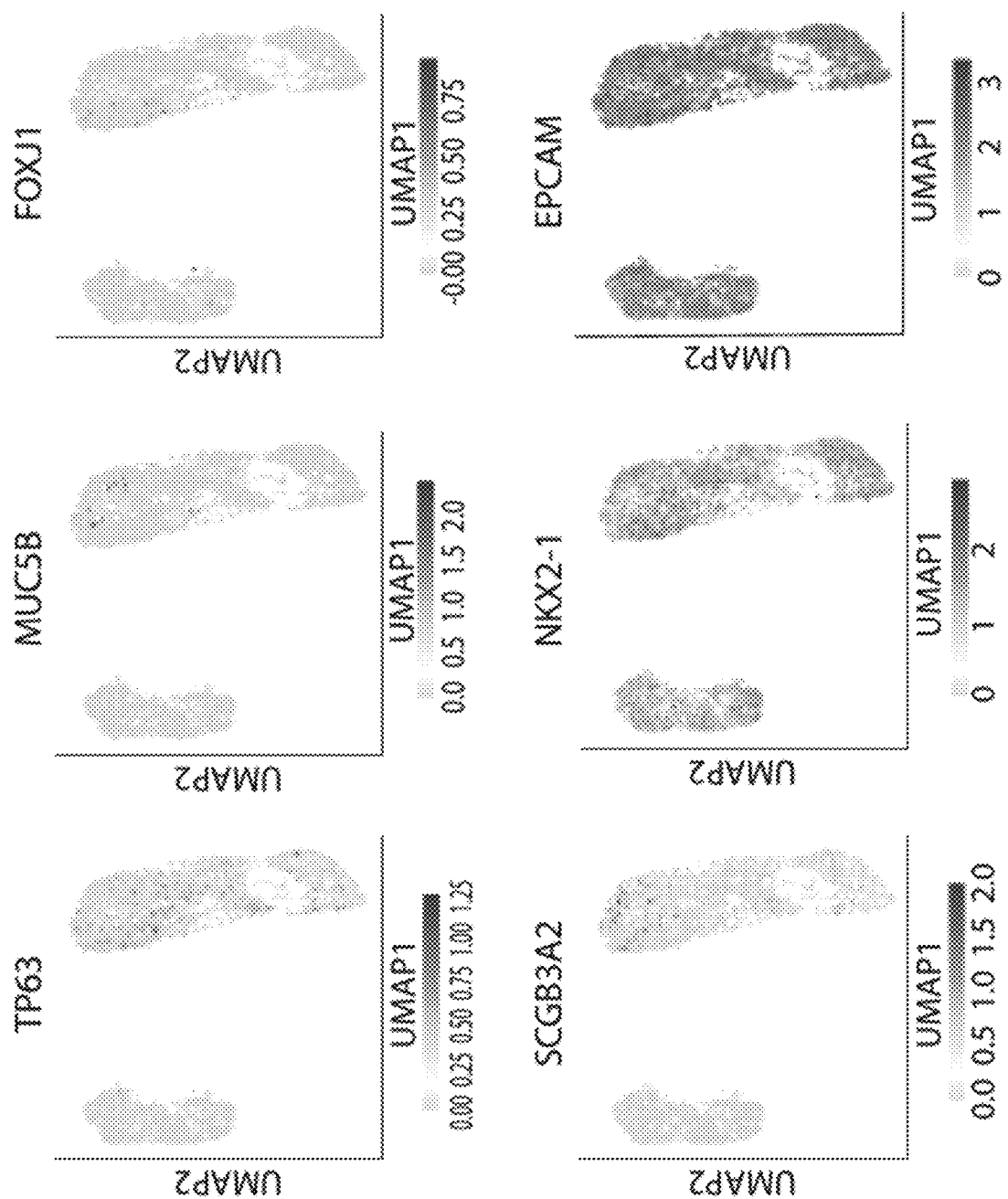

We employed Louvain clustering (resolution 0.05) to identify three distinct cell clusters (FIG. 3E), which we annotated based on the top 50 differentially expressed genes enriched in each cluster (FIGS. 3F, 10C). Both iAT2s and proliferating iAT2s expressed similarly high levels of AT2 marker genes such as SFTPC, SFTPB, and NAPSA, whereas proliferating iAT2s were uniquely enriched in expression of proliferation markers such as MKI67 and TOP2A (FIGS. 3F, 3G). The YAP5SA driven cluster's top differentially expressed genes included YAP downstream targets ANKRD1 and CYR61 as well as AT1 marker genes such as AGER, CAV1, CAV2, CLIC3, CLIC5, VEGFA, and EMP2 (FIGS. 3F, 3G). Known markers for transitional or aberrant KRT17+/ KRT5–AT2-derived cells were not enriched at significant levels in our YAP5SA transduced cells (FIG. 10D), and markers of airway epithelia (SCGB3A2, FOXJ1, TP63) were expressed very rarely, if at all (FIG. 10D).

Figure 3H:
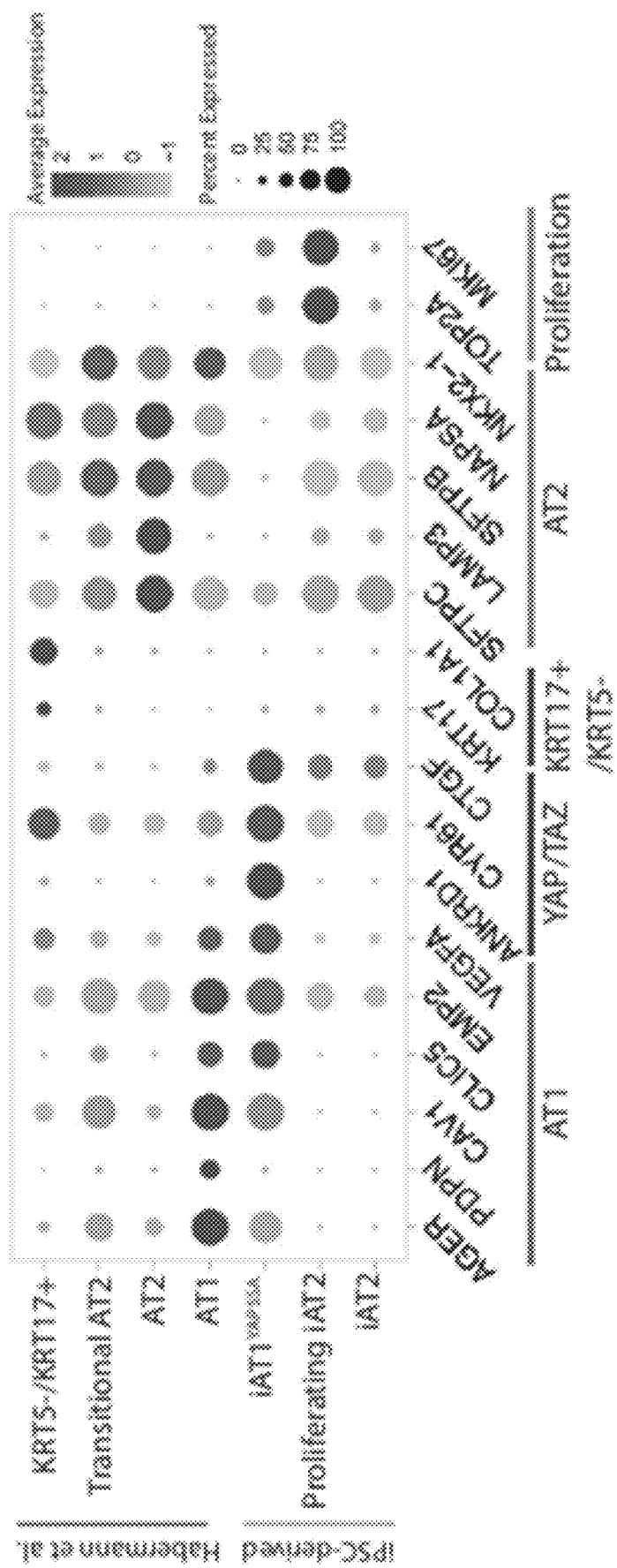
Figure 10E:
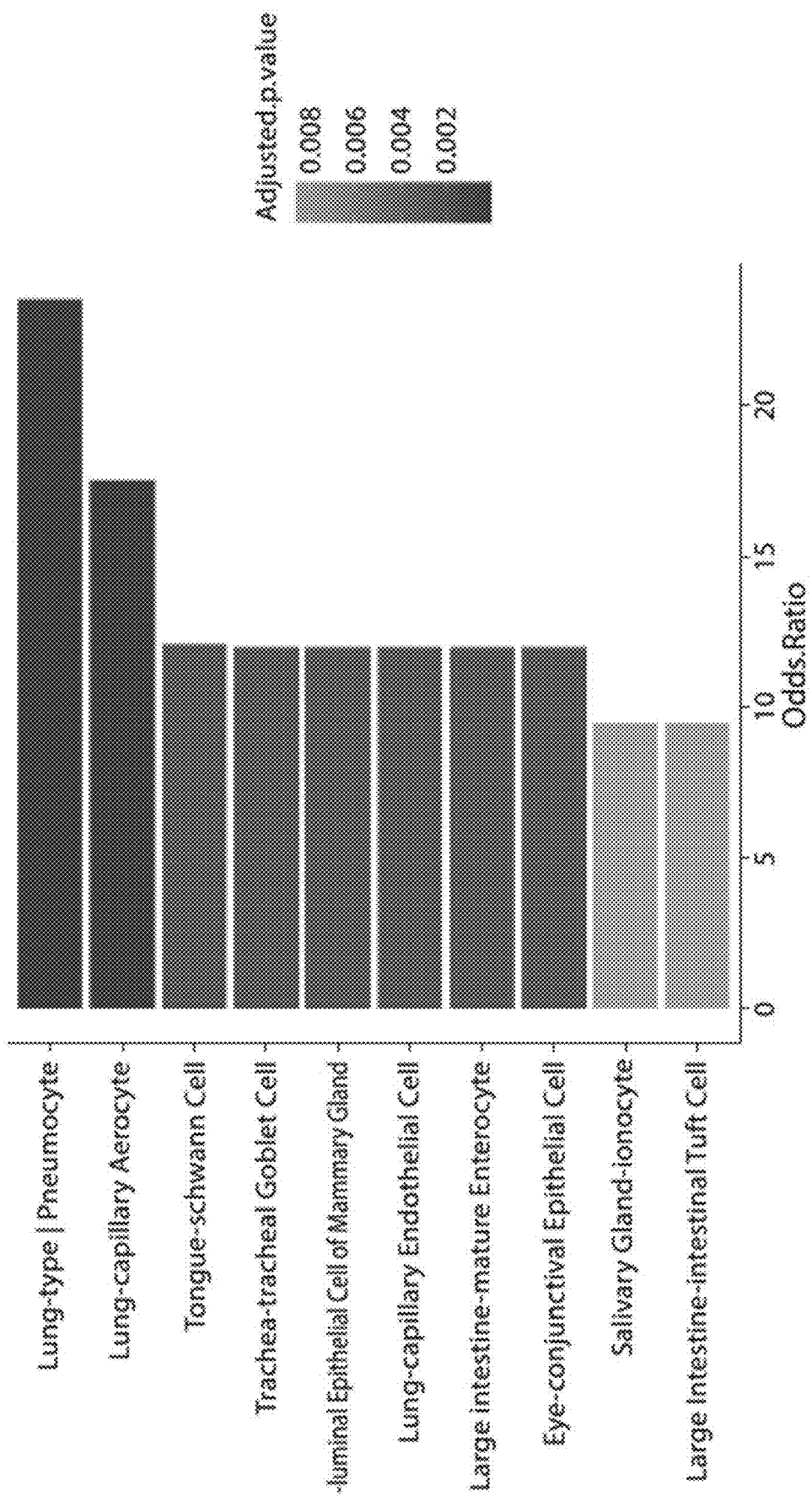

To provide an unbiased assessment of the lineage identity of our YAP5SA induced cell cluster, hereafter iAT1YAP5SA, based on the top differentially expressed genes enriched in this cluster (FDR<0.05, log FC>1; 92 genes), we employed the Tabula Sapiens gene set library,[63] and found primary lung-type I pneumocyte to be the top enriched term in our cluster (ranked by either p value or odds ratio). compared to all profiled tissue lineages (FIG. 10E). Additional comparisons to primary human lung scRNA-seq datasets published by Habermann et al.[49] indicated similar expression frequencies of individual AT1 markers in iAT1YAP5SA cells compared to primary AT1s in vivo (FIG. 3H). However. iAT1s expressed higher frequencies of YAP downstream targets, ANKRD1, CYR61, and CTGF, consistent with forced over-expression of activated nuclear YAP (FIG. 3H). Taken together our results suggest that overexpression of nuclear YAP drives the downregulation of the AT2 program and upregulation of the AT1 program in human iAT2s. Since cells grown in the same well but not transduced with the YAP5SA lentivirus maintained their iAT2 identity and clustered with the WT YAP control cells, this suggests nuclear YAP acts in a cell-autonomous manner to initiate this differentiation program without evidence of paracrine effects on other cells.

Cre Excision of YAP5SA Lentivirus Results in Reversion to the iAT2 State

Figure 11A:
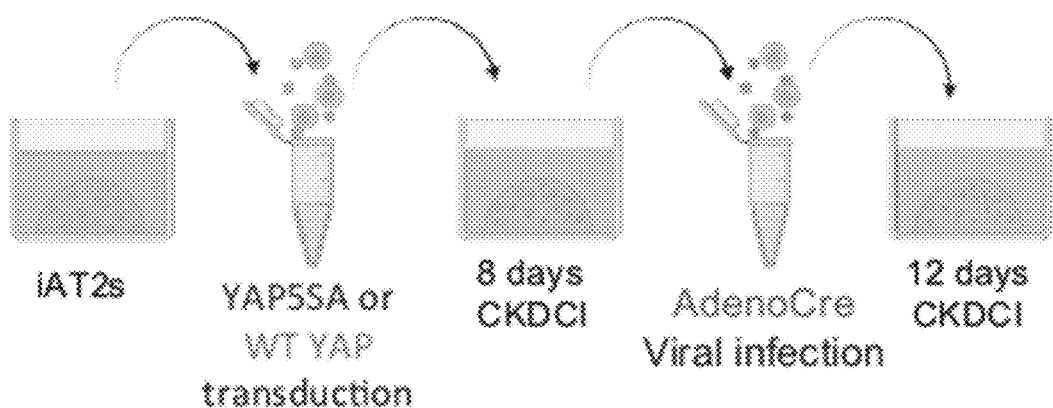
FIGS. 11A-11F demonstrate that Cre excision of YAP5SA lentivirus leads to reversion to iAT2-like phenotype.
Figure 11B:
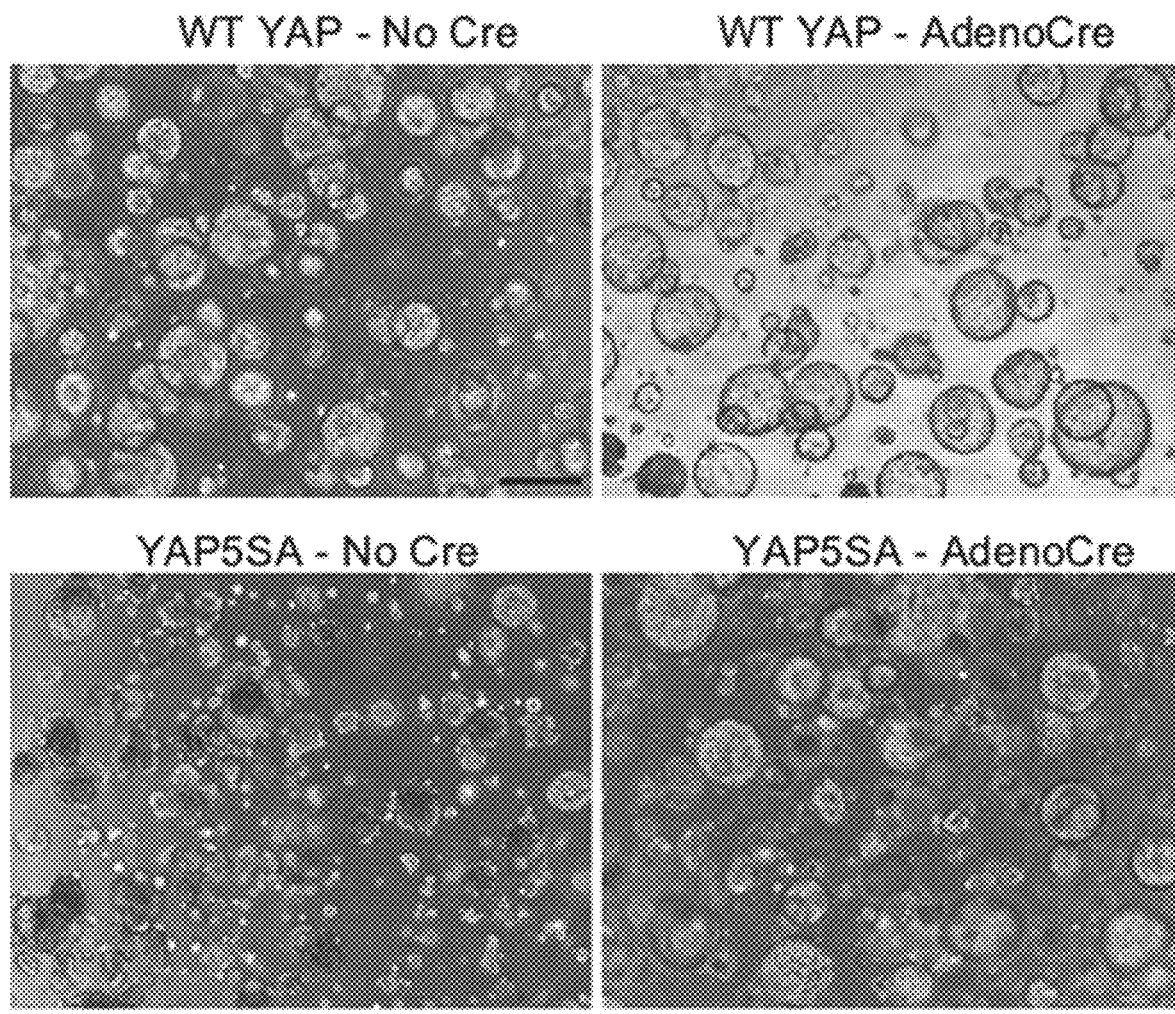
Figure 11C:
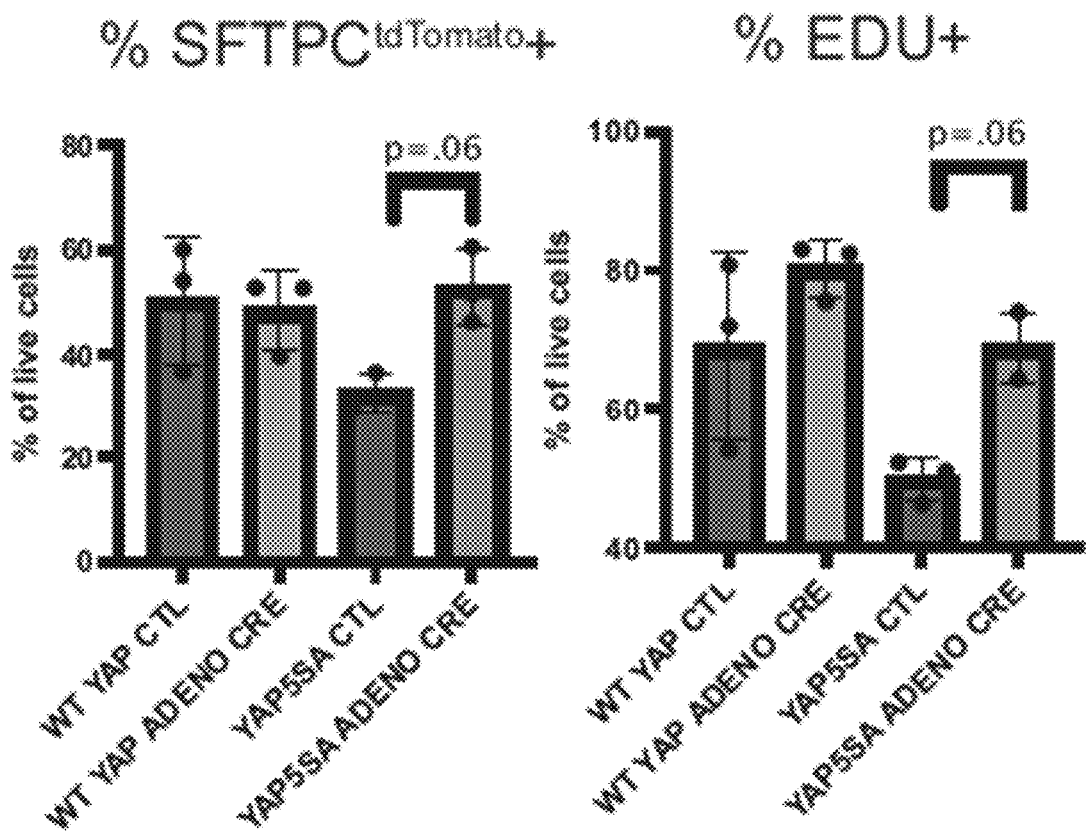
Figure 11D:
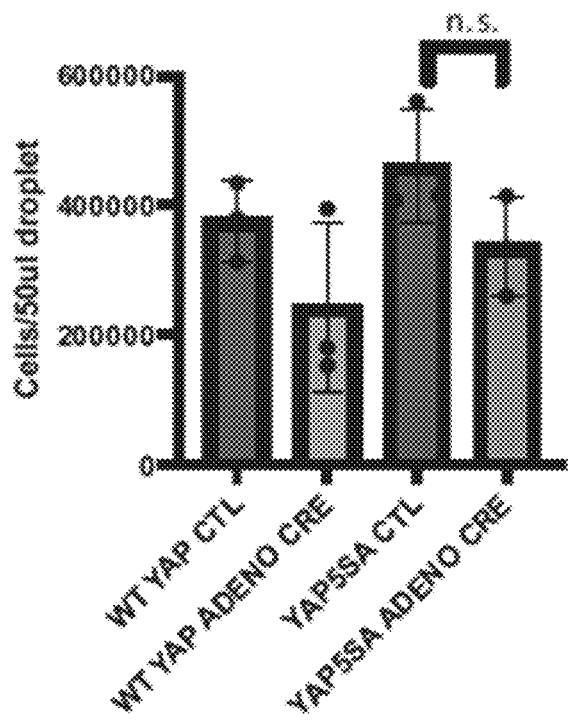
Figure 11E:
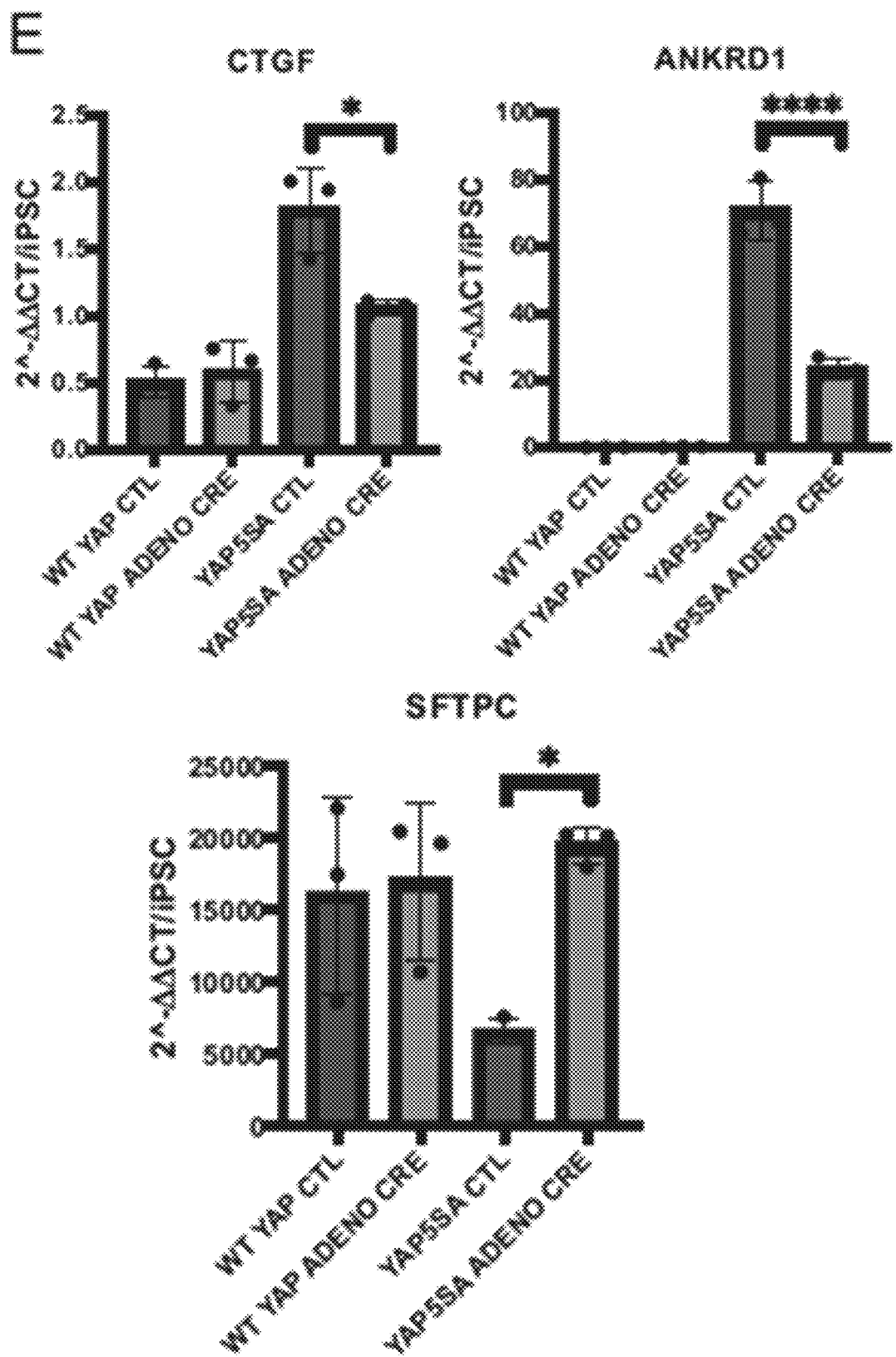
Figure 11F:
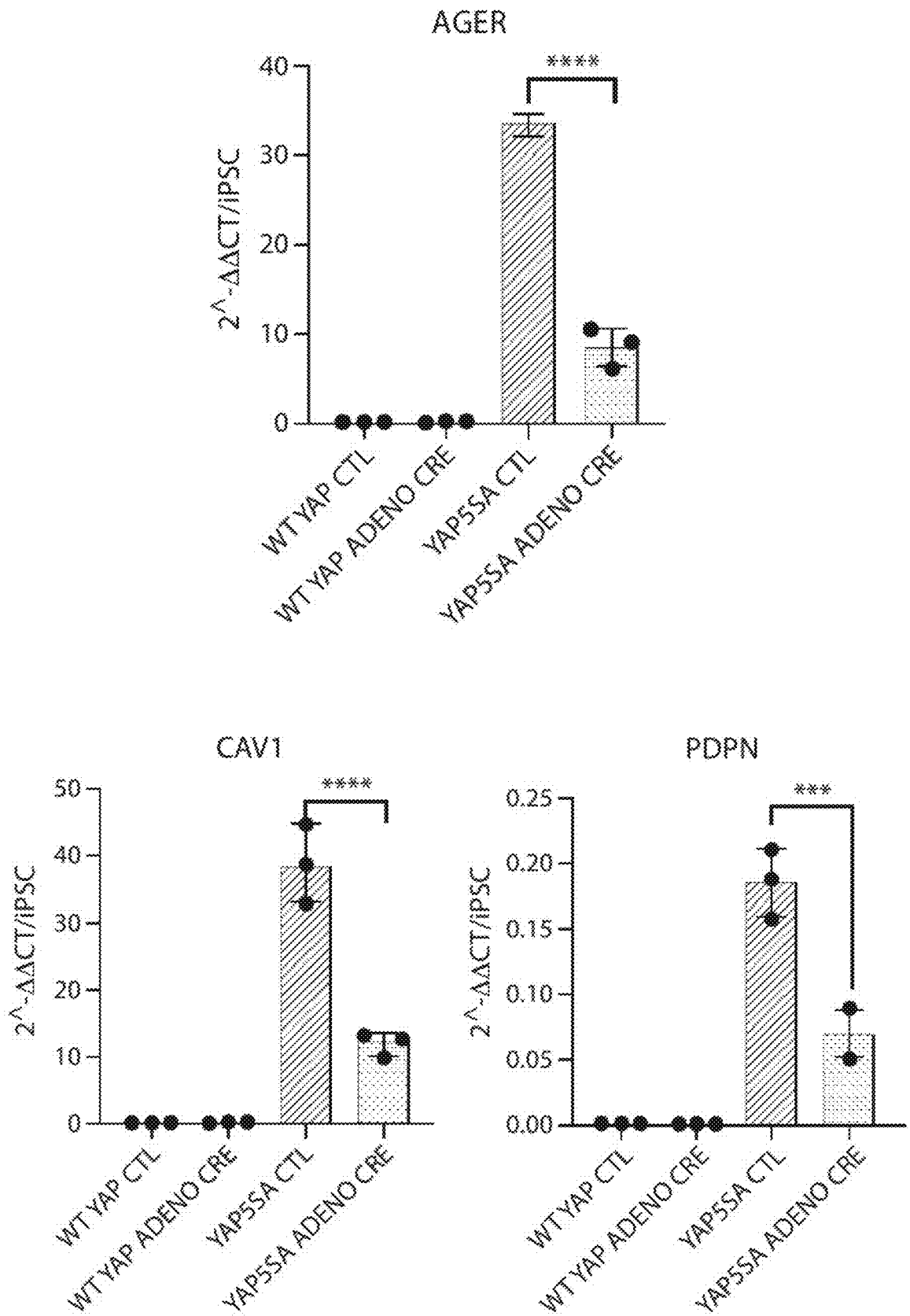

We next sought to determine whether iAT1YAP5SAcells stably maintain this cell program after removal of forced over-expression of YAP5SA. Recent publications indicate that YAP/TAZ KO in murine AT1s leads to a loss of AT1 markers and expression of AT2 markers suggesting a reversion to AT2 cells.[64,65] Since we engineered the lentiviral YAP5SA vector to carry a loxP site in the lentiviral 3'LTR which is copied to the 5'LTR after infection, resulting in a floxed vector after genomic integration (FIGS. 2A, 9B), we employed adenoviral Cre-mediated vector excision (Adeno-Cre) and assayed the phenotype of the resulting cells after removal of YAP5SA (11A). By fluorescence microscopy and flow cytometry, AdenoCre infected cells augmented SFTPCtdTomatoexpression compared to uninfected YAP5SA cells (FIGS. 11B, 11C). Additionally, YAP5SA-AdenoCre infected cells resumed proliferation at rates comparable to WT YAP spheres as quantified by Edu incorporation (FIG. 11C). However, cell counts at this stage were not significantly different between conditions, possibly due to cell loss or toxicity from adenoviral infection as suggested by the WT YAP Adeno-Cre control sample (FIG. 11D). YAP5SA-AdenoCre treated cells decreased expression of YAP downstream targets CTGF and ANKRD1, although not to levels of WT YAP suggesting only partial cre excision. YAP5SA-AdenoCre cells also decreased expression of AT1 markers AGER and CAV1 (although still present) and increased SFTPC expression, reverting to levels similar to WT YAP control iAT2s (FIGS. 11E-11F). Together, this data suggests that AT1-like cells generated through forced activation of nuclear YAP signaling do not exhibit a stable AT1 phenotype, at least when maintained in CK+DCI medium, a condition that has been optimized for iAT2 maintenance.

Development of AGER Reporter iPSC's to Track iAT1s

Figure 4A:
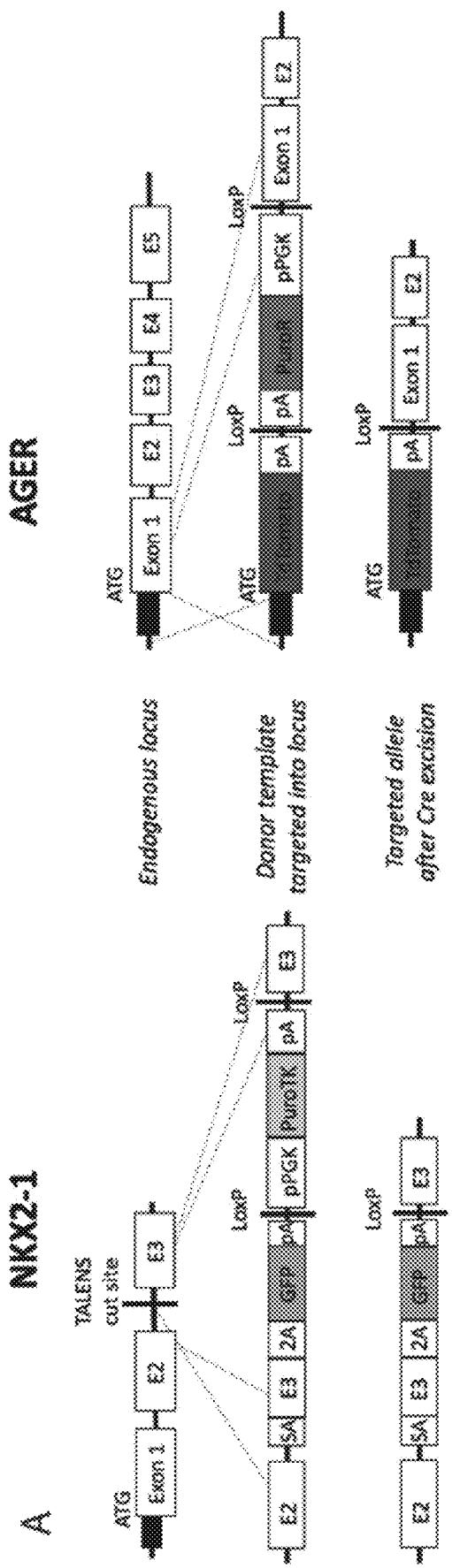
Figure 12A:
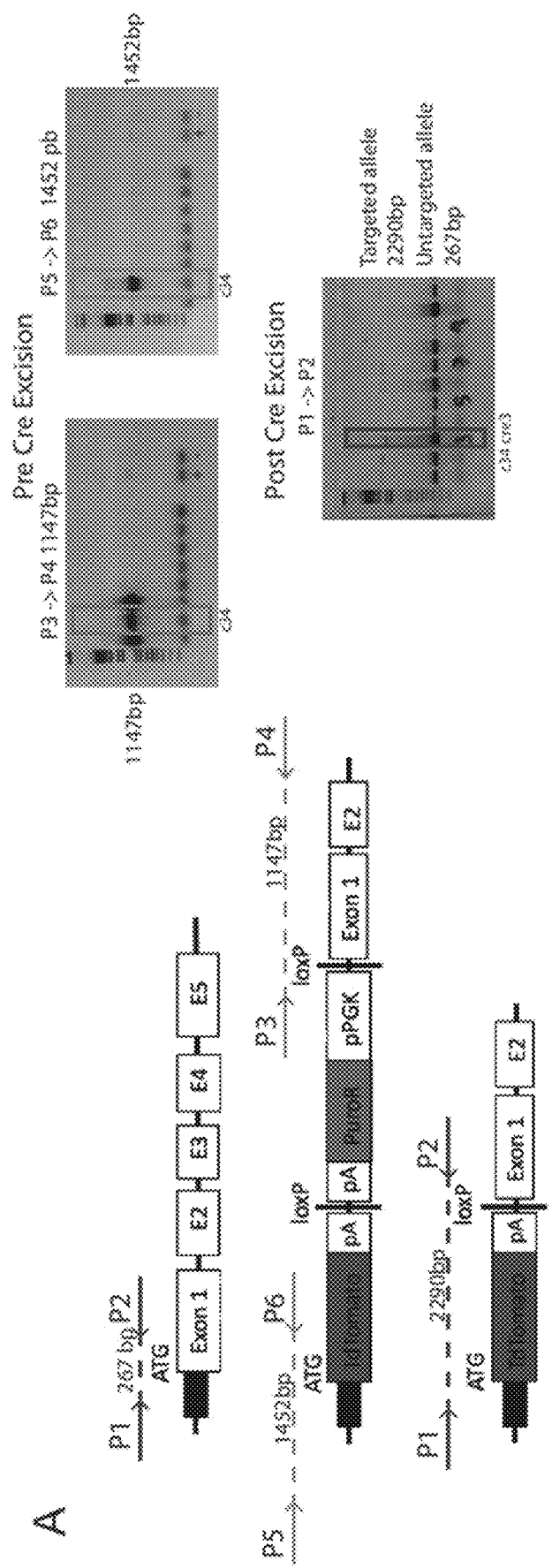
FIGS. 12A-12C depict the NKX2-1GFP/AGERtdTomatodual reporter iPSC line.
Figure 12B:
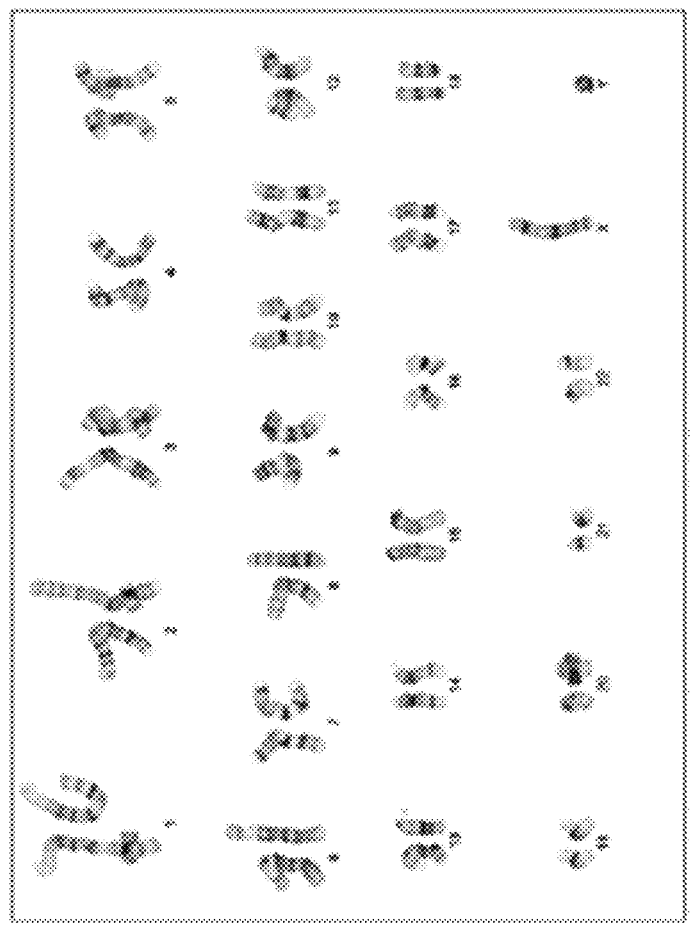

We next sought to engineer a fluorescent reporter to identify, monitor, and purify human iAT1s. Due to its high expression in and specificity to AT1 cells in our human primary single cell dataset (FIG. 1F), AGER was selected as a candidate human AT1 marker locus for reporter targeting. Our lab has previously published the use of gene editing to create an NKX2-1GFPreporter iPSC line (BU3 NG; Hawkins et al. 2017)[24] for the visualization and purification of NKX2-1+ lung epithelial cells. Using CRISPR/Cas9 targeting of iPSCs, we inserted a second fluorophore-encoding cassette, tdTomato, into the start codon of the endogenous human AGER locus of this same line (FIGS. 4A, 12A, 12B), generating a karyotypically normal bifluorescent reporter line carrying NKX2-1GFPand AGERtdTomato, hereafter BU3 "NGAT".

Figure 4B:
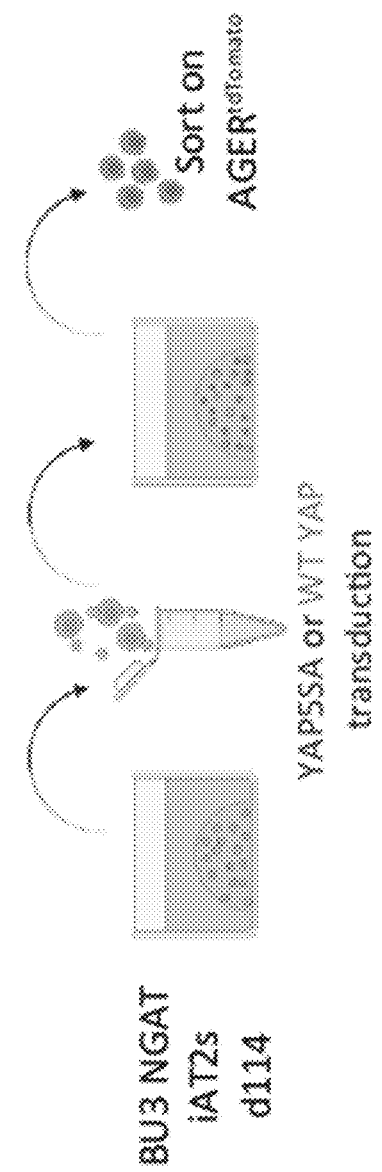
Figure 4C:
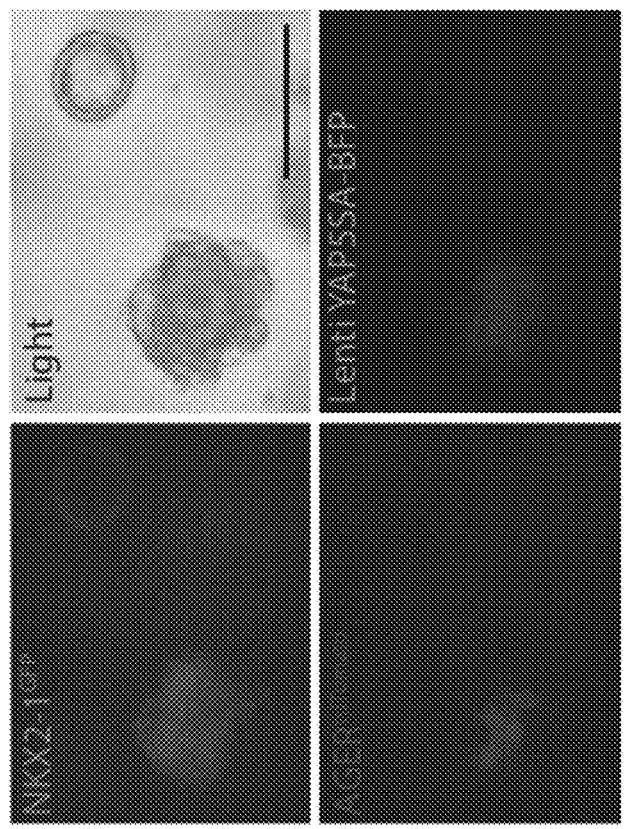
Figure 4E:
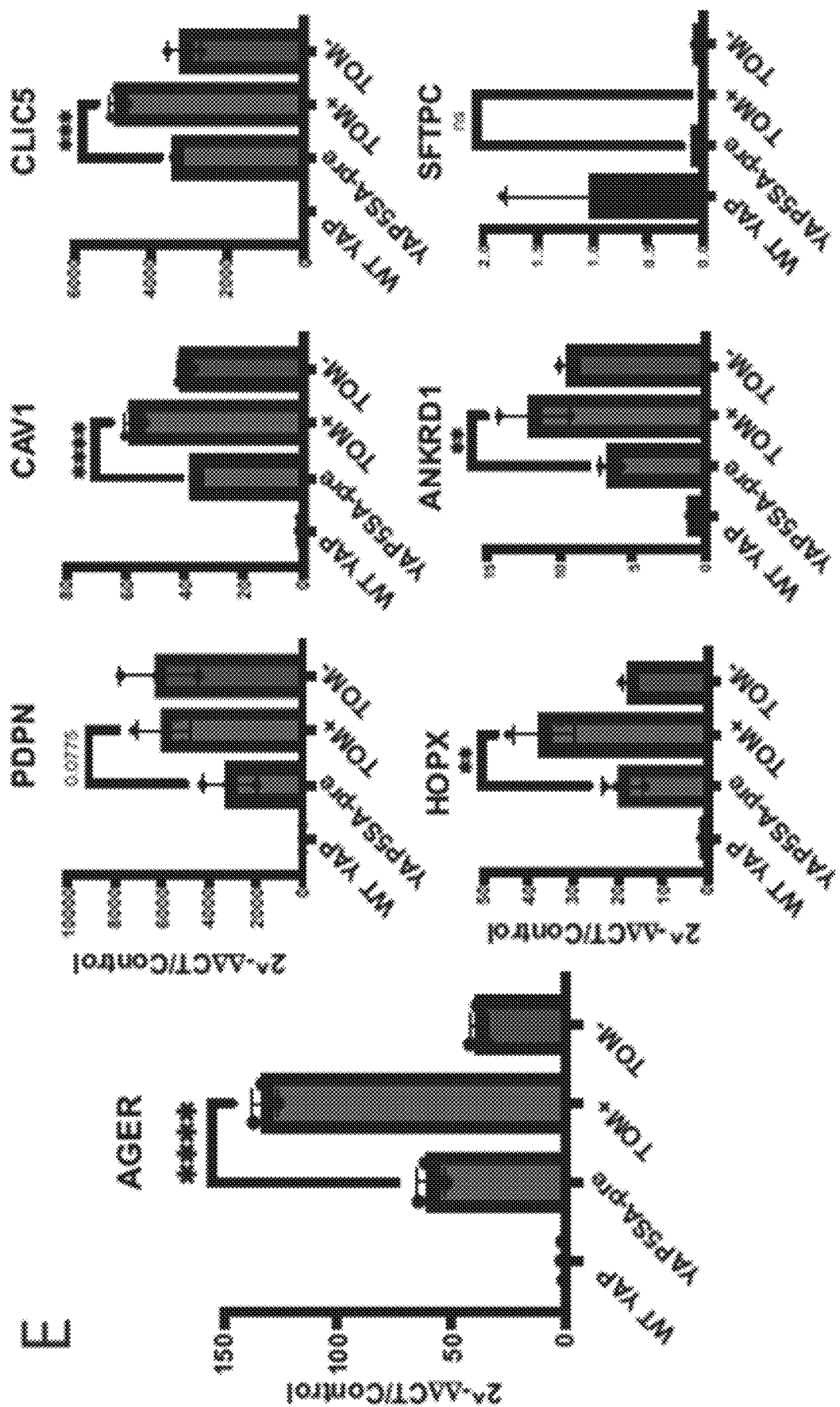
Figure 4F:
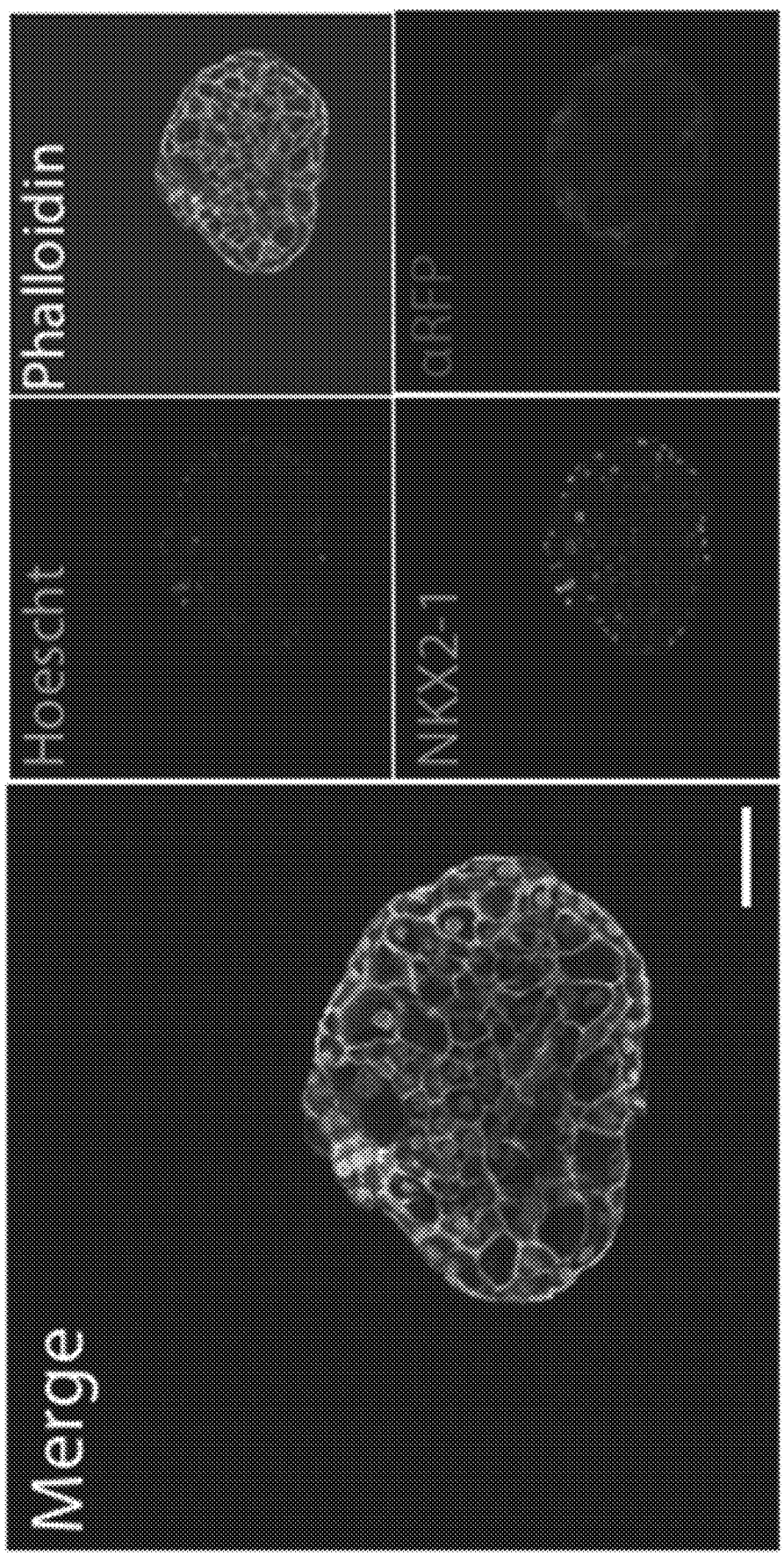
Figure 12C:
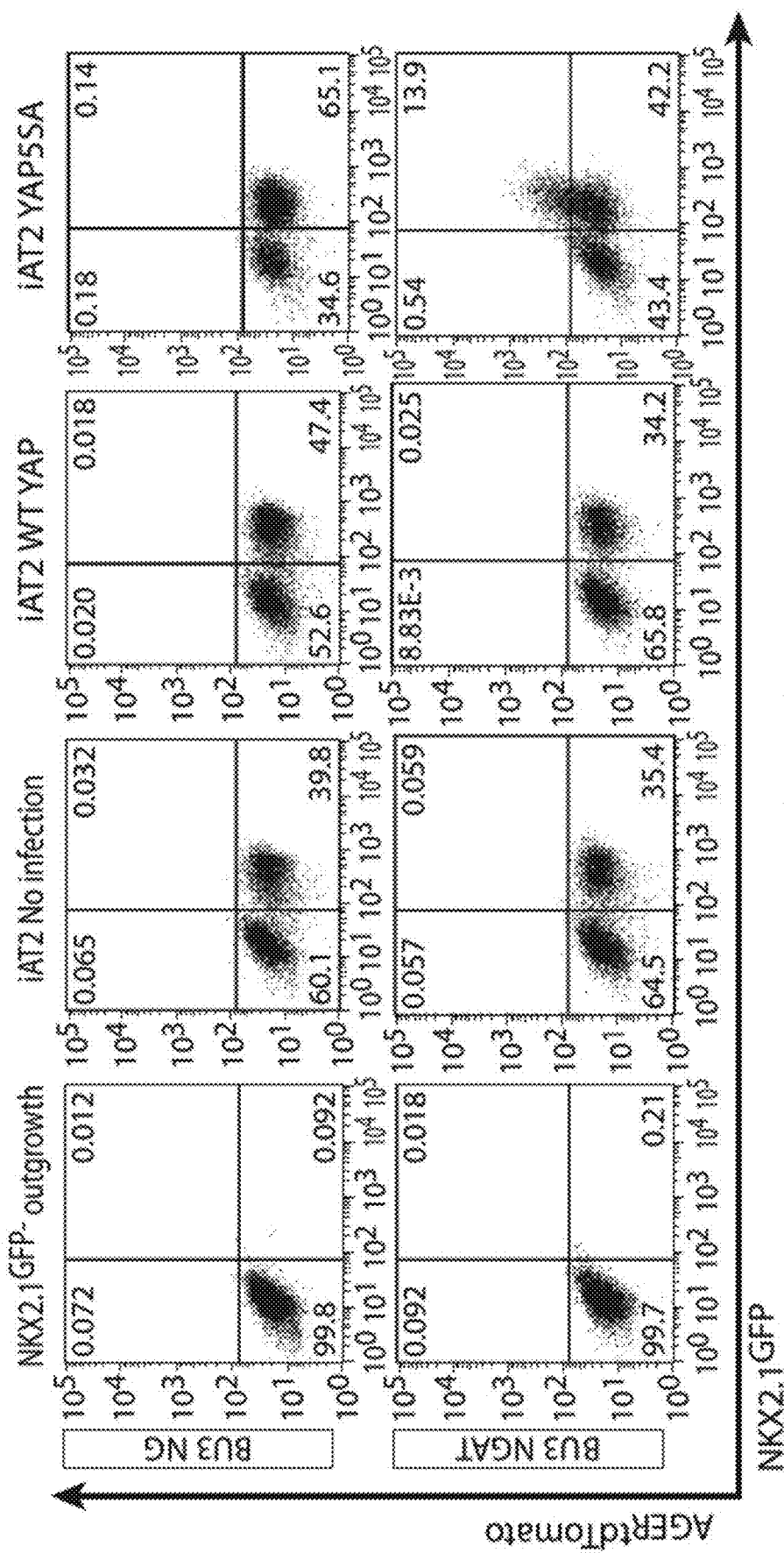

We characterized BU3 NGAT iPSCs after directed differentiation into distal lung epithelium followed by YAP5SA lentiviral transduction (FIG. 4B). Cells transduced with the WT YAP lentivirus did not express tdTomato, while YAP5SA transduced cells expressed AGERtdTomatospecifically in the NKX2-1GFP+ lung epithelial population (FIGS. 4C, 4D). Additionally, the parental BU3 NG line when transduced with YAP5SA showed no tdTomato expression (FIG. 12C). BU3 NGAT-derived AGERtdTomato+ cells were sorted and their expression levels of YAP downstream targets, AT2 markers, and AT1 marker genes were compared to that of YAP5SA-transduced unsorted ("presort") cells, tdTomato-sorted cells, or control unsorted cells from WT YAP transduced samples (FIG. 4E). AGERtdTomato+ cells were enriched in expression of AGER as well as AT1 markers CAV1, PDPN, and CLIC5 (FIG. 4E), suggesting the utility of the reporter to track and sort iAT1s. Immunofluorescence microscopy further confirmed tdTomato protein expression was specific to cells co-expressing nuclear NKX2-1 protein, and the altered clumped organoid morphology observed in YAP5SA transduced SPC2B2 iAT2s was recapitulated in transduced cells derived from the BU3 NGAT line (FIGS. 2A-2G, 4F).

Serum Free Medium-Based Induction of iAT1s

Figure 5A:
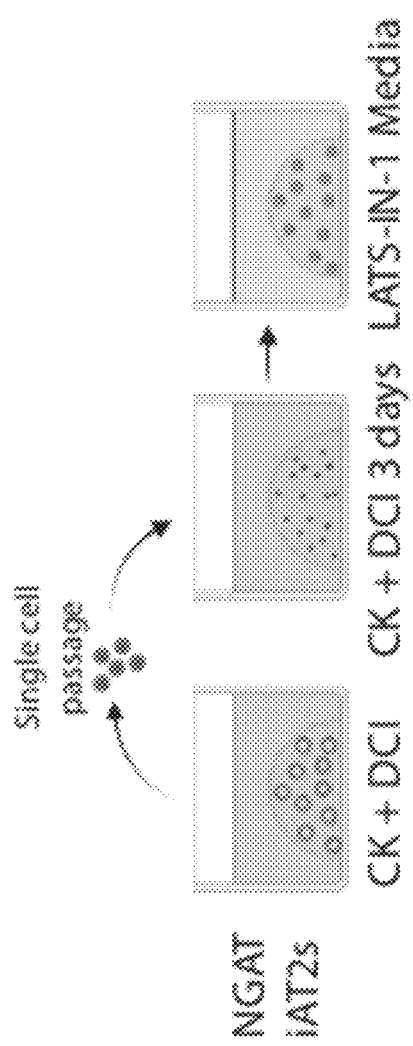
Figure 5B:
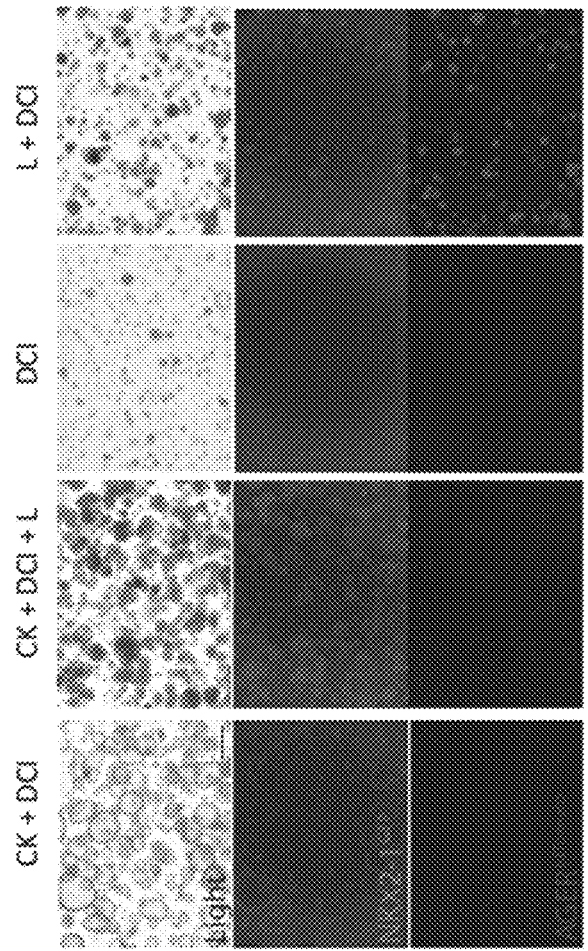
Figure 5D:
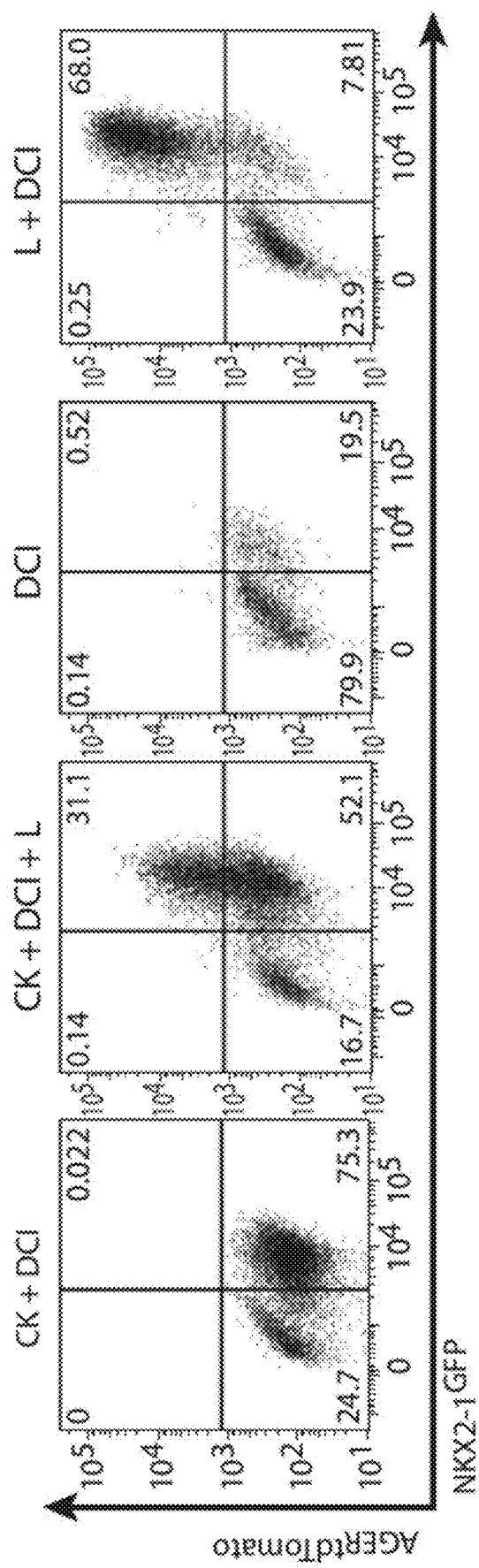
Figure 5E:
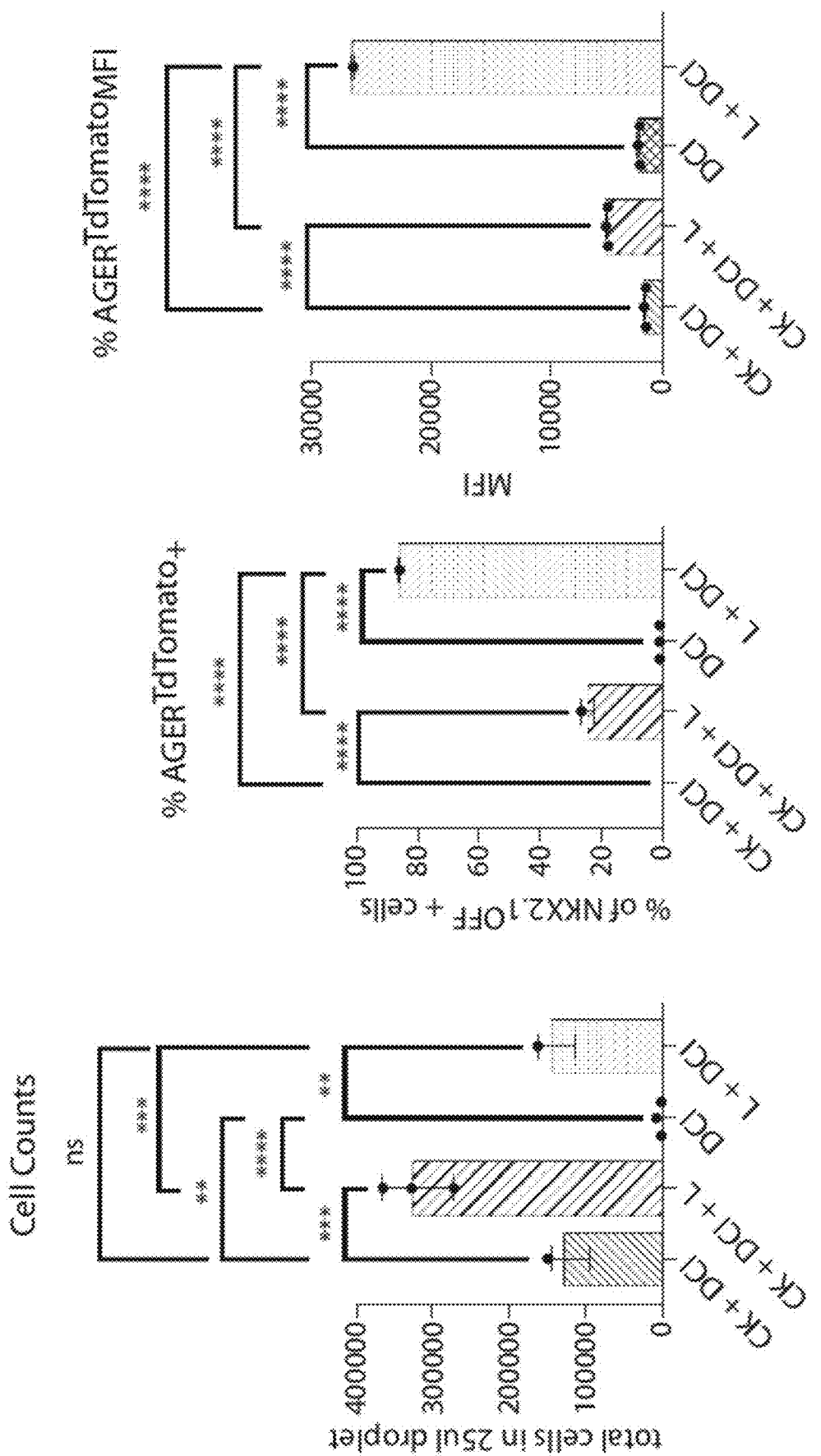

We next sought to identify factors that could be added to a defined medium to recapitulate iAT2 to iAT1 differentiation without requiring lentiviral forced YAP over-expression. Nantie et al have previously used genetic mouse models to show that transgenic over-expression of activated YAP or conditional deletion of the Hippo kinases LATS1 and LATS2 in the developing lung epithelium results in increased expression of mouse AT1 markers, suggesting a role for Hippo-LATS-YAP signaling in AT1 differentiation.[57] More recently, the small molecule LATS inhibitor LATS-IN-1 (hereafter "L") has been shown to drive nuclear YAP in vitro.[66] Thus, we tested the effect of L supplementation on iAT2s cultured with and without the iAT2 supportive growth factors Chir ("C") and KGF ("K") (FIGS. 5A-5E). We found L induced rapid and robust changes in iAT2s including: 1) morphologic changes within 48 hours, resembling those of the YAP5SA-transduced cells, and 2) AGERtdTomatoinduction, detectable within 72 hours in the NKX2-1+ population and increasing over the following 2 weeks to 84.97±1.23% of the NKX2-1GFP+cells in L+DCI (FIGS. 5B-5D). Comparing L supplemented conditions with/without Chir and KGF, the AGERtdTomato expression was brightest and most frequent in wells without Chir or KGF, suggesting inhibitory effects of these growth factors (FIGS. 5B, 5D, 5E). There was little to no AGERtdTomatoexpression observed in cells exposed to DCI without L (FIGS. 5B, 5D, and 5E).

Figure 13A:
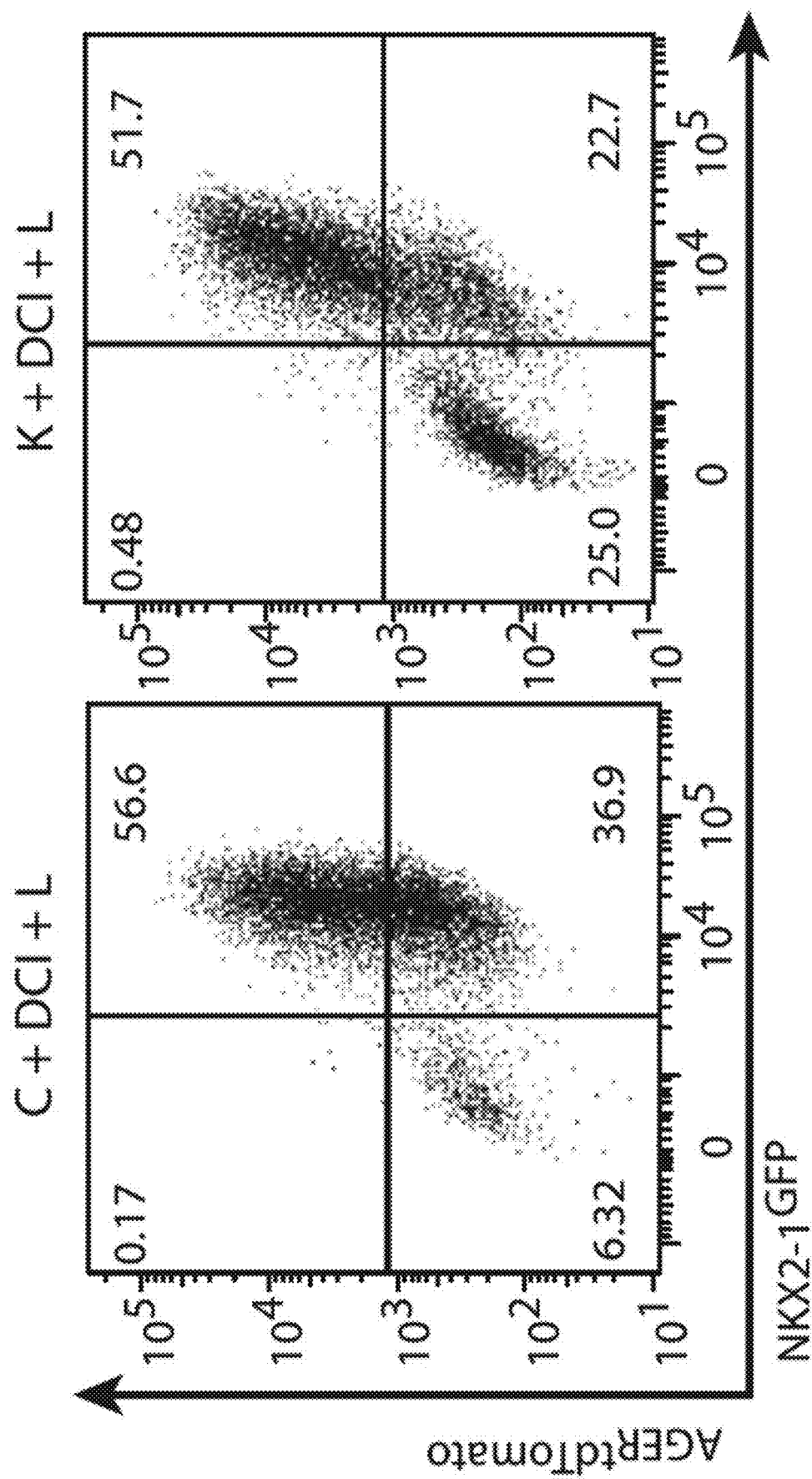
FIGS. 13A-13H demonstrate that both Chir and KGF are inhibitory towards AT1 program induced by both serum-free media and YAP5SA lentivirus.
Figure 13B:
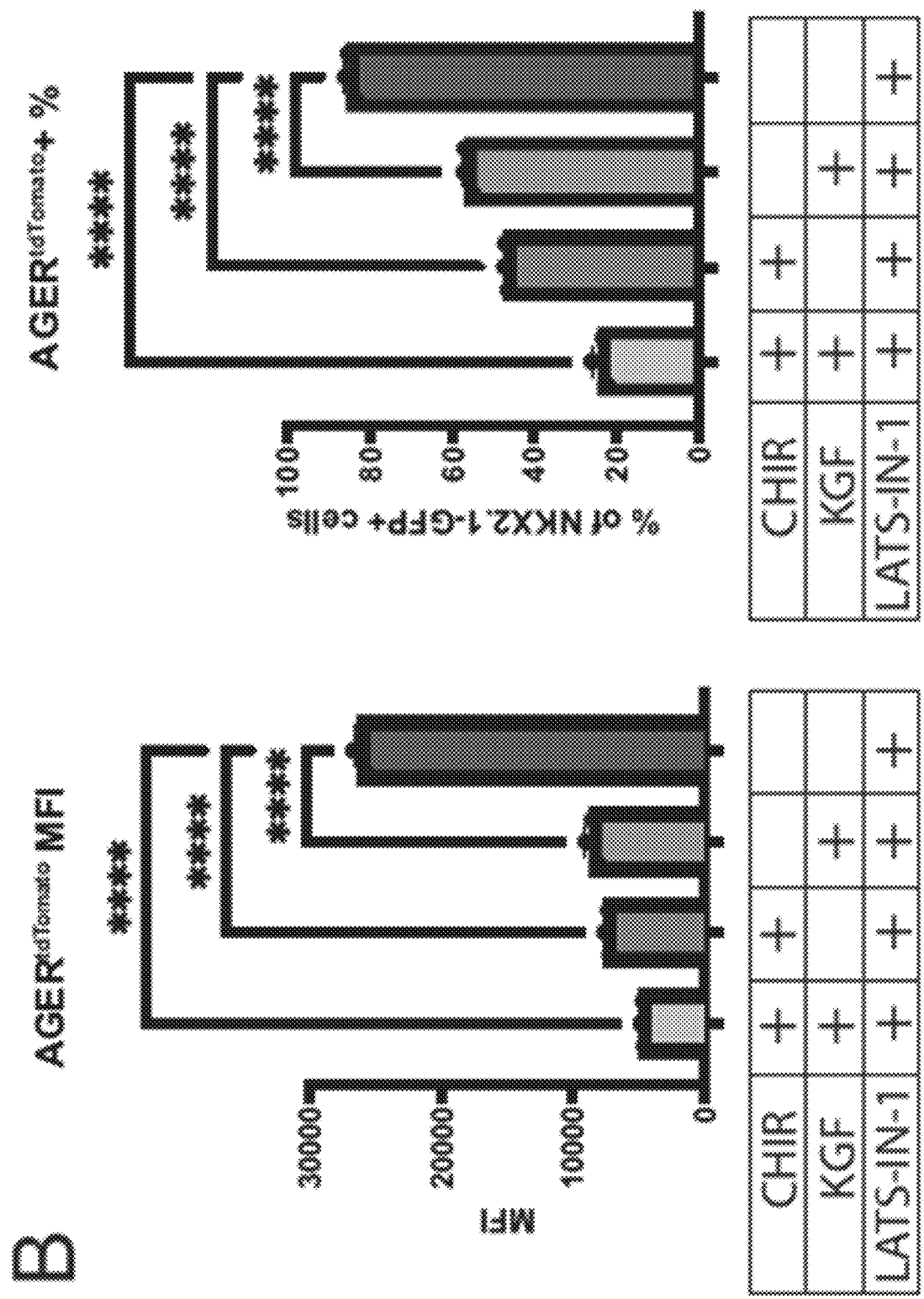
Figure 13C:
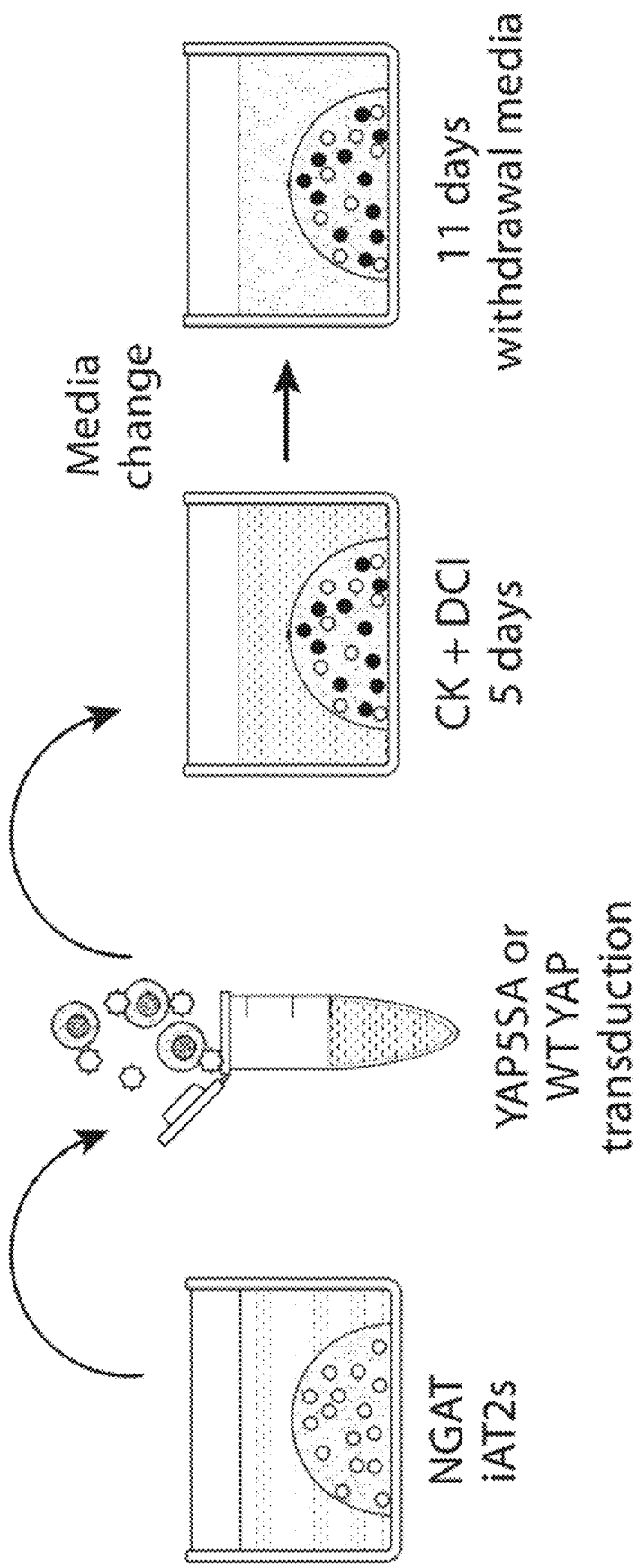
Figure 13D:
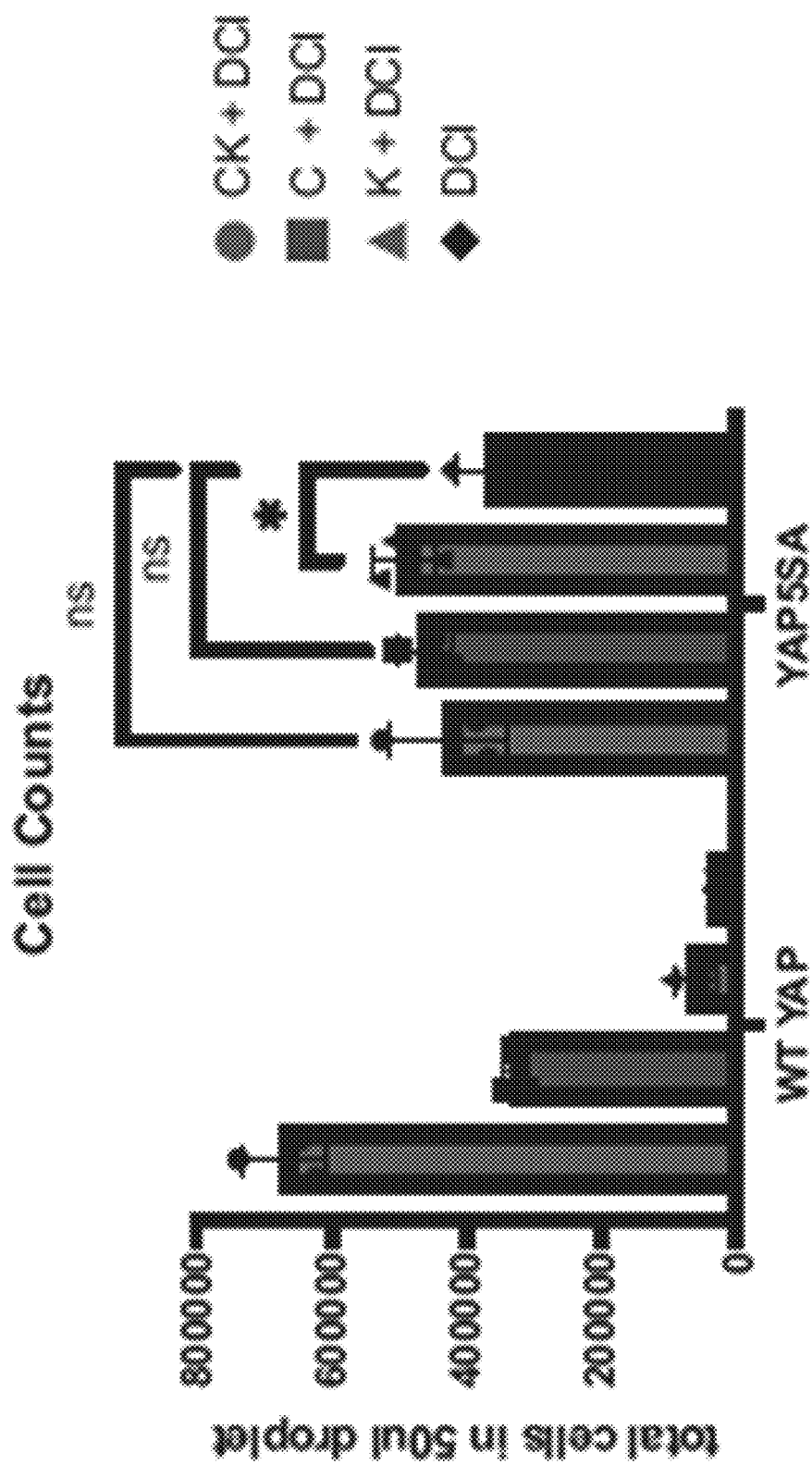
Figure 13E:
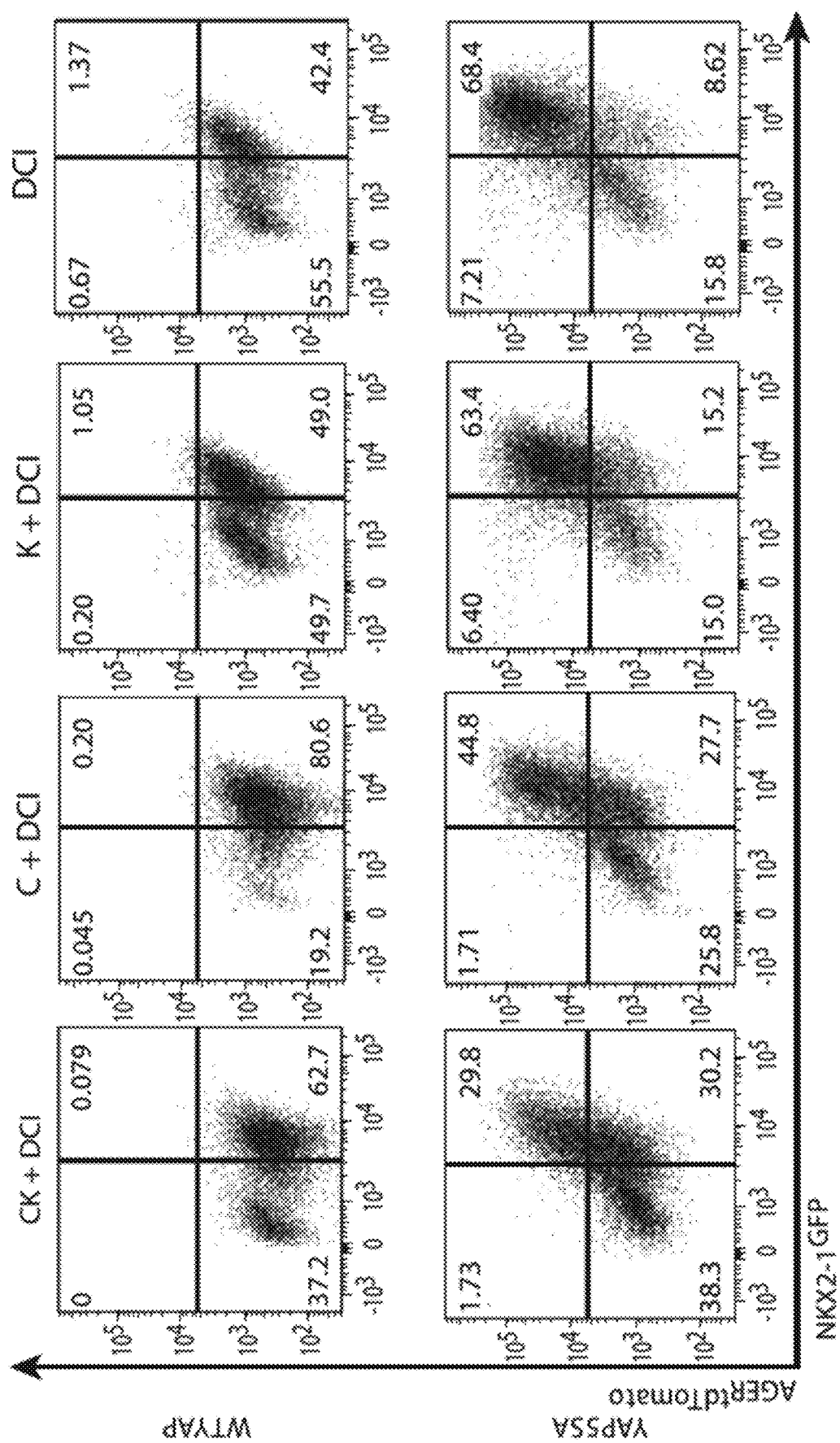
Figure 13F:
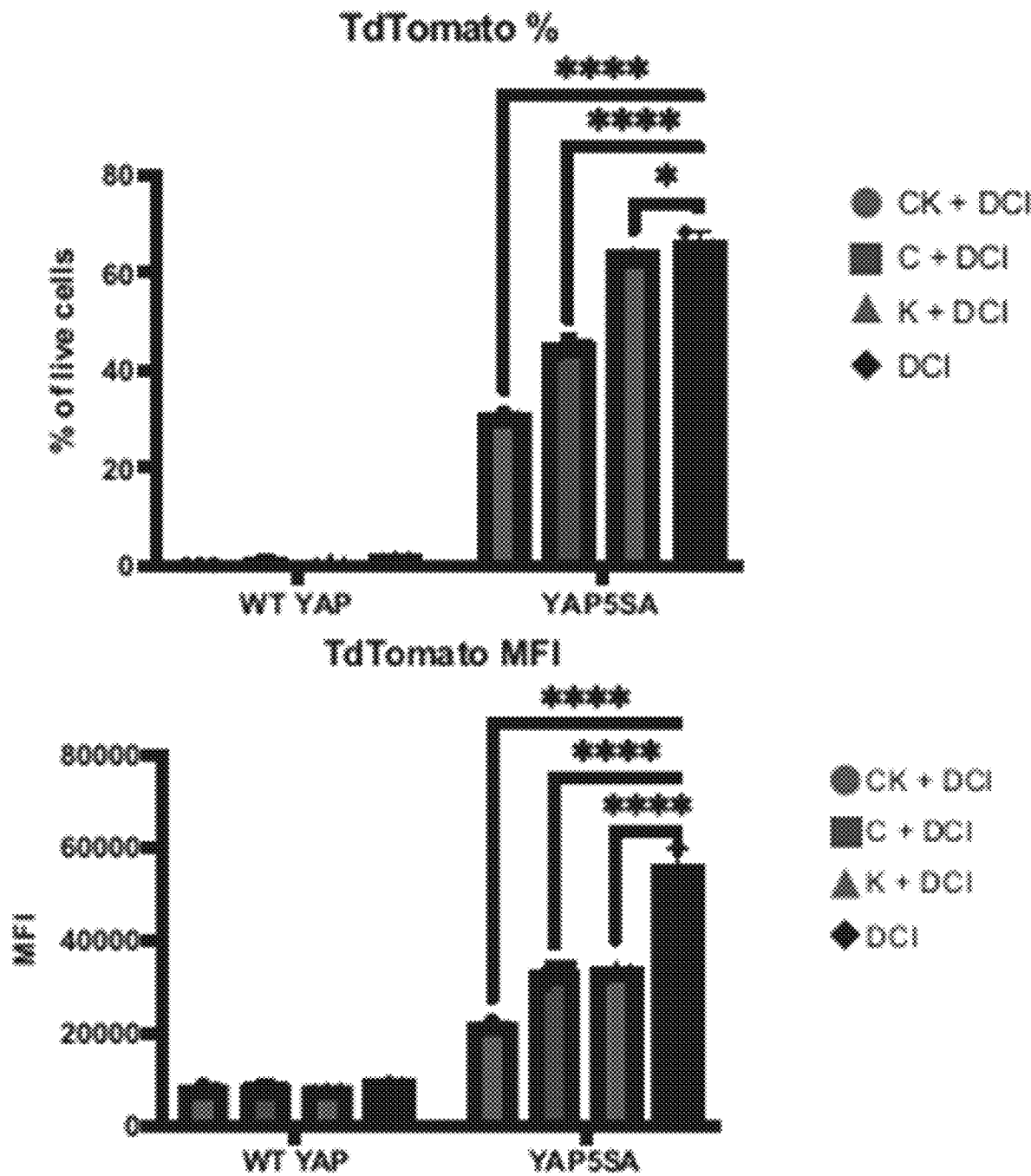
Figure 13G:
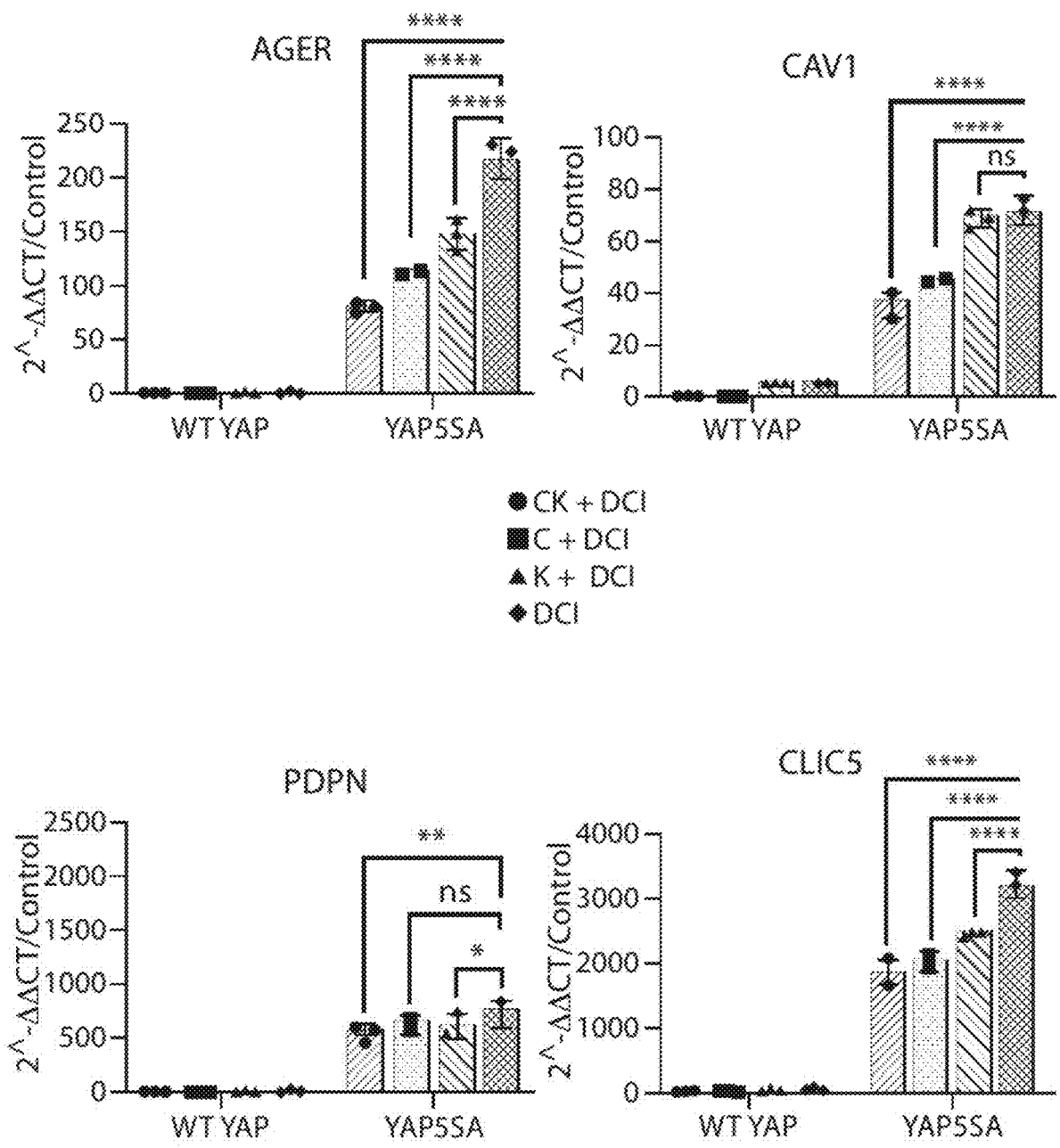
Figure 13H:
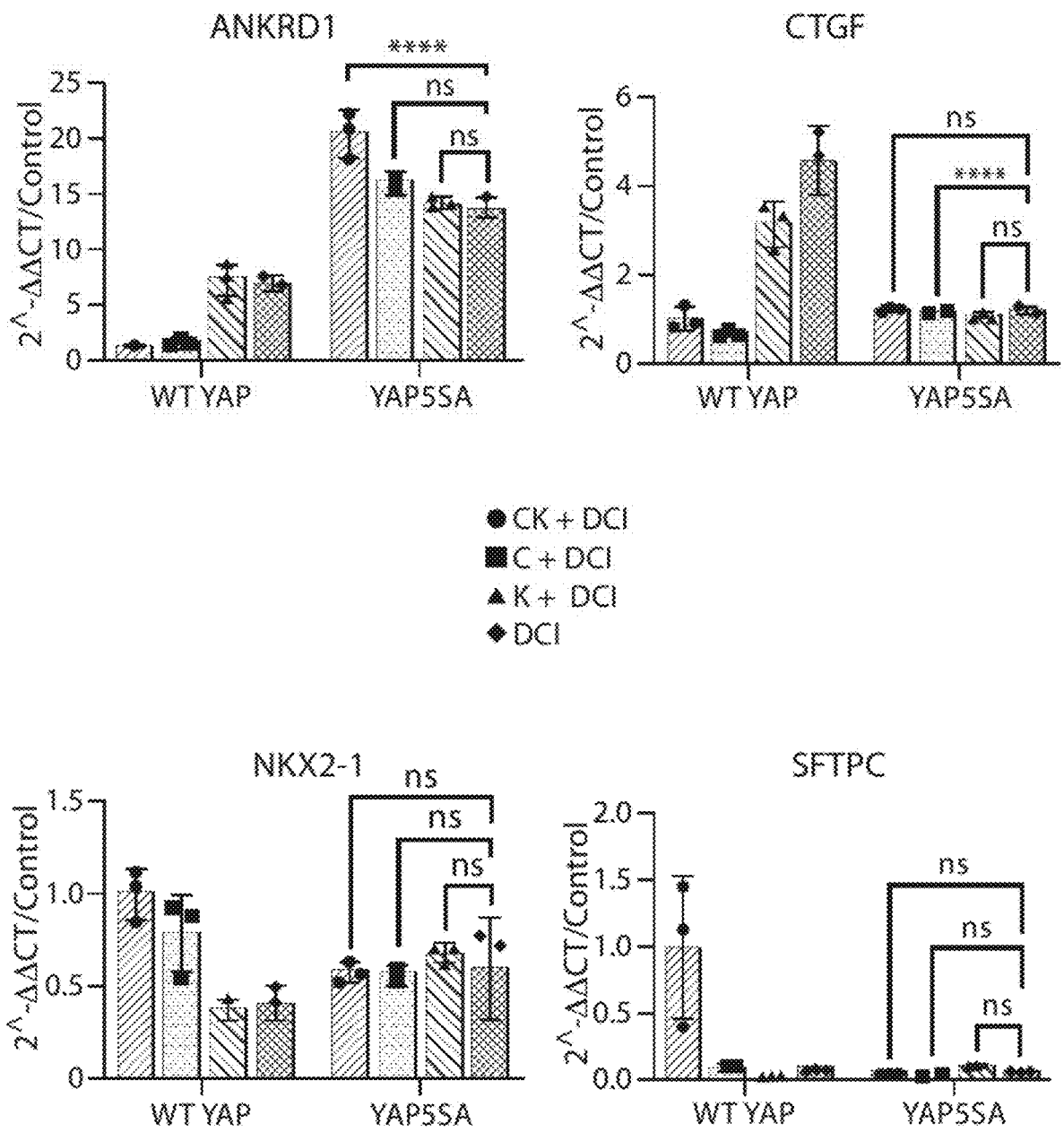

We then examined the individual effects of Chir and KGF in inhibiting AGERtdTomatoin media containing L and saw that both were significantly inhibitory to both AGERtdTomatopercentage and MFI (FIGS. 13A, 13B). To test whether this was specific to the LATS inhibitor media-based differentiation, we also tested withdrawal of each of these factors in our YAP5SA differentiation model. We saw inhibitory effects of both molecules on AGERtdTomatoas well as AT1 markers by bulk RT-qPCR, suggesting both Chir and KGF need to be removed for the efficient differentiation of iAT1s (FIGS. 13C-13H). This is consistent with prior publications suggesting canonical Wnt or KGF signaling are inhibitory to expression of the AT1 program.[6,20,43]

Figure 5F:
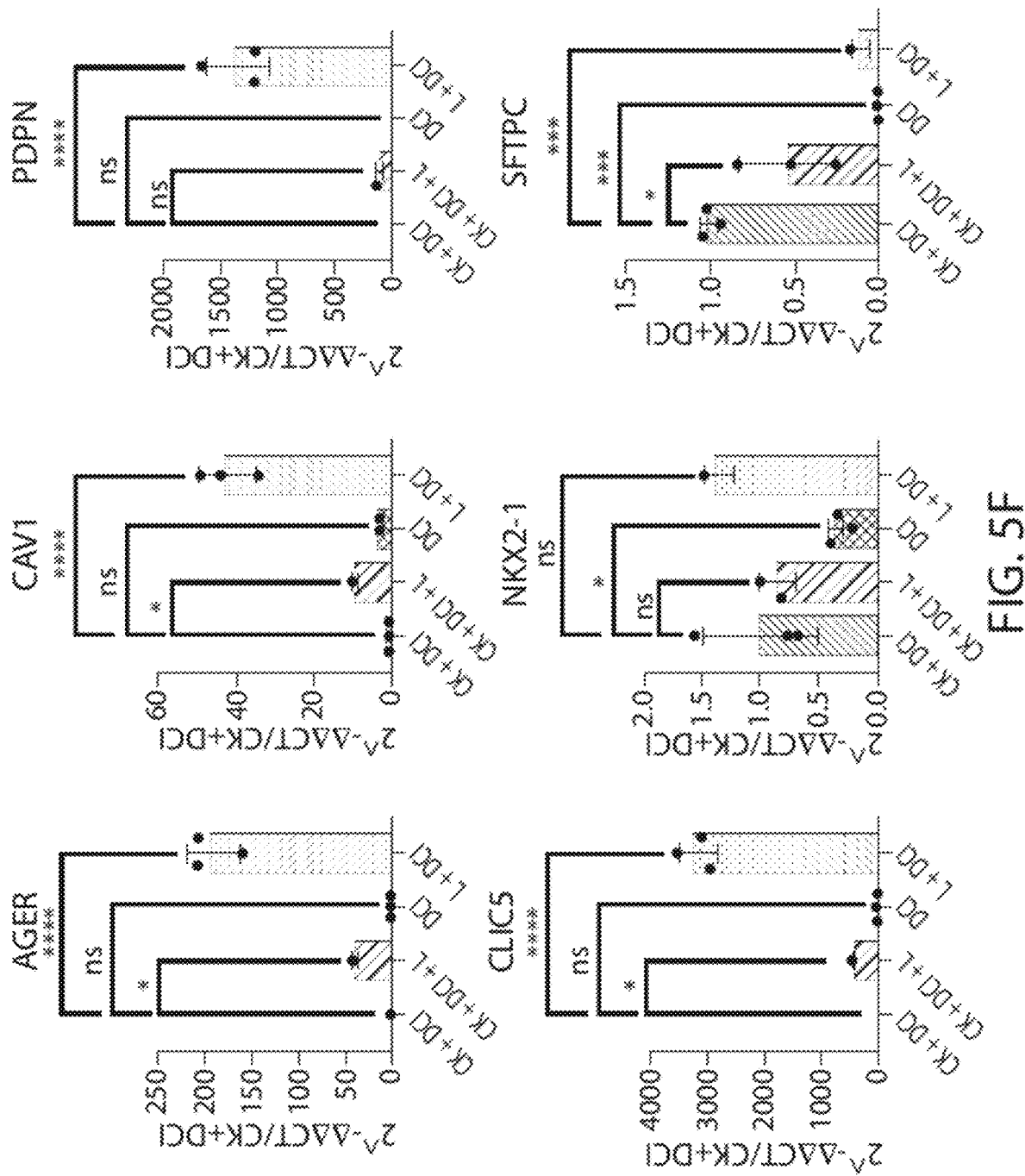
Figure 5G:
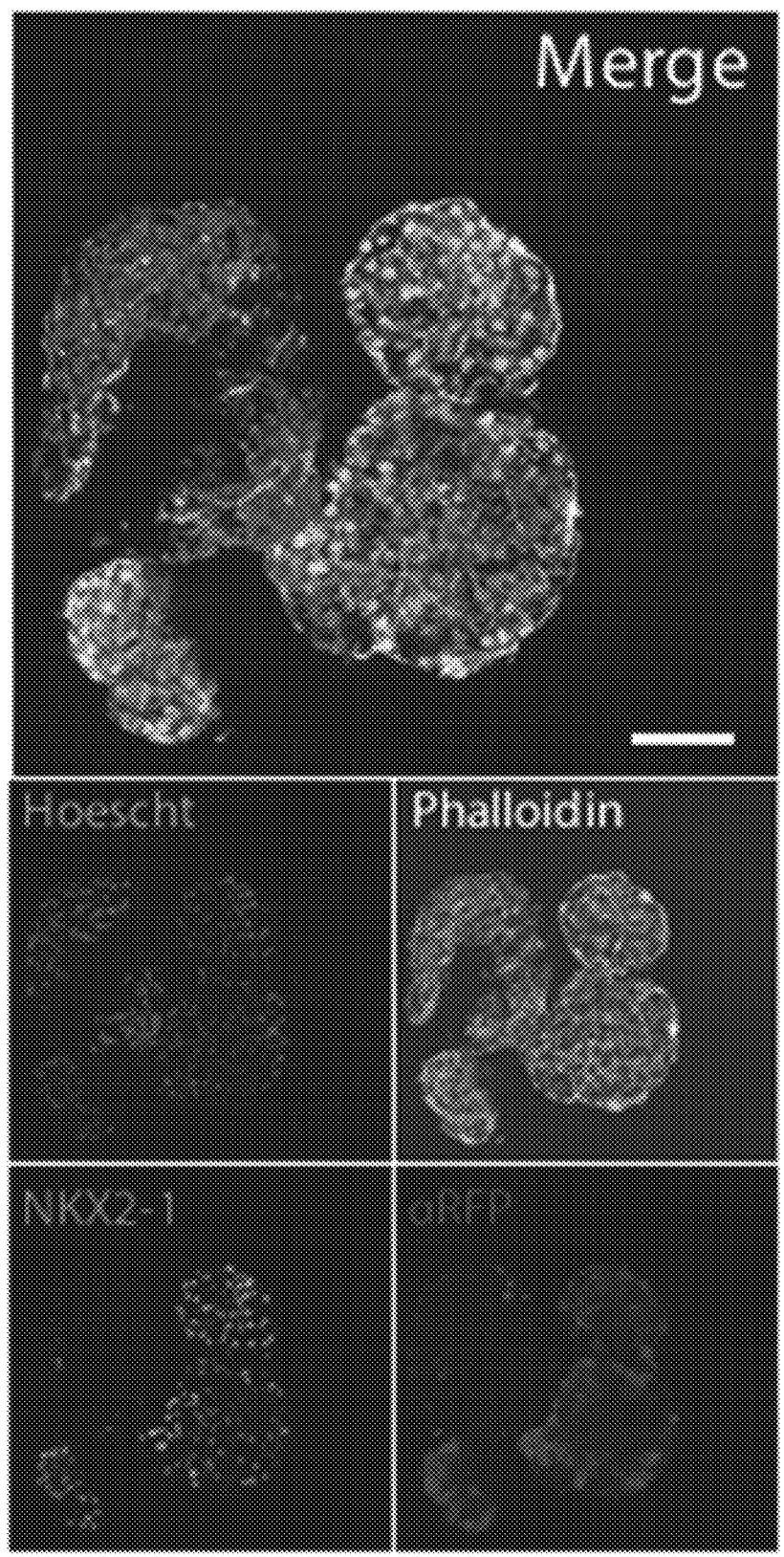
Figure 14A:
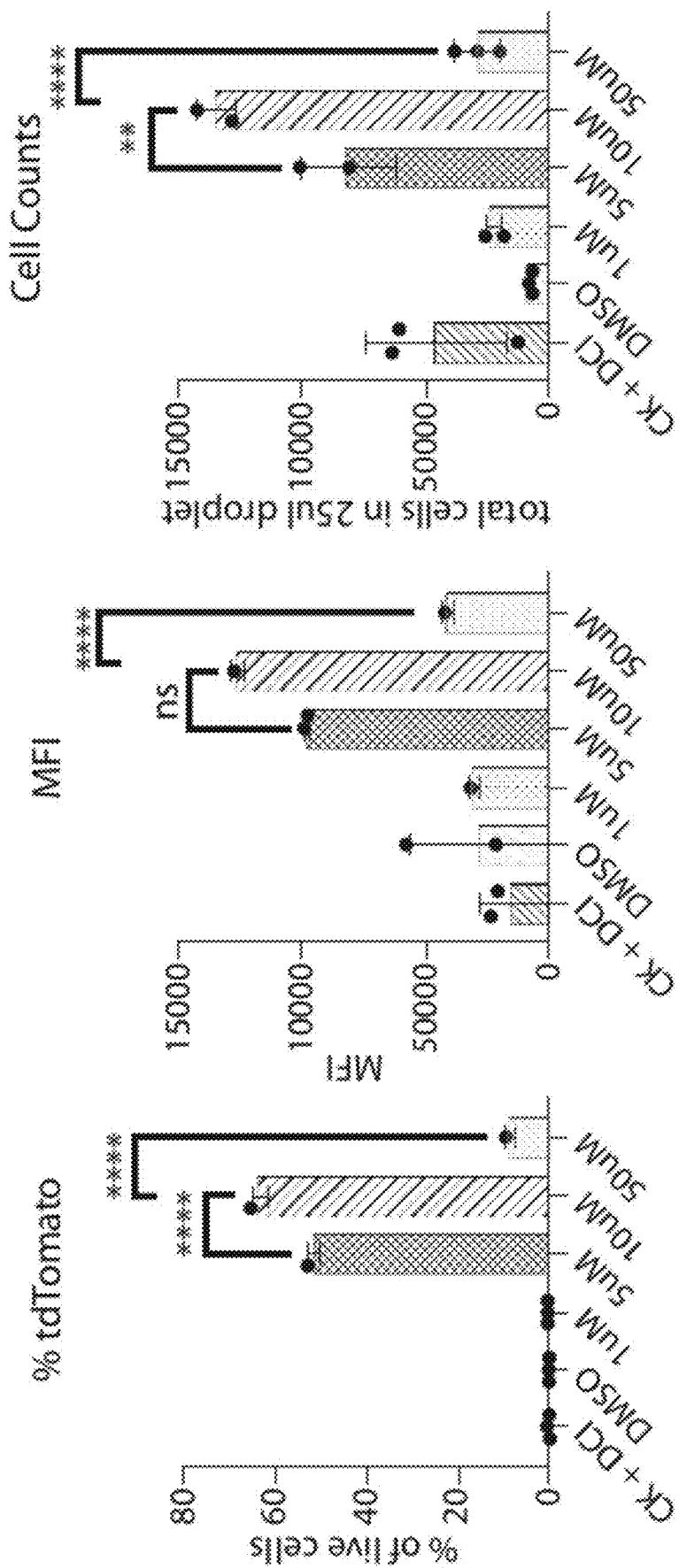
FIGS. 14A-14G depict optimization of LATS inhibitor-containing media for iAT1 induction.
Figure 14B:
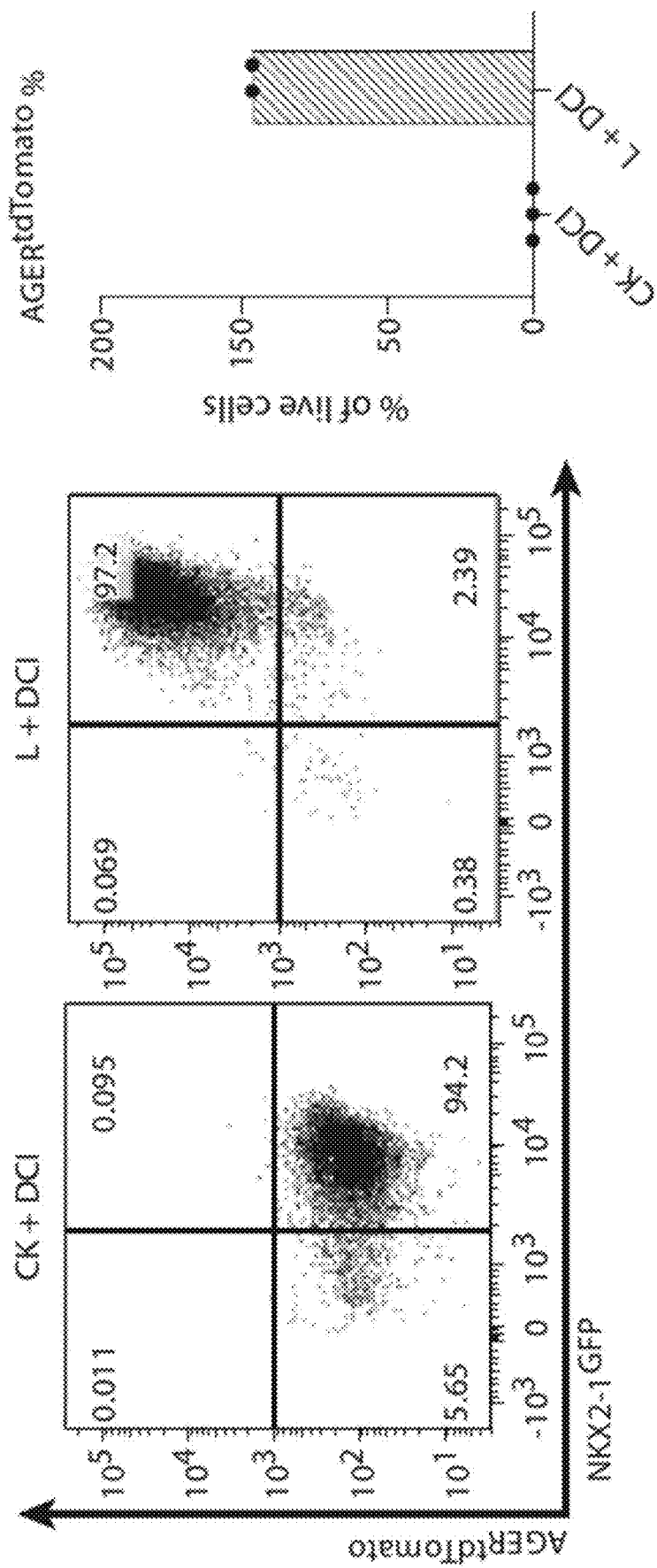
Figure 14C:
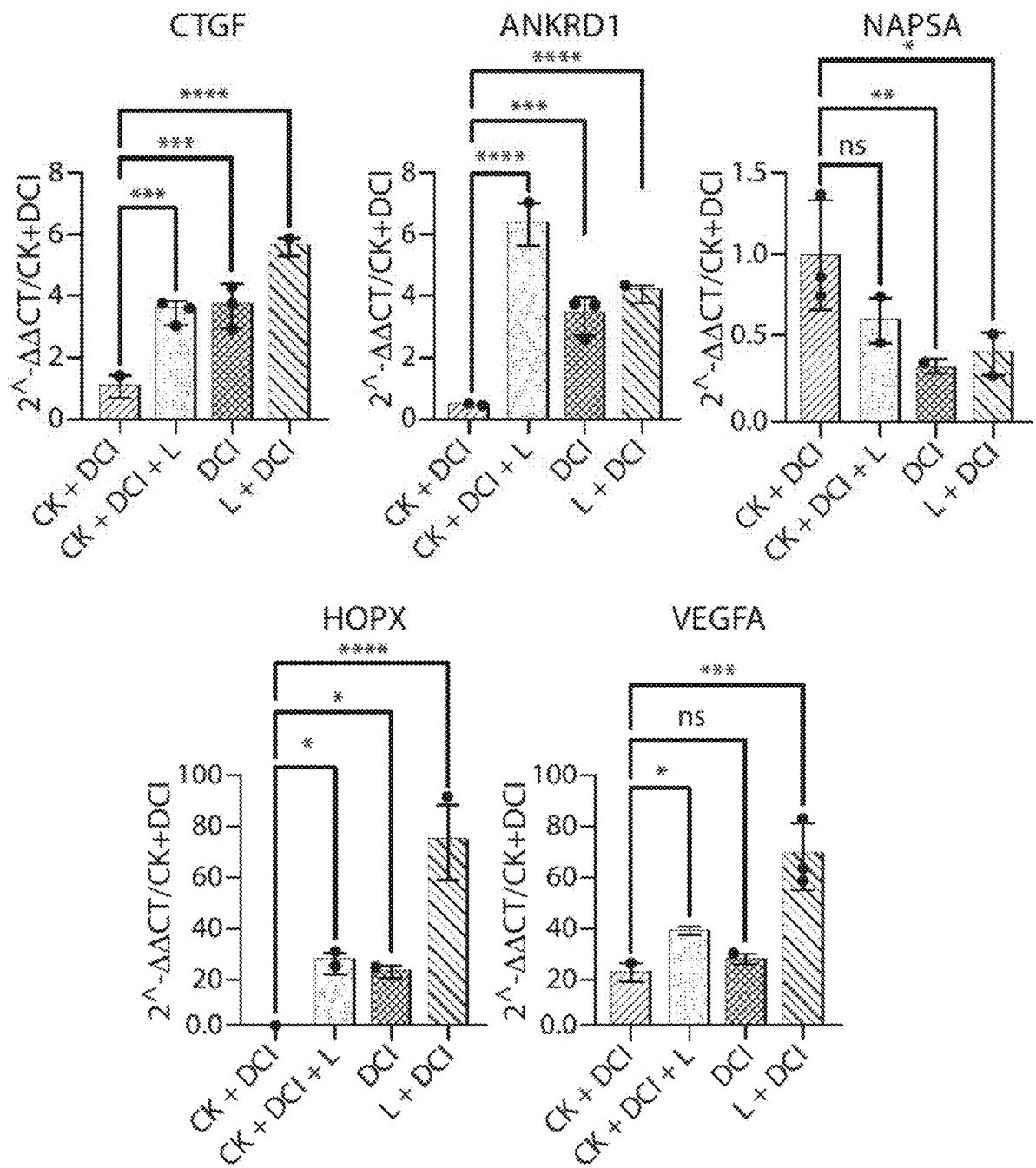
Figure 14D:
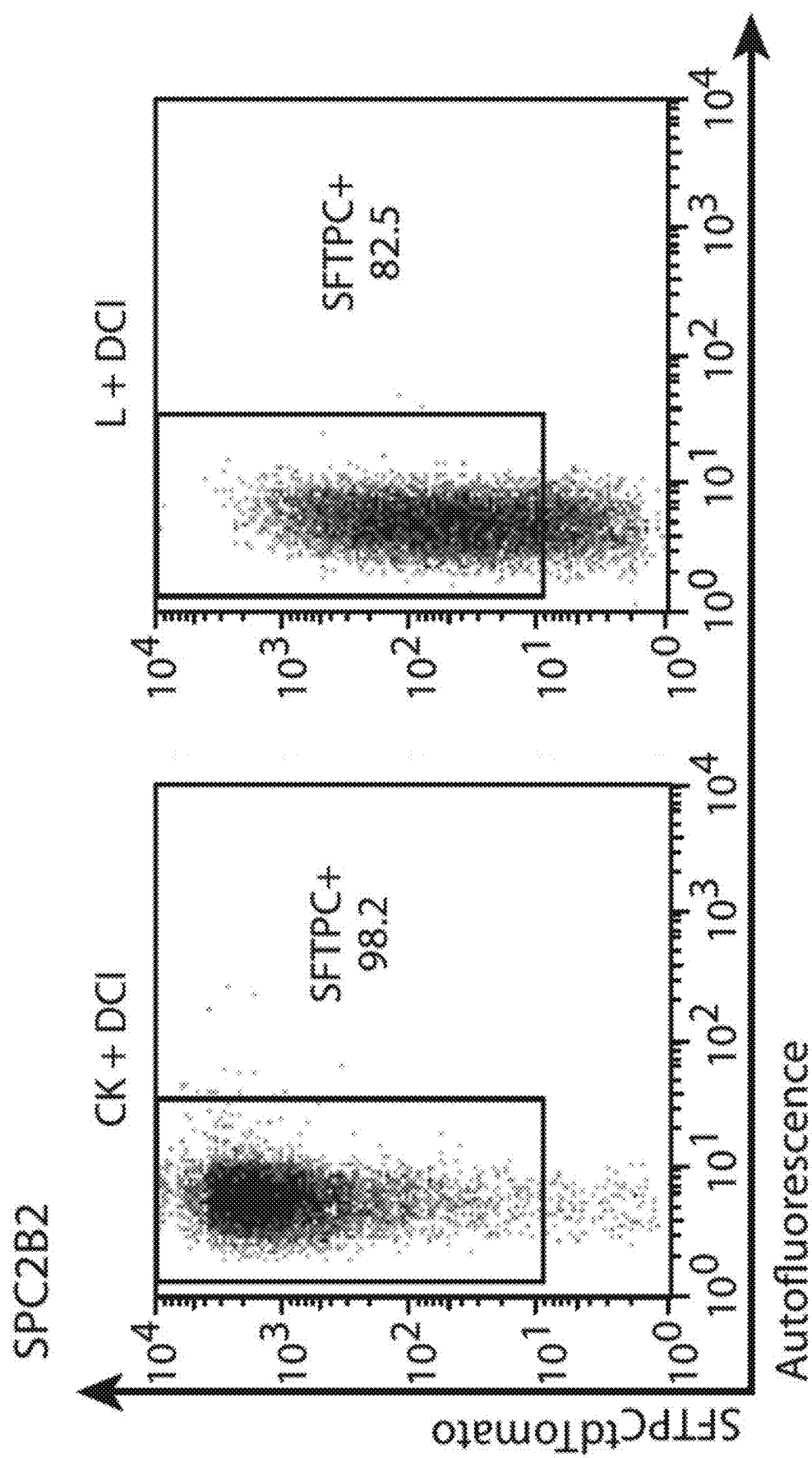
Figure 14E:
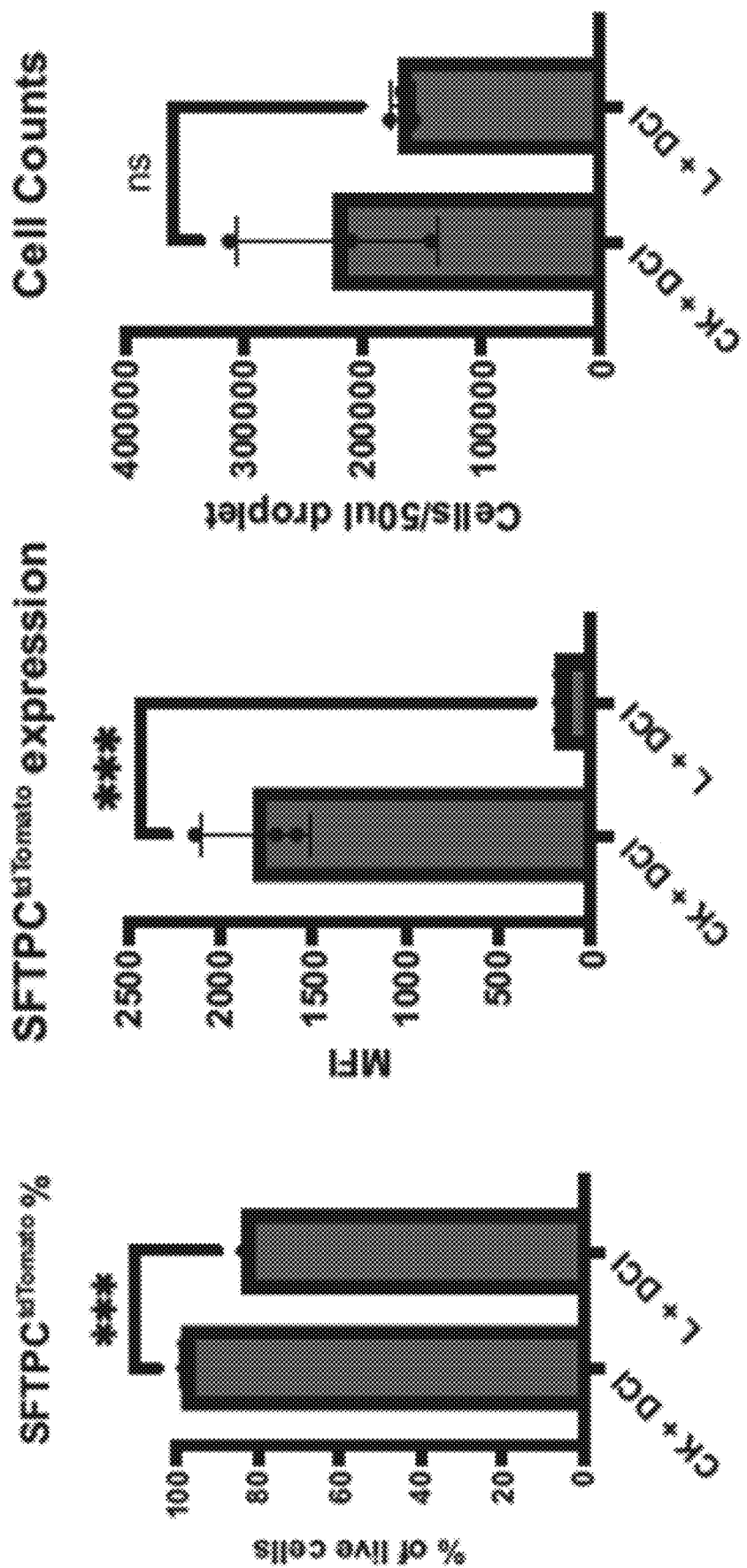
Figure 14F:
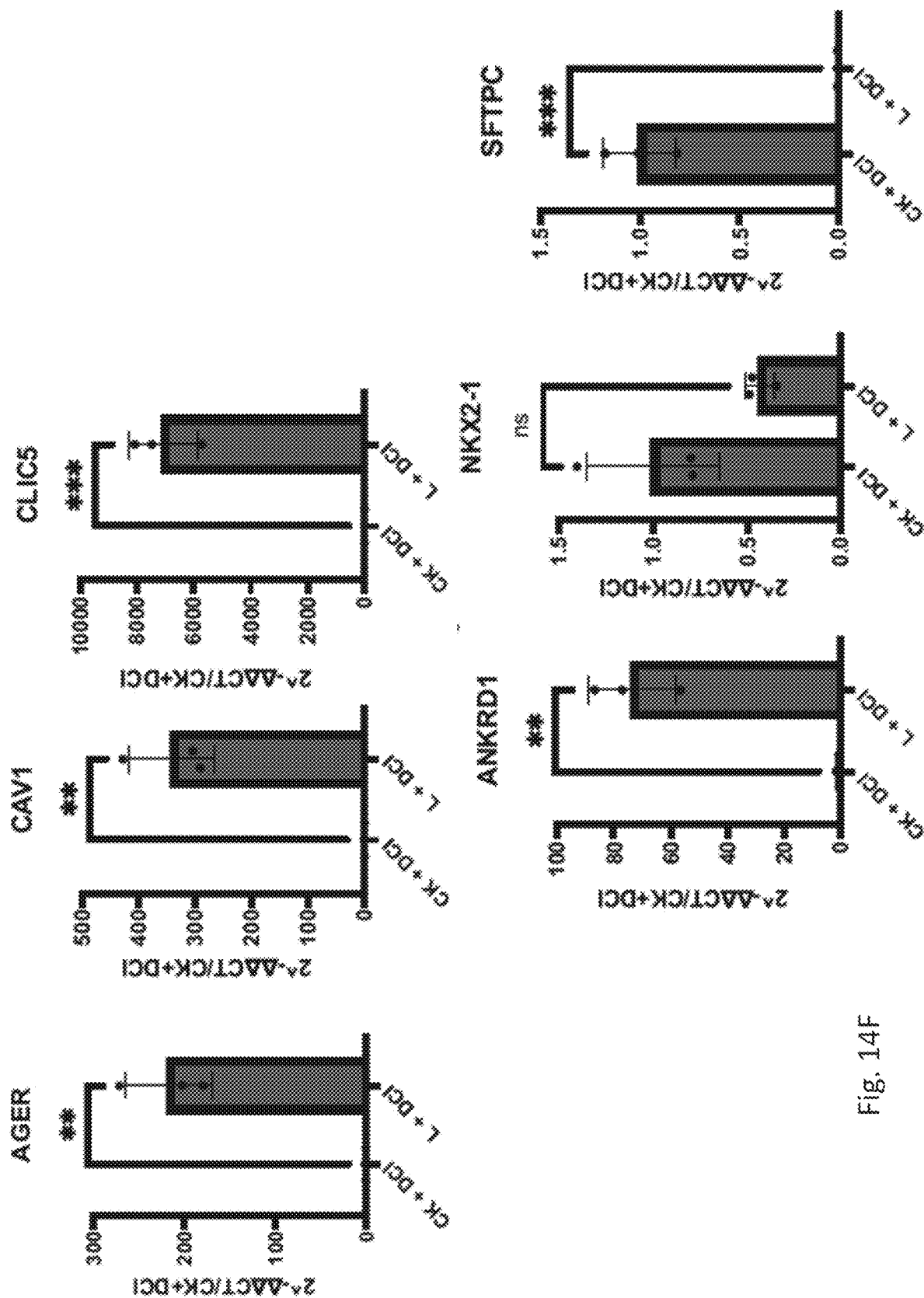

After dose response testing to identify an optimal dose of L, replacing the CK+DCI medium on day 3 after passaging iAT2s with a medium consisting of L+DCI using a 10 uM dose of LATS-IN-1, yielded the greatest frequency and brightness (MFI) of NKX2-1GFP/AGERtdTomato+ cells 2 weeks post passage (FIG. 14A). When NKX2-1GFP+ cells were resorted to purify the lung epithelial population and exposed to L+DCI beginning 3 days post sort, up to 97% of all cells were AGERtdTomato+ by day 14 (FIG. 14B). By whole well RT-qPCR, AGER, CAV1, PDPN, and CLIC5 were significantly upregulated in wells containing the LATS inhibitor, consistent with induction of a broad AT1 program, with higher levels expressed in conditions without KGF and Chir (FIGS. 5F, 14C). NKX2-1 remained unchanged between iAT2 media and medias containing LATS-IN-1, suggesting maintenance of the lung epithelial program, whereas SFTPC was decreased (though not entirely absent) indicating downregulation of the AT2 program (FIGS. 5F, 14C). Similar trends were seen in SPC2B2 iAT2s grown in L+DCI (FIGS. 14D-14F). Immunostaining showed similar organoid shape to that of YAP5SA-transduced organoids, with AGERtdTomatoonly being expressed in NKX2-1+ cells (FIG. 5G). Taken together these results indicate that treatment with the LATS inhibitor, L, in the absence of Chir and KGF efficiently differentiates iAT2s into iAT1s.

Figure 14G:
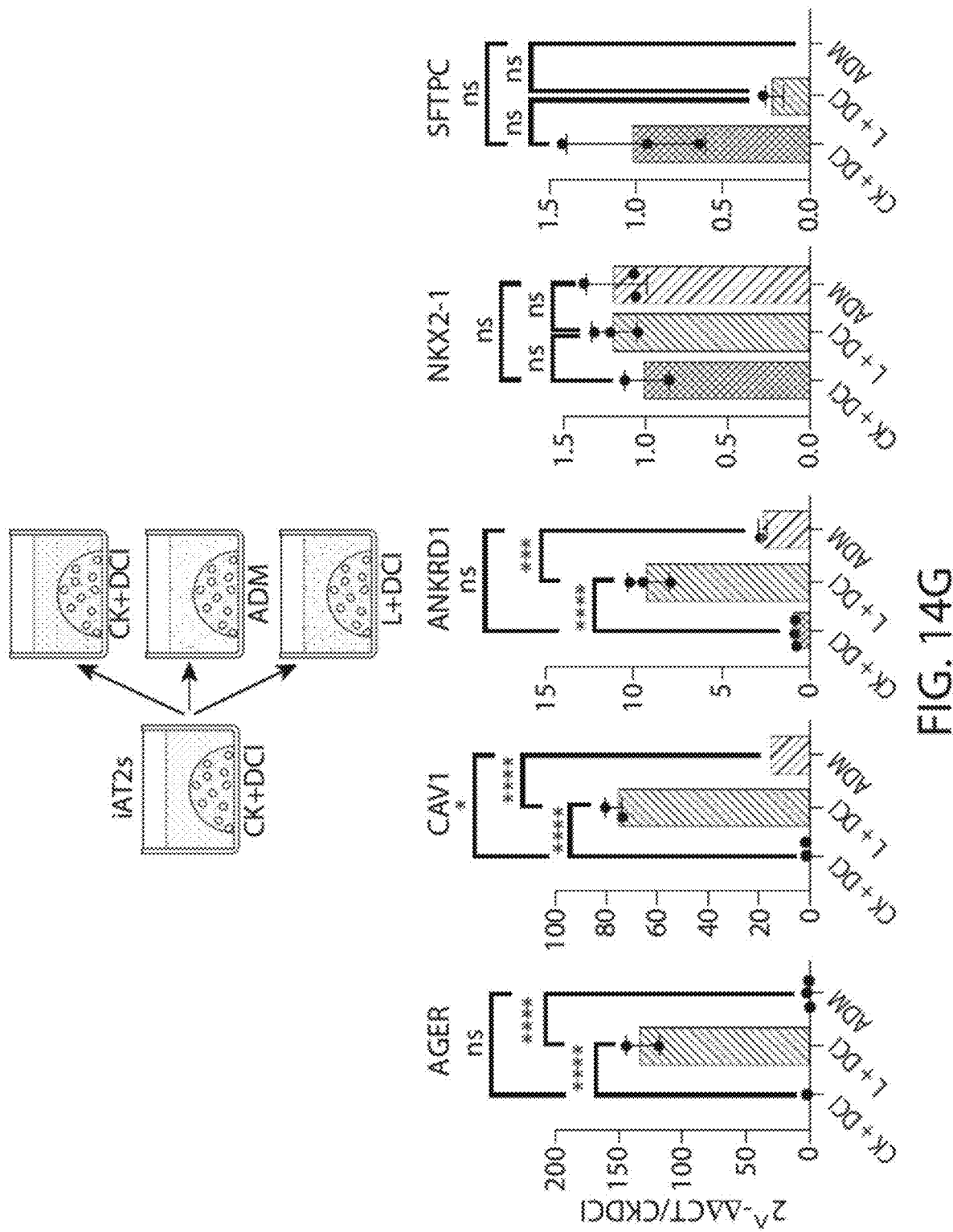

To determine whether L+DCI medium similarly induces the AT1 program in primary adult human AT2s, we first culture-expanded primary AT2s in serum-free, feeder-free conditions (SFFF) as reported.$_5$ After seven days in SFFF, medium was either continued as SFFF or switched to published human serum-containing Alveolar Differentiation Medium (ADM) or L+DCI. Seven days later. NKX2-1 expression was similar for all conditions, while AGER was significantly upregulated in both L+DCI and ADM conditions and was not significantly different between the two media. CAV1 and ANKRD1 expression was higher in L+DCI than ADM, suggesting this differentiation medium is effective in the differentiation of primary human AT2s into AT1s (FIG. 5H). In repeat tests using iAT2s instead of primary AT2s, only L+DCI and not ADM promoted iAT1 differentiation based on low induction of CAV1 in response to ADM and no induction of AGER or ANKRD1 (FIG. 14G).

Figure 5I:
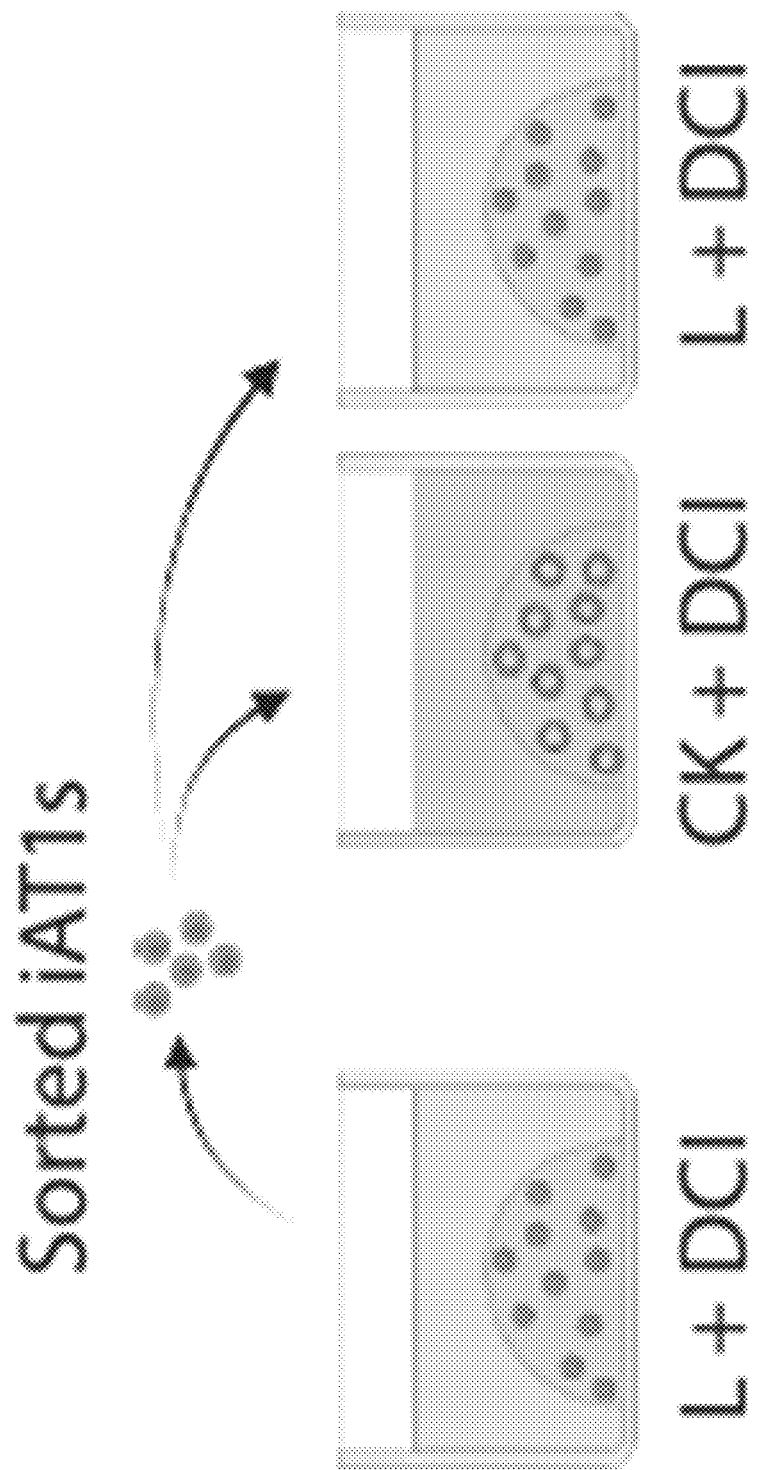
Figure 5J:
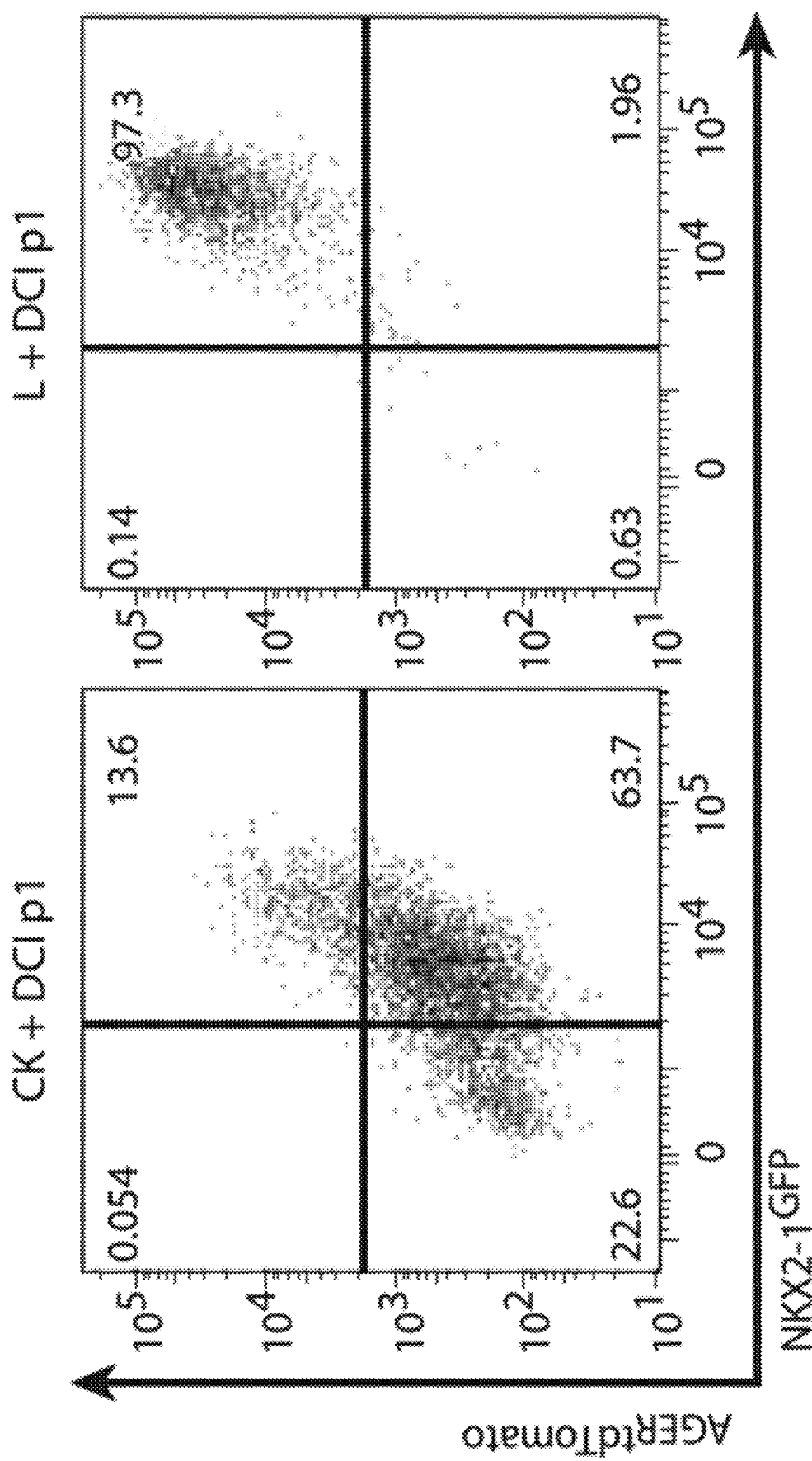
Figure 5K:
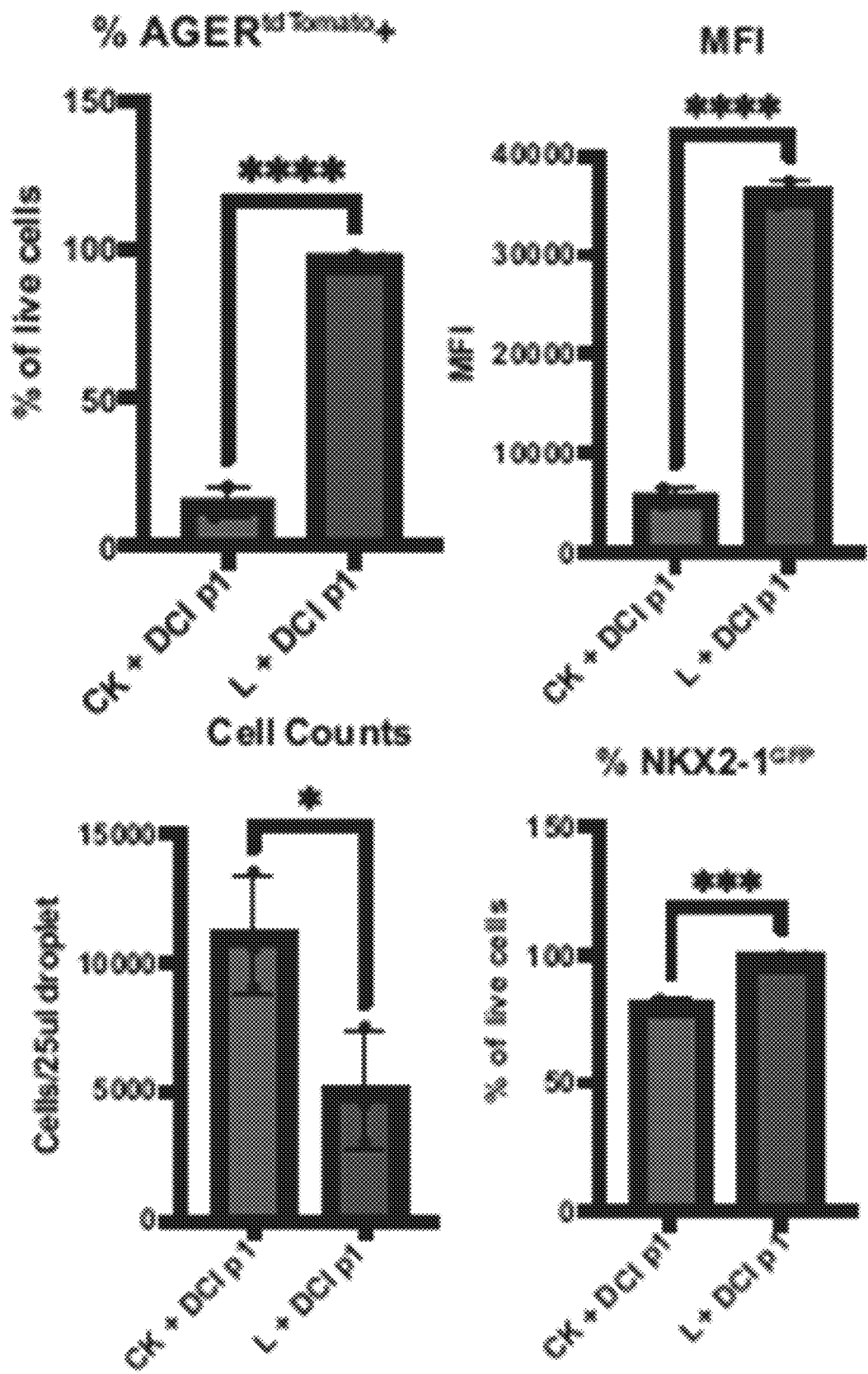
Figure 5L:
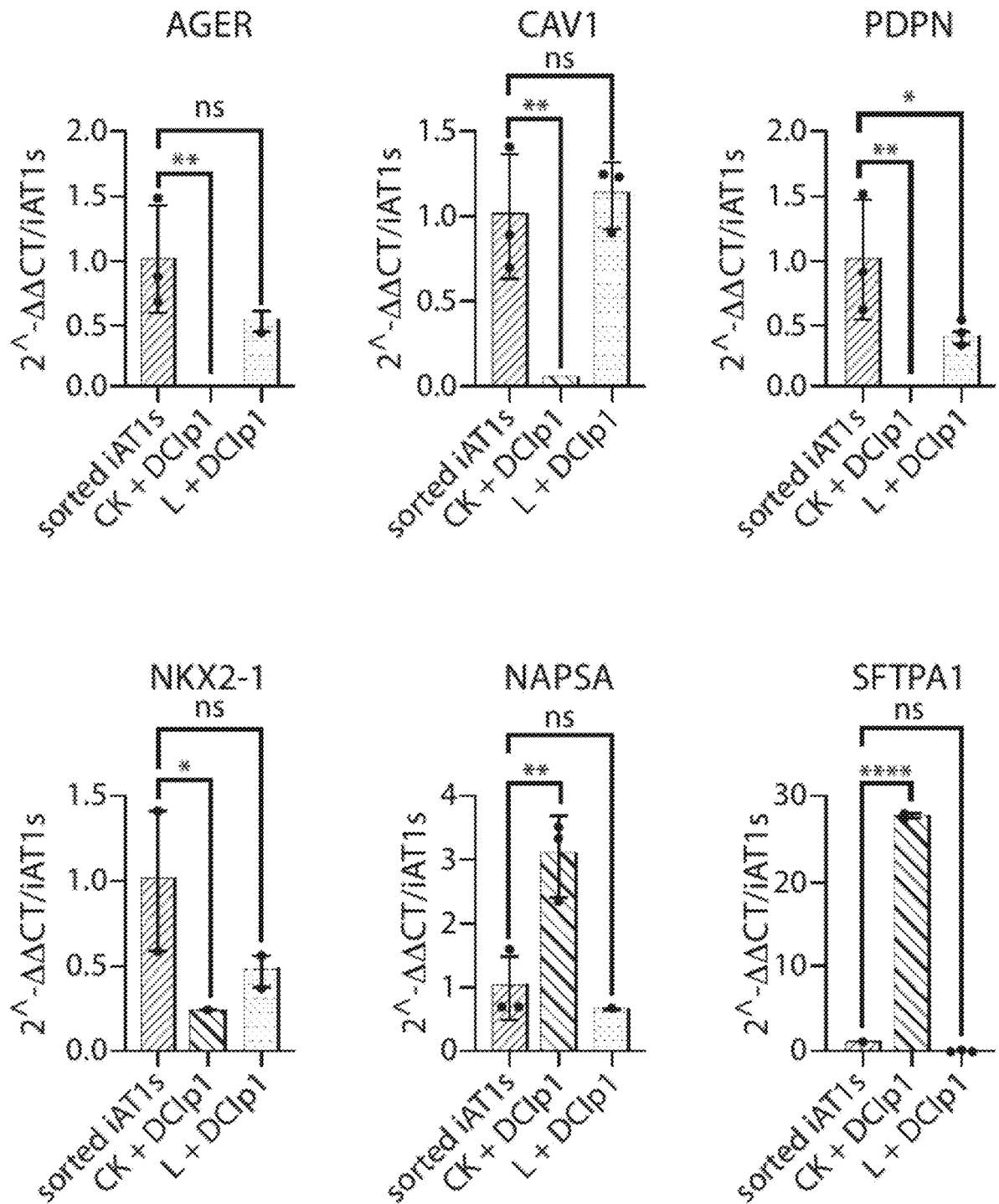

To determine whether iAT1s maintain their phenotype when transitioned back into iAT2-maintenance medium (CK+DCI). AGERtdTomato+ cells were sorted after 11 days in L+DCI and replated into 3D Matrigel in either L+DCI or CK+DCI (FIG. 5I). After 9 further days in culture, cells in L+DCI maintained >95% AGERtdTomato+, while those in CK+DCI showed 10-20% AGERtdTomato+ cells (FIGS. 5I-5L) and re-expressed AT2 markers consistent with residual plasticity in iAT1s. Those iAT1s maintained in L+DCI, compared to CK+DCI better maintained the AT1 program as evidenced by retained expression of AGER and CAV1 and suppression of AT2 markers (FIGS. 5J-5L).

Transcriptomic Profiling by scRNA-seq of iAT1s

Figure 6A:
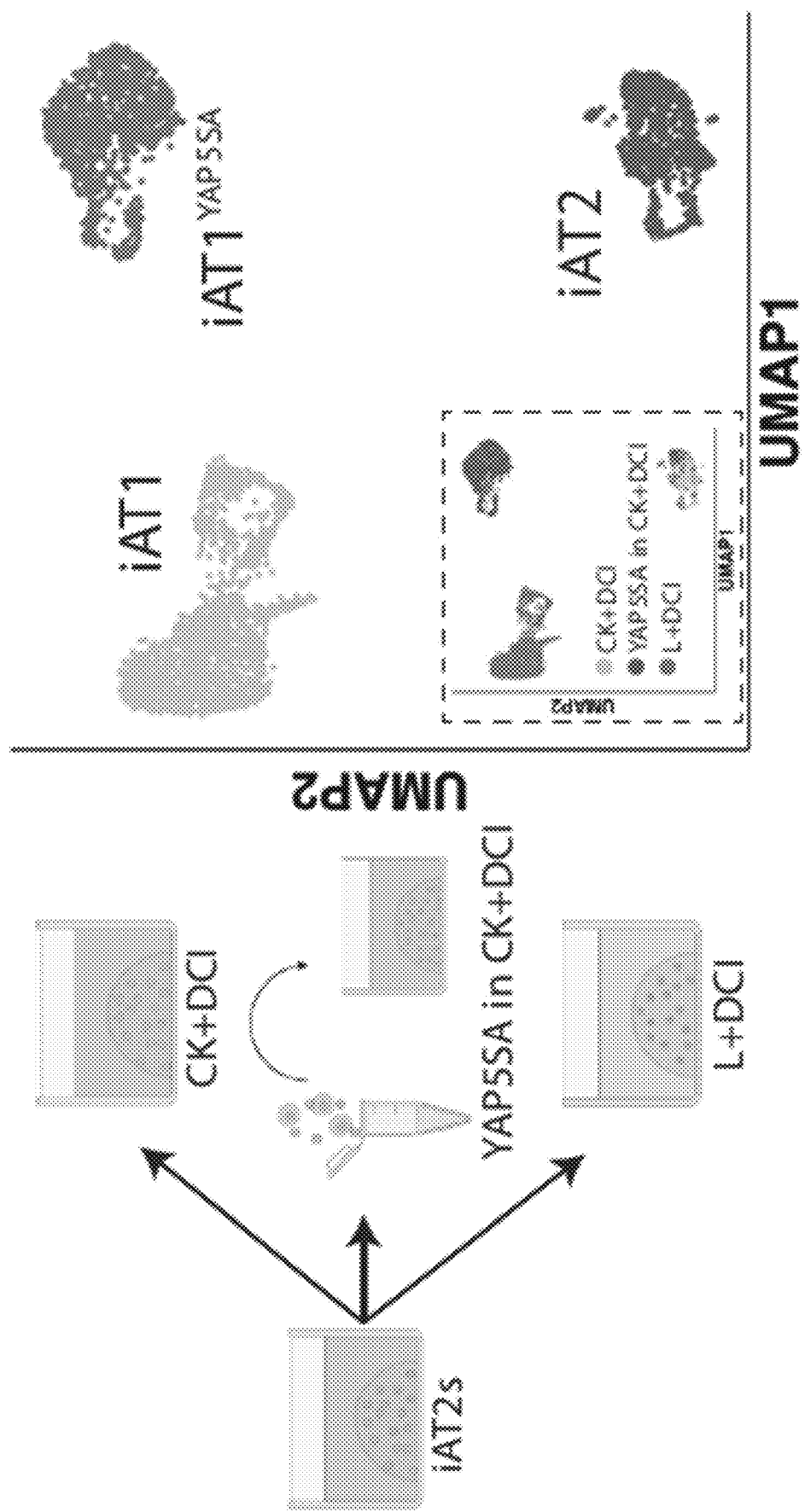
FIGS. 6A-6G demonstrate that iAT1s generated by either a defined medium or by lentiviral activated nuclear YAP express a broad AT1 transcriptomic program.
Figure 6B:
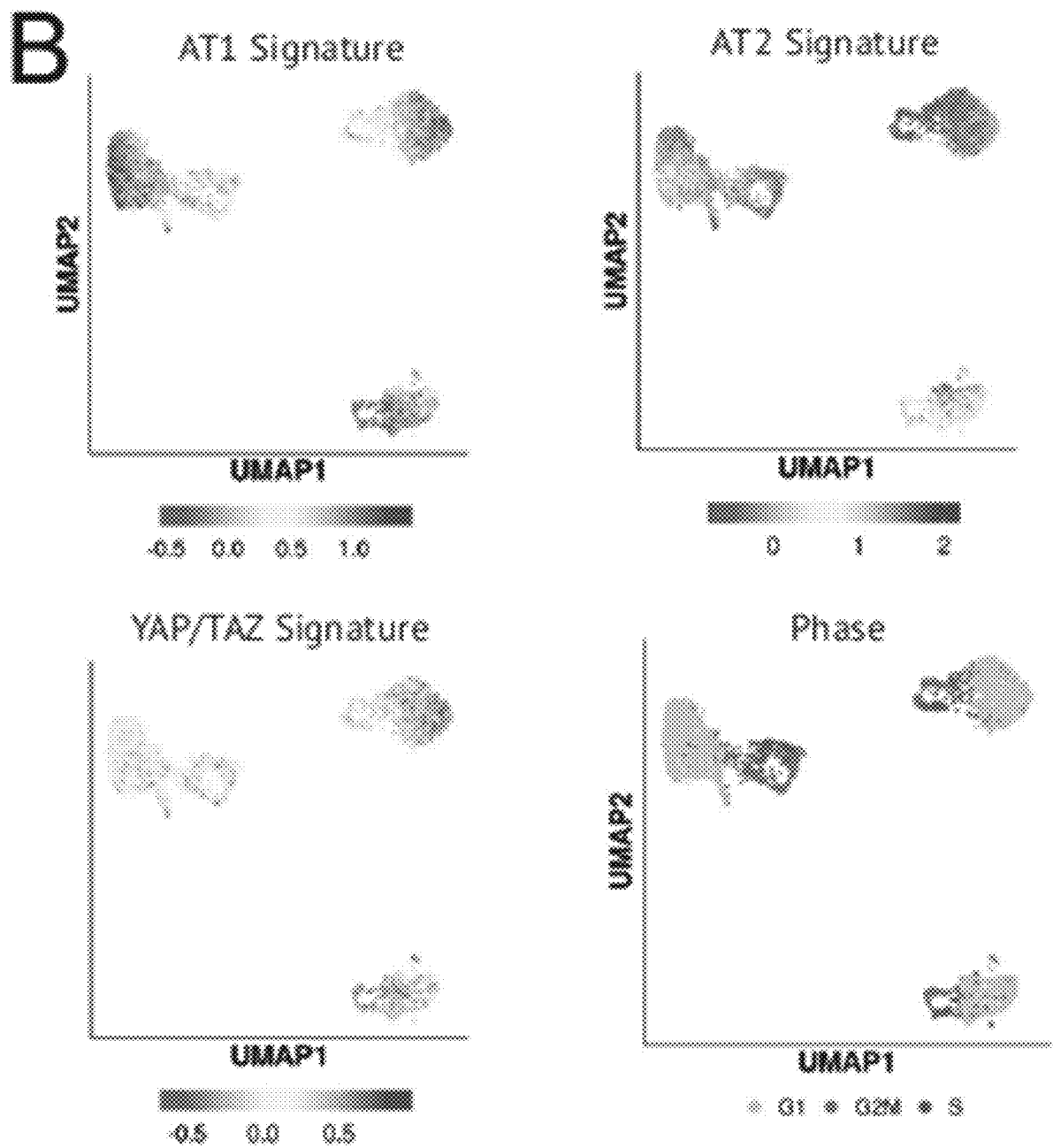

To comprehensively compare the transcriptomic programs of iAT1s generated through our defined iAT1 medium (L+DCI) vs our method of lentiviral forced over-expression of YAP5SA in CK+DCI, we performed head-to-head profiling of iAT1s prepared by either method vs their siblings that were maintained as iAT2s, hereafter named iAT1, iAT1YAP5SA, and iAT2 respectively (SPC2B2 iPSCs; FIG. 6A). Visualization of transcriptomes by UMAP revealed 3 predominant clusters (Louvain; resolution=0.05; FIGS. 6A, 6B) segregated based on the method used to generate the cells. As in FIG. 3, cells from the YAP5SA sample segregated into either the iAT1YAP5SAcluster or the iAT2 cluster, depending on whether they were successfully transduced (iAT1YAP5SA) or not transduced (iAT2s) with the lentiviral vector (see inset FIG. 6A).

Figures 1, 15A:
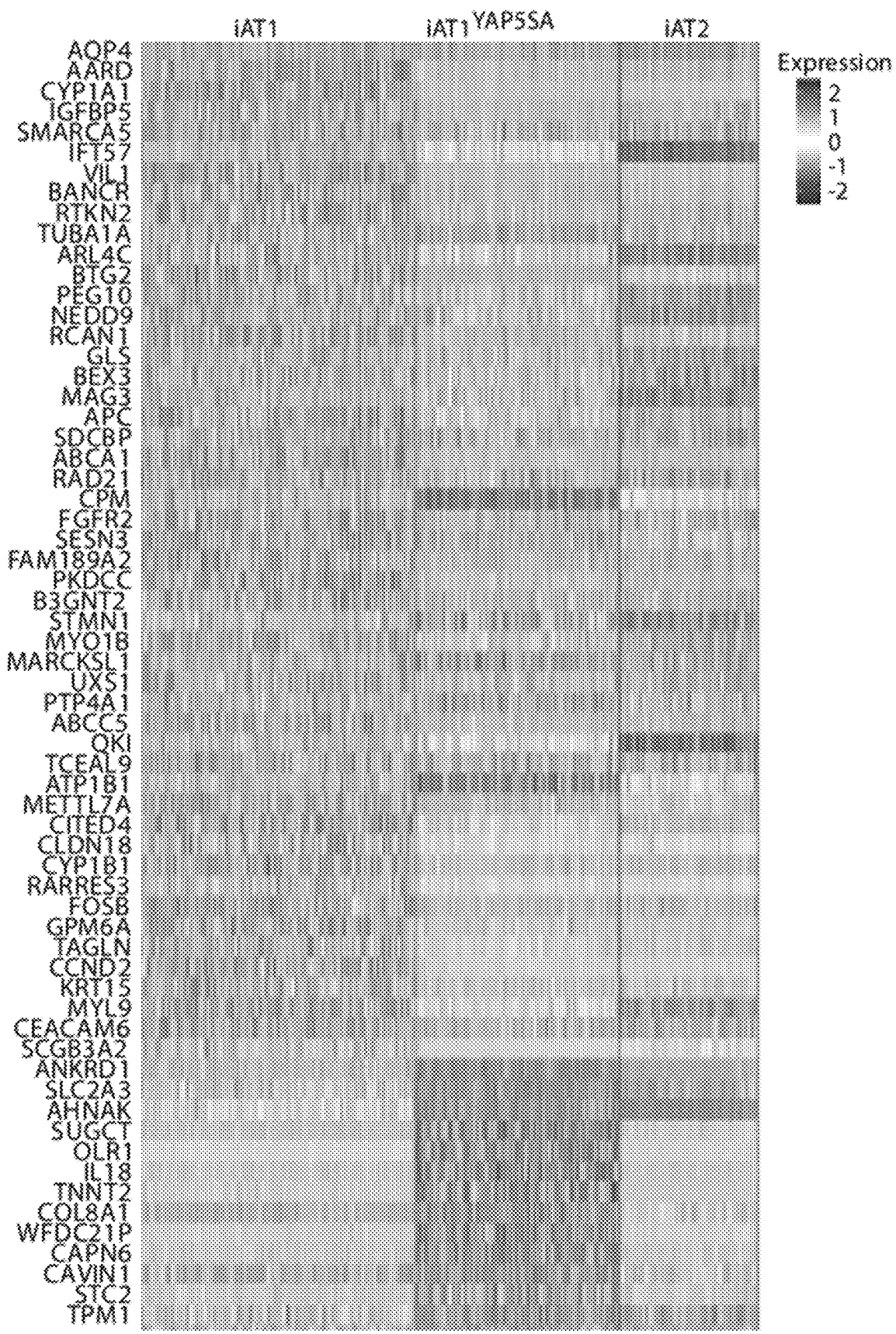
Figures 2, 15A:
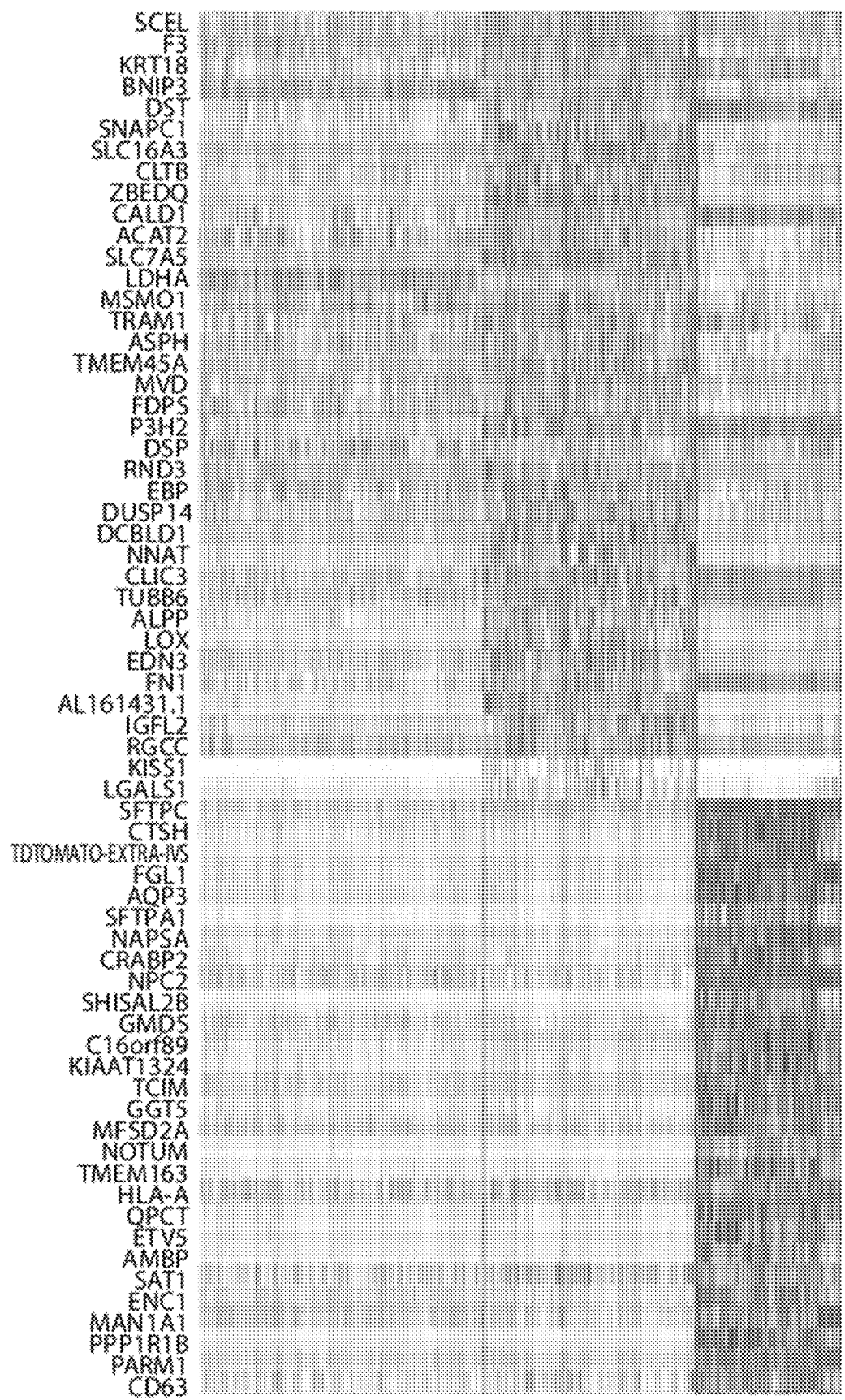
Figures 3, 15A:
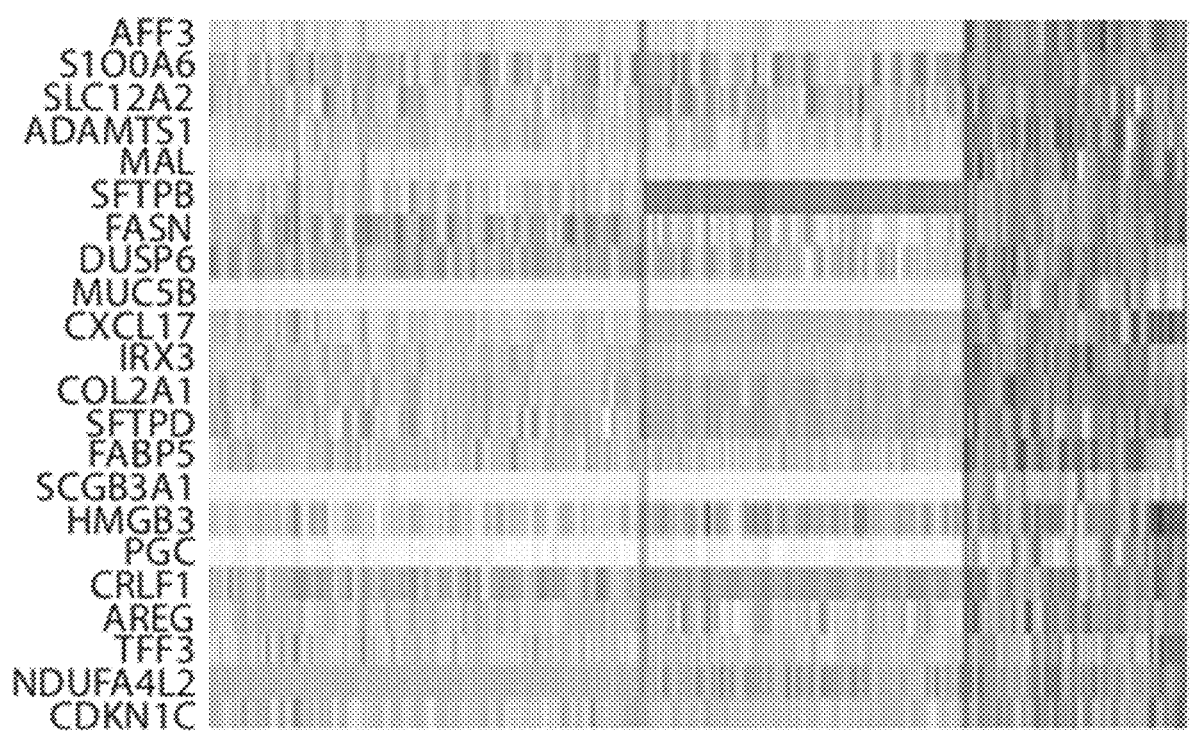

We observed that both iAT1 and iAT1YAP5SApopulations exhibited downregulation of the AT2 signature with frequent and robust upregulation of the AT1 50-gene set signature (FIG. 6B) as well as individual AT1 marker genes (AGER, CAV1, PDPN, and CLIC5; FIGS. 6C-6H, 15A-15D), consistent with differentiation of iAT2 into AT1-like cells using either method. Upregulation of AT1 transcripts, AGER, PDPN, and CAV1 was validated by RT-qPCR (FIG. 6H), and the frequency of expression of most AT1 marker transcripts was similar to expression profiles of published primary AT1s (FIG. 6G), although absolute expression levels for AGER and PDPN were lower than in primary control distal lung tissue by RT-qPCR (FIGS. 6H, 15E).

Figure 6C:
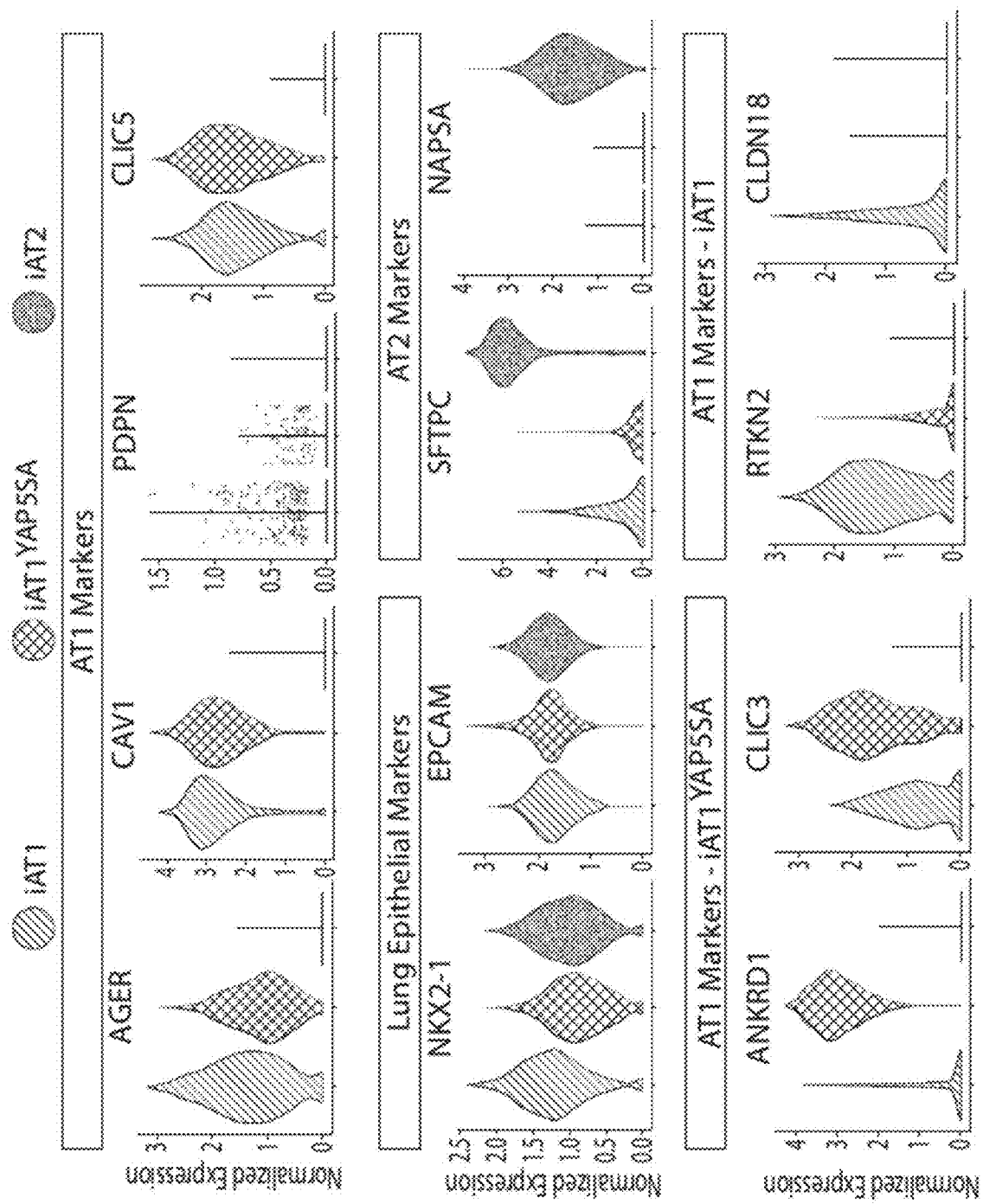
Figure 6D:
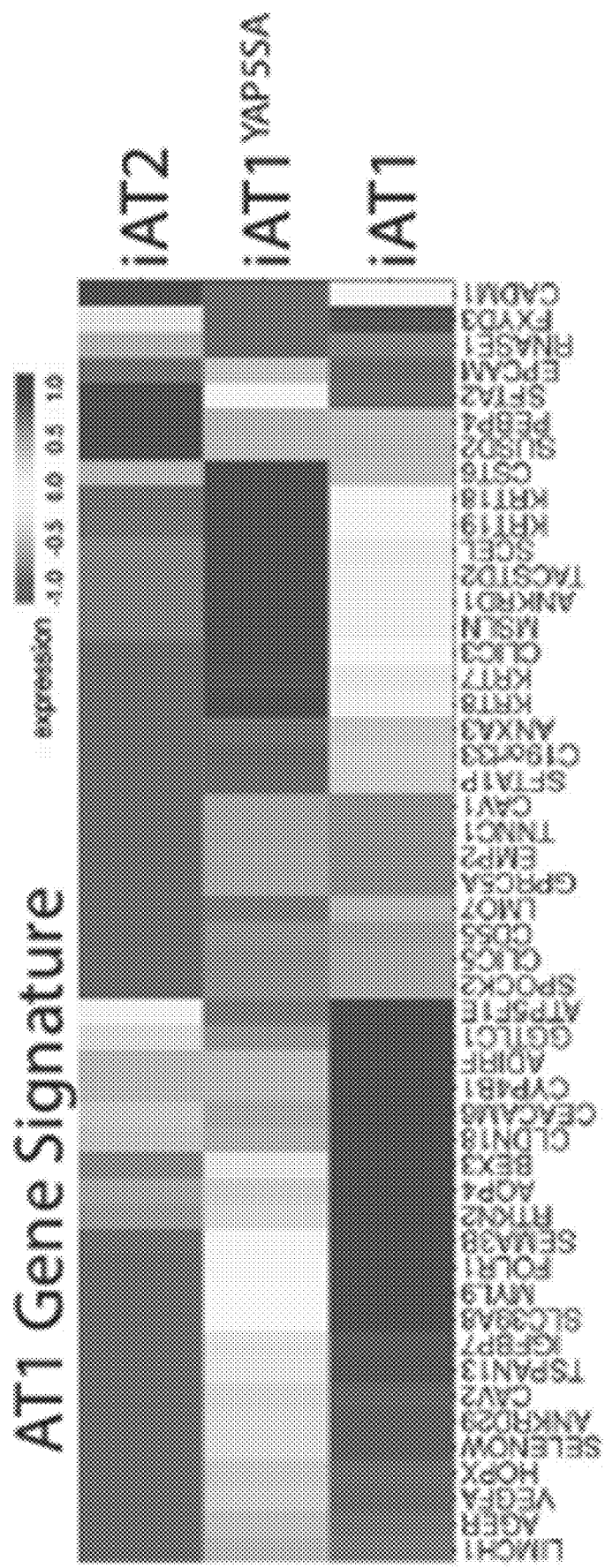
Figure 6E:
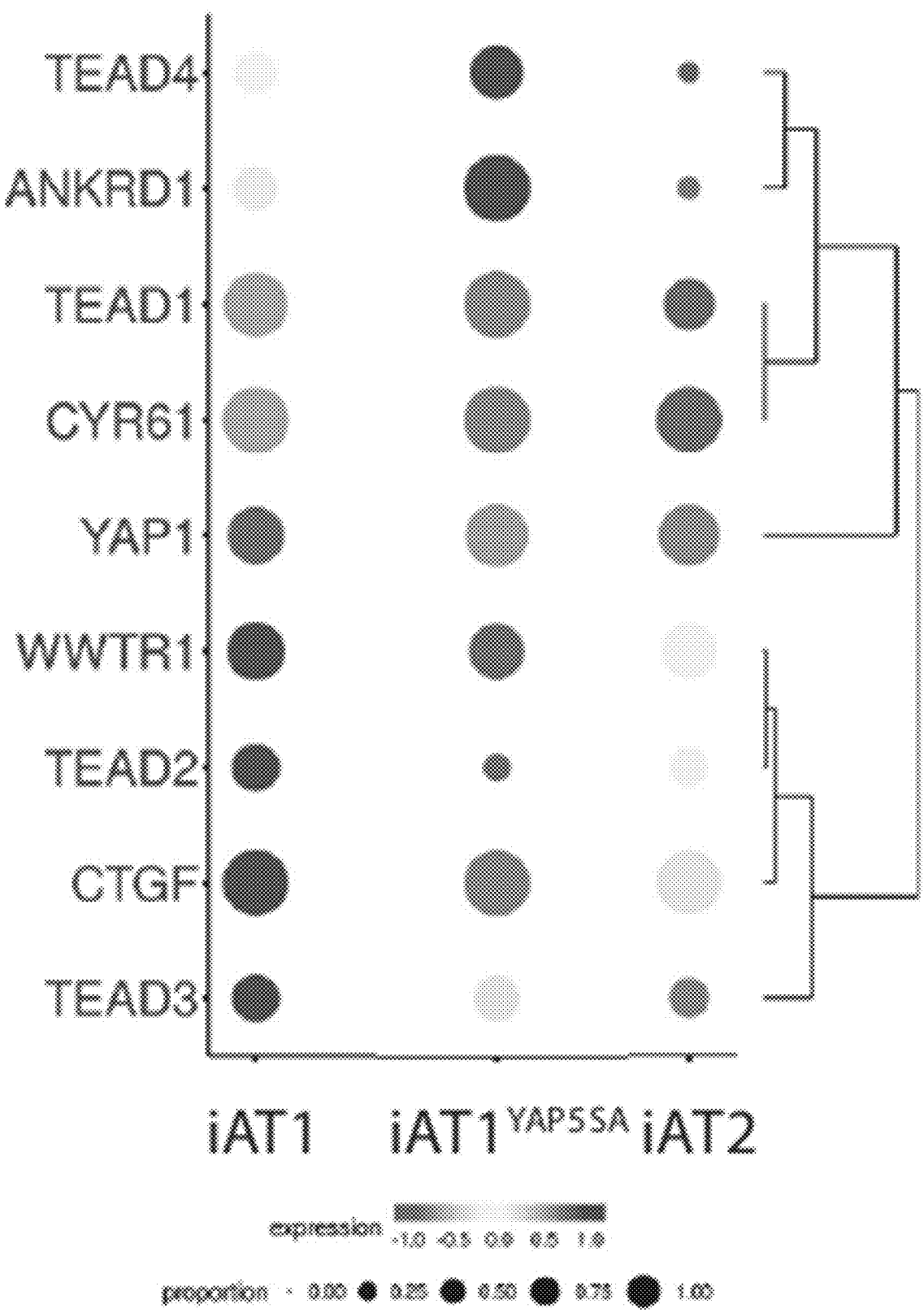
Figure 6F:
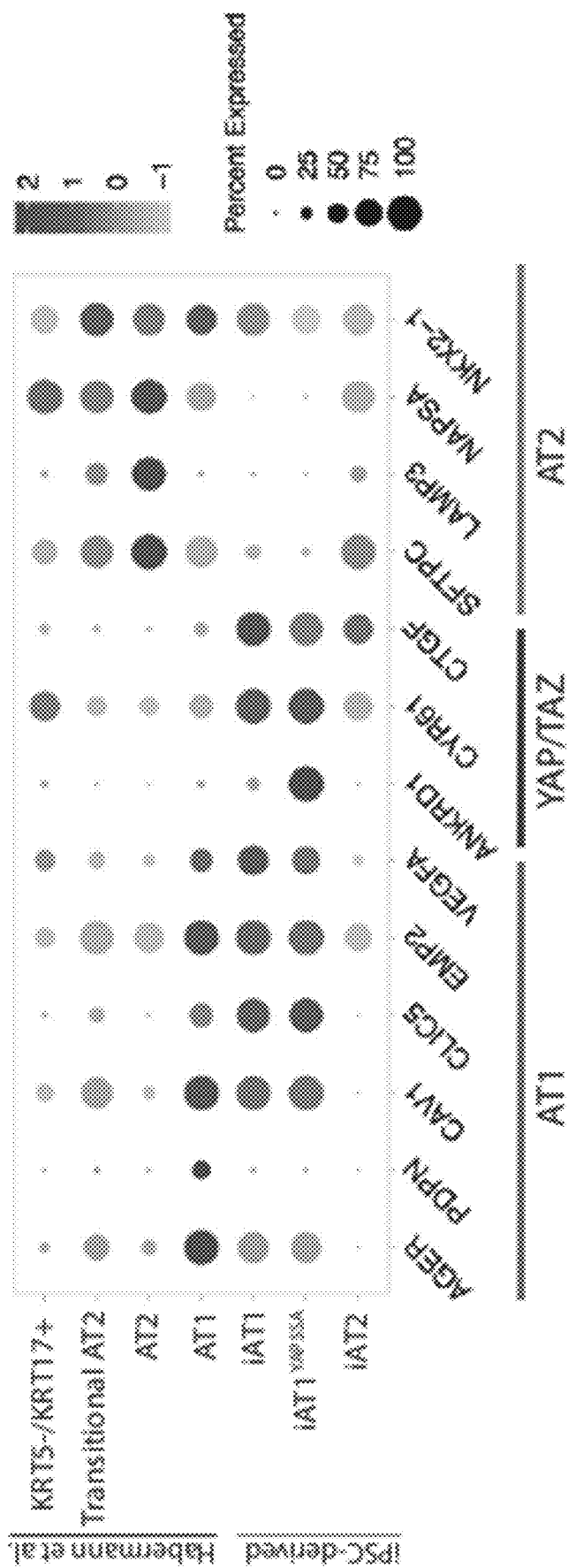
Figure 6G:
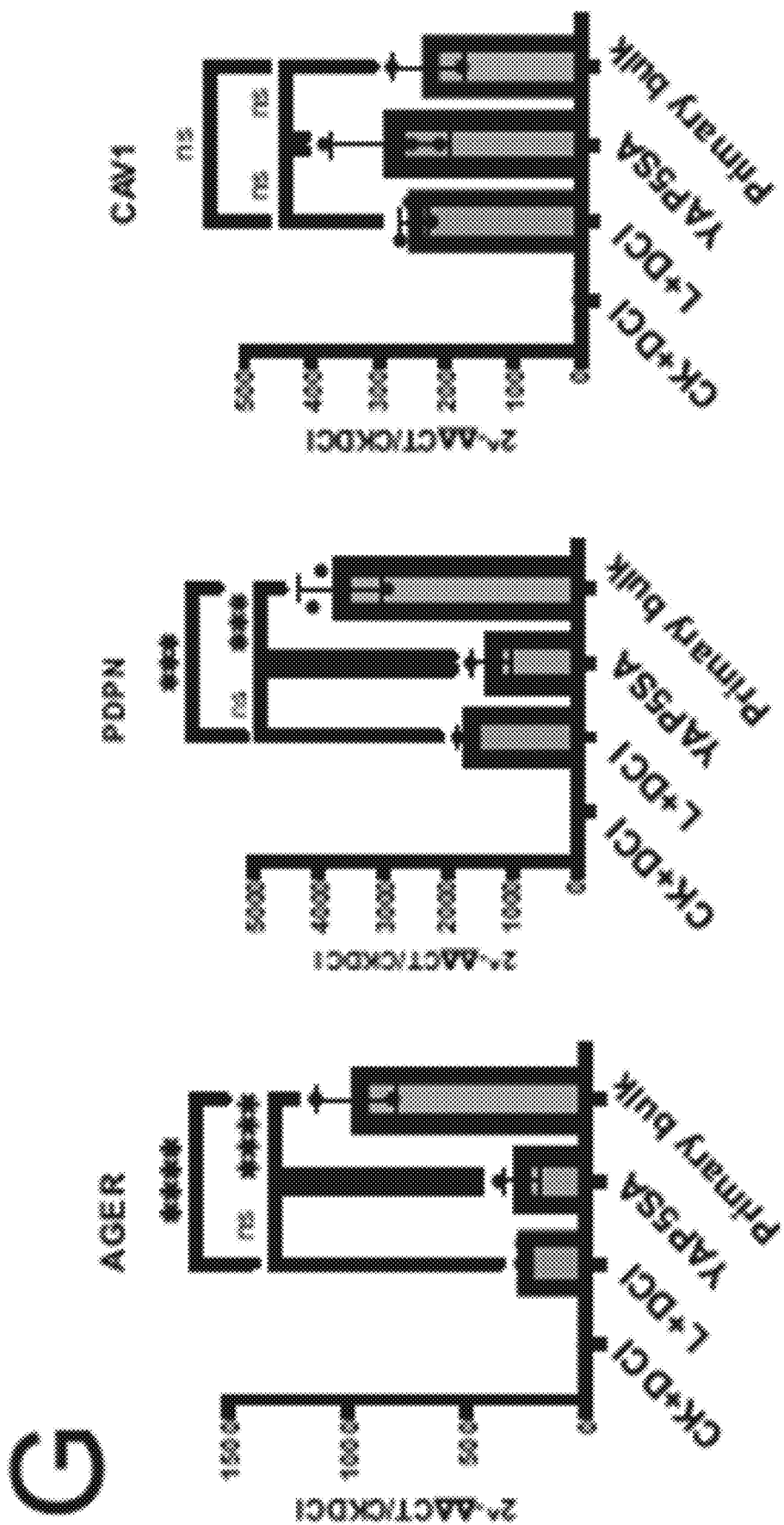

Despite these similarities, iAT1 and iAT1YAP5SAcells clustered separately with 298 transcripts differentially expressed (FDR<0.05, log FC>1). These differences include: 1) differential upregulation of a YAP/TAZ 22 gene target signature67(FIG. 6B), likely reflecting the higher levels of YAP signaling induced by forced over-expression of the YAP5SA driver compared to milder upregulation resulting from the LATS inhibitor, and 2) differential expression of other AT1 marker genes in our AT1 50 marker set, such as ANKRD1 and CLIC3 which were more highly expressed in the iAT1YAP5SA cluster, or RTKN2 and CLDN18, which were more highly expressed in the iAT1s (FIGS. 6C, 6D, 15A). Consistent with the above differences in the YAP/TAZ signature set were notable differences in specific Hippo-LATS-YAP signaling targets. For example. YAP and TEAD4 were upregulated in iAT1YAP5SAcells, whereas TAZ (WWTR1), TEAD2, TEAD3, and CTGF were upregulated in iAT1s (FIG. 6E). While it is possible that some of these differences are due to the LATS inhibitor affecting both YAP and TAZ whereas the lentivirus is YAP-specific, they could also be due to the effect of Chir and KGF in the medium of the lentiviral-transduced iAT1YAP5SAcells.

Figure 7B:
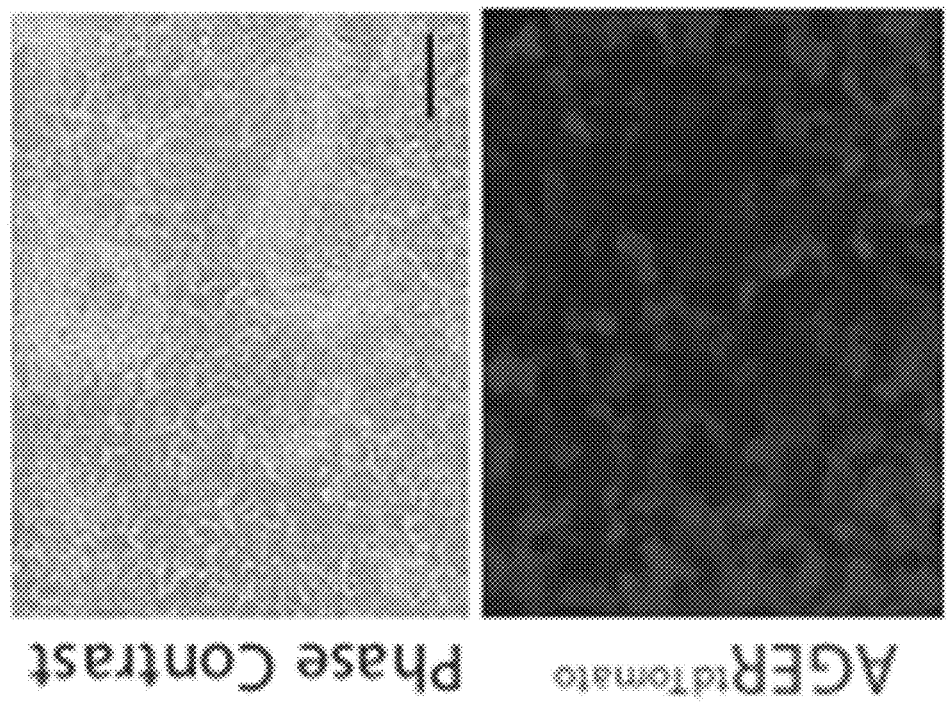
FIG. 7B) Live cell imaging showing retention of AGERtdTomatoin iAT1s after ALI culture. scale bar=100 um.
Figure 7A:
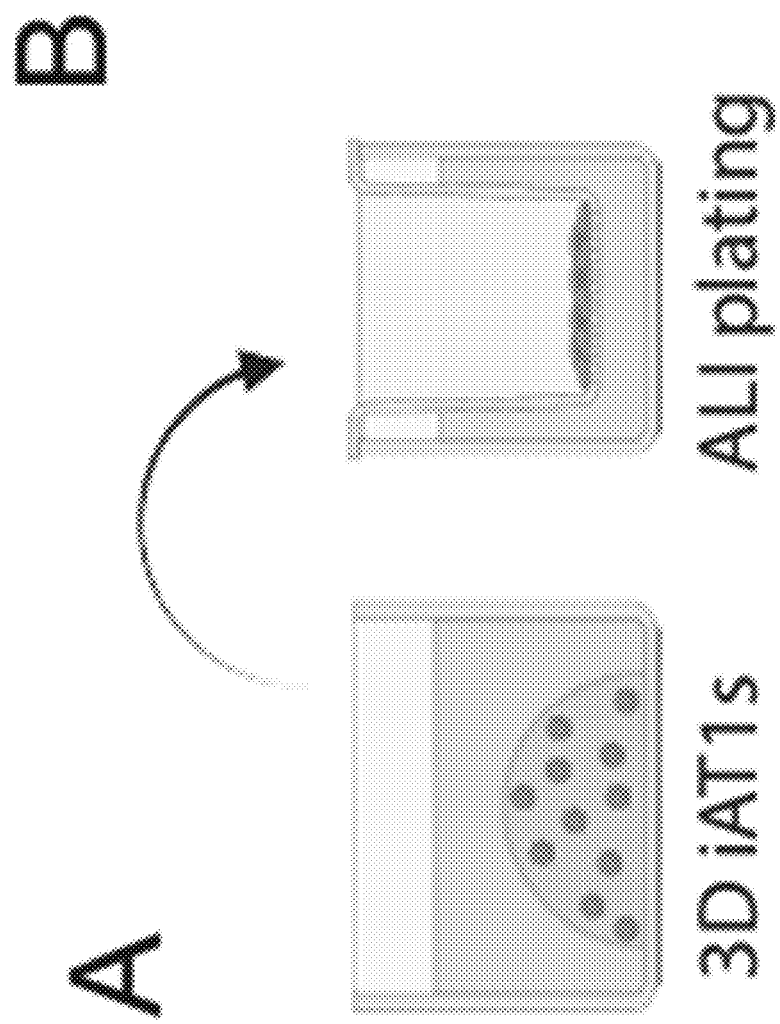
Figure 7C:
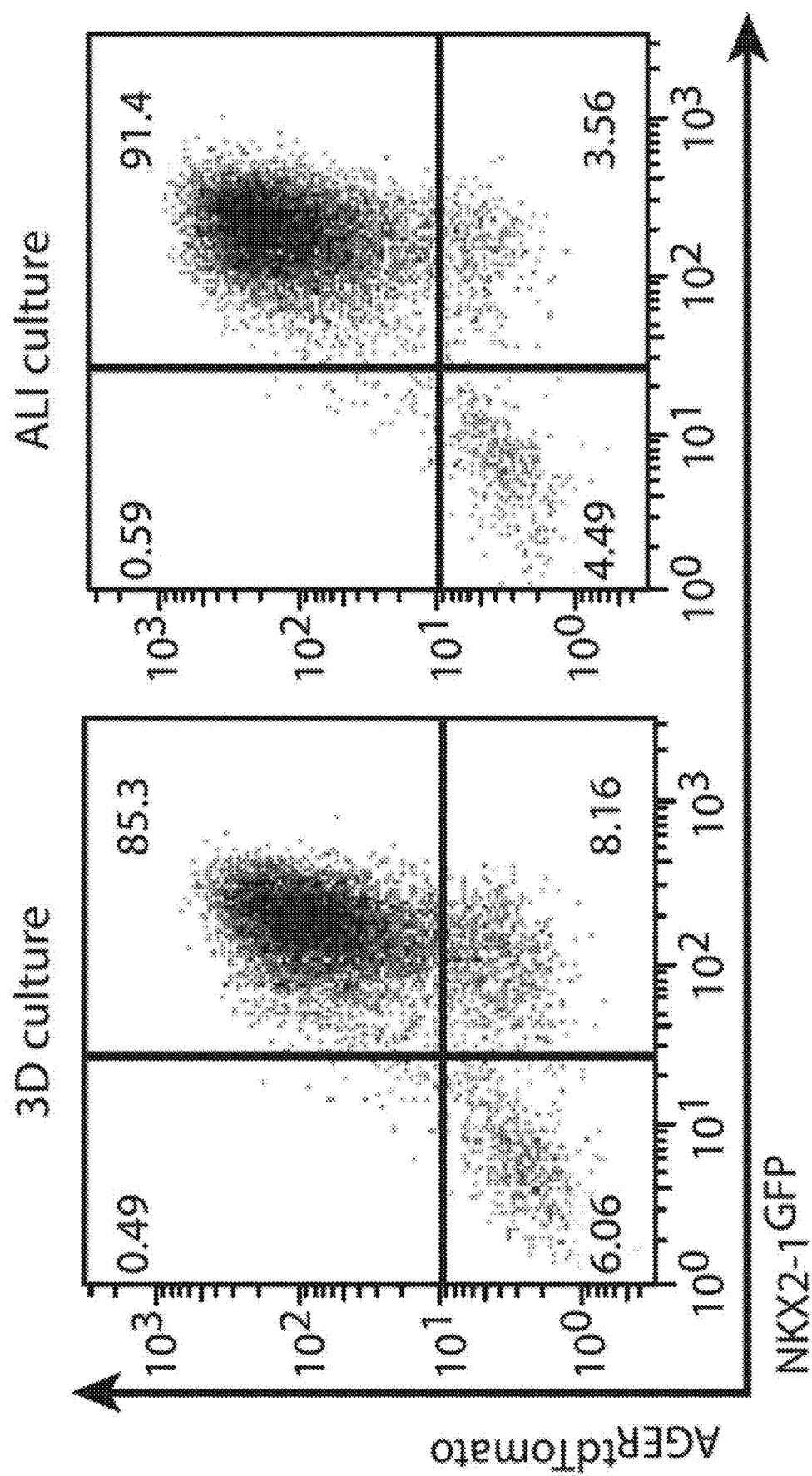
FIG. 7C) Flow cytometric analysis of NKX2-1GFPand AGERtdTomatoreporter expression in 3D or ALI cultures of iAT1s (6 days).
Figure 7D:
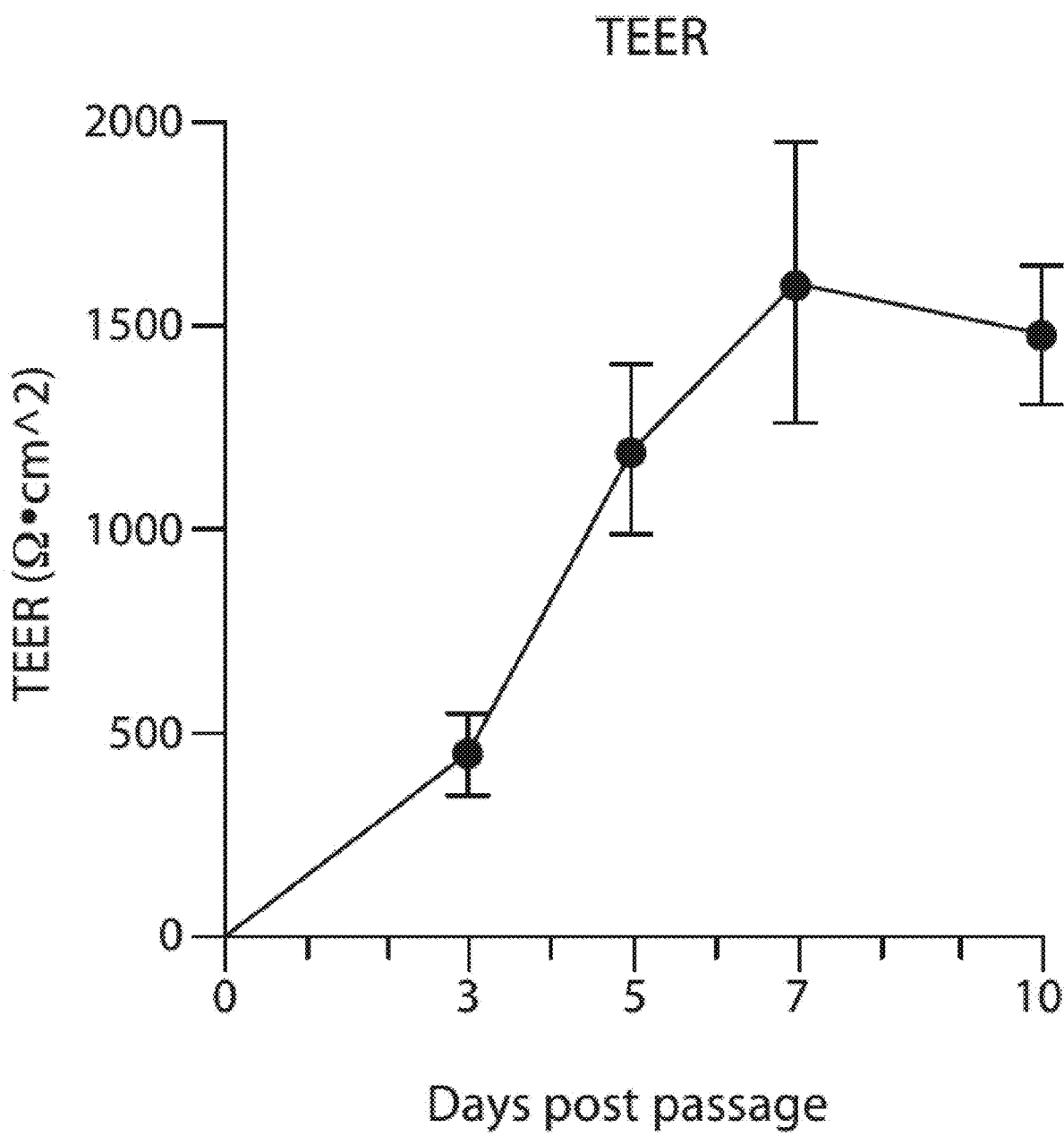
FIG. 7D) Transepithelial electrical resistance (TEER) measurements of BU3 NGAT iAT1s over 10 days of ALI cultures (Air lifted at day 3; N=3).
Figure 7E:
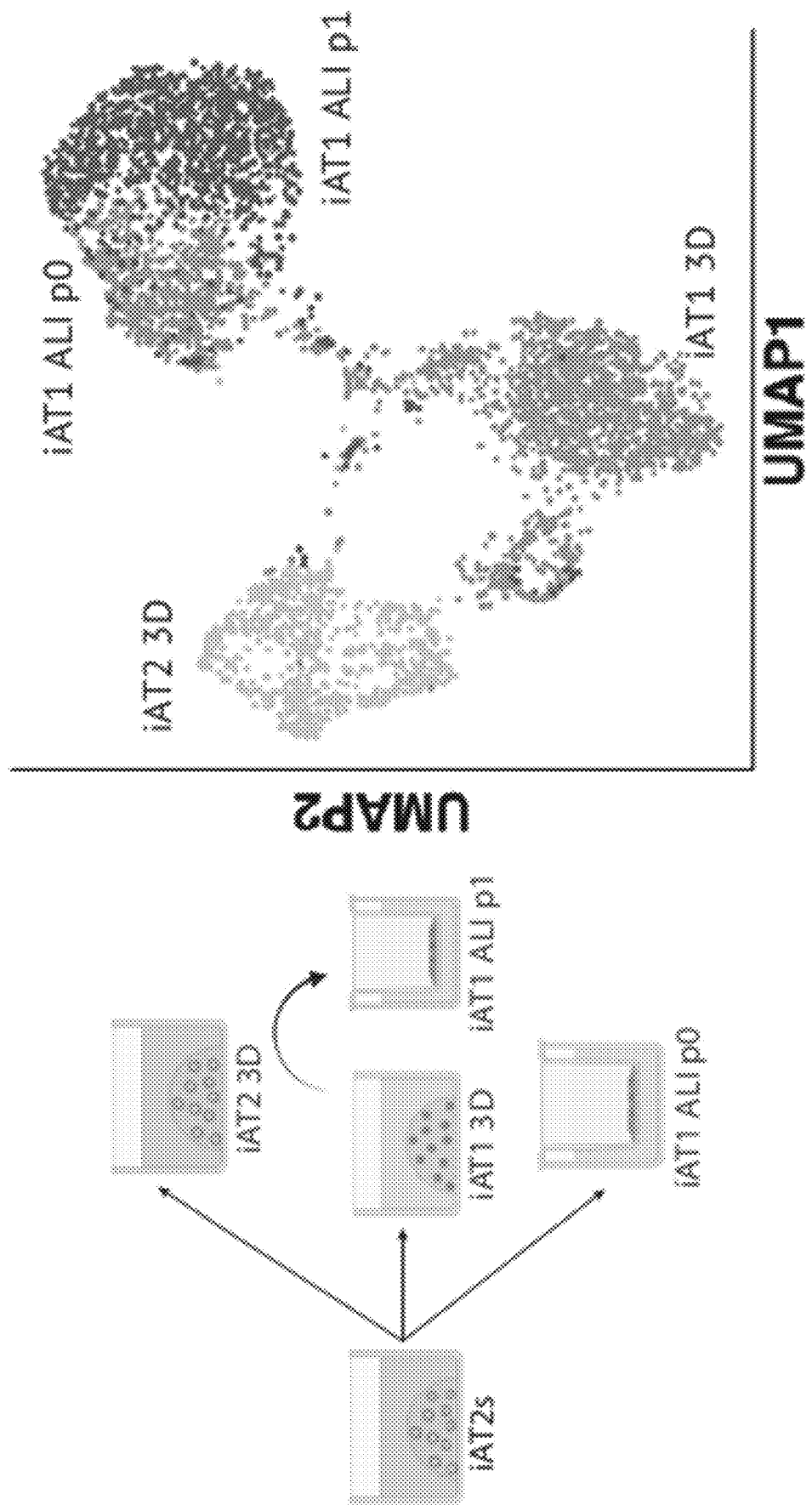
FIG. 7E) Profiling by scRNA-seq of BU3 NGATiAT2s in 3D CK+DCI, iAT1s in 3D L+DCI, or iAT1s in ALI cultures. iAT1s in ALI cultures were plated either from iAT2s into L+DCI (iAT1 ALI P0) or were plated from 3D iAT1s after 9 days of pre-culturing in 3D L+DCI prior to transfer to ALI culture (iAT1 ALI P1). UMAP projection shows the 3D cultures cluster separately while the two iAT1 ALI cultures cluster closer together.
Figure 15B:
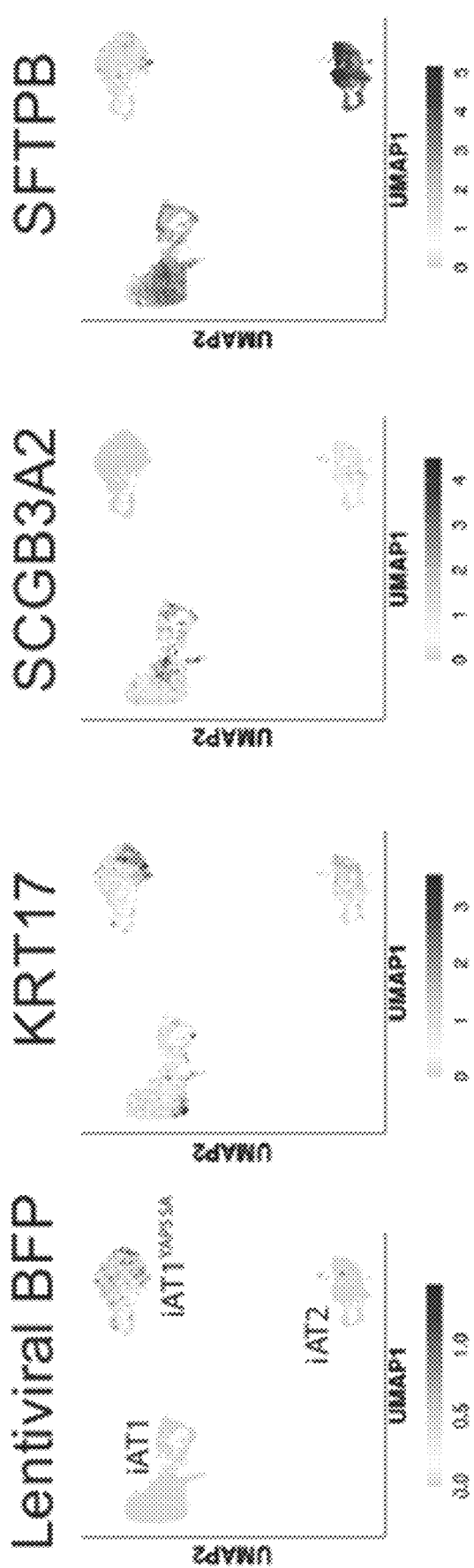
Figure 15C:
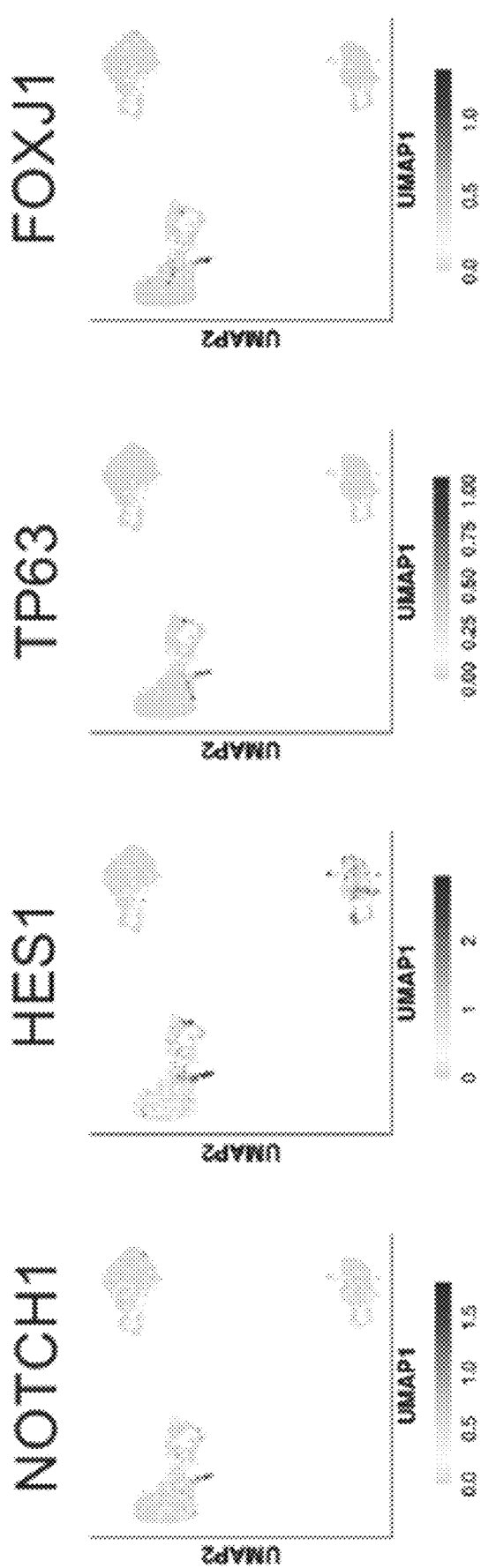
Figure 15D:
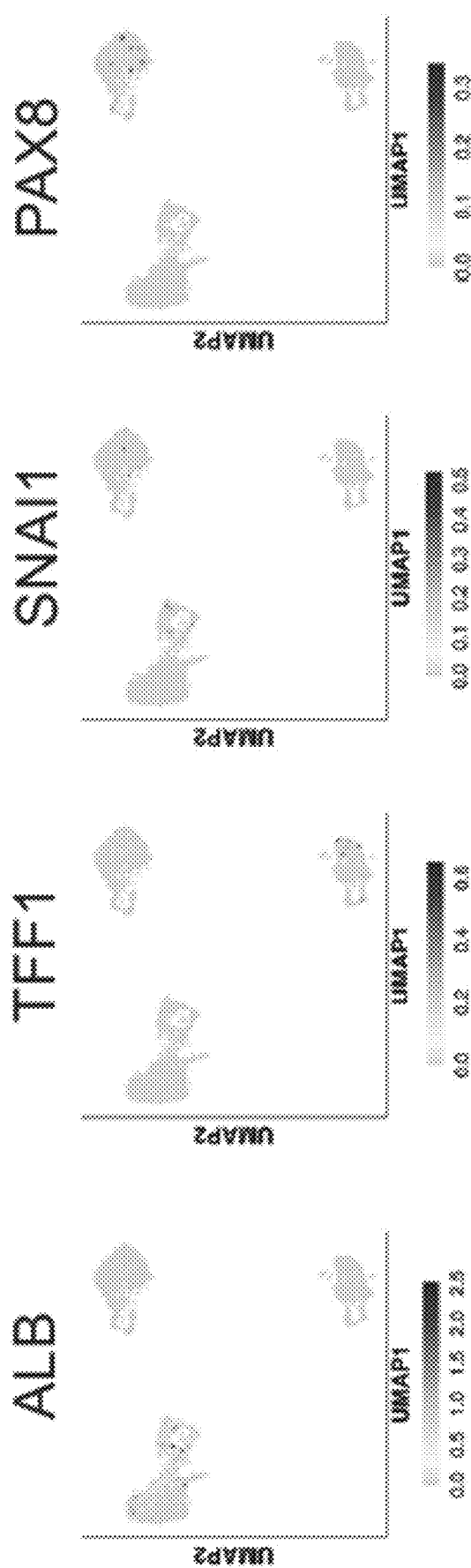
Figure 15E:
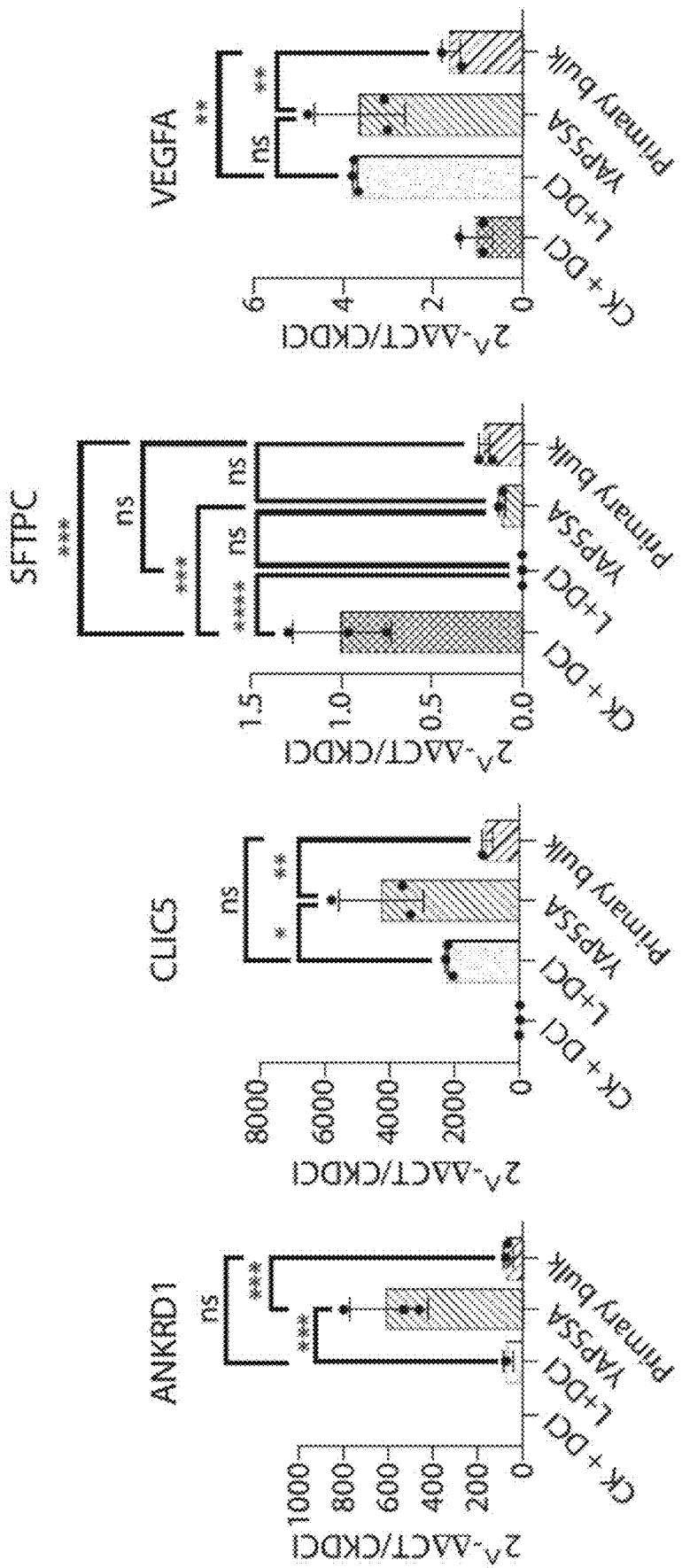

We found that both iAT1YAP5SA and iAT1 populations included a subset of cells in active cycle (FIG. 6B) and both contained minor subsets expressing detectable levels of some, but not all, transitional state markers, such as KRT17 (FIGS. 15B-15D). Importantly, neither population showed significant expression of nonlung endoderm, EMT, or airway (FOXJ1, TP63, or SCGB1A1) markers, except for SCGB3A2 which was differentially upregulated in iAT1s (FIGS. 15B-15D). A small subpopulation appeared in the iAT1 population that is high in expression of Notch signaling targets such as HES1 but is lower in AT1 gene signature. Taken together these results indicate efficient induction of the AT1 program without the need for lentiviral transduction via a serum-free differentiation medium, L+DCI.

iAT1s Display Functional Capacities to Form a Flattened Epithelial Barrier, Secrete Signaling Ligands, and Express Extracellular Matrix-Encoding Transcripts We next evaluated the functional capacity of iAT1s generated in defined L+DCI medium. An emerging literature has established several functions that characterize primary AT1s in vivo, including their potential to: form flattened cells that contribute to an epithelial barrier;$_1$ produce a characteristic alveolar extracellular matrix;$_{68}$ and serve as signaling hubs in the lung through secretion of ligands that bind receptors on adjacent lung mesenchymal lineages.$_{69}$ Since iAT1s in 3D soft Matrigel cultures are still proliferative and do not discernably form flattened epithelial barriers, we transitioned BU3 NGAT iAT1s into transwell cultures in L+DCI, and 3 days later aspirated apical medium to establish air-liquid interface (ALI) cultures in L+DCI, hereafter "iAT1 ALI P1". We observed maintenance of AGERtdTomatoreporter expression in the outgrowth cells at ALI, suggesting maintenance of the AT1 program (FIGS. 7A-7C), comparable to 3D L+DCI culture conditions. We also noted formation of an epithelial barrier after ALI culture, based on prevention of apical medium leakage and increasing transepithelial resistance (TEER) over time to 1479±166Ω·cm2 by day 10 (FIG. 7D).

Figure 7G:
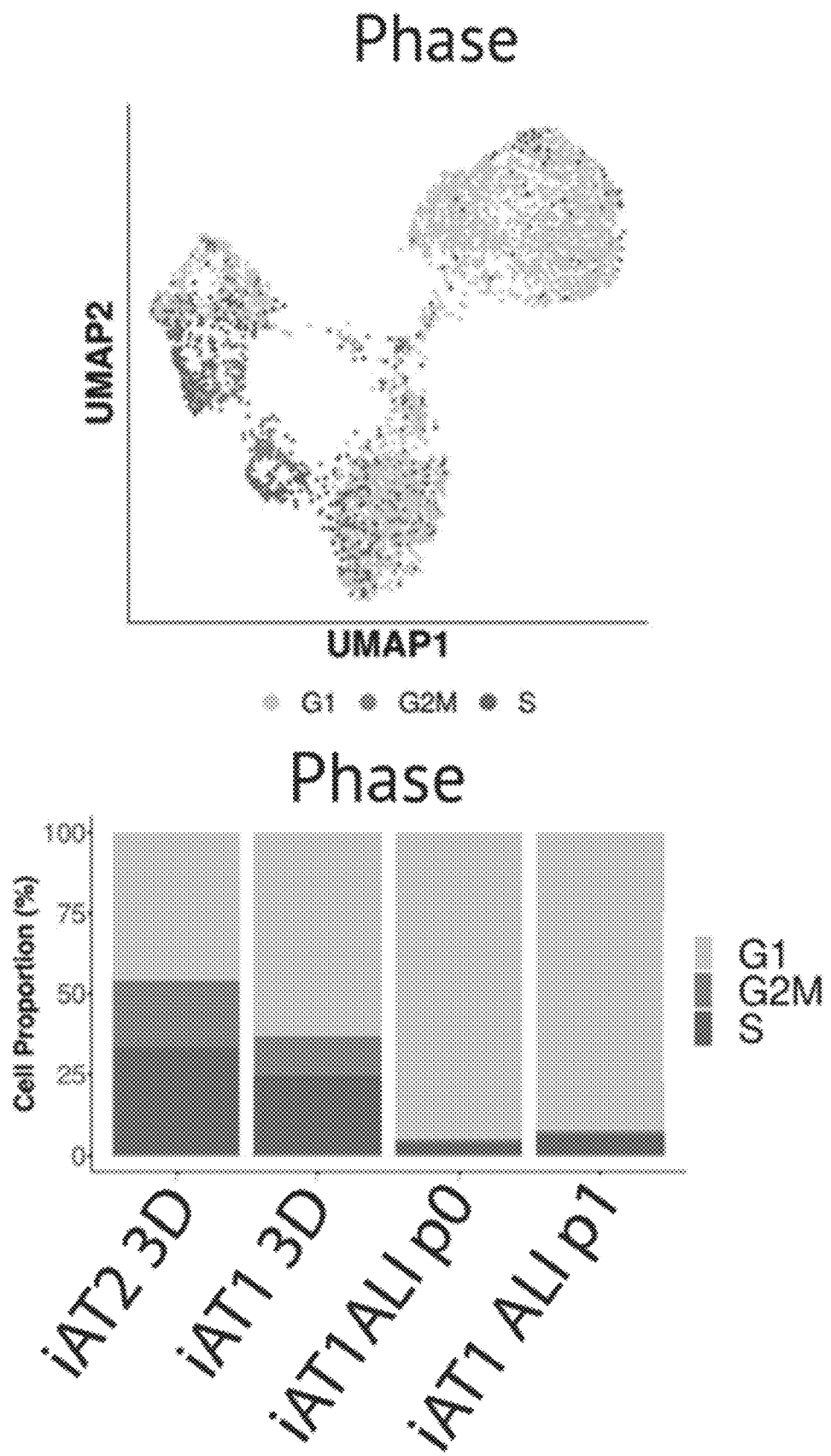
FIG. 7G) Cell cycle phase distribution across all samples.
Figure 16A:
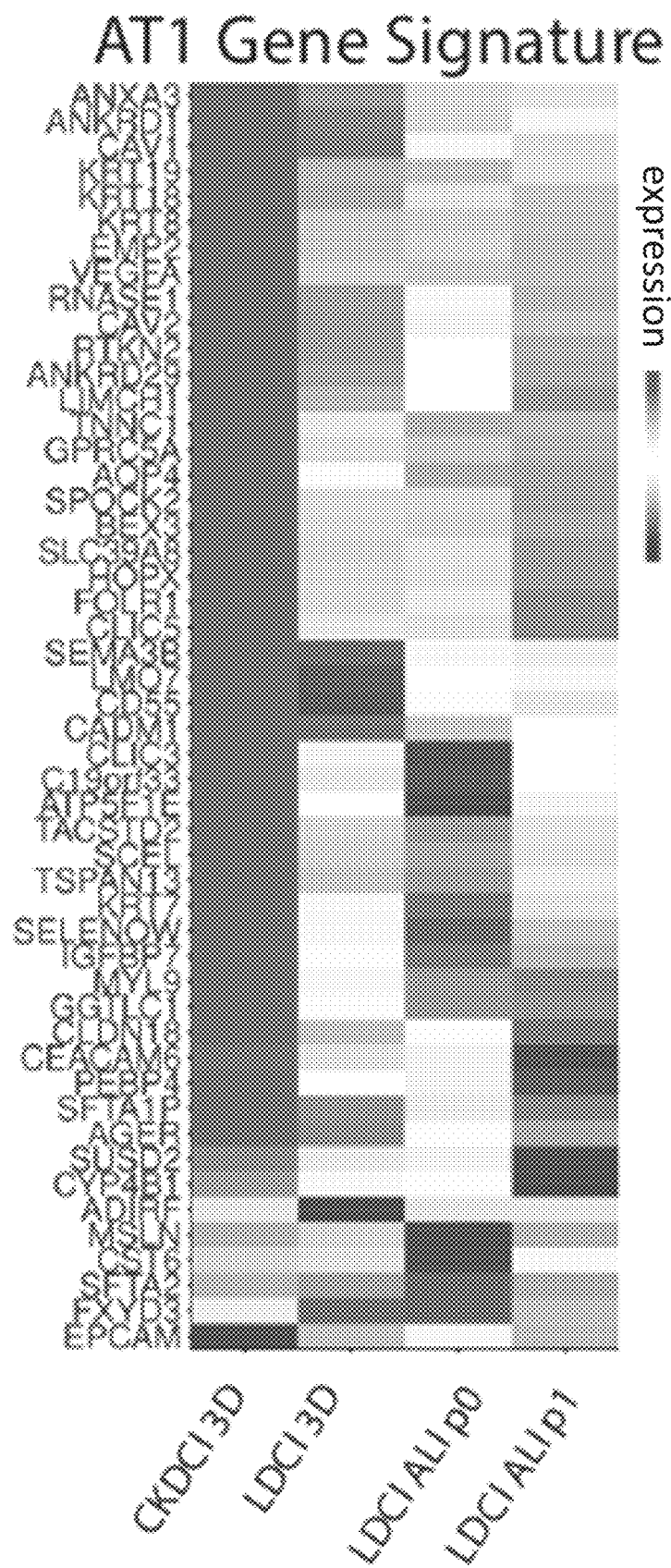
Figure 16B:
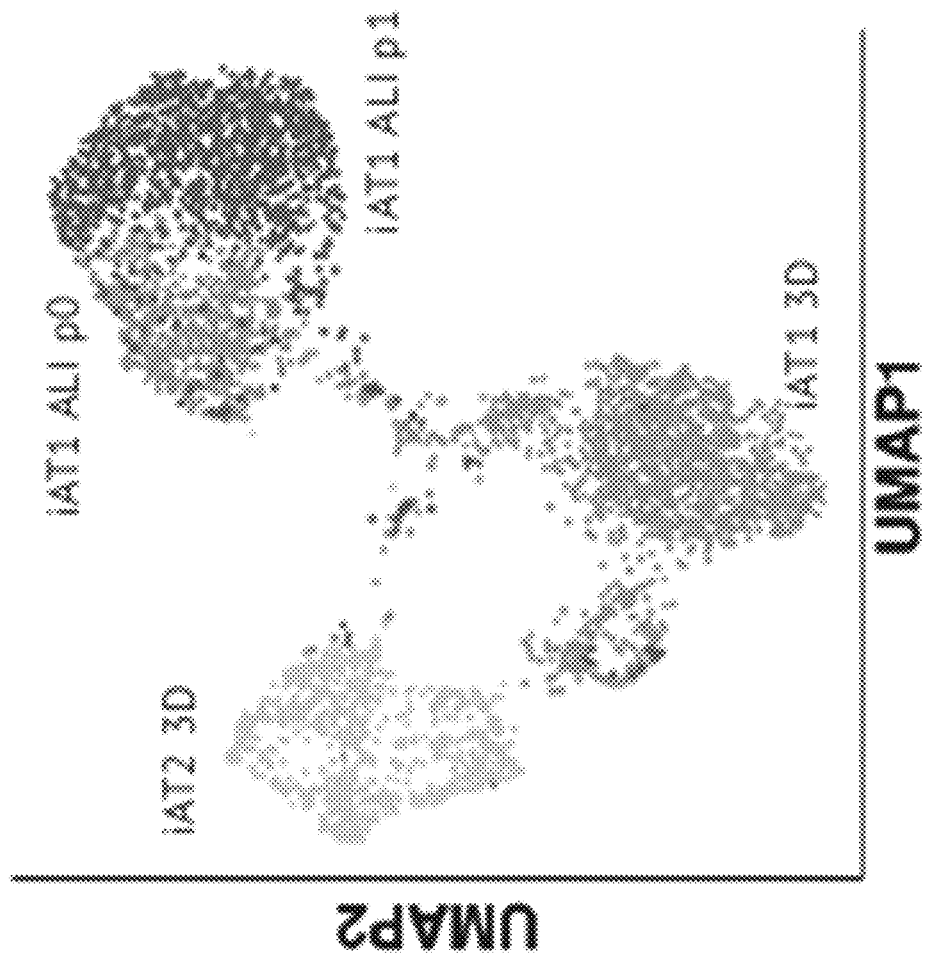
Figure 16C:
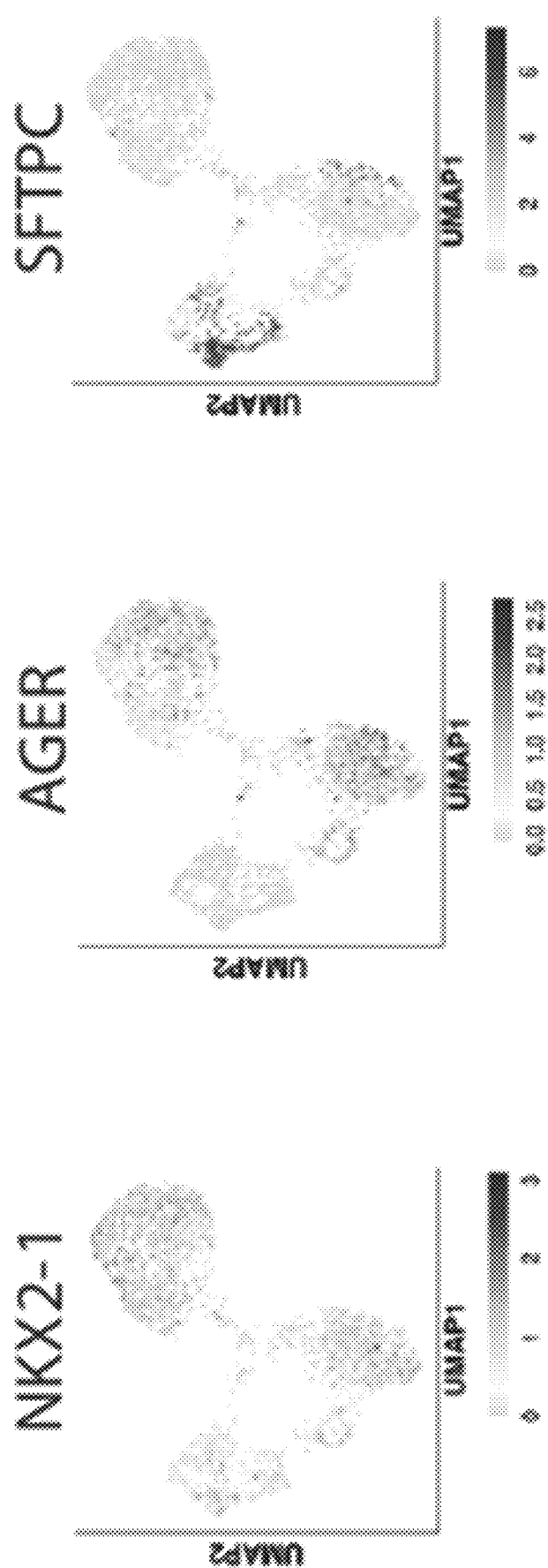
Figure 16F:
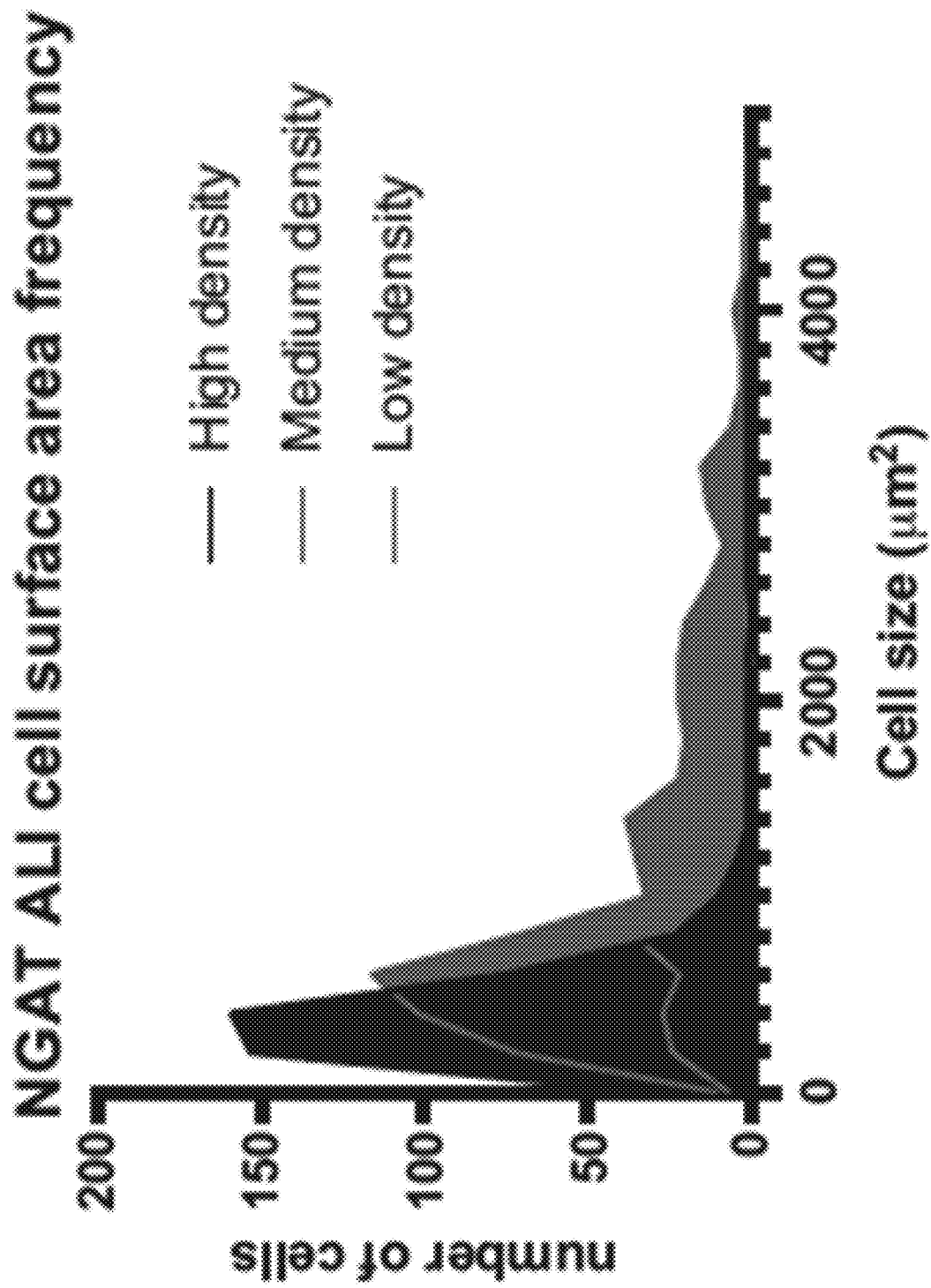
Figure 16H:
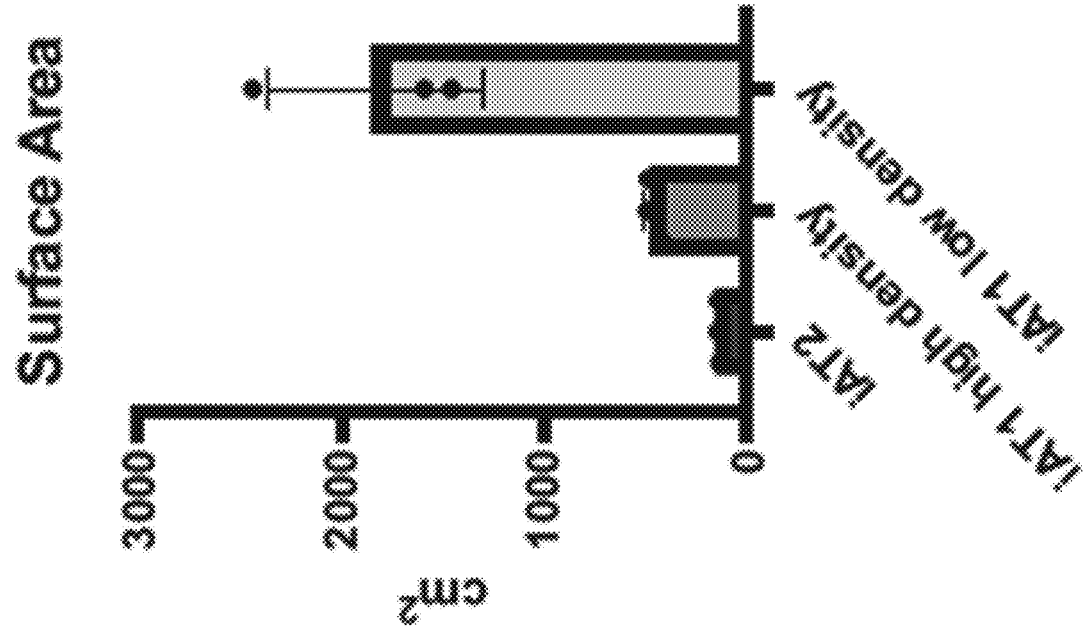
Figure 16G:
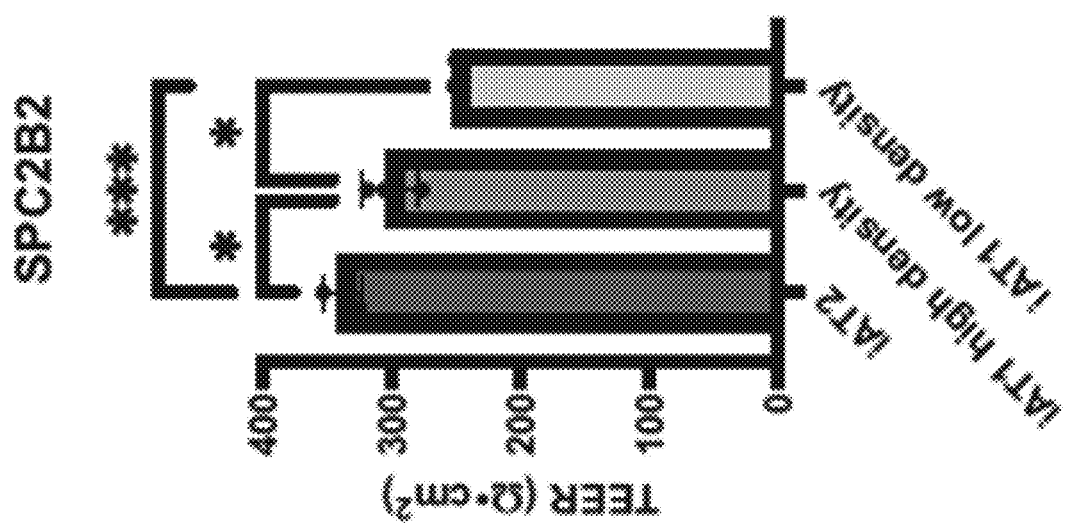
Figure 16I:
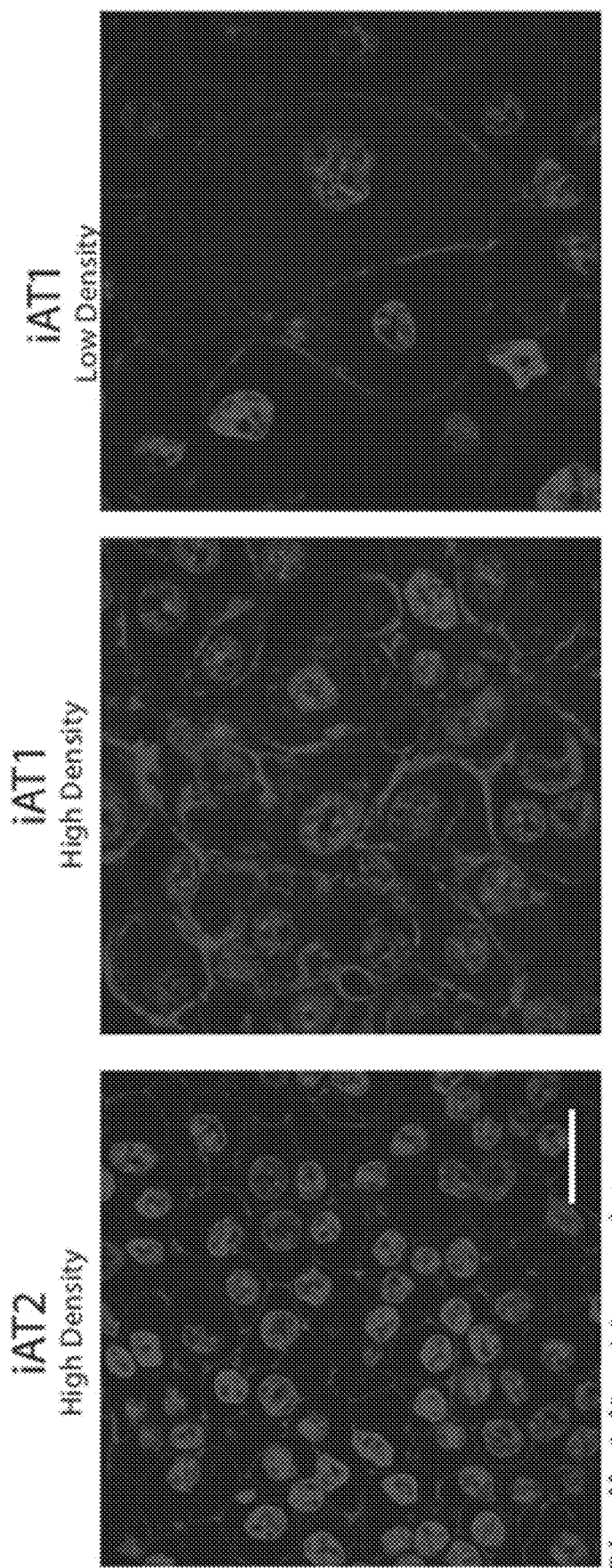

We profiled the iAT1s produced in 3D L+DCI (iAT1 3D) vs iAT1 ALI P1 conditions as well as iAT1s produced in a second ALI condition where iAT2s are only exposed to L+DCI coincident with transwell plating (hereafter "iAT1 ALI P0"; FIGS. 7E-7I, FIGS. 16A-16E). Compared to their siblings maintained as control iAT2s, we found downregulation of the AT2 program and upregulation of the YAP/TAZ and AT1 programs in iAT1s grown in both ALI cultures, similar to those iAT1s produced in 3D-L+DCI, but with significantly reduced active cell cycling (reduced G2/ M phases; FIGS. 7F-7G, 16A) and significantly less TOP2A (data not shown). These results indicate that iAT1s transition to a more a quiescent state after either ALI culture. As we have previously reported for iAT2s,$_{70}$ a are subset of cells plated in these conditions upregulated markers of non-lung endoderm (ALB, AFP) suggesting some degree of residual plasticity in rare cells plated in all 4 conditions (FIGS. 16B-16E).

Figure 7H:
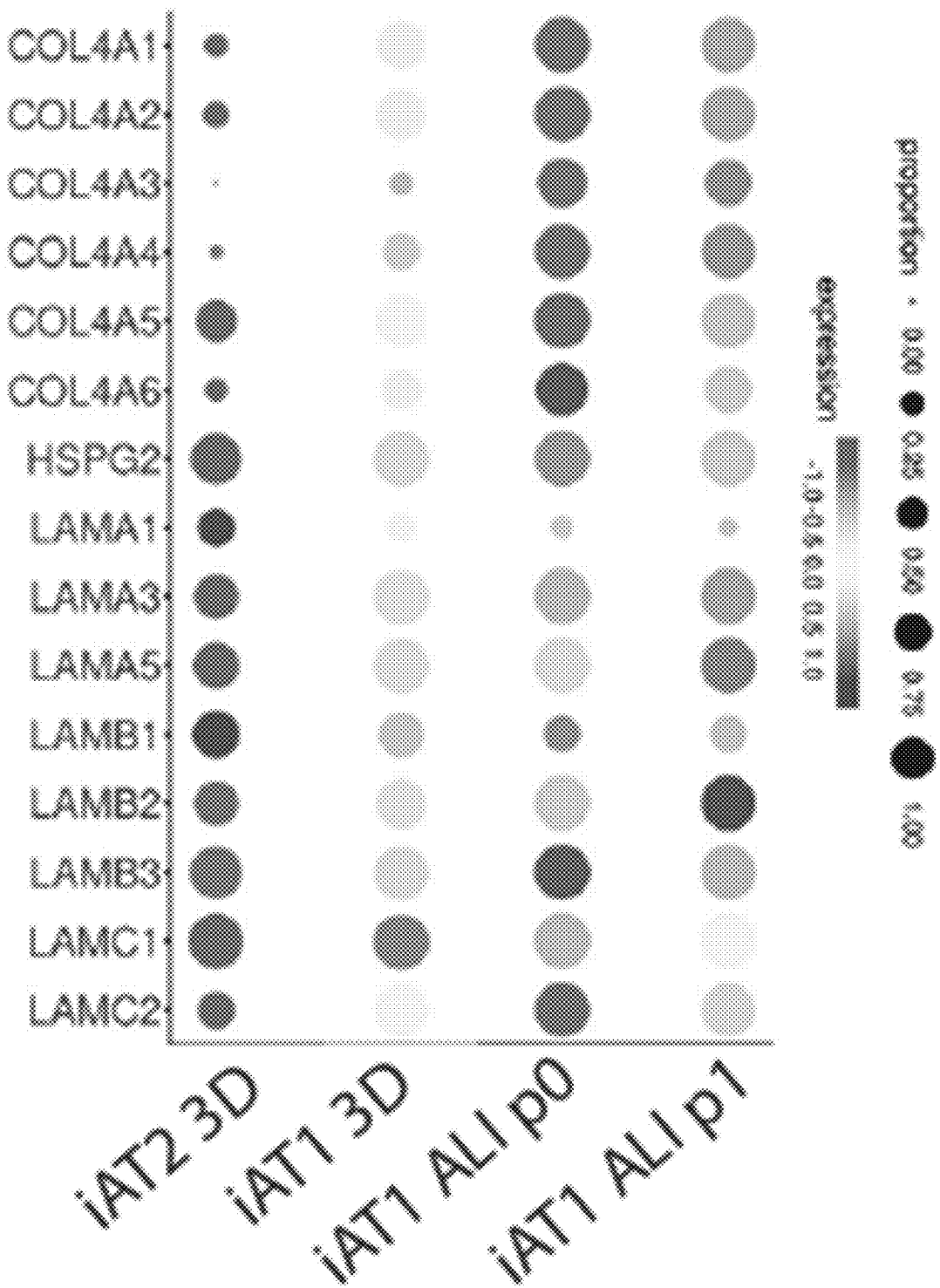
FIG. 7H) Expression of transcripts encoding extracellular matrix (ECM) components.
Figure 71:
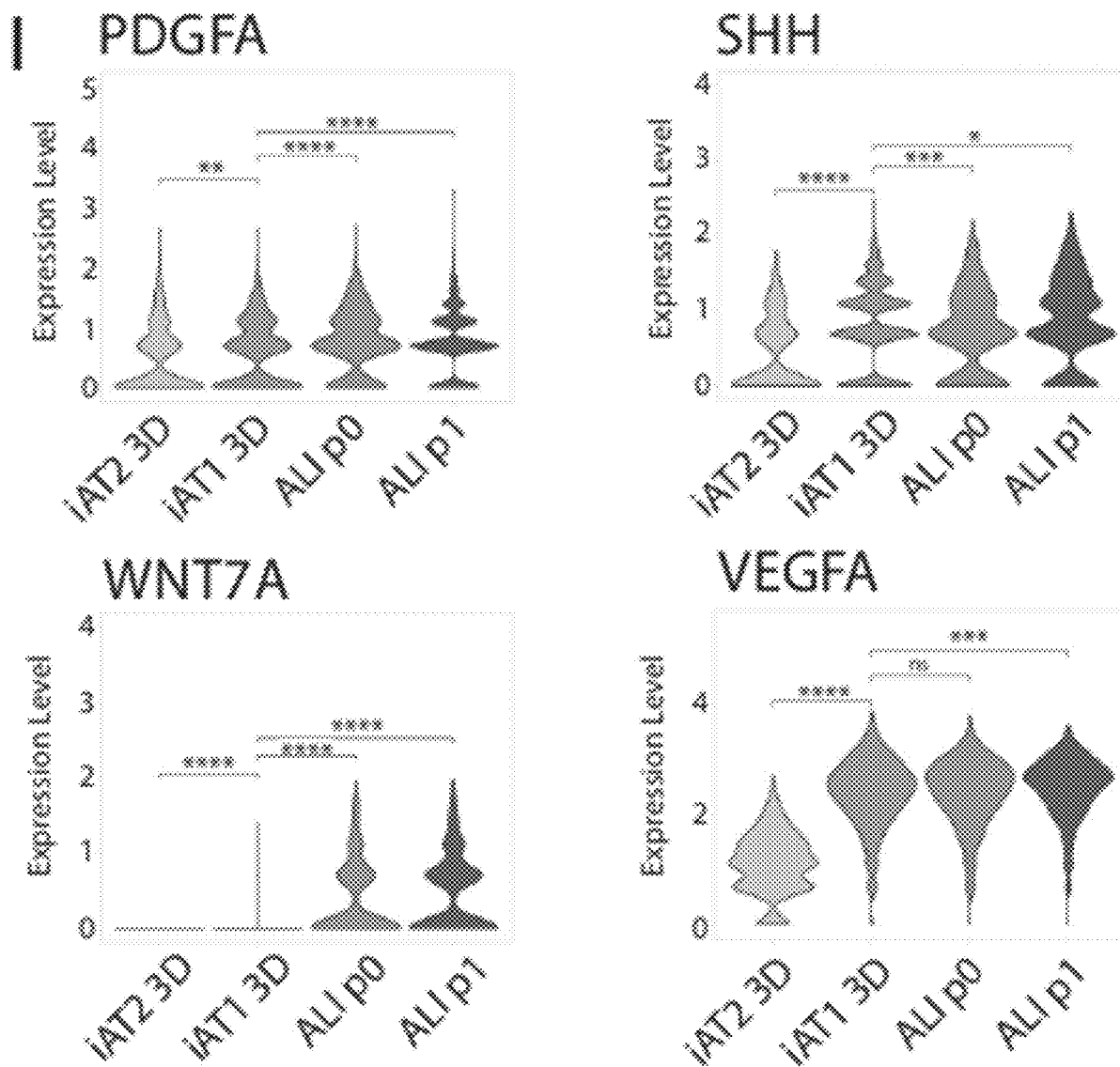

Despite the similarities in expression levels of AT1 marker genes in cells cultured with vs without ALI conditions, iAT1s after ALI culture clustered separately from iAT1 3D, and genes encoding extracellular matrix components, such as COL4A4, featured prominently in those transcripts upregulated after ALI culture (FIG. 7H). Given the recent reported role of extracellular matrix generation by mouse AT1s during development,$_{68}$ we looked at the other components of collagen IV, as well as laminins, including the components of laminin-332 (LAMA3, LAMB3, LAMC2). As reported for mouse AT1s in vivo.$_{68}$ human iAT1s after ALI culture expressed all 6 components of collagen IV (with more frequent expression of COL4A6 than the mouse), as well as patterns of laminin expression similar to published mouse single cell data (FIG. 7H). Notably, in this mouse dataset, expression of the components of laminin-332 was associated with more mature AT1 cells, only turning on around E18 and continuing postnatally. However, the expression pattern of these laminins in human lung development is unknown.

Figure 7J:
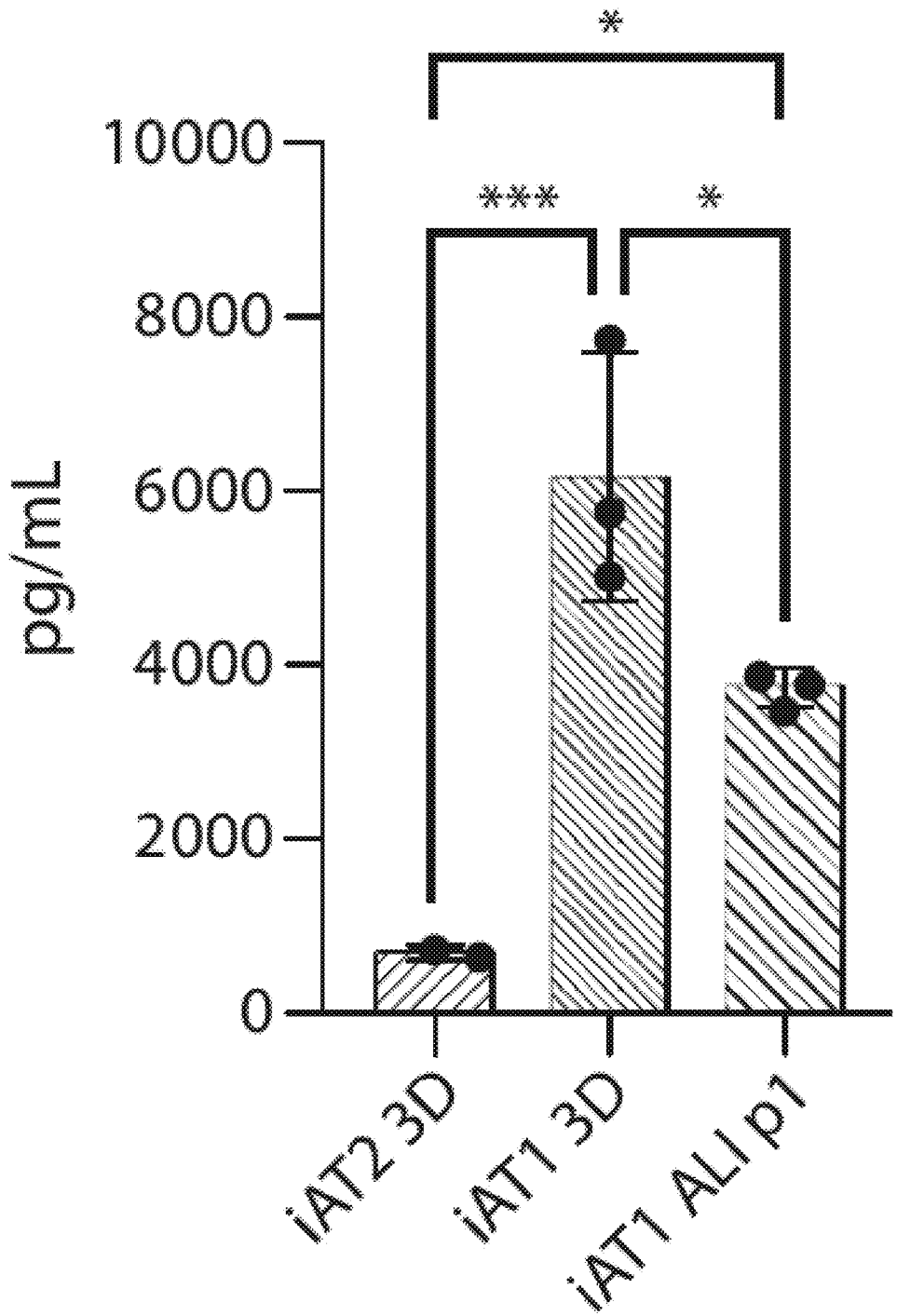
FIG. 7J) Analysis of secreted VEGFA protein in conditioned media at day 10 of culture of each indicated sample.

One recently recognized function of AT1s in vivo is their role as signaling hubs in the distal lung, based on mouse and human scRNA-seq profiles and genetic mouse models that suggest AT1s stimulate local alveolar Shh, Wnt, PDGF, and VEGF signaling in adjacent alveolar mesenchymal or vascular endothelial lineages during alveologenesis or tissue maintenance.$_{68,69}$ Consistent with these reports, we found iAT1s after ALI culture upregulated transcripts encoding the signaling ligands, PDGFA, SHH, WNT7A, and VEGFA (FIG. 7I) that were also enriched in primary AT1s from 2 month old human infants as reported by Zepp et al.$_{69}$ At the protein level, we verified secreted VEGFA was present in conditioned medium from both 3D and ALI iAT1 culture conditions. (FIG. 7J).

Figure 7K:
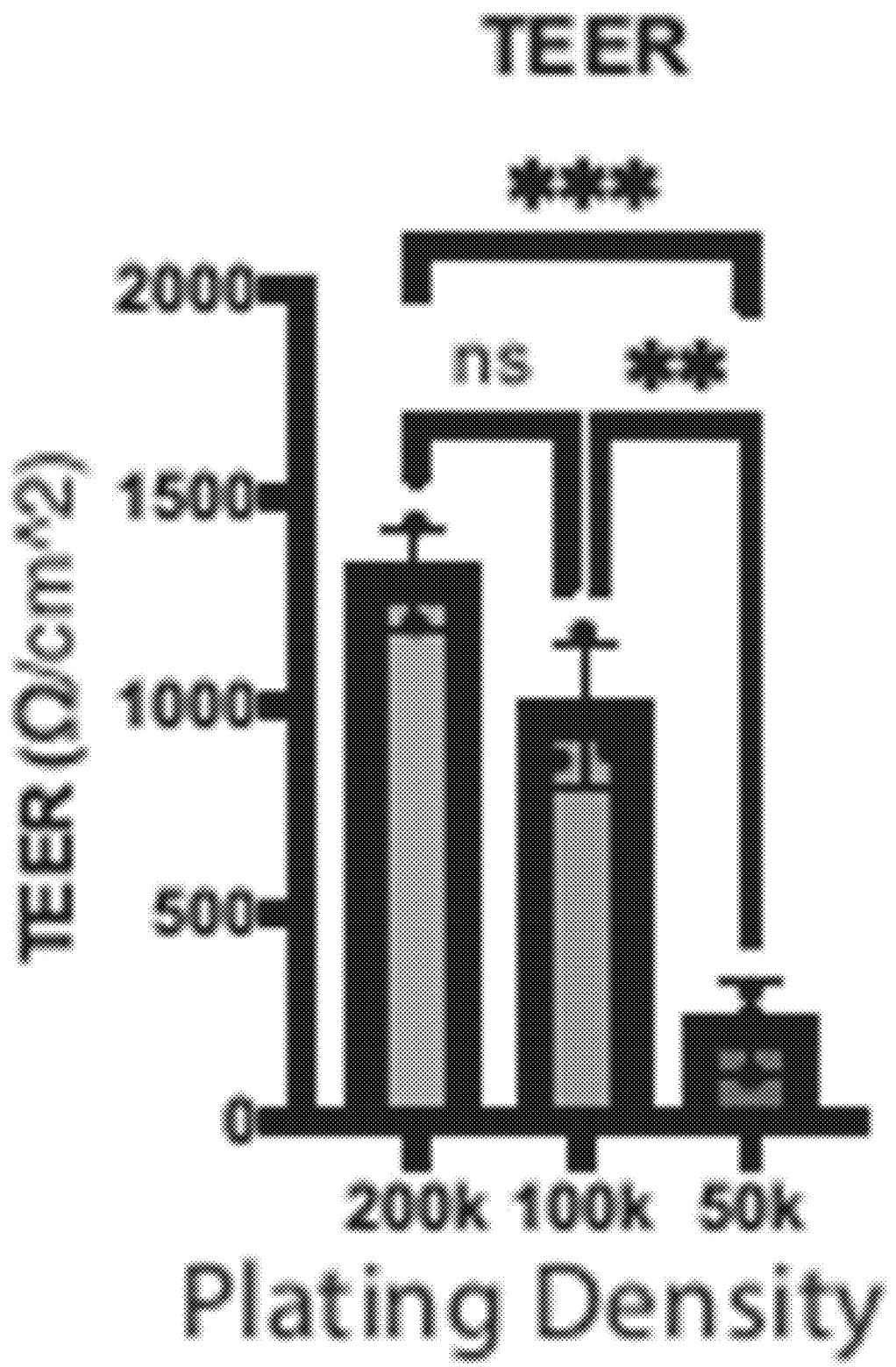
FIG. 7K) TEER of iAT1s after plating at High, Medium, and Low densities and outgrowth in ALI cultures in L+DCI. One-way ANOVA, N=3 per condition.
Figure 7M:
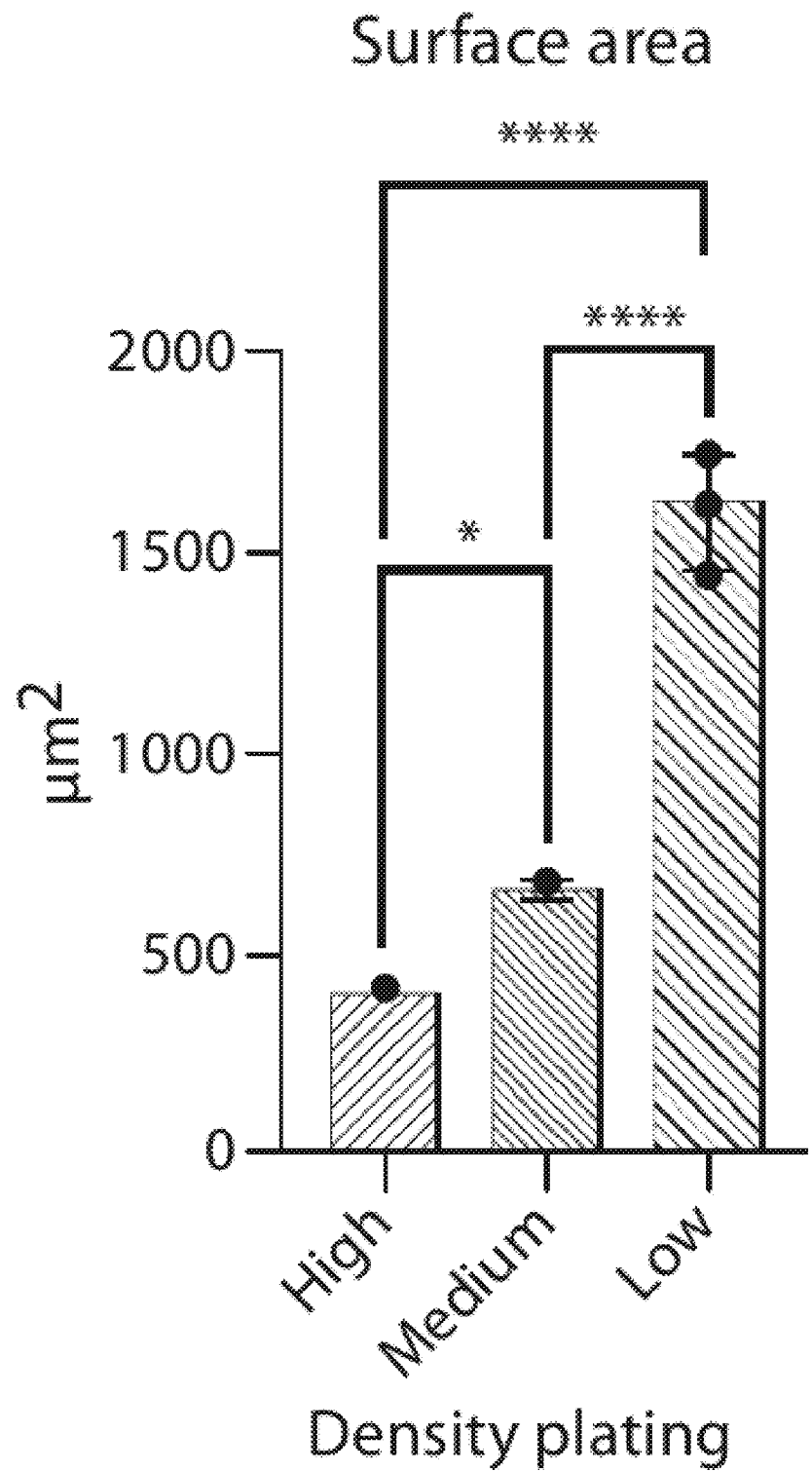
FIG. 7M) Average surface area of cells calculated using ZO-1 cell outlines at three different iAT1 ALI plating densities. N=3 per condition, averaged from ~150 cells per sample.
Figure 7L:
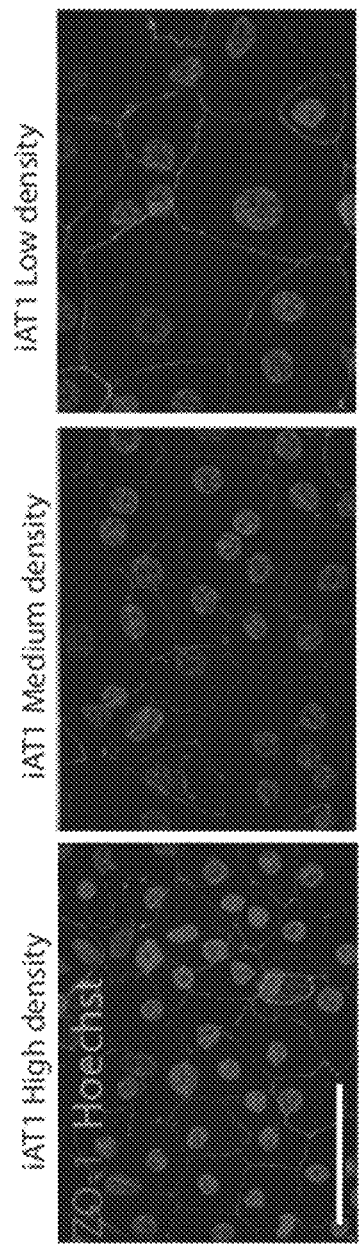
FIG. 7L) Tight junction protein ZO-1 staining at high, medium, and low plating density outgrowths at day 10 Scale bar=50 um.
Figure 7N:
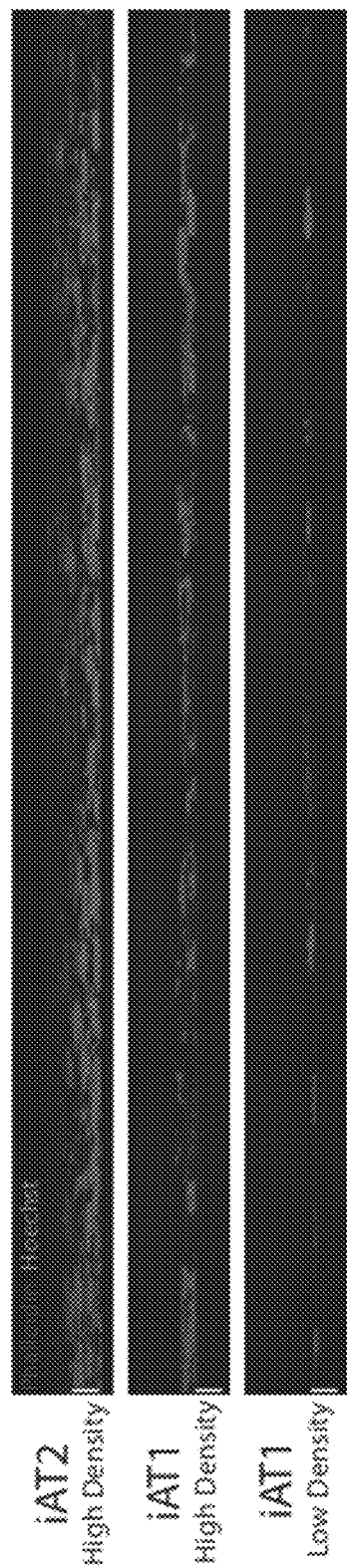
FIG. 7N) Orthogonal projection from confocal Z stacks of SPC2B2 iAT2s at ALI as previously published (ref 76 of Example 2), and SPC2B2 iAT1s plated at high and low densities in L+DCI. Scale bar=20 um.
Figure 70:
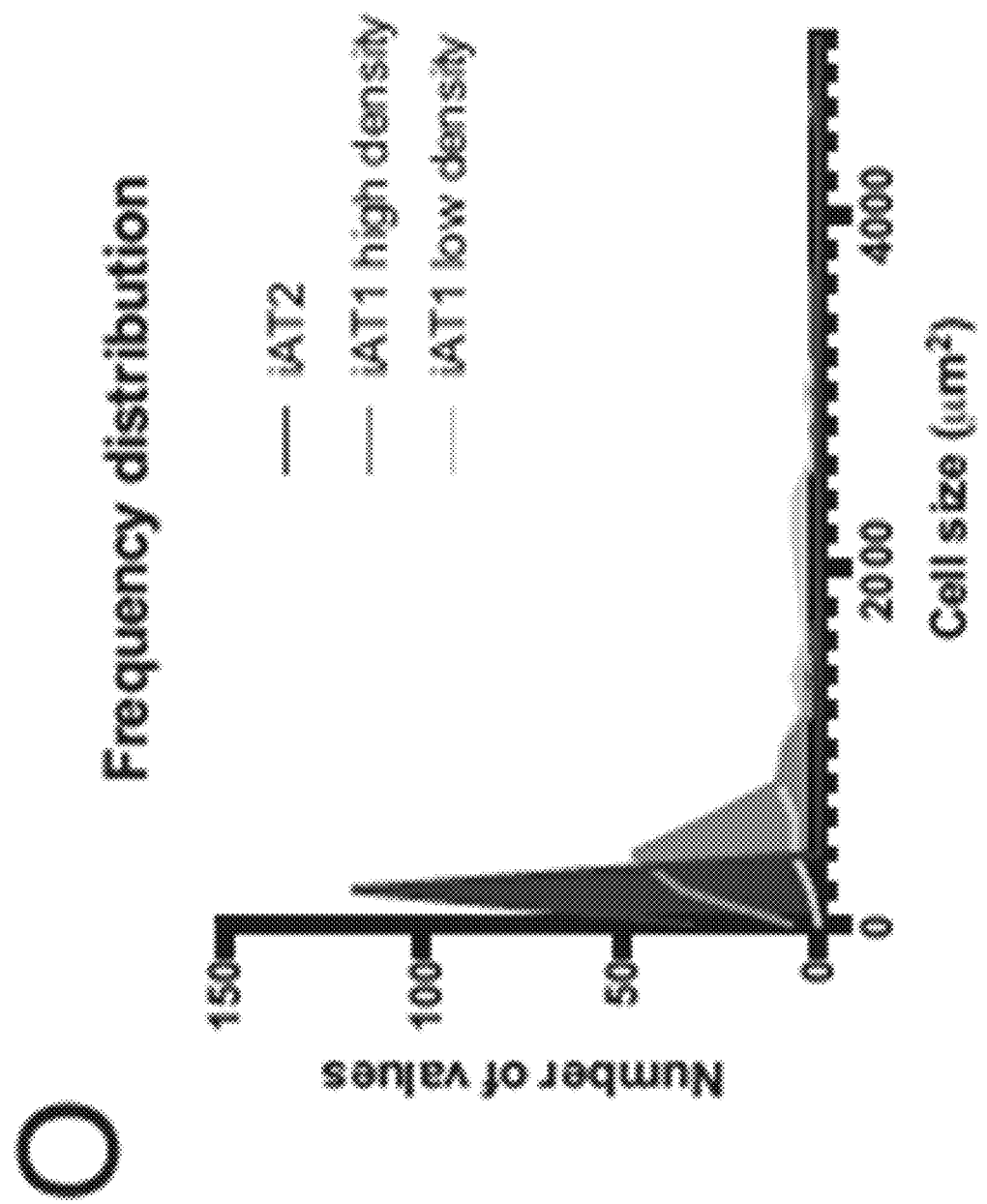

Finally, we evaluated whether iAT1s were capable of forming the characteristic flattened epithelial barrier that defines their unique morphology. We tested whether BU3 NGAT iAT1s would form a flattened monolayer at lower density plating, potentially stretching out to cover the available surface area, while still forming tight junctions necessary to form a functional epithelial barrier. Cells were plated at 3 separate densities in ALI cultures for 10 days. The ALI barrier remained intact for all 3 conditions with measurable TEER and formation of tight junctions, evident based on ZO-1 staining (FIGS. 7K, 7L). Average cell surface area was calculated, and cells plated at lower densities had significantly larger cell surface areas on average (FIGS. 7M, 17F). Similar results were observed for SPC2B2 iAT1s plated at high- and low-density ALI cultures, and iAT1s occupied larger cell surface areas than iAT2s plated at an identical initial cell density (FIGS. 7N, 7O; 17F-17H). Reported average surface areas of adult human AT1s range from 3960 µm2 to 8290 µm2, averaging around 5100 µm2.$_{1,2,71}$ At the above plating density, iAT1s reached the size of cells on the smaller end of this range (FIGS. 7O, 16E). Additionally, confocal Z stacks of SPC2B2 iAT1s show a flatter cross section than iAT2s plated at the same density and appearing even thinner when plated at a lower cell density. These results suggest iAT1s readily flatten and stretch to cover available surface area in order to form and maintain a thin epithelial barrier.

Discussion:

In this study we employed directed differentiation of iPSCs in vitro to efficiently generate cells expressing several key features reminiscent of human AT1 cells. Using multiple human iPSC lines, we first derived iAT2s and found activated nuclear YAP signaling was sufficient to drive a global transcriptomic shift from the AT2 to the AT1 program. This transition could be recapitulated with 97% efficiency using a defined serum-free medium containing a LATS inhibitor, producing cells that broadly upregulated a YAP/TAZ signaling gene set, expressed the molecular phenotype of human AT1 cells, and exhibited AT1 functional features, including the potential to form a flattened epithelial barrier that expresses AT1-associated ligands and matrix components.

Our finding that Hippo-LATS-YAP signaling activates the human AT1 program in lung epithelia is consistent with several recent reports that employed various mouse genetic models to activate this pathway in vivo, similarly finding resultant emergence of mouse AT1 markers.$_{46,56-58,65}$ While nuclear YAP activation was sufficient to drive the transcriptomic shift from iAT2 to iAT1, withdrawal of canonical Wnt or FGF signaling activators (CHIR and KGF) alone was not sufficient to robustly induce this differentiation, as measured by AGERtdTomato expression. We found these AT2-sustaining factors were inhibitory to the AT1 program, thus their withdrawal helped to promote the Hippo-LATS-YAP induced AT1 transition. In the 2 activating conditions we developed, we found that iAT1s grown in our defined medium (L+DCI) resembled YAP5SA-transduced iAT1s in terms of their structure, growth, and expression of most but not all canonical AT1 marker transcripts. While neither population was detectably more mature than the other, they clustered separately and differed in several ways with higher expression of the YAP target, ANKRD1, as well as expression of several keratins, KRT18, KRT19, and KRT7, all higher in the YAP5SA-transduced iAT1s, findings of unclear significance that will require further study. Importantly, our L+DCI medium, without requiring any lentivirus, also induced upregulation of several AT1 markers in cultured primary adult human AT2 cells, providing an identical serum-free defined medium-based approach that can now be studied using cells prepared from multiple sources, either primary or engineered.

Key to benchmarking our in vitro cells was the identification of gene set markers and pathways that define the in vivo transcriptomic program of human AT1 cells. Single cell RNA sequencing of adult primary human AT1 cells provided a comprehensive gene signature as well as a quartet of canonical markers (AGER, PDPN, CAV1, and CLIC5) that can be used for future profiling of these cells. Additionally, these datasets help to distinguish differences between human and mouse marker genes. While mice are the most common in vivo lung model, several mouse AT1 markers are not identically expressed in humans, including marker genes HOPX and AQP5, which are commonly used mouse AT1-specific genetic drivers that do not share this specificity in the human lung.[3,51] In prior mouse studies, AT1-selective fluorescent reporters or tracing approaches have revealed much about AT1 cell biology and lineage relationships.[3,50,51] Similarly, we engineered a human AGER-targeted tdTomato fluorescent reporter iPSC line, providing a key reagent for the tracking, quantification, and purification of candidate human AT1-like cells. In combination with an NKX2-1GFPreporter, we employed this bifluorescent system to understand the differentiation kinetics and characteristics of iAT1s as they emerge in various culture conditions from parental NKX2-1+ distal lung epithelial cells.

Additional mouse genetic models have shown that deletion of YAP/TAZ in mature AT1s in vivo leads to reversion to an AT2-like state.[45,46] Upon cre-mediated excision of the YAP5SA lentivirus in our human iAT1YAP5SAcells, we saw an upregulation of AT2 markers and an increase in iAT2 sphere morphology consistent with these mouse studies. Our medium employed in these studies (CK+DCI) has been optimized to support iAT2 differentiation and proliferation, and thus may have increased this iAT1-iAT2 reversion; however, overall, our findings suggest the necessity for activated nuclear YAP in the maintenance of AT1 program in human systems as well.

Our results raise several questions that will require further study. First, while our defined medium leads to robust differentiation of iAT2s into iAT1s by single cell RNA sequencing, it remains unclear whether this transition proceeds through the recently described transitional or basaloid cell state.[10,72,73] Although a very minor subset of iAT1s at the end point of our experiments expressed a few markers potentially associated with the transitional state (e.g. KRT17), most transitional markers were absent and further kinetic studies are needed at single cell resolution, potentially including bar-coded lineage tracing approaches, to understand whether differentiation fate trajectories in our model include transitional or other intermediate phenotypes. A second priority in future work will be further maturing the iAT1s produced by our methods. While our iAT1s show some functional properties and transcriptomic similarities to that of in vivo human AT1 cells, expression levels of most canonical AT1 markers are still significantly lower than in primary cell controls, and a variety of future approaches can now be tested in an effort to augment maturation, such as introducing biomechanical cues or different matrix substrata that more closely recapitulate the distal lung microenvironment. Lastly, our reductionist model which includes only 2 cell types in our studies (iAT1s and/or iAT2s), can be augmented in complexity in the future, beginning with the introduction of other alveolar lineages into co-cultures that might include mesenchymal, vascular, and immune lineages.

Thus, our work shows the generation of AT1-like cells from iPSC-derived AT2 cells. providing an in vitro model of human alveolar epithelial differentiation and a potential source of human cells that until now have been challenging to viably obtain from patients. Access to these cells, either in pure form or combined with other lineages should facilitate a variety of basic developmental studies. disease models, and potential engineering of future regenerative therapies.

Materials and Methods iPSC Generation and Maintenance

The reprogramming and characterization of the original human iPSC clones employed in this study (BU3 and SPC2-ST-B2) were previously published.[24,70,74] All iPSC lines had a normal karyotype (Cell Line Genetics G-banding analysis), both before and after gene-editing, and were maintained on hESC qualified Matrigel (Corning, 8774552) in feeder-free conditions in mTeSRI medium (STEMCELL Technologies, 05850). Gentle Cell Dissociation Reagent (STEMCELL Technologies, 07174) was used for passaging. All iPSC differentiations were performed under regulatory approval of the Institutional Review Board of Boston University. Additional details and protocols for iPSC derivation, culture, and characterization can be downloaded at crem.b-u.edu/cores-protocols/. All iPSC lines are available from the CREM repository upon request, stemcellbank.bu.edu.

CRISPR Targeting of tdTomato to AGER Locus in iPSCs

The iPSC line BU3 NG,[24] previously engineered to carry an NKX2-1GFPreporter was used for targeting a tdTomato reporter to the human AGER endogenous locus using CRISPR gene editing as follows. Left and right homology arms of about 700 bp in length to the left and right of the AGER endogenous start codon were generated by PCR amplification using gDNA extracts from BU3 NG iPSCs. These arms were cloned into our previously published plasmid backbone p1303-DV-SFTPC-tdTomato 16replacing the SFTPC homology arms, generating the p2701-AGER-tdTomato plasmid. Guide RNAs (gRNA1: CACCGCCAGGCTCCAACTGCTGTTC (SEQ ID NO: 11); gRNA2: CACCGATGGCTGCCGGAACAGCAGT (SEQ ID NO: 12); gRNA3: CACCGCTGTGGCCTCCGCCCTAGGT (SEQ ID NO: 13)) were selected and cloned into the pSpCas9(BB)-2A-GFP plasmid (Addgene plasmid #48138). BU3 NG iPSCs were pretreated with Rock Inhibitor (Y-27632) for three hours prior to nucleofection using the Lonza P3 Primary Cell 4DNucleofector™ X Kit (Lonza, cat. no. V4XP-3024) and replated for puromycin resistancescreening. Clones were passaged and gDNA was isolated for PCR screening using the following primer pairs (Fig S5): 5' CTGATCCCCTCAGACATTCTCAGGA 3' (SEQ ID NO: 14) to 5' GAGCTGCCGCTGCCGGT 3' (SEQ ID NO: 15) for outside the left homology arm to the tdTomato cassette and 5' ACTTGTGTAGCGCCAAGTGC 3' (SEQ ID NO: 16) to 5' ACACACACTCGCCTCCTGTT 3' (SEQ ID NO: 17) for within the puromycin resistance cassette to outside the right homology arm. HEK293 cells that had been transfected with the targeting plasmids or not were used as controls. Clones that showed insertion of tdTomato by PCR were sequenced to confirm insertion, and further expanded. The floxed PGK-Puromycin resistance cassette was excised using transient transfection with Cre plasmid (pHAGE2 EF1aL-Cre-IRES-NeoR-W; plasmid map available at kottonlab.com as previously published 16 with transient G418 selection of candidate targeted. Cre-excised clones.

Mono-allelic targeting and puromycin resistance excision was confirmed by PCR with primers 5'AGGACTCTTGTCCCAAAGGC 3" (SEQ ID NO: 18) to 5' CTGGGGTGTGGGGTTAAAGT 3' (SEQ ID NO: 19) yielding both a 267 bp long band for the untargeted allele and a 2290 bp long band for the targeted allele with the puromycin cassette excised. Cells were then assessed by G-banding to identify karyotypically normal clones (Cell Line Genetics).

iPSC Differentiation into iAT2 Cells (Alveolospheres)

Human iPSC lines (BU3 NG, BU3 NGAT, SPC2-ST-B2 were differentiated into iAT2s as previously described75, with detailed protocols and characterizations available for free download at www.kottonlab.com. Briefly, the STEMdiff Definitive Endoderm Kit (STEMCELL Technologies, 05110), was used for differentiation into endoderm, which was scored by co-expression of CKIT and CXCR4 by flow cytometry. Cells were then passaged using Gentle Cell Dissociation Reagent, replated onto Matrigel coated plate, and cultured in "DS/SB" media consisting of complete serum free differentiation media (cSFDM)[75] with 2 uM Dorsomorphin ("DS"; Stemgent) and 10 uM SB431542 ("SB"; Tocris) for 72 hours for anteriorization, the first 24 hours being supplemented with 10 uM Y-27632 (Tocris). Media was then changed to cSFDM with 3 uM CHIR99021 ("C"; Tocris), recombinant human BMP4 (10 ng/ml; "B"; R&D Systems), and 100 nM retinoic acid ("Ra"; Sigma-Aldrich) called "CBRa" for lung specification. Between days 14-16 of differentiation, cells were sorted for lung progenitors either using NKX2-1GFPknock-in reporters or using antibody staining for CPM (FUJIFILM) for lines not containing an NKX2-1 reporter. Sorted cells were resuspended in growth-factor reduced Matrigel (Corning 356231) droplets and covered with alveolar differentiation medium, "CK+DCI" containing a base of cSFDM with 3 uM CHIR99021 (C), rhKGF (10 ng/m; "K"; R&D Systems), 50 nM dexamethasone ("D"; Sigma-Aldrich), 0.1 mM 8-bromoadenosine 3',5'cyclic monophosphate sodium salt (Sigma-Aldrich), and 0.1 mM 3-isobutyl-1-methylxanthine (IBMX; Sigma-Aldrich) ("CI"). 10 uM Y-27632 (Tocris) was supplemented for 72 hours post sort and cells were refed with CK+DCI every 48-72 hours. For iAT2 maintenance, cells were passaged every 10-14 days as single cells as previously described.[75] iAT2s at Air-liquid interface were plated onto 6.5 mm transwell inserts (Corning) coated with hESC qualified Matrigel (Corning. 8774552) as previously published.[76,77]

Lentiviral and Adenoviral Transduction

For introduction of lentiviral and adenoviral constructs to iAT2s, alveolospheres were dissociated to single cells as with passaging 75. Cells were then incubated for 4 hours at 37 C in suspension with virus in CK+DCI supplemented with 10 uM Y-27632 and 5 ug/mL polybrene. WT YAP and YAP5SA lentiviral transduction was performed at a multiplicity of infection (MOI) of 10, as previously published.[75] An MOI of 200 was used for infections with Adeno-Cre-GFP virus. Cells were then replated in Matrigel droplets in CK+DCI.

iAT1 Differentiation in "L+DCI" Medium and Air-Liquid Interface (ALI) Culture iPSCs were first differentiated into iAT2s and passaged as above in 3D cultures in iAT2 medium (CK+DCI) supplemented for the first 3 days after passaging with 10 uM Y-27632 (Tocris). To generate iAT1s, 3 days after passaging iAT2s in 3D, the medium was replaced with "L+DCI", consisting of [10 uM LATS-IN-1 ("L"; MedChemExpress Cat. No.: HY-138489), 50 nM dexamethasone ("D"; Sigma-Aldrich), 0.1 mM 8-bromoadenosine 3',5'cyclic monophosphate sodium salt (Sigma-Aldrich; "C"), and 0.1 mM 3-isobutyl-1-methylxanthine (IBMX; Sigma-Aldrich; "I")]. Cells were cultured up to 16 days in L+DCI in 3D while monitoring AGERtdTomatoexpression as detailed in the text.

ALI versions of iAT1 cultures were prepared as follows. To prepare "iAT1 ALI p0" cultures. first a single cell suspension of iAT2s was passaged onto 6.5 mm transwell inserts (Corning) coated with hESC qualified Matrigel (Corning, 8774552) as previously published,[76,77] but switching CK+DCI medium to L+DCI at the time of plating. To prepare "iAT1 ALI p1" cultures, iAT2s in 3D Matrigel culture were first switched to L+DCI medium in 3D for 9 days before being passaged as singlecells onto Matrigel coated transwells for continued L+DCI culture. (High density=200 k cells/6.5 mm insert, medium=100 k cells/insert, low density=50 k cells/insert.) For all ALI culturing conditions, rock inhibitor was added to LDCI media for the first 3 days post passaging and then removed. At the same time (day 3), liquid was aspirated from the apical chamber (air lift) to form the air liquid interface (ALI). Cells in ALI cultures were maintained for up to 10 days (7 days post air lift). Accutase (Innovative Cell Technologies) was used to dissociate cells for FACS analysis and single cell RNA sequencing.

Reverse Transcription Quantitative Polymerase Chain Reaction (RT-qPCR)

For RT-qPCR, whole well or sorted cells were collected and stored in Qiazol (Qiagen, 79306) prior to RNA isolation using RNeasy Plus Mini Kit according to the manufacturer's protocol (Qiagen, 74104), cDNA was then synthesized using MultiScribe™ Reverse Transcriptase (ThermoFisher 4311235). A QuantStudio instrument (Applied Biosciences) and predesigned Taqman probes were used and run in a 384-well format for 40 cycles. Relative expression was normalized to an 18S control and fold change over control cells was calculated using $2^{-\Delta\Delta Ct}$. Where indicated in the text, RNA extracts from adult primary human distal lung tissue explants, the kind gift of Barry Stripp (Cedars Sinai, Los Angeles) were employed as RT-qPCR controls. RNA was isolated via RNeasy Plus Mini Kit following manufacturer's protocol.

Flow Cytometry and FACS 0.05% trypsin was used to generate single cell suspensions which were resuspended in sort buffer [HBSS (ThermoFisher) with 2% FBS, 10 uM Y-27632 (Tocris)] with Live/dead stain [Calcein blue (Life technologies) or DRAQ7 (Abcam)]. Cells were sorted based on reporter expression: NKX2-1GFP and AGERtdTomatofor BU3 NGAT, or SFTPCtdTomatofor SPC2B2, as indicated in the text. Cell sorting was performed on a Moflo Astrios EQ (Beckman Coulter) and flow cytometry analysis was performed on an LSRII SORP (BD Biosciences) at the Boston University Flow Cytometry Core Facility. For Edu assays, the Click-iT Plus EdU Alexa Fluor 647 Flow Cytometry Assay Kit (Thermo Fisher Scientific) was used with EdU added 24 hours before cell isolation, and cells fixed in 4% paraformaldehyde (PFA) were analyzed on a Stratedigm (S1000EXI) cytometer with post-processing using Flow Jo software (BD Biosciences). For all other analyses, live non-fixed cells were sorted or analyzed as indicated in the text.

Immunofluorescence Microscopy

Organoids (3D cultured epithelial spheres or clumps) or cells were fixed in 4% PFA for 20 minutes at room temperature. For whole mount staining, organoids were immediately stained in solution and mounted on cavity slides (Elisco). For sectioning, samples were dehydrated via ethanol and paraffin embedded, or dehydrated using sucrose and frozen in OCT. Prior to staining, paraffin sections were rehydrated, and antigen retrieval was performed using heated citrate buffer. For both paraffin- and cryo-embedded sections, permeabilization was performed using 0.1% Triton and blocking was done with 4% Normal Donkey Serum. Samples were incubated in primary antibody overnight at 4 C and incubated in secondary antibody with Hoechst for 2 hrs at RT. Primary antibodies used included ProSFTPC (Pro-SPC): Seven Hills WRAB-9337; HTI-56: Terrace Biotech TB-29AHT1-56; ZO-1: Thermo Fisher Cat# 61-7300; and RFP: Rockland 600-401-379. Confocal images were taken on either a Leica SP5 or Zeiss LSM 710-Live Duo and were processed using Fiji.

VEGFA ELISA

To measure secreted VEGFA protein, conditioned media after 48 hours of exposure to cells was harvested from each sample indicated in the text and figure legends on day 10 of ALI culture. VEGFA ELISA was performed using the Human VEGFA ELISA kit (Abcam) according to manufacturer's instructions.

Cell Surface Area Calculations iAT1 ALI p1 cells were grown in LDCI medium for 10 days, aspirating apical medium on day 3 (air lift) to form an air liquid interface. Day 10 post plating (7 days after air lift) cells were fixed in 4% PFA and stained for tight junction protein ZO-1 (Thermo Fisher Cat# 61-7300). Randomized Z stack images were taken at 20× in 3 different places of each transwell for three transwells and imported into ImageJ. Cell outlines denoted by ZO-1 were traced by hand and area was calculated using ImageJ for around 50 cells per image.

Transepithelial Electrical Resistance

To measure TEER, a Millicell ERS-2 Coltohmmeter (Moillipore Sigma, MERS00002) was used. Electrodes were sterilized by dipping in 70% EtOH followed by conditioned cell media. 200 uL media was added to the apical chamber of Transwell culture inserts prior to taking measurements. For each sample, readings were taken at 3 locations in the well. TEER was calculated by subtracting the "blank" Matrigel coated well from the mean and multiplying by the tissue culture growth area.

Generation of YAP5SA and WT YAP Lentivirus

Coding sequences for YAP5SA and WT YAP were PCR amplified from pLVX-Tight-Puro-3F-YAP-5SA and pLVX-Tight-Puro-3F-YAP, respectively,[78] adding NotI and BglII restriction sites for ligation into a pHAGE2-EF1aL-dsRed-UBC-tagBFP-WPRE backbone in place of the dsRed cassette. We have previously published the dual promoter lentiviral vector for dual transgenesis [79] and the pHAGE2 version includes a loxP cassette in the 3'LTR as previously published.[80] This cloning strategy generated the following loxP containing plasmids for the current project: pHAGE2-EF1aL-YAP5SA-UBC-tagBFP-WPRE and pHAGE2-EF1aL-WTYAP-UBC-tagBFP-WPRE. The YAP5SA coding sequence was also cloned into a pHAGE1 backbone generating pHAGE1-EF1aL-YAP5SA-UBC-GFP-WPRE. Lentiviral packaging and titering protocols (as we have previously published), was well as plasmid maps and primer design protocols for cloning into pHAGE lentiviral backbones are all available at kottonlab.com.

Single Cell RNA Sequencing of iAT2s and iAT1s

For single cell RNA sequencing of iPSC-derived alveolar epithelial cells, cells were dissociated to single cell suspensions using 0.05% trypsin. Live cells were sorted via DRAQ7 using Moflo Astrios EQ (Beckman Coulter) at the Boston University Flow Cytometry Core Facility. Single Cell RNA sequencing was then preformed using the Chromium Single Cell 3'system according to manufacturers' instructions (10× Genomics) at the Single Cell Sequencing Core at Boston University Medical Center. Sequencing files were mapped to the human genome reference (which one? GRCh37?) supplemented with GFP, tdTomato, and BFP sequences. Seurat v3.2.3 was used for downstream analysis and quality control. Cells with less than 800 genes detected and doublets were excluded, as well as cells with high mitochondrial gene counts (manual thresholds set for each dataset between 15% and 35%). We used SCTransform for normalization and PCAfor initial linear dimensionality reduction. Data was plotted using UMAP and clustering was done using Louvain algorithm.

Statistical Analysis

Unpaired student's t-tests were used to compare two groups while one-way Analysis of Variance (ANOVA) with Tukey multiple comparisons test was used to compare the means between three or more groups, $p<0.05$ was used to determine statistical significance unless otherwise indicated in the text.

REFERENCES

1. Weibel, E. R. On the tricks alveolar epithelial cells play to make a good lung. *Am. J. Respir. Crit. Care Med.* 191, 504-513 (2015).
2. Schneider, J. P, et al. On the topological complexity of human alveolar epithelial type 1 cells. *American Journal of Respiratory and Critical Care Medicine* (2019).doi: 10.1164/ rccm.201810-1866LE
3. Jain, R, et al. Plasticity of Hopx+ type I alveolar cells to regenerate type II cells in the lung. (2015). doi: 10.1038/ ncomms7727. Plasticity
4. Gonzalez, R. F., Allen, L. & Dobbs, L. G. Rat alveolar type I cells proliferate, express OCT-4, and exhibit phenotypic plasticity in vitro. *Am. J. Physiol. Cell. Mol. Physiol.* 297, L1045-L1055 (2009).
5. Katsura, H. et al. Human Lung Stem Cell-Based Alveolospheres Provide Insights into SARS-COV-2-Mediated Interferon Responses and Pneumocyte Dysfunction. *Cell Stem Cell* 27, 890-904. e8 (2020).
6. Qiao, R, et al. Effects of KGF on alveolar epithelial cell transdifferentiation are mediated by JNK signaling. *Am. J. Respir. Cell Mol. Biol.* (2008). doi: 10.1165/ rcmb.2007-01720C
7. Evans, M. J., Cabral, L. J., Stephens, R. J. & Freeman, G. Transformation of alveolar Type 2 cells to Type 1 cells following exposure to NO2. *Exp. Mol. Pathol.* 22, 142-150 (1975).
8. Adamson, I. Y. R. & Bowden, D. H. The type 2 cell as progenitor of alveolar epithelial regeneration. A cytodynamic study in mice after exposure to oxygen. *Lab. Invest.* 30, 35-42 (1974).
9. Barkauskas, C. et al. Type 2 alveolar cells are stem cells in adult lung. *J Clin Invest* 123, 3025-3036 (2013).
10. Kobayashi, Y, et al. Persistence of a regeneration-associated, transitional alveolar epithelial cell state in pulmonary fibrosis. *Nat. Cell Biol.* 22, 934-946 (2020).
11. Choi, J. et al. Inflammatory Signals Induce AT2 Cell-Derived Damage-Associated Transient Progenitors that Mediate Alveolar Regeneration. *Cell Stem Cell* 27, 366-382. e7 (2020).
12. Zacharias, W. J. et al. Regeneration of the lung alveolus by an evolutionarily conserved epithelial progenitor. *Nature* 555, 251-255 (2018).
13. Wang, J. et al. Differentiated Human Alveolar Epithelial Cells and Reversibility of their Phenotype In Vitro. *Am. J. Respir. Cell Mol. Biol.* 36, 661 (2007).
14. Fehrenbach, H. et al. Keratinocyte growth factor-induced hyperplasia of rat alveolar type II cells in vivo is resolved by differentiation into type I cells and by apoptosis. *Eur Respir J* 14, 534-544 (1999).

15. Danto, S. I., Shannon, J. M., Borok, Z., Zabski, S. M. & Crandall, E. D. Reversible transdifferentiation of alveolar epithelial cells. *Am. J. Respir. Cell Mol. Biol.* 12, 497-502 (1995).

16. Jacob, A, et al. Differentiation of Human Pluripotent Stem Cells into Functional Lung Alveolar Epithelial Cells. *Cell Stem Cell* 21, 472-488. e10 (2017).

17. Alysandratos, K.-D. et al. Impact of cell culture on the transcriptomic programs of primary and iPSC-derived human alveolar type 2 cells, doi: 10.1101/2022.02.08.479591

18. Yamamoto, Y. et al. Long-term expansion of alveolar stem cells derived from human iPS cells in organoids. *Nat. Methods* 14, 1097-1106 (2017).

19. Kadur Lakshminarasimha Murthy, P. et al. Human distal lung maps and lineage hierarchies reveal a bipotent progenitor. *Nature* 604, 111-119 (2022).

20. Kanagaki, S. et al. Directed induction of alveolar type I cells derived from pluripotent stem cells via Wnt signaling inhibition. *Stem Cells* 39, 156-169 (2021).

21. Salahudeen, A. A. et al. Progenitor identification and SARS-COV-2 infection in human distal lung organoids. *Nat.* 2020 5887839 588, 670-675 (2020).

22. Desai, T. J., Brownfield, D. G. & Krasnow, M. A. Alveolar progenitor and stem cells in lung development, renewal and cancer. *Nature* 507, 190-194 (2014).

23. Frank, D. B. et al. Early lineage specification defines alveolar epithelial ontogeny in the murine lung. *Proc. Natl. Acad. Sci.* (2019), doi: 10.1073/ pnas. 1813952116

24. Hawkins, F. et al. Prospective isolation of NKX2-1— expressing human lung progenitors derived from pluripotent stem cells. 127, 1-18 (2017).

25. Longmire, T. A. et al. Efficient derivation of purified lung and thyroid progenitors from embryonic stem cells. *Cell Stem Cell* 10, 398-411 (2012).

26. Serls, A. E., Doherty, S., Parvatiyar, P., Wells, J. M. & Deutsch, G. H. Different thresholds of fibroblast growth factors pattern the ventral foregut into liver and lung. *Development* 132, 35-47 (2005).

27. Serra, M. et al. Pluripotent stem cell differentiation reveals distinct developmental pathways regulating Lung-Versus Thyroid-Lineage specification. *Dev.* 144, 3879-3893 (2017).

28. Ikonomou, L. & Kotton, D. N. Derivation of endodermal progenitors from pluripotent stem cells. *J. Cell Physiol.* 230, 246-258 (2015).

29. Ikonomou, L. et al. The in vivo genetic program of murine primordial lung epithelial progenitors. *Nat. Commun.* 11, (2020).

30. Treutlein, B. et al. Reconstructing lineage hierarchies of the distal lung epithelium using single-cell RNA-seq. *Nature* 509, 371-375 (2014).

31. Liu, Z. et al. MAPK-Mediated YAP Activation Controls Mechanical-Tension-Induced Pulmonary Alveolar Regeneration. *Cell Rep.* 16, 1810-1819 (2016).

32. Frank, D. B. et al. Emergence of a Wave of Wnt Signaling that Regulates Lung Alveologenesis by Controlling Epithelial Self-Renewal and Differentiation. *Cell Rep.* 17, 2312-2325 (2016).

33. Rieger, M. E. et al. P300/ β-Catenin Interactions Regulate Adult Progenitor Cell Differentiation Downstream of WNT5a/Protein Kinase C (PKC). *J. Biol. Chem.* 291, 6569-6582 (2016).

34. Li, J. et al. The Strength of Mechanical Forces Determines the Differentiation of Alveolar Epithelial Cells. *Dev. Cell* 44, 297-312. e5 (2018).

35. Barkauskas, C. E. et al. Type 2 alveolar cells are stem cells in adult lung. *J. Clin. Invest.* 123, 3025-3036 (2013).

36. Rock, J. R. et al. Multiple stromal populations contribute to pulmonary fibrosis without evidence for epithelial to mesenchymal transition. *Proc. Natl. Acad. Sci.* 108, E1475-E1483 (2011).

37. Liberti, D. C. et al. Alveolar epithelial cell fate is maintained in a spatially restricted manner to promote lung regeneration after acute injury. *Cell Rep.* 35, (2021).

38. Zhao, L., Yee, M. & O'Reilly, M. A. Transdifferentiation of alveolar epithelial type II to type I cells is controlled by opposing TGF- and BMP signaling. *AJP Lung Cell. Mol. Physiol.* 305, L409-L418 (2013).

39. Riemondy, K. A. et al. Single-cell RNA sequencing identifies TGF-βas a key regenerative cue following LPS-induced lung injury. *JCI Insight* (2019). doi: 10.1172/jci.insight.123637

40. Nabhan, A. N., Brownfield, D. G., Harbury, P. B., Krasnow, M. A. & Desai, T. J. Single-cell Wnt signaling niches maintain stemness of alveolar type 2 cells. *Science* (80-.). 359, 1118-1123 (2018).

41. Chung, M.-I., Bujnis, M., Barkauskas, C. & Hogan, B. L. M. Niche-mediated BMP/SMAD signaling regulates lung alveolar stem cell proliferation and differentiation. *Development* 145, dev163014 (2018).

42. Little, D. R. et al. Transcriptional control of lung alveolar type 1 cell development and maintenance by NK homeobox 2-1. *Proc. Natl. Acad. Sci.* 116, 20545-20555 (2019).

43. Borok, Z. et al. Keratinocyte growth factor modulates alveolar epithelial cell phenotype in vitro: expression of aquaporin 5. *Am. J. Respir. Cell Mol. Biol.* 18, 554-561 (1998).

44. Sun, T. et al. TAZ is required for lung alveolar epithelial cell differentiation after injury. *JCI insight* 5, (2019).

45. Little, D. R. et al. Differential chromatin binding of the lung lineage transcription factor NKX2-1 resolves opposing murine alveolar cell fates in vivo. *Nat. Commun.* 12, (2021).

46. Penkala, I. J. et al. Age-dependent alveolar epithelial plasticity orchestrates lung homeostasis and regeneration. *Cell Stem Cell* 28, 1775-1789. e5 (2021).

47. Matthay, M. A. et al. Acute respiratory distress syndrome. *Nat. Rev. Dis. Prim.* 5, (2019).

48. Strunz, M. et al. Alveolar regeneration through a Krt8+ transitional stem cell state that persists in human lung fibrosis. *Nat. Commun.* 11, (2020).

49. Habermann, A. C. et al. Single-cell RNA-sequencing reveals profibrotic roles of distinct epithelial and mesenchymal lineages in pulmonary fibrosis, *bioRxiv* (2019), doi: 10.1101/753806

50. Chung, M. I. & Hogan, B. L. M. Ager-CreERT2: A new genetic tool for studying lung alveolar development, homeostasis, and repair. *Am. J. Respir. Cell Mol. Biol.* (2018), doi: 10.1165/ rcmb.2018-0125OC 51. Flodby, P. et al. Directed Expression of Cre in Alveolar Epithelial Type 1 Cells. *Am. J. Respir. Cell Mol. Biol.* 43, 173 (2010).

52. Basil, M. C. et al. Human distal airways contain a multipotent secretory cell that can regenerate alveoli. *Nature* (2022). doi: 10.1038/ s41586-022-04552-0

53. Sun, X. et al. A census of the lung: CellCards from LungMAP. *Dev. Cell* 57, 112-145. e2 (2022).

54. Du, Y. et al. Lung Gene Expression Analysis (LGEA): an integrative web portal for comprehensive gene expression data analysis in lung development. *Thorax* 72, 481-484 (2017).
55. Ardini-Poleske, M. E. et al. LungMAP: The molecular atlas of lung development program. *Am. J. Physiol.—Lung Cell. Mol. Physiol.* 313, L733-L740 (2017).
56. Gokey, J. J. et al. YAP regulates alveolar epithelial cell differentiation and AGER via NFIB/KLF5/ NKX2-1. *iScience* 24, 102967 (2021).
57. Nantie, L. B. et al. Lats1/2 inactivation reveals Hippo function in alveolar type I cell differentiation during lung transition to air breathing. *Development* (2018). doi: 10.1242/ dev.163105
58. van Soldt, B. J. et al. Yap and its subcellular localization have distinct compartment-specific roles in the developing lung. *Development* (2019). doi: 10.1242/ dev.175810
59. Wang, Y. et al. Pulmonary alveolar type I cell population consists of two distinct subtypes that differ in cell fate. *Proc. Natl. Acad. Sci. U.S.A.* 115, 2407-2412 (2018).
60. Zhao, B. et al. Inactivation of YAP oncoprotein by the Hippo pathway is involved in cell contact inhibition and tissue growth control. (2007), doi: 10.1101/ gad.1602907
61. Jacob, A. et al. Derivation of self-renewing lung alveolar epithelial type II cells fromhuman pluripotent stem cells HHS Public Access. doi: 10.1038/ s41596-019-0220-0
62. Little, D. R. et al. Transcriptional control of lung alveolar type 1 cell development and maintenance by NK homeobox 2-1. *Proc. Natl. Acad. Sci. U.S.A.* 116, 20545-20555 (2019).
63. Jones, R. C. et al. The Tabula Sapiens: A multiple-organ, single-cell transcriptomic atlas of humans. *Science* (80-.). 376, (2022).
64. Penkala, I. J. et al. Age-dependent alveolar epithelial plasticity orchestrates lung homeostasis and regeneration. *Cell Stem Cell* (2021). doi: 10.1016/ j.stem.2021.04.026
65. Little, D. R. et al. Differential chromatin binding of the lung lineage transcription factor NKX2-1 resolves opposing murine alveolar cell fates in vivo. *Nat. Commun.* 12, 1-18 (2021).
66. Kastan, N. et al. Small-molecule inhibition of Lats kinases may promote Yap-dependent proliferation in post-mitotic mammalian tissues. *Nat. Commun.* 2021 121 12, 1-12 (2021).
67. Wang, Y. et al. Comprehensive Molecular Characterization of the Hippo Signaling Pathway in Cancer. *Cell Rep.* 25, 1304-1317. e5 (2018).
68. Negretti, N. M. et al. A single-cell atlas of mouse lung development. *Dev.* 148, (2021).
69. Zepp, J. A. et al. Genomic, epigenomic, and biophysical cues controlling the emergence of the lung alveolus. *Science* (80-.). 371, (2021).
70. Hurley, K. et al. Reconstructed Single-Cell Fate Trajectories Define Lineage Plasticity Windows during Differentiation of Human PSC-Derived Distal Lung Progenitors. *Cell Stem Cell* 26, 593-608. e8 (2020).
71. Crapo, J. D., Barry, B. E., Gehr, P., Bachofen, M. & Weibel, E. R. Cell number and cell characteristics of the normal human lung. *Am. Rev. Respir. Dis.* 126, 332-337 (1982).
72. Habermann, A. C. et al. *Single-cell RNA sequencing reveals profibrotic roles of distinct epithelial and mesenchymal lineages in pulmonary fibrosis. Sci. Adv* 6, (2020).
73. Kathiriya, J. J. et al. Human alveolar type 2 epithelium transdifferentiates into metaplastic KRT5+ basal cells. *Nat. Cell Biol.* 24, 10-23 (2022).
74. Alysandratos, K. D. et al. Patient-specific iPSCs carrying an SFTPC mutation reveal the intrinsic alveolar epithelial dysfunction at the inception of interstitial lung disease. *Cell Rep.* 36, (2021).
75. Jacob, A. et al. Derivation of self-renewing lung alveolar epithelial type II cells from human pluripotent stem cells. *Nat. Protoc.* 14, 3303 (2019).
76. Abo, K. M. et al. Air-liquid interface culture promotes maturation and allows environmental exposure of pluripotent stem cell-derived alveolar epithelium. *JCI Insight* 7, (2022).
77. Huang, J. et al. SARS-COV-2 Infection of Pluripotent Stem Cell-Derived Human Lung Alveolar Type 2 Cells Elicits a Rapid Epithelial-Intrinsic Inflammatory Response. *Cell Stem Cell* 27, 962-973. e7 (2020).
78. Hiemer, S. E., Szymaniak, A. D. & Varelas, X. The Transcriptional Regulators TAZ and YAP Direct Transforming Growth Factor β2-induced Tumorigenic Phenotypes in Breast Cancer Cells*âTMİ. *J. Biol. Chem.* 289, 13461-13474 (2014).
79. Wilson, A. A. et al. Sustained expression of alpha1-antitrypsin after transplantation of manipulated hematopoietic stem cells. *Am. J. Respir. Cell Mol. Biol.* 39, 133-141 (2008).
80. Sommer, C. A. et al. Excision of reprogramming transgenes improves the differentiation potential of iPS cells generated with a single excisable vector. *Stem Cells* 28, 64-74 (2010).

What is claimed herein is:

1. A method comprising culturing at least one alveolar epithelial cell type II (AT2) cell and/or lung epithelial progenitor cell in a medium comprising a Large Tumor Suppressor Kinase (LATS) inhibitor;
wherein said culturing results in the differentiation of the at least one AT2 cell and/or lung epithelial progenitor cell to an alveolar epithelial cell type I (AT1) cell.

2. The method of claim 1, wherein the medium is a complete serum free defined medium.

3. The method of claim 1, wherein the LATS inhibitor is selected from the group consisting of:
LATS-IN-1 (TRULI; N-(3-benzylthiazol-2(3H)-ylidene)-1H-pyrrolo[2,3-b]pyridine-3-carboxamide); GA-017; and TDI-011536.

4. The method of claim 1, wherein the medium does not comprise, or the at least one AT2 cell and/or lung epithelial progenitor cell is not in contact with, CHIR99021 and/or keratinocyte growth factor (KGF) protein.

5. The method of claim 1, wherein the medium does not comprise, or the at least one AT2 cell and/or lung epithelial progenitor cell is not in contact with, ectopic epidermal growth factor (EGF) protein and/or ectopic fibroblast growth factor 10 (FGF10) protein.

6. The method of claim 1, wherein the medium further comprises, or the at least one AT2 cell and/or lung epithelial progenitor cell is further contacted with, ectopic epidermal growth factor (EGF) protein and/or ectopic fibroblast growth factor 10 (FGF10) protein.

7. The method of claim 1, whereby the culturing at least one AT2 cell and/or lung epithelial progenitor cell in a medium comprising a LATS inhibitor induces YAP signaling.

8. The method of claim 1, wherein the at least one AT2 cell is a human AT2 cell, a primary AT2 cell, or an induced AT2 cell; and/or
the at least one lung epithelial progenitor cell is a human lung epithelial progenitor cell; a primary lung epithelial progenitor cell; or an induced lung epithelial progenitor cell.

9. The method of claim 1, further comprising contacting the at least one AT2 cell and/or lung epithelial progenitor cell, or a cell produced by the method, with:
a nucleic acid encoding a reporter protein;
a virus;
smoke; and/or
Transforming Growth Factor Beta (TGFB) and/or bleomycin.

10. The method of claim 1, wherein the at least one AT2 cell and/or lung epithelial progenitor cell comprises a pulmonary fibrosis (PF) inducing mutation.

11. The method of claim 1, further comprising inducing ectopic Yes Associated Protein (YAP) expression in at least one AT2 cell and/or lung epithelial progenitor cell.

12. The method of claim 11, wherein the YAP comprises:
mutation of the serine of at least one HXRXXS consensus sequence;
mutation of the serine of at least one HXRXXS consensus sequence to alanine;
mutation of the serine of every HXRXXS consensus sequence;
mutation of the serine of every HXRXXS consensus sequence to alanine;
mutation of each serine corresponding to S61, S109, S127, S164, and S397 of SEQ ID NO: 1; or mutation of each serine corresponding to S61, S109, S127, S164, and S397 of SEQ ID NO: 1 to alanine.

13. The method of claim 11, wherein inducing comprises contacting the at least one AT2 cell and/or lung epithelial progenitor cell with an expression vector encoding a YAP protein.

* * * * *